(12) United States Patent
Sakai et al.

(10) Patent No.: US 10,451,967 B2
(45) Date of Patent: Oct. 22, 2019

(54) ACID- AND RADICAL-GENERATING AGENT AND METHOD FOR GENERATING ACID AND RADICAL

(71) Applicant: FUJIFILM Wako Pure Chemical Corporation, Osaka-shi, Osaka (JP)

(72) Inventors: Nobuhiko Sakai, Kawagoe (JP); Kosuke Yanaba, Kawagoe (JP)

(73) Assignee: FUJIFILM Wako Pure Chemical Corporation, Osaka (JP)

( * ) Notice: Subject to any disclaimer, the term of this patent is extended or adjusted under 35 U.S.C. 154(b) by 483 days.

(21) Appl. No.: 15/038,955

(22) PCT Filed: Nov. 21, 2014

(86) PCT No.: PCT/JP2014/080985
§ 371 (c)(1),
(2) Date: May 24, 2016

(87) PCT Pub. No.: WO2015/076395
PCT Pub. Date: May 28, 2015

(65) Prior Publication Data
US 2016/0342084 A1    Nov. 24, 2016

(30) Foreign Application Priority Data

Nov. 25, 2013 (JP) .................. 2013-243388

(51) Int. Cl.
C07D 335/16        (2006.01)
G03F 7/004         (2006.01)
(Continued)

(52) U.S. Cl.
CPC .......... *G03F 7/0045* (2013.01); *B01J 19/127* (2013.01); *C07C 317/24* (2013.01); *C07C 317/44* (2013.01); *C07D 335/16* (2013.01); *G03F 7/029* (2013.01); *G03F 7/031* (2013.01); *C07C 2603/24* (2017.05)

(58) Field of Classification Search
None
See application file for complete search history.

(56) References Cited

U.S. PATENT DOCUMENTS 4,058,401 A    11/1977 Crivello
4,136,102 A    1/1979 Crivello
(Continued)

FOREIGN PATENT DOCUMENTS

JP    S50-151997    12/1975
JP    H04-45159     2/1992
(Continued)

OTHER PUBLICATIONS

Chang et al, "Synthesis of 2-Substituted 9,10-Anthraquinones," Synthetic Communications vol. 43, pp. 3363-3372, 2013 (Year: 2013).*
(Continued)

*Primary Examiner* — Heidi Reese
(74) *Attorney, Agent, or Firm* — Hamre, Schumann, Mueller & Larson, P.C.

(57) ABSTRACT

It is a subject of the present invention to provide an acid- and radical-generating agent which has high sensitivity to an active energy ray having a wavelength of around 300 to 450 nm, and can exert both high acid-generating performance and high radical-generating performance, and has heat resistance; and a method for generating an acid and a radical.

The present invention relates to a compound represented by the general formula (A); an acid- and radical-generating agent comprising the compound; and a method for generating an acid and a radical:

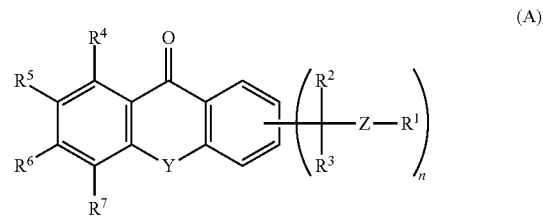

(A)

wherein n pieces of $R^1$ each independently represent an alkyl group, which may have a specific functional group in the chain, or in which a hydrogen atom may be substituted by a halogen atom; an alkoxy group, in which a hydrogen atom may be substituted by a halogen atom; an aryl group or an aryloxy group, in which a hydrogen atom may be substituted by a halogen atom, an alkyl group or a haloalkyl group; or an arylalkyl group or an arylalkyloxy group, in which a hydrogen atom may be substituted by a halogen atom, an alkyl group or a haloalkyl group; n pieces of $R^2$ and $R^3$ each independently represent a hydrogen atom, an alkyl group or an alkoxycarbonyl group; $R^4$ to $R^7$ each independently represent a hydrogen atom, a halogen atom, an alkyl group, an alkoxy group, an alkenyl group, an aryl group, an alkoxycarbonyl group, a dialkylamino group or a nitro group; Y represents an oxygen atom, a sulfur atom, or a carbonyl group; n pieces of Z each independently represent a sulfonyl group or an alkoxyphosphoryl group; n represents 1 or 2.

12 Claims, No Drawings

(51) Int. Cl.
  *B01J 19/12* (2006.01)
  *C07C 317/24* (2006.01)
  *C07C 317/44* (2006.01)
  *G03F 7/029* (2006.01)
  *G03F 7/031* (2006.01)

(56) References Cited

U.S. PATENT DOCUMENTS

| | | |
|---|---|---|
| 4,161,478 A | 7/1979 | Crivello |
| 4,173,551 A | 11/1979 | Crivello |
| 4,175,972 A | 11/1979 | Crivello |
| 4,219,654 A | 8/1980 | Crivello |
| 4,234,732 A | 11/1980 | Crivello |
| 4,250,311 A | 2/1981 | Crivello |
| 4,407,759 A | 10/1983 | Crivello |
| 4,417,061 A | 11/1983 | Crivello |
| 6,093,753 A | 7/2000 | Takahashi |

FOREIGN PATENT DOCUMENTS

| | | |
|---|---|---|
| JP | H09-118663 | 5/1997 |
| JP | H10-213899 | 8/1998 |
| JP | 2008-266495 | 11/2008 |
| JP | 2011-252147 | 12/2011 |
| JP | 2012-1453 | 1/2012 |
| JP | 2013-1821 | 1/2013 |

OTHER PUBLICATIONS

Chang, M.-Y. et al., Synthetic Communications 2013, vol. 43, pp. 3363-3372.*

H.D. Scharf and R. Weitz, "Synthesis of Anthraquinonyl-Methanesulfonic Acids as Catalysts for Photoredox Reaction," Tetrahedron, vol. 35 (1979), p. 2263-2267.

M.V. Gorelik et al., "Interaction of alpha-Halogen- and alpha-Nitroanthraquinones with CH-acid Anions I: Synthesis of 1-alkyl-, 1,5-dialkyl- and 1-aroylanthraquinones," Russian Journal of Organic Chemistry, vol. 28, No. 11 (1992), p. 2294-2300.

M.V. Gorelik et al., "Interaction of alpha-Halogen- and alpha-Nitroanthraquinones with CH-acid Anions III: Peri-Cyclizations in Case of Interaction with Ketones, Malonic and Phenylsulfonylacetic Esters, Nitromethane," Russian Journal of Organic Chemistry, vol. 28, No. 12 (1992), p. 2534-2540.

"STN Document 1" CAS Registry No. 1456629-46-1, 1456629-38-1, (Enter STN Oct. 9, 2013); CAS Registry No. 208759-14-2, 208759-12-0 (Enter STN) Jul. 22, 1998); CAS Registry No. 152486-25-4 (Enter STN Jan. 26, 1994); CAS Registry No. 152190-76-6, 152190-68-6, 152190-67-5, 152190-64-2 (Enter STN Jan. 11, 1994); CAS Registry No. 102468-68-8 (Enter STN May 31, 1986); and CAS Registry No. 74215-10-04, 74215-01-3, 742414-99-6 (Enter STN Nov. 16, 1984).

"STN Document 2" CAS Registry No. 114089-59-7, 114089-58-6, 114089-57-5, 114089-56-4 (Enter STN Apr. 23, 1988).

Jean-Pierre Fouassier and Jacques Lalevee, "Photoinitiators for Polymer Synthesis: Scope, Reactivity, and Efficiency," Wiley-VCH, 2012, p. 144-147.

Meng-Yang Chang and Hang-Yi Tai, "Synthesis of 2-substituted 9,10-anthraquinones," Synthetic Communications, 2013, vol. 43, p. 3363-3372.

A. Wada et al., "Retinoids and Related Compounds; 18: A Convenient Synthesis of Retinoic Acid Analogs Having an Anthraquinone Ring," Synthesis, Sep. 1995, No. 9, p. 1107-1110.

M. Makosza et al., "Reactions of Chloromethyl Aryl Sulfones Carbanions with Anthraquinone Derivatives," Tetrahedron, 1998, vol. 54, p. 6147-6158.

H.D. Scharf and R. Weitz, "Synthese Von Anthrachinonyl-Methanosulfonsauren als Katalysatoren fur Photoredoxreaktionen," Tetrahedron, 1979, vol. 35, p. 2263-2267.

A. Chiarini et al., "Chromone and xanthone derivatives related to Fostedil," Acta Pharm. Suec., 1987, vol. 24, p. 257-262.

Zhurnal Organicheskoj Khimii, 1992, vol. 28, No. 11, p. 2294-2300, Compound Va, XVa; cited in International Search Report.

Zhurnal Organicheskoj Khimii, 1992, vol. 28, No. 12, p. 2534-2540, Compound VIa, XIa, XI6; cited in International Search Report.

Krohn, et al., "Product Class 5: Anthra-9,10-quinones, Anthra-1,2-quinones, Anthra-1,4-quinones, Anthra-2,9-qinones, and Their Higher Fused Analogues", Science of Synthesis 28 (2006) 367-506.

* cited by examiner

ACID- AND RADICAL-GENERATING AGENT AND METHOD FOR GENERATING ACID AND RADICAL

TECHNICAL FIELD

The present invention relates to a compound useful as an acid-generating agent, a radical-generating agent, or the like, to be used in a resist field or the like, and for more detail, relates to a compound which has property to generate an acid and a radical by irradiation of an active energy ray having a wavelength of around 300 to 450 nm; an acid- and radical-generating agent comprising these; and a method for generating an acid and a radical.

BACKGROUND ART

Conventionally, as a resist material to be used in a photolithography process, there has been known a resin composition containing a resin, which is changed to alkali-soluble by a reaction of a carboxylic acid derivative or a phenol derivative by an action of an acid, for example, a tert-butyl ester of a carboxylic acid, or a tert-butyl ether or a silyl ether of phenol or the like, and a photo-acid-generating agent. By irradiation of an active energy ray of, for example, UV-rays and the like onto such a resin composition to decompose the photo-acid-generating agent, and to generate a strong acid, and still more by carrying out post exposure baking (PEB), deprotection of the carboxylic acid derivative or the phenol derivative in the resin is induced by an action of the strong acid generated from the photo-acid-generating agent, and a carboxylic acid or a phenol is generated. By such chemical change, a resin at an exposed part, where the active energy ray are irradiated, changes to easy-soluble to an alkaline developing solution, and then by an action of the alkaline developing solution to the resin, pattern formation is carried out. Usually, in such pattern formation, the active energy ray of far-ultraviolet light (wavelength 200 nm or shorter), KrF excimer laser light (wavelength 248 nm), ArF excimer laser light (wavelength 193 nm), as well as F2 laser light (wavelength 157 nm), extreme ultraviolet light (wavelength 1 to 30 nm), and the like, are used in exposure, however, in recent years, application researches have also been carried out, using a photo-reaction, where the active energy ray of a long wavelength region, such as near-ultraviolet light (wavelength 200 to 380 nm), visible light (wavelength 380 to 750 nm), and the like are used as a light source. For example, as a resist for i-ray lithography using a wavelength of 365 nm, a diazonaphtho-quinone (DNQ) resist is generally used, however, i-ray lithography using a chemically amplified resist has been received attention, because the chemically amplified resist is capable of preparing a resist having high sensitivity and high thickness, not attainable by the DNQ resist. Accompanying with this, as for the photo-acid-generating agent, such one has been required that is sensitive to the active energy ray of a long wavelength region, such as for using i-ray lithography or the like. In addition, a cross-linking reaction using an acid generated from a photo-acid-generating agent as a catalyst has also been attempted, and as application fields of a material utilizing such a cross-linking reaction, there are a semiconductor device (an interlayer insulating film, a buffer layer, a bump layer), 127 MEMS (Micro Electro Mechanical System), a liquid crystal display, an organic EL display, a sensor, a solar cell, printing and the like.

As the acid-generating agent having sensitivity to such an active energy ray, ionic-type or nonionic-type ones have been known. As the ionic-type acid-generating agent, for example, an aryl sulfonium salt compound (for example, PATENT LITERATURE 1 and 2), or the like has been known. As the nonionic-type acid-generating agent, for example, sulfonate esters, for example, a nitrobenzyl sulfonate compound, a N-oximesulfonate compound, a N-imidesulfonate compound and the like have been known conventionally, and as for these sulfonate esters, various investigations have been carried out, because of relatively easy chemical modification and superior solubility (for example, PATENT LITERATURE 3 and 4). In addition, as a different type from the sulfonate esters, a diazodisulfonyl-methane compound (for example, PATENT LITERATURE 5), or a α-sulfonylketone compound (for example, NON-PATENT LITERATURE 1) having function as a photo-radical initiator, or the like has been known to generate an acid by irradiation of an active energy ray.

CITATION LIST

Patent Literature

PATENT LITERATURE 1: JP-A-50-151997
PATENT LITERATURE 2: JP-A-9-118663
PATENT LITERATURE 3: JP-A-2008-266495
PATENT LITERATURE 4: JP-A-2013-1821
PATENT LITERATURE 5: JP-A-10-213899

Non-Patent Literature

NON-PATENT LITERATURE 1: Photoinitiators for Polymer Synthesis Scope, Reactivity and Efficiency (Wiley-VCH), P144

SUMMARY OF INVENTION

Technical Problem

Conventional acid-generating agents as described above, however, have low sensitivity to an active energy ray of a long wavelength region, such as near-ultraviolet light, visible light and the like, and thus have a problem of inferior acid generation efficiency in the long wavelength region. In addition, an ionic-type acid-generating agent, having an elongated conjugated system by incorporation of an aromatic ring, such as an anthracene ring, a pyrene ring or the like, as a substituent to an aryl group, for example, an arylsulfonium salt or the like, generally has a problem of not enabling to be stored for several weeks or easily changing resist performance (for example, dimensional change, sensitivity change, shape change, or the like), due to having generally poor solubility, causing easy deposition as a solid in a resin composition, or inferior stability in an organic solvent. In addition, in recent years, in view of energy saving, such an UV-LED exposure machine having high output in a narrow wavelength region has been used, and for example, in using such an exposure machine in pattern formation, it is necessary to select a photo-acid-generating agent suitable for such a narrow light emitting region (for example 365 nm, 396 nm). Up to now, however, there has been little photo-acid-generating agents having superior performance to a light emitting region of the UV-LED of i-ray having a wavelength of 365 nm, or the like, or an active energy ray of h-ray having a wavelength of 405 nm, which makes application thereof a difficult situation. Under such a background, there has been desired development of an acid-generating agent which has high sensitivity to an active energy ray having a wavelength of around 300 to 450 nm, and can exert high acid-generating performance.

The present invention has been proposed in view of such circumstances as described above, and a subject is to provide an acid-generating agent which has high sensitivity to an active energy ray having a wavelength of around 300 to 450 nm, which is a near-ultraviolet light region and a visible light region, and can generate an acid efficiently by irradiation of the active energy ray of these wavelengths, in a short time; and a method for generating an acid.

Solution to Problem

The present invention is composed of the following constitution.
(1) A compound represented by the general formula (A).

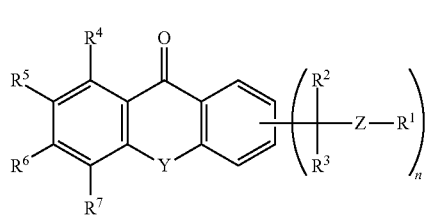

(wherein n pieces of $R^1$ each independently represent an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an alkoxy group having 1 to 10 carbon atoms, in which a hydrogen atom may be substituted by a halogen atom; an aryl group having 6 to 10 carbon atoms, in which a hydrogen atom may be substituted by a halogen atom, an alkyl group or a haloalkyl group; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group; n pieces of $R^2$ and n pieces of $R^3$ each independently represent a hydrogen atom, an alkyl group having 1 to 10 carbon atoms or an alkoxycarbonyl group having 2 to 7 carbon atoms; $R^4$ to $R^7$ each independently represent a hydrogen atom, a halogen atom, an alkyl group having 1 to 6 carbon atoms, an alkoxy group having 1 to 6 carbon atoms, an alkenyl group having 2 to 6 carbon atoms, an aryl group having 6 to 10 carbon atoms, an alkoxycarbonyl group having 2 to 7 carbon atoms, a dialkylamino group having 2 to 8 carbon atoms, or a nitro group; Y represents an oxygen atom, a sulfur atom or a carbonyl group; n pieces of Z each independently represent a sulfonyl group or an alkoxyphosphoryl group having 1 to 6 carbon atoms; n represents 1 or 2.)
 (2) An acid- and radical-generating agent comprising the compound represented by the above-described general formula (A).
 (3) A method for generating an acid and a radical, which comprises irradiating an active energy ray onto the compound represented by the above-described general formula (A).

Advantageous Effects of Invention

The compound represented by the general formula (A) of the present invention is a compound having a tricyclic photo absorbing group and an acid-generating group (an acid generation unit), and is a compound generating a strong acid, for example, sulfinic acid, or the like, as well as generating a radial by irradiation of an active energy ray. These compounds have high sensitivity to an active energy ray having a wavelength of around 300 to 450 nm, and in particular, to an active energy ray having a wavelength of 405 nm (h-ray); as well as can generate an acid and a radical efficiently by irradiation of an active energy ray in a short time; and still more have heat resistance. The compound represented by the general formula (A) of the present invention can be used in either purpose as an acid-generating agent or a radical-generating agent, because of having such performance, and still more, it exerts such an effect that it can be used also as an acid- and radical-generating agent having both performances of the acid-generating agent and the radical-generating agent. In addition, because the compound represented by the general formula (A) of the present invention is capable of having two acid generation units in the molecule, such a compound exerts an effect of being capable of generating two times acid as compared with conventional one.

The method for generating an acid and a radical of the present invention is a method for generating both of an acid and a radical by irradiation of an active energy ray, in particular, an active energy ray having a wavelength of around 300 to 450 nm, onto the compound represented by the general formula (A) of the present invention, which exerts such an effect of being capable of generating a strong acid, for example, sulfenic acid, or the like, as well as generating a radial from the compound represented by the general formula (A) of the present invention, more efficiently as compared with a method for generating an acid and a radical by thermal energy.

The present inventors have intensively studied to attain the above-described objects, and as a result, have discovered that not only a strong acid but also a radial are generated from the compound represented by the general formula (A) by irradiation of an active energy ray, in particular, an active energy ray having a wavelength of around 300 to 450 nm, onto the compound represented by general formula (A) having in combination a tricyclic photo absorbing group and an acid generation unit for generating a strong acid. Still more, the present inventors have discovered that, because the compound represented by the general formula (A) has heat resistance, the compound represented by general formula (A) can be used not only in any purposes as an acid-generating agent or a radical-generating agent, but also as an acid- and radical-generating agent having both performances of the acid-generating agent and the radical-generating agent, and thus have completed the present invention.

DESCRIPTION OF EMBODIMENTS

In the present invention, active energy ray includes, except for the case where a wavelength is specified, not only an electromagnetic wave having a wavelength of a visible light region (visible rays), but also an electromagnetic wave having a wavelength of a non-visible light region, such as, for example, an electromagnetic wave having a wavelength of an ultraviolet light region (UV rays), an electromagnetic wave having a wavelength of an infrared light region (infrared rays), X-rays or the like. In the present invention, there may be the case where an acid-generating agent sensitive to an active energy ray (an acid-generating agent generating an acid by irradiation of an active energy ray) is referred to as a photo-acid-generating agent, a radical-generating agent sensitive to an active energy ray (a radical-generating agent generating a radical by irradiation of an active energy ray) is referred to as the photo-radical-generating agent, and an acid- and radical-generating agent sensitive to an active energy ray (an acid- and radical-generating agent generating both of an acid and a radical by irradiation of an active energy ray) is referred to as a photo-acid- and radical-generating agent. In addition, there may be the case where an active energy ray having a wavelength of 365 nm, 405 nm and 436 nm are represented as i-ray, h-ray and g-ray, respectively.

—A Compound Represented by the General Formula (A) of the Present Invention—

The compound of the present invention is a compound represented by the following general formula (A).

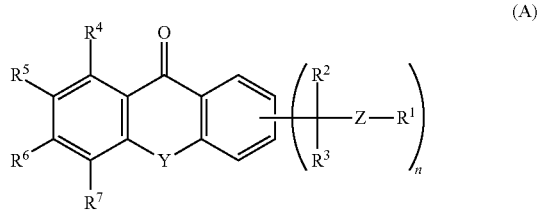

(wherein n pieces of $R^1$ each independently represent an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an alkoxy group having 1 to 10 carbon atoms, in which a hydrogen atom may be substituted by a halogen atom; an aryl group having 6 to 10 carbon atoms, in which a hydrogen atom may be substituted by a halogen atom, an alkyl group or a haloalkyl group; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group; n pieces of $R^2$ and n pieces of $R^3$ each independently represent a hydrogen atom, an alkyl group having 1 to 10 carbon atoms or an alkoxycarbonyl group having 2 to 7 carbon atoms; $R^4$ to $R^7$ each independently represent a hydrogen atom, a halogen atom, an alkyl group having 1 to 6 carbon atoms, an alkoxy group having 1 to 6 carbon atoms, an alkenyl group having 2 to 6 carbon atoms, an aryl group having 6 to 10 carbon atoms, an alkoxycarbonyl group having 2 to 7 carbon atoms, a dialkylamino group having 2 to 8 carbon atoms, or a nitro group; Y represents an oxygen atom, a sulfur atom or a carbonyl group; n pieces of Z each independently represent a sulfonyl group or an alkoxyphosphoryl group having 1 to 6 carbon atoms; n represents 1 or 2.)

In an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom, represented by $R^1$ in general formula (A); an alkyl group having 1 to 20 carbon atoms, in which a hydrogen atom may be substituted by a halogen atom, may be any of a straight chained, branched or cyclic group, and specifically includes an unsubstituted (not substituted by a halogen atom) alkyl group having 1 to 20 carbon atoms, such as, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, an undecyl group, a dodecyl group, a tridecyl group, a tetradecyl group, a pentadecyl group, a hexadecyl group, a heptadecyl group, an octadecyl group, a nonadecyl group, an icosyl group, a norbornyl group (a norbornane-X-yl group), a bornyl group (a bornane-X-yl group), a menthyl group (a mentha-X-yl group), an adamantyl group, a decahydronaphthyl group, or the like; an alkyl group having 1 to 20 carbon atoms, in which a hydrogen atom bonded to the carbon atom is substituted by a halogen atom, such as, for example, an alkyl group having 1 to 20 carbon atoms, in which a hydrogen atom bonded to the carbon atoms is substituted by a fluorine atom, such as, for example, a trifluoromethyl group, a pentafluoroethyl group, a heptafluoro-n-propyl group, a heptafluoroisopropyl group, a nonafluoro-n-butyl group, a nonafluoroisobutyl group, a nonafluoro-sec-butyl group, a nonafluoro-tert-butyl group, a nonafluorocyclobutyl group, a perfluoro-n-pentyl group, a perfluoroisopentyl group, a perfluoro-sec-pentyl group, a perfluoro-tert-pentyl group, a perfluoroneopentyl group, a perfluoro-2-methylbutyl group, a perfluoro-1,2-dimethylpropyl group, a perfluoro-1-ethylpropyl group, a perfluorocyclopentyl group, a perfluoro-n-hexyl group, a perfluoroisohexyl group, a perfluoro-sec-hexyl group, a perfluoro-tert-hexyl group, a perfluoroneohexyl group, a perfluoro-2-methylpentyl group, a perfluoro-1,2-dimethylbutyl group, a perfluoro-2,3-dimethylbutyl group, a perfluoro-1-ethylbutyl group, a perfluorocyclohexyl group, a perfluoro-n-heptyl group, a perfluoroisoheptyl group, a perfluoro-sec-heptyl group, a perfluoro-tert-heptyl group, a perfluoroneoheptyl group, a perfluorocycloheptyl group, a perfluoro-n-octyl group, a perfluoroisooctyl group, a perfluoro-sec-octyl group, a perfluoro-tert-octyl group, a perfluoroneooctyl group, a perfluoro-2-ethylhexyl group, a perfluorocyclooctyl group, a perfluoro-n-nonyl group, a perfluoroisononyl group, a perfluoro-sec-nonyl group, a perfluoro-tert-nonyl group, a perfluoroneononyl group, a perfluorocyclononyl group, a perfluoro-n-decyl group, a perfluoroisodecyl group, a perfluoro-sec-decyl group, a perfluoro-tert-decyl group, a perfluoroneodecyl group, a perfluorocyclodecyl group, a perfluoroundecyl group, a perfluorododecyl group, a perfluorotridecyl group, a perfluorotetradecyl group, a perfluoropentadecyl group, a perfluorohexadecyl group, a perfluoroheptadecyl group, a perfluorooctadecyl group, a perfluorononadecyl group, a perfluoroicosyl group, a perfluoronorbornyl group (a perfluoronorbornane-X-yl group), a perfluorobornyl group (a perfluorobornane-X-yl group), a perfluoromenthyl group (a perfluoromentha-X-yl group), a perfluoroadamantyl group, a perfluorodecahydronaphthyl group, or the like; an alkyl group having 1 to 20 carbon atoms, in which a hydrogen atom bonded to the carbon atoms is substituted by a chlorine atom, such as, for example, a trichloromethyl group, a pentachloroethyl group, a heptachloro-n-propyl group, a heptachloroisopropyl group, a nonachloro-n-butyl group, a nonachloroisobutyl group, a nonachloro-sec-butyl group, a nonachloro-tert-butyl group, a nonachlorocyclobutyl group, a perchloro-n-pentyl group, a perchloroisopentyl group, a perchloro-sec-pentyl group, a perchloro-tert-pentyl group, a perchloroneopentyl group, a perchloro-2-methylbutyl group, a perchloro-1,2-dimethylpropyl group, a perchloro-1-ethylpropyl group, a perchlorocyclopentyl group, a perchloro-n-hexyl group, a perchloroisohexyl group, a perchloro-sec-hexyl group, a perchloro-tert-hexyl group, a perchloroneohexyl group, a perchloro-2-methylpentyl group, a perchloro-1,2-dimethylbutyl group, a perchloro-2,3-dimethylbutyl group, a perchloro-1-ethylbutyl group, a perchlorocyclohexyl group, a perchloro-n-heptyl group, a perchloroisoheptyl group, a perchloro-sec-heptyl group, a perchloro-tert-heptyl group, a perchloroneoheptyl group, a perchlorocycloheptyl group, a perchloro-n-octyl group, a perchloroisooctyl group, a perchloro-sec-octyl group, a perchloro-tert-octyl group, a perchloroneooctyl group, a perchloro-2-ethylhexyl group, a perchlorocyclooctyl group, a perchloro-n-nonyl group, a perchloroisononyl group, a perchloro-sec-nonyl group, a perchloro-tert-nonyl group, a perchloroneononyl group, a perchlorocyclononyl group, a perchloro-n-decyl group, a perchloroisodecyl group, a perchloro-sec-decyl group, a perchloro-tert-decyl group, a perchloroneodecyl group, a perchlorocyclodecyl group, a perchloroundecyl group, a perchlorododecyl group, a perchlorotridecyl group, a perchlorotetradecyl group, a perchloropentadecyl group, a perchlorohexadecyl group, a perchloroheptadecyl group, a perchlorooctadecyl group, a perchlorononadecyl group, a perchloroicosyl group, a perchloronorbornyl group (a perchloronorbornane-X-yl group), a perchlorobornyl group (a perchlorobornane-X-yl group), a perchloromenthyl group (a perchloromentha-X-yl group), a perchloroadamantyl group, a perchlorodecahydronaphthyl group, or the like; an alkyl group having 1 to 20 carbon atoms, in which a hydrogen atom bonded to the carbon atoms is substituted by a bromine atom, such as, for example, a tribromomethyl group, a pentabromoethyl group, a heptabromo-n-propyl group, a heptabromoisopropyl group, a nonabromo-n-butyl group, a nonabromoisobutyl group, a nonabromo-sec-butyl group, a nonabromo-tert-butyl group, a nonabromocyclobutyl group, a perbromo-n-pentyl group, a perbromoisopentyl group, a perbromo-sec-pentyl group, a perbromo-tert-pentyl group, a perbromoneopentyl group, a perbromo-2-methylbutyl group, a perbromo-1,2-dimethylpropyl group, a perbromo-1-ethylpropyl group, a perbromocyclopentyl group, a perbromo-n-hexyl group, a perbromoisohexyl group, a perbromo-sec-hexyl group, a perbromo-tert-hexyl group, a perbromoneohexyl group, a perbromo-2-methylpentyl group, a perbromo-1,2-dimethylbutyl group, a perbromo-2,3-dimethylbutyl group, a perbromo-1-ethylbutyl group, a perbromocyclohexyl group, a perbromo-n-heptyl group, a perbromoisoheptyl group, a perbromo-sec-heptyl group, a perbromo-tert-heptyl group, a perbromoneoheptyl group, a perbromocycloheptyl group, a perbromo-n-octyl group, a perbromoisooctyl group, a perbromo-sec-octyl group, a perbromo-tert-octyl group, a perbromoneooctyl group, a perbromo-2-ethylhexyl group, a perbromocyclooctyl group, a perbromo-n-nonyl group, a perbromoisononyl group, a perbromo-sec-nonyl group, a perbromo-tert-nonyl group, a perbromoneononyl group, a perbromocyclononyl group, a perbromo-n-decyl group, a perbromoisodecyl group, a perbromo-sec-decyl group, a perbromo-tert-decyl group, a perbromoneodecyl group, a perbromocyclodecyl group, a perbromoundecyl group, a perbromododecyl group, a perbromotridecyl group, a perbromotetradecyl group, a perbromopentadecyl group, a perbromohexadecyl group, a perbromoheptadecyl group, a perbromooctadecyl group, a perbromononadecyl group, a perbromoicosyl group, a perbromonorbornyl group (a perbromonorbornane-X-yl group), a perbromobornyl group (a perbromobornane-X-yl group), a perbromomenthyl group (a perbromomentha-X-yl group), a perbromoadamantyl group, a perbromodecahydronaphthyl group, or the like; an alkyl group having 1 to 20 carbon atoms, in which a hydrogen atom bonded to the carbon atoms is substituted by an iodine atom, such as, for example, a triiodomethyl group, a pentaiodoethyl group, a heptaiodo-n-propyl group, a heptaiodoisopropyl group, a nonaiodo-n-butyl group, a nonaiodoisobutyl group, a nonaiodo-sec-butyl group, a nonaiodo-tert-butyl group, a nonaiodocyclobutyl group, a periodo-n-pentyl group, a periodoisopentyl group, a periodo-sec-pentyl group, a periodo-tert-pentyl group, a periodoneopentyl group, a periodo-2-methylbutyl group, a periodo-1,2-dimethylpropyl group, a periodo-1-ethylpropyl group, a periodocyclopentyl group, a periodo-n-hexyl group, a periodoisohexyl group, a periodo-sec-hexyl group, a periodo-tert-hexyl group, a periodoneohexyl group, a periodo-2-methylpentyl group, a periodo-1,2-dimethylbutyl group, a periodo-2,3-dimethylbutyl group, a periodo-1-ethylbutyl group, a periodocyclohexyl group, a periodo-n-heptyl group, a periodoisoheptyl group, a periodo-sec-heptyl group, a periodo-tert-heptyl group, a periodoneoheptyl group, a periodocycloheptyl group, a periodo-n-octyl group, a periodoisooctyl group, a periodo-sec-octyl group, a periodo-tert-octyl group, a periodoneooctyl group, a periodo-2-ethylhexyl group, a periodocyclooctyl group, a periodo-n-nonyl group, a periodoisononyl group, a periodo-sec-nonyl group, a periodo-tert-nonyl group, a periodoneononyl group, a periodocyclononyl group, a periodo-n-decyl group, a periodoisodecyl group, a periodo-sec-decyl group, a periodo-tert-decyl group, a periodoneodecyl group, a periodocyclodecyl group, a periodoundecyl group, a periodododecyl group, a periodotridecyl group, a periodotetradecyl group, a periodopentadecyl group, a periodohexadecyl group, a periodoheptadecyl group, a periodooctadecyl group, a periodononadecyl group, a periodoicosyl group, a periodonorbornyl group (a periodonorbornane-X-yl group), a periodobornyl group (a periodobornane-X-yl group), a periodomenthyl group (a periodomentha-X-yl group), a periodoadamantyl group, a periododecahydronaphthyl group, or the like.

Among these alkyl groups, an unsubstituted (not substituted by a halogen atom) alkyl group having 1 to 15 carbon atoms, such as, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, an undecyl group, a dodecyl group, a tridecyl group, a tetradecyl group, a pentadecyl group, a norbornyl group (a norbornane-X-yl group), a bornyl group (a bornane-X-yl group), a menthyl group (a mentha-X-yl group), an adamantyl group, a decahydronaphthyl group or the like; and an alkyl group having 1 to 15 carbon atoms, in which a hydrogen atom bonded to the carbon atoms is substituted by a fluorine atom, such as, for example, a trifluoromethyl group, a pentafluoroethyl group, a heptafluoro-n-propyl group, a heptafluoroisopropyl group, a nonafluoro-n-butyl group, a nonafluoroisobutyl group, a nonafluoro-sec-butyl group, a nonafluoro-tert-butyl group, a nonafluorocyclobutyl group, a perfluoro-n-pentyl group, a perfluoroisopentyl group, a perfluoro-sec-pentyl group, a perfluoro-tert-pentyl group, a perfluoroneopentyl group, a perfluoro-2-methylbutyl group, a perfluoro-1,2-dimethylpropyl group, a perfluoro-1-ethylpropyl group, a perfluorocyclopentyl group, a perfluoro-n-hexyl group, a perfluoroisohexyl group, a perfluoro-sec-hexyl group, a perfluoro-tert-hexyl group, a perfluoroneohexyl group, a perfluoro-2-methylpentyl group, a perfluoro-1,2-dimethylbutyl group, a perfluoro-2,3-dimethylbutyl group, a perfluoro-1-ethylbutyl group, a perfluorocyclohexyl group, a perfluoro-n-heptyl group, a perfluoroisoheptyl group, a perfluoro-sec-heptyl group, a perfluoro-tert-heptyl group, a perfluoroneoheptyl group, a perfluorocycloheptyl group, a perfluoro-n-octyl group, a perfluoroisooctyl group, a perfluoro-sec-octyl group, a perfluoro-tert-octyl group, a perfluoroneooctyl group, a perfluoro-2-ethylhexyl group, a perfluorocyclooctyl group, a perfluoro-n-nonyl group, a perfluoroisononyl group, a perfluoro-sec-nonyl group, a perfluoro-tert-nonyl group, a perfluoroneononyl group, a perfluorocyclononyl group, a perfluoro-n-decyl group, a perfluoroisodecyl group, a perfluoro-sec-decyl group, a perfluoro-tert-decyl group, a perfluoroneodecyl group, a perfluorocyclodecyl group, a perfluoroundecyl group, a perfluorododecyl group, a perfluorotridecyl group, a perfluorotetradecyl group, a perfluoropentadecyl group, a perfluoronorbornyl group (a perfluoronorbornane-X-yl group), a perfluorobornyl group (a perfluorobornane-X-yl group), a perfluoromenthyl group (a perfluoromentha-X-yl group), a perfluoroadamantyl group, a perfluorodecahydronaphthyl group or the like are preferable.

Such an alkyl group having 1 to 20 carbon atoms, in which a hydrogen atom may be substituted by a halogen atom, may have a functional group selected from the group consisting of a carbonyloxy group, a carbonylamino group, an ether group, and a sulfide group in the chain. A specific example of an alkyl group having 1 to 20 carbon atoms, in which a hydrogen atom may be substituted by a halogen atom, in the case of having a functional group selected from the group consisting of a carbonyloxy group, a carbonylamino group, an ether group and a sulfide group in the chain, includes, for example, the following general formulae (B-1) or (B-2):

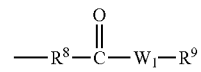
(B-1)

(wherein $R^8$ represents an alkylene group having 1 to 7 carbon atoms, in which a hydrogen atom may be substituted by a halogen atom, $R^9$ represents an alkyl group having 1 to 12 carbon atoms, in which a hydrogen atom may be substituted by a halogen atom, $W_1$ represents an oxygen atom or a NH group.)

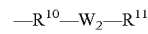
(B-2)

(wherein $R^{19}$ represents an alkylene group having 1 to 8 carbon atoms, in which a hydrogen atom may be substituted by a halogen atom, $R^{11}$ represents an alkyl group having 1 to 12 carbon atoms, in which a hydrogen atom may be substituted by a halogen atom, $W_2$ represents an oxygen atom or a sulfur atom.)

A specific example of an alkylene group having 1 to 7 carbon atoms, in which a hydrogen atom may be substituted by a halogen atom, represented by $R^8$ in the general formula (B-1), includes an unsubstituted (not substituted by a halogen atom) alkylene group having 1 to 7 carbon atoms, such as, for example, a methylene group, a dimethylene group (an ethylene group), a trimethylene group, a propylene group, a tetramethylene group, a pentamethylene group, a hexamethylene group, a heptamethylene group or the like; an alkylene group having 1 to 7 carbon atoms, in which a hydrogen atom bonded to the carbon atoms is substituted by a halogen atom, such as, for example, an alkylene group having 1 to 7 carbon atoms, in which a hydrogen atom bonded to the carbon atoms is substituted by a fluorine atom, such as, for example, a perfluoromethylene group, a perfluorodimethylene group (a perfluoroethylene group), a perfluorotrimethylene group, a perfluoropropylene group, a perfluorotetramethylene group, a perfluoropentamethylene group, a perfluorohexamethylene group, a perfluoroheptamethylene group or the like; an alkylene group having 1 to 7 carbon atoms, in which a hydrogen atom bonded to the carbon atoms is substituted by a chlorine atom, such as, for example, a perchloromethylene group, a perchlorodimethylene group (a perchloroethylene group), a perchlorotrimethylene group, a perchloropropylene group, a perchlorotetramethylene group, a perchloropentamethylene group, a perchlorohexamethylene group, a perchloroheptamethylene group or the like; an alkylene group having 1 to 7 carbon atoms, in which a hydrogen atom bonded to the carbon atoms is substituted by a bromine atom, such as, for example, a perbromomethylene group, a perbromodimethylene group (a perbromoethylene group), a perbromotrimethylene group, a perbromopropylene group, a perbromotetramethylene group, a perbromopentamethylene group, a perbromohexamethylene group, a perbromoheptamethylene group or the like; an alkylene group having 1 to 7 carbon atoms, in which a hydrogen atom bonded to the carbon atoms is substituted by an iodine atom, such as, for example, a periodomethylene group, a periododimethylene group (a periodoethylene group), a periodotrimethylene group, a periodopropylene group, a periodotetramethylene group, a periodopentamethylene group, a periodohexamethylene group, a periodoheptamethylene group or the like.

Among these alkylene groups, an unsubstituted (not substituted by a halogen atom) alkylene group having 1 to 4 carbon atoms, such as, for example, a methylene group, a dimethylene group (an ethylene group), a trimethylene group, a propylene group, a tetramethylene group or the like;

and an alkylene group having 1 to 4 carbon atoms, in which a hydrogen atom bonded to the carbon atoms is substituted by a fluorine atom, such as, for example, a perfluoromethylene group, a perfluorodimethylene group (a perfluoroethylene group), a perfluorotrimethylene group, a perfluoropropylene group, a perfluorotetramethylene group or the like are preferable, and among them, an unsubstituted (not substituted by a halogen atom) alkylene group having 1 to 4 carbon atoms, such as, for example, a methylene group, a dimethylene group (an ethylene group), a trimethylene group, a propylene group, a tetramethylene group or the like is preferable.

A specific example of an alkyl group having 1 to 12 carbon atoms, in which a hydrogen atom may be substituted by a halogen atom, represented by $R^9$ in the general formula (B-1), includes the same as a specific example of an alkyl group having 1 to 12 carbon atoms, in which a hydrogen atom may be substituted by a halogen atom represented by $R^1$ in the general formula (A).

Among these alkyl groups, an unsubstituted (not substituted by a halogen atom) alkyl group having 1 to 10 carbon atoms; and an alkyl group having 1 to 10 carbon atoms, in which a hydrogen atom bonding to the carbon atoms is substituted by a fluorine atom are preferable, and among them, an unsubstituted (not substituted by a halogen atom) alkyl group having 1 to 10 carbon atoms is more preferable. These (more) preferable specific examples also include the same as a specific example of an unsubstituted (not substituted by a halogen atom) alkyl group having 1 to 10 carbon atoms; and an alkyl group having 1 to 10 carbon atoms, in which a hydrogen atom bonding to the carbon atoms is substituted by a fluorine atom, represented by $R^1$ in the general formula (A).

As $W_1$ in the general formula (B-1), an oxygen atom is more preferable.

A specific example of an alkylene group having 1 to 8 carbon atoms, in which a hydrogen atom may be substituted by a halogen atom, represented by $R^{10}$ in the general formula (B-2), includes an unsubstituted (not substituted by a halogen atom) alkylene group having 1 to 8 carbon atoms, such as, for example, a methylene group, a dimethylene group (an ethylene group), a trimethylene group, a propylene group, a tetramethylene group, a pentamethylene group, a hexamethylene group, a heptamethylene group, an octamethylene group or the like; an alkylene group having 1 to 8 carbon atoms, in which a hydrogen atom bonded to the carbon atoms is substituted by a halogen atom, such as, for example, an alkylene group having 1 to 8 carbon atoms, in which a hydrogen atom bonded to the carbon atoms is substituted by a fluorine atom, such as, for example, a perfluoromethylene group, a perfluorodimethylene group (a perfluoroethylene group), a perfluorotrimethylene group, a perfluoropropylene group, a perfluorotetramethylene group, a perfluoropentamethylene group, a perfluorohexamethylene group, a perfluoroheptamethylene group, a perfluorooctamethylene group or the like; an alkylene group having 1 to 8 carbon atoms, in which a hydrogen atom bonded to the carbon atoms is substituted by a chlorine atom, such as, for example, a perchloromethylene group, a perchlorodimethylene group (a perchloroethylene group), a perchlorotrimethylene group, a perchloropropylene group, a perchlorotetramethylene group, a perchloropentamethylene group, a perchlorohexamethylene group, a perchloroheptamethylene group, a perchlorooctamethylene group or the like; an alkylene group having 1 to 8 carbon atoms, in which a hydrogen atom bonded to the carbon atoms is substituted by a bromine atom, such as, for example, a perbromomethylene group, a perbromodimethylene group (a perbromoethylene group), a perbromotrimethylene group, a perbromopropylene group, a perbromotetramethylene group, a perbromopentamethylene group, a perbromohexamethylene group, a perbromoheptamethylene group, a perbromooctamethylene group or the like; an alkylene group having 1 to 8 carbon atoms, in which a hydrogen atom bonded to the carbon atoms is substituted by an iodine atom, such as, for example, a periodomethylene group, a periododimethylene group (a periodoethylene group), a periodotrimethylene group, a periodopropylene group, a periodotetramethylene group, a periodopentamethylene group, a periodohexamethylene group, a periodoheptamethylene group, a periodooctamethylene group or the like.

Among these alkylene groups, an unsubstituted (not substituted by a halogen atom) alkylene group having 1 to 5 carbon atoms, such as, for example, a methylene group, a dimethylene group (an ethylene group), a trimethylene group, a propylene group, a tetramethylene group, a pentamethylene group or the like; and an alkylene group having 1 to 5 carbon atoms, in which a hydrogen atom bonded to the carbon atoms is substituted by a fluorine atom, such as, for example, a perfluoromethylene group, a perfluorodimethylene group (a perfluoroethylene group), a perfluorotrimethylene group, a perfluoropropylene group, a perfluorotetramethylene group, perfluoropentamethylene group or the like are preferable, and among them, an unsubstituted (not substituted by a halogen atom) alkylene group having 1 to 5 carbon atoms, such as, for example, a methylene group, a dimethylene group (an ethylene group), a trimethylene group, a propylene group, a tetramethylene group, a pentamethylene group or the like are more preferable.

A specific example of an alkyl group having 1 to 12 carbon atoms, in which a hydrogen atom may be substituted by a halogen atom, represented by $R^{11}$ in the general formula (B-2), includes the same as a specific example of an alkyl group having 1 to 12 carbon atoms, in which a hydrogen atom may be substituted by a halogen atom, represented by $R^1$ in the general formula (A).

Among these alkyl groups, an unsubstituted (not substituted by a halogen atom) alkyl group having 1 to 10 carbon atoms; and an alkyl group having 1 to 10 carbon atoms, in which a hydrogen atom bonding to the carbon atoms is substituted by a fluorine atom are preferable, and among them, an unsubstituted (not substituted by a halogen atoms) alkyl group having to 10 carbon atoms is more preferable. These (more) preferable specific examples also include to the same as a specific example of an unsubstituted (not substituted by a halogen atom) alkyl group having 1 to 10 carbon atoms; and an alkyl group having 1 to 10 carbon atoms, in which a hydrogen atom bonding to the carbon atoms is substituted by a fluorine atom, represented by $R^1$ in the general formula (A).

As $W_2$ in the general formula (B-2), an oxygen atom is more preferable.

An alkoxy group having 1 to 10 carbon atoms, in which a hydrogen atom may be substituted by a halogen atom, represented by $R^1$ in the general formula (A), may be any of a straight chained, branched or cyclic group, and specifically includes an unsubstituted (not substituted by a halogen atom) alkoxy group having 1 to 10 carbon atoms, such as, for example, a methoxy group, an ethoxy group, a n-propoxy group, an isopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, a n-heptyloxy group, an isoheptyloxy group, a sec-heptyloxy group, a tert-heptyloxy group, a neoheptyloxy group, a cycloheptyloxy group, a n-octyloxy group, an isooctyloxy group, a sec-octyloxy group, a tert-octyloxy group, a neooctyloxy group, a 2-ethylhexyloxy group, a cyclooctyloxy group, a n-nonyloxy group, an isononyloxy group, a sec-nonyloxy group, a tert-nonyloxy group, a neononyloxy group, a cyclononyloxy group, a n-decyloxy group, an isodecyloxy group, a sec-decyloxy group, a tert-decyloxy group, a neodecyloxy group, a cyclodecyloxy group, a norbornyloxy group (a norbornane-X-yloxy group), a bornyloxy group (a bornane-X-yloxy group), a menthyloxy group (a mentha-X-yloxy group), an adamantyloxy group, a decahydronaphthyloxy group or the like; an alkoxy group having 1 to 10 carbon atoms, in which a hydrogen atom bonded to the carbon atoms is substituted by a halogen atom, such as, for example, an alkoxy group having 1 to 10 carbon atoms, in which a hydrogen atom bonded to the carbon atoms is substituted by a fluorine atom, such as, for example, a trifluoromethoxy group, a pentafluoroethoxy group, a heptafluoro-n-propoxy group, a heptafluoroisopropoxy group, a nonafluoro-n-butoxy group, a nonafluoro-n-butoxy group, a nonafluoroisobutoxy group, a nonafluoro-sec-butoxy group, a nonafluoro-tert-butoxy group, a nonafluorocyclobutoxy group, a perfluoro-n-pentyloxy group, a perfluoroisopentyloxy group, a perfluoro-sec-pentyloxy group, a perfluoro-tert-pentyloxy group, a perfluoroneopentyloxy group, a perfluoro-2-methylbutoxy group, a perfluoro-1,2-dimethylpropoxy group, a perfluoro-1-ethylpropoxy group, a perfluorocyclopentyloxy group, a perfluoro-n-hexyloxy group, a perfluoroisohexyloxy group, a perfluoro-sec-hexyloxy group, a perfluoro-tert-hexyloxy group, a perfluoroneohexyloxy group, a perfluoro-2-methylpentyloxy group, a perfluoro-1,2-dimethylbutoxy group, a perfluoro-2,3-dimethylbutoxy group, a perfluoro-1-ethylbutoxy group, a perfluorocyclohexyloxy group, a perfluoro-n-heptyloxy group, a perfluoroisoheptyloxy group, a perfluoro-sec-heptyloxy group, a perfluoro-tert-heptyloxy group, a perfluoroneoheptyloxy group, a perfluorocycloheptyloxy group, a perfluoro-n-octyloxy group, a perfluoroisooctyloxy group, a perfluoro-sec-octyloxy group, a perfluoro-tert-octyloxy group, a perfluoroneooctyloxy group, a perfluoro-2-ethylhexyloxy group, a perfluorocyclooctyloxy group, a perfluoro-n-nonyloxy group, a perfluoroisononyloxy group, a perfluoro-sec-nonyloxy group, a perfluoro-tert-nonyloxy group, a perfluoroneononyloxy group, a perfluorocyclononyloxy group, a perfluoro-n-decyloxy group, a perfluoroisodecyloxy group, a perfluoro-sec-decyloxy group, a perfluoro-tert-decyloxy group, a perfluoroneodecyloxy group, a perfluorocyclodecyloxy group, a perfluoronorbornyloxy group (a perfluoronorbornane-X-yloxy group), a perfluorobornyloxy group (a perfluorobornane-X-yloxy group), a perfluoromenthyloxy group (a perfluoromentha-X-yloxy group), a perfluoroadamantyloxy group, a perfluorodecahydronaphthyloxy group or the like; an alkoxy group having 1 to 10 carbon atoms, in which a hydrogen atom bonded to the carbon atoms is substituted by a chlorine atom, such as, for example, a trichloromethoxy group, a pentachloroethoxy group, a heptachloro-n-propoxy group, a heptachloroisopropoxy group, a nonachloro-n-butoxy group, a nonachloroisobutoxy group, a nonachloro-sec-butoxy group, a nonachloro-tert-butoxy group, a nonachlorocyclobutoxy group, a perchloro-n-pentyloxy group, a perchloroisopentyloxy group, a perchloro-sec-pentyloxy group, a perchloro-tert-pentyloxy group, a perchloroneopentyloxy group, a perchloro-2-methylbutoxy group, a perchloro-1,2-dimethylpropoxy group, a perchloro-1-ethylpropoxy group, a perchlorocyclopentyloxy group, a perchloro-n-hexyloxy group, a perchloroisohexyloxy group, a perchloro-sec-hexyloxy group, a perchloro-tert-hexyloxy group, a perchloroneohexyloxy group, a perchloro-2-methylpentyloxy group, a perchloro-1,2-dimethylbutoxy group, a perchloro-2,3-dimethylbutoxy group, a perchloro-1-ethylbutoxy group, a perchlorocyclohexyloxy group, a perchloro-n-heptyloxy group, a perchloroisoheptyloxy group, a perchloro-sec-heptyloxy group, a perchloro-tert-heptyloxy group, a perchloroneoheptyloxy group, a perchlorocycloheptyloxy group, a perchloro-n-octyloxy group, a perchloroisooctyloxy group, a perchloro-sec-octyloxy group, a perchloro-tert-octyloxy group, a perchloroneooctyloxy group, a perchloro-2-ethylhexyloxy group, a perchlorocyclooctyloxy group, a perchloro-n-nonyloxy group, a perchloroisononyloxy group, a perchloro-sec-nonyloxy group, a perchloro-tert-nonyloxy group, a perchloroneononyloxy group, a perchlorocyclononyloxy group, a perchloro-n-decyloxy group, a perchloroisodecyloxy group, a perchloro-sec-decyloxy group, a perchloro-tert-decyloxy group, a perchloroneodecyloxy group, a perchlorocyclodecyloxy group, a perchloronorbornyloxy group (a perchloronorbornane-X-yloxy group), a perchlorobornyloxy group (a perchlorobornane-X-yloxy group), a perchloromenthyloxy group (a perchloromentha-X-yloxy group), a perchloroadamantyloxy group, a perchlorodecahydronaphthyloxy group or the like; an alkoxy group having 1 to 10 carbon atoms, in which a hydrogen atom bonded to the carbon atoms is substituted by a bromine atom, such as, for example, a tribromomethoxy group, a pentabromoethoxy group, a heptabromo-n-propoxy group, a heptabromoisopropoxy group, a nonabromo-n-butoxy group, a nonabromoisobutoxy group, a nonabromo-sec-butoxy group, a nonabromo-tert-butoxy group, a nonabromocyclobutoxy group, a perbromo-n-pentyloxy group, a perbromoisopentyloxy group, a perbromo-sec-pentyloxy group, a perbromo-tert-pentyloxy group, a perbromoneopentyloxy group, a perbromo-2-methylbutoxy group, a perbromo-1,2-dimethylpropoxy group, a perbromo-1-ethylpropoxy group, a perbromocyclopentyloxy group, a perbromo-n-hexyloxy group, a perbromoisohexyloxy group, a perbromo-sec-hexyloxy group, a perbromo-tert-hexyloxy group, a perbromoneohexyloxy group, a perbromo-2-methylpentyloxy group, a perbromo-1,2-dimethylbutoxy group, a perbromo-2,3-dimethylbutoxy group, a perbromo-1-ethylbutoxy group, a perbromocyclohexyloxy group, a perbromo-n-heptyloxy group, a perbromoisoheptyloxy group, a perbromo-sec-heptyloxy group, a perbromo-tert-heptyloxy group, a perbromoneoheptyloxy group, a perbromocycloheptyloxy group, a perbromo-n-octyloxy group, a perbromoisooctyloxy group, a perbromo-sec-octyloxy group, a perbromo-tert-octyloxy group, a perbromoneooctyloxy group, a perbromo-2-ethylhexyloxy group, a perbromocyclooctyloxy group, a perbromo-n-nonyloxy group, a perbromoisononyloxy group, a perbromo-sec-nonyloxy group, a perbromo-tert-nonyloxy group, a perbromoneononyloxy group, a perbromocyclononyloxy group, a perbromo-n-decyloxy group, a perbromoisodecyloxy group, a perbromo-sec-decyloxy group, a perbromo-tert-decyloxy group, a perbromoneodecyloxy group, a perbromocyclodecyloxy group, a perbromonorbornyloxy group (a perbromonorbornane-X-yloxy group), a perbromobornyloxy group (a perbromobornane-X-yloxy group), a perbromomenthyloxy group (a perbromomentha- X-yloxy group), a perbromoadamantyloxy group, a perbromodecahydronaphthyloxy group or the like; an alkoxy group having 1 to 10 carbon atoms, in which a hydrogen atom bonded to the carbon atoms is substituted by an iodine atom, such as, for example, a triiodomethoxy group, a pentaiodoethoxy group, a heptaiodo-n-propoxy group, a heptaiodoisopropoxy group, a nonaiodo-n-butoxy group, a nonaiodoisobutoxy group, a nonaiodo-sec-butoxy group, a nonaiodo-tert-butoxy group, a nonaiodocyclobutoxy group, a periodo-n-pentyloxy group, a periodoisopentyloxy group, a periodo-sec-pentyloxy group, a periodo-tert-pentyloxy group, a periodoneopentyloxy group, a periodo-2-methylbutoxy group, a periodo-1,2-dimethylpropoxy group, a periodo-1-ethylpropoxy group, a periodocyclopentyloxy group, a periodo-n-hexyloxy group, a periodoisohexyloxy group, a periodo-sec-hexyloxy group, a periodo-tert-hexyloxy group, a periodoneohexyloxy group, a periodo-2-methylpentyloxy group, a periodo-1,2-dimethylbutoxy group, a periodo-2,3-dimethylbutoxy group, a periodo-1-ethyl butoxy group, a periodocyclohexyloxy group, a periodo-n-heptyloxy group, a periodoisoheptyloxy group, a periodo-sec-heptyloxy group, a periodo-tert-heptyloxy group, a periodoneoheptyloxy group, a periodocycloheptyloxy group, a periodo-n-octyloxy group, a periodoisooctyloxy group, a periodo-sec-octyloxy group, a periodo-tert-octyloxy group, a periodoneooctyloxy group, a periodo-2-ethylhexyloxy group, a periodocyclooctyloxy group, a periodo-n-nonyloxy group, a periodoisononyloxy group, a periodo-sec-nonyloxy group, a periodo-tert-nonyloxy group, a periodoneononyloxy group, a periodocyclononyloxy group, a periodo-n-decyloxy group, a periodoisodecyloxy group, a periodo-sec-decyloxy group, a periodo-tert-decyloxy group, a periodoneodecyloxy group, a periodocyclodecyloxy group, a periodonorbornyloxy group (a periodonorbornane-X-yloxy group), a periodobornyloxy group (a periodobornane-X-yloxy group), a periodomenthyloxy group (a periodomentha-X-yloxy group), a periodoadamantyloxy group, a periododecahydronaphthyloxy group or the like.

Among these alkoxy groups, an unsubstituted (not substituted by a halogen atom) alkoxy group having 1 to 10 carbon atoms, such as, for example, a methoxy group, an ethoxy group, a n-propoxy group, an isopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group, a n-heptyloxy group, an isoheptyloxy group, a sec-heptyloxy group, a tert-heptyloxy group, a neoheptyloxy group, a cycloheptyloxy group, a n-octyloxy group, an isooctyloxy group, a sec-octyloxy group, a tert-octyloxy group, a neooctyloxy group, a 2-ethylhexyloxy group, a cyclooctyloxy group, a n-nonyloxy group, an isononyloxy group, a sec-nonyloxy group, a tert-nonyloxy group, a neononyloxy group, a cyclononyloxy group, a n-decyloxy group, an isodecyloxy group, a sec-decyloxy group, a tert-decyloxy group, a neodecyloxy group, a cyclodecyloxy group, a norbornyloxy group (a norbornane-X-yloxy group), a bornyloxy group (a bornane-X-yloxy group), a menthyloxy group (a mentha-X-yloxy group), an adamantyloxy group, a decahydronaphthyloxy group or the like; and an alkoxy group having 1 to 10 carbon atoms, in which a hydrogen atom bonded to the carbon atoms is substituted by a fluorine atom, such as, for example, a trifluoromethoxy group, a pentafluoroethoxy group, a heptafluoro-n-propoxy group, a heptafluoroisopropoxy group, a nonafluoro-n-butoxy group, a nonafluoroisobutoxy group, a nonafluoro-sec-butoxy group, a nonafluoro-tert-butoxy group, a nonafluorocyclobutoxy group, a perfluoro-n-pentyloxy group, a perfluoroisopentyloxy group, a perfluoro-sec-pentyloxy group, a perfluoro-tert-pentyloxy group, a perfluoroneopentyloxy group, a perfluoro-2-methylbutoxy group, a perfluoro-1,2-dimethylpropoxy group, a perfluoro-1-ethylpropoxy group, a perfluorocyclopentyloxy group, a perfluoro-n-hexyloxy group, a perfluoroisohexyloxy group, a perfluoro-sec-hexyloxy group, a perfluoro-tert-hexyloxy group, a perfluoroneohexyloxy group, a perfluoro-2-methylpentyloxy group, a perfluoro-1,2-dimethylbutoxy group, a perfluoro-2,3-dimethylbutoxy group, a perfluoro-1-ethylbutoxy group, a perfluorocyclohexyloxy group, a perfluoro-n-heptyloxy group, a perfluoroisoheptyloxy group, a perfluoro-sec-heptyloxy group, a perfluoro-tert-heptyloxy group, a perfluoroneoheptyloxy group, a perfluorocycloheptyloxy group, a perfluoro-n-octyloxy group, a perfluoroisooctyloxy group, a perfluoro-sec-octyloxy group, a perfluoro-tert-octyloxy group, a perfluoroneooctyloxy group, a perfluoro-2-ethylhexyloxy group, a perfluorocyclooctyloxy group, a perfluoro-n-nonyloxy group, a perfluoroisononyloxy group, a perfluoro-sec-nonyloxy group, a perfluoro-tert-nonyloxy group, a perfluoroneononyloxy group, a perfluorocyclononyloxy group, a perfluoro-n-decyloxy group, a perfluoroisodecyloxy group, a perfluoro-sec-decyloxy group, a perfluoro-tert-decyloxy group, a perfluoroneodecyloxy group, a perfluorocyclodecyloxy group, a perfluoronorbornyloxy group, (a perfluoronorbornane-X-yloxy group), a perfluorobornyloxy group, (a perfluorobornane-X-yloxy group), a perfluoromenthyloxy group, (a perfluoromentha-X-yloxy group), a perfluoroadamantyloxy group, a perfluorodecahydronaphthyloxy group or the like are preferable, and among them, an unsubstituted (not substituted by a halogen atom) alkoxy group having 1 to 6 carbon atoms, such as, for example, a methoxy group, an ethoxy group, a n-propoxy group, an isopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group or the like; and an alkoxy group having 1 to 6 carbon atoms, in which a hydrogen atom bonded to the carbon atoms is substituted by a fluorine atom, such as, for example, a trifluoromethoxy group, a pentafluoroethoxy group, a heptafluoro-n-propoxy group, a heptafluoroisopropoxy group, a nonafluoro-n-butoxy group, a nonafluoroisobutoxy group, a nonafluoro-sec-butoxy group, a nonafluoro-tert-butoxy group, a nonafluorocyclobutoxy group, a perfluoro-n-pentyloxy group, a perfluoroisopentyloxy group, a perfluoro-sec-pentyloxy group, a perfluoro-tert-pentyloxy group, a perfluoroneopentyloxy group, a perfluoro-2-methylbutoxy group, a perfluoro-1,2-dimethylpropoxy group, a perfluoro-1-ethylpropoxy group, a perfluorocyclopentyloxy group, a perfluoro-n-hexyloxy group, a perfluoroisohexyloxy group, a perfluoro-sec-hexyloxy group, a perfluoro-tert-hexyloxy group, a perfluoroneohexyloxy group, a perfluoro-2-methylpentyloxy group, a perfluoro-1,2-dimethylbutoxy group, a perfluoro-2,3-dimethylbutoxy group, a perfluoro-1-ethylbutoxy group, a perfluorocyclohexyloxy group are more preferable, and among them, an unsubstituted (not substituted by a halogen atom) alkoxy group having 1 to 4 carbon atoms, such as, for example, a methoxy group, an ethoxy group, a n-propoxy group, an isopropoxy group, a n-butoxy group, an isobutoxy group, a sec-butoxy group, a tert-butoxy group, a cyclobutoxy group; and an alkoxy group having 1 to 4 carbon atoms, in which a hydrogen atom bonded to the carbon atoms is substituted by a fluorine atom, such as, for example, a trifluoromethoxy group, a pentafluoroethoxy group, a heptafluoro-n-propoxy group, a heptafluoroisopropoxy group, a nonafluoro-n-butoxy group, a nonafluoroisobutoxy group, a nonafluoro-sec-butoxy group, a nonafluoro-tert-butoxy group, a nonafluorocyclobutoxy group or the like are further preferable.

An aryl group having 6 to 10 carbon atoms, in which a hydrogen atom may be substituted by a halogen atom, an alkyl group or haloalkyl group, represented by $R^1$ in the general formula (A), may be any of a monocyclic or a condensed polycyclic group, and specifically includes an unsubstituted (having no substituent) aryl group having 6 to 10 carbon atoms, such as, for example, a phenyl group, a naphthyl group or the like; an aryl group having 6 to 10 carbon atoms, in which a hydrogen atom bonded to the carbon atoms is substituted by a halogen atom (having a halogen atom as a substituent), such as, for example, an aryl group having 6 to 10 carbon atoms, in which a hydrogen atom bonded to the carbon atoms is substituted by a fluorine atom (having a fluorine atom as a substituent), such as, for example, a 2-fluorophenyl group, a 3-fluorophenyl group, a 4-fluorophenyl group, a 2,4-difluorophenyl group, a 2,6-difluorophenyl group, a 2,4,6-trifluorophenyl group, a 1-fluoronaphthyl group, a 2-fluoronaphthyl group, a 3-fluoronaphthyl group, a 4-fluoronaphthyl group, a 5-fluoronaphthyl group, a 6-fluoronaphthyl group, a 7-fluoronaphthyl group, a 8-fluoronaphthyl group or the like; an aryl group having 6 to 10 carbon atoms, in which a hydrogen atom bonded to the carbon atoms is substituted by a chlorine atom (having a chlorine atom as a substituent), such as, for example, a 2-chlorophenyl group, a 3-chlorophenyl group, a 4-chlorophenyl group, a 2,4-dichlorophenyl group, a 2,6-dichlorophenyl group, a 2,4,6-trichlorophenyl group, a 1-chloronaphthyl group, a 2-chloronaphthyl group, a 3-chloronaphthyl group, a 4-chloronaphthyl group, a 5-chloronaphthyl group, a 6-chloronaphthyl group, a 7-chloronaphthyl group, a 8-chloronaphthyl group or the like; an aryl group having 6 to 10 carbon atoms, in which a hydrogen atom bonded to the carbon atoms is substituted by a bromine atom (having a bromine atom as a substituent), such as, for example, a 2-bromophenyl group, a 3-bromophenyl group, a 4-bromophenyl group, a 2,4-dibromophenyl group, a 2,6-dibromophenyl group, a 2,4,6-tribromophenyl group, a 1-bromonaphthyl group, a 2-bromonaphthyl group, a 3-bromonaphthyl group, a 4-bromonaphthyl group, a 5-bromonaphthyl group, a 6-bromonaphthyl group, 7-bromonaphthyl group, a 8-bromonaphthyl group or the like; an aryl group having 6 to 10 carbon atoms, in which a hydrogen atom bonded to the carbon atoms is substituted by an iodine atom (having an iodine atom as a substituent), such as, for example, a 2-iodophenyl group, a 3-iodophenyl group, a 4-iodophenyl group, a 2,4-diiodophenyl group, a 2,6-diiodophenyl group, a 2,4,6-triiodophenyl group, a 1-iodonaphthyl group, a 2-iodonaphthyl group, a 3-iodonaphthyl group, a 4-iodonaphthyl group, a 5-iodonaphthyl group, a 6-iodonaphthyl group, a 7-iodonaphthyl group, a 8-iodonaphthyl group or the like; an aryl group having 6 to 10 carbon atoms, in which a hydrogen atom bonded to the carbon atoms is substituted by an alkyl group having 1 to 4 carbon atoms (having an alkyl group having 1 to 4 carbon atoms as a substituent), such as, for example, an aryl group having 6 to 10 carbon atoms, in which a hydrogen atom bonded to the carbon atoms is substituted by a methyl group (having a methyl group as a substituent), such as, for example, a 2-tolyl group, a 3-tolyl group, a 4-tolyl group, a 2,4-xylyl group, a 2,6-xylyl group, a mesityl group (a 2,4,6-trimethylphenyl group), a 1-methylnaphthyl group, a 2-methylnaphthyl group, a 3-methylnaphthyl group, a 4-methylnaphthyl group, a 5-methylnaphthyl group, a 6-methylnaphthyl group, a 7-methylnaphthyl group, a 8-methylnaphthyl group or the like; an aryl group having 6 to 10 carbon atoms, in which a hydrogen atom bonded to the carbon atoms is substituted by an ethyl group (having an ethyl group as a substituent), such as, for example, a 2-ethylphenyl group, a 3-ethylphenyl group, a 4-ethylphenyl group, a 2,4-diethylphenyl group, a 2,6-diethylphenyl group, a 2,4,6-triethylphenyl group, a 1-ethylnaphthyl group, a 2-ethylnaphthyl group, a 3-ethylnaphthyl group, a 4-ethylnaphthyl group, a 5-ethylnaphthyl group, a 6-ethylnaphthyl group, a 7-ethylnaphthyl group, a 8-ethylnaphthyl group or the like; an aryl group having 6 to 10 carbon atoms, in which a hydrogen atom bonded to the carbon atoms is substituted by a propyl group (having a propyl group as a substituent), such as, for example, a 2-propylphenyl group, a 3-propylphenyl group, a 4-propylphenyl group, a 2,4-dipropylphenyl group, a 2,6-dipropylphenyl group, a 2,4,6-tripropylphenyl group, a 1-propylnaphthyl group, a 2-propylnaphthyl group, a 3-propylnaphthyl group, a 4-propylnaphthyl group, a 5-propylnaphthyl group, a 6-propylnaphthyl group, a 7-propylnaphthyl group, a 8-propylnaphthyl group or the like; an aryl group having 6 to 10 carbon atoms, in which a hydrogen atom bonded to the carbon atoms is substituted by a butyl group (having a butyl group as a substituent), such as, for example, a 2-butylphenyl group, a 3-butylphenyl group, a 4-butylphenyl group, a 2,4-dibutylphenyl group, a 2,6-dibutylphenyl group, a 2,4,6-tributylphenyl group, a 1-butylnaphthyl group, a 2-butylnaphthyl group, a 3-butylnaphthyl group, a 4-butylnaphthyl group, a 5-butylnaphthyl group, a 6-butylnaphthyl group, a 7-butylnaphthyl group, a 8-butylnaphthyl group or the like; an aryl group having 6 to 10 carbon atoms, in which a hydrogen atom bonded to the carbon atoms is substituted by a haloalkyl group having 1 to 4 carbon atoms (having a haloalkyl group having 1 to 4 carbon atoms as a substituent), such as, for example, a fluoroalkyl group having 1 to 4 carbon atoms or a chloroalkyl group having 1 to 4 carbon atoms, such as, for example, an aryl group having 6 to 10 carbon atoms, in which a hydrogen atom bonded to the carbon atoms is substituted by a fluoromethyl group (having a fluoromethyl group as a substituent), such as, for example, a 2-trifluoromethylphenyl group, a 3-trifluoromethylphenyl group, a 4-trifluoromethylphenyl group, a 2,4-bis(trifluoromethyl)phenyl group, a 2,6-bis(trifluoromethyl)phenyl group, a 2,4,6-tris(trifluoromethyl)phenyl group, a 1-trifluoromethylnaphthyl group, a 2-trifluoromethylnaphthyl group, a 3-trifluoromethylnaphthyl group, a 4-trifluoromethylnaphthyl group, a 5-trifluoromethylnaphthyl group, a 6-trifluoromethylnaphthyl group, a 7-trifluoromethylnaphthyl group, a 8-trifluoromethylnaphthyl group or the like; an aryl group having 6 to 10 carbon atoms, in which a hydrogen atom bonded to the carbon atoms is substituted by a chloromethyl group (having a chloromethyl group as a substituent), such as, for example, a 2-trichloromethylphenyl group, a 3-trichloromethylphenyl group, a 4-trichloromethylphenyl group, a 2,4-bis(trichloromethyl)phenyl group, a 2,6-bis(trichloromethyl)phenyl group, a 2,4,6-tris(trichloromethyl)phenyl group, a 1-trichloromethylnaphthyl group, a 2-trichloromethylnaphthyl group, a 3-trichloromethylnaphthyl group, a 4-trichloromethylnaphthyl group, a 5-trichloromethylnaphthyl group, a 6-trichloromethylnaphthyl group, a 7-trichloromethylnaphthyl group, a 8-trichloromethylnaphthyl group or the like; an aryl group having 6 to 10 carbon atoms, in which a hydrogen atom bonded to the carbon atoms is substituted by a fluoroethyl group (having a fluoroethyl group as a substituent), such as, for example, a 2-pentafluoroethylphenyl group, a 3-pentafluoroethylphenyl group, a 4-pentafluoroethylphenyl group, a 2,4-bis(pentafluoroethyl)phenyl group, a 2,6-bis(pentafluoroethyl)phenyl group, a 2,4,6-tris(pentafluoroethyl)phenyl group, a 1-pentafluoroethylnaphthyl group, a 2-pentafluoroethylnaphthyl group, a 3-pentafluoroethylnaphthyl group, a 4-pentafluoroethylnaphthyl group, a 5-pentafluoroethylnaphthyl group, a 6-pentafluoroethylnaphthyl group, a 7-pentafluoroethylnaphthyl group, a 8-pentafluoroethylnaphthyl group or the like; an aryl group having 6 to 10 carbon atoms, in which a hydrogen atom bonded to the carbon atoms is substituted by a chloroethyl group (having a chloroethyl group as a substituent), such as, for example, a 2-pentachloroethylphenyl group, a 3-pentachloroethylphenyl group, a 4-pentachloroethylphenyl group, a 2,4-bis(pentachloroethyl)phenyl group, a 2,6-bis(pentachloroethyl)phenyl group, a 2,4,6-tris(pentachloroethyl)phenyl group, a 1-pentachloroethylnaphthyl group, a 2-pentachloroethylnaphthyl group, a 3-pentachloroethylnaphthyl group, a 4-pentachloroethylnaphthyl group, a 5-pentachloroethylnaphthyl group, a 6-pentachloroethylnaphthyl group, a 7-pentachloroethylnaphthyl group, a 8-pentachloroethylnaphthyl group or the like; an aryl group having 6 to 10 carbon atoms, in which a hydrogen atom bonded to the carbon atoms is substituted by a fluoropropyl group (having a fluoropropyl group as a substituent), such as, for example, a 2-heptafluoropropylphenyl group, a 3-heptafluoropropylphenyl group, a 4-heptafluoropropylphenyl group, a 2,4-bis(heptafluoropropyl)phenyl group, a 2,6-bis(heptafluoropropyl)phenyl group, a 2,4,6-tris(heptafluoropropyl)phenyl group, a 1-heptafluoropropylnaphthyl group, a 2-heptafluoropropylnaphthyl group, a 3-heptafluoropropylnaphthyl group, a 4-heptafluoropropylnaphthyl group, a 5-heptafluoropropylnaphthyl group, a 6-heptafluoropropylnaphthyl group, a 7-heptafluoropropylnaphthyl group, a 8-heptafluoropropylnaphthyl group or the like; an aryl group having 6 to 10 carbon atoms, in which a hydrogen atom bonded to the carbon atoms is substituted by a chloropropyl group (having a chloropropyl group as a substituent), such as, for example, a 2-heptachloropropylphenyl group, a 3-heptachloropropylphenyl group, a 4-heptachloropropylphenyl group, a 2,4-bis(heptachloropropyl)phenyl group, a 2,6-bis(heptachloropropyl)phenyl group, a 2,4,6-tris(heptachloropropyl)phenyl group, a 1-heptachloropropylnaphthyl group, a 2-heptachloropropylnaphthyl group, a 3-heptachloropropylnaphthyl group, a 4-heptachloropropylnaphthyl group, a 5-heptachloropropylnaphthyl group, a 6-heptachloropropylnaphthyl group, a 7-heptachloropropylnaphthyl group, a 8-heptachloropropylnaphthyl group or the like; an aryl group having 6 to 10 carbon atoms, in which a hydrogen atom bonded to the carbon atoms is substituted by a fluorobutyl group (having a fluorobutyl group as a substituent), such as, for example, a 2-nonafluorobutylphenyl group, a 3-nonafluorobutylphenyl group, a 4-nonafluorobutylphenyl group, a 2,4-bis(nonafluorobutyl)phenyl group, a 2,6-bis(nonafluorobutyl)phenyl group, a 2,4,6-tris(nonafluorobutyl)phenyl group, a 1-nonafluorobutylnaphthyl group, a 2-nonafluorobutylnaphthyl group, a 3-nonafluorobutylnaphthyl group, a 4-nonafluorobutylnaphthyl group, a 5-nonafluorobutylnaphthyl group, a 6-nonafluorobutylnaphthyl group, a 7-nonafluorobutylnaphthyl group, a 8-nonafluorobutylnaphthyl group or the like; an aryl group having 6 to 10 carbon atoms, in which a hydrogen atom bonded to the carbon atoms is substituted by a chlorobutyl group (having a chlorobutyl group as a substituent), such as, for example, a 2-nonachlorobutylphenyl group, a 3-nonachlorobutylphenyl group, a 4-nonachlorobutylphenyl group, a 2,4-bis(nonachlorobutyl)phenyl group, a 2,6-bis(nonachlorobutyl)phenyl group, a 2,4,6-tris(nonachlorobutyl)phenyl group, a 1-nonachlorobutylnaphthyl group, a 2-nonachlorobutylnaphthyl group, a 3-nonachlorobutylnaphthyl group, a 4-nonachlorobutylnaphthyl group, a 5-nonachlorobutylnaphthyl group, a 6-nonachlorobutylnaphthyl group, a 7-nonachlorobutylnaphthyl group, a 8-nonachlorobutylnaphthyl group, or the like. It should be noted that, in the above-described specific examples, an alkyl group or a haloalkyl group substituted (bonded) to an aryl group is not limited to a normal-form, and may be an alkyl group or a haloalkyl group of a branched group, such as, for example, a sec-form, a tert-form, an iso-form and a neo-form, or an alkyl group or a haloalkyl group of a cyclic group, such as, for example, a cyclo-form. In addition, the carbon atoms constituting an alkyl group or a haloalkyl group substituted (bonded) to an aryl group should not be contained in number of the carbon atoms constituting an aryl group to which they bond (6 to 10 carbon atoms). In other words, sum of the carbon atoms of an aryl group in which 1 to 3 pieces of a hydrogen atom in hydrogen atoms bonded to the carbon atoms are substituted by an alkyl group or a haloalkyl group having 1 to 4 carbon atoms (having an alkyl group or a haloalkyl group having 1 to 4 carbon atoms as a substituent), are 7 to 22.

Among these aryl groups, an unsubstituted (having no substituent) aryl group having 6 carbon atoms, such as, for example, a phenyl group; an aryl group having 6 carbon atoms, in which a hydrogen atom bonded to the carbon atoms is substituted by a halogen atom (having a halogen atom as a substituent), such as, for example, an aryl group having 6 carbon atoms, in which a hydrogen atom bonded to the carbon atoms is substituted by a fluorine atom (having a fluorine atom as a substituent), such as, for example, a 2-fluorophenyl group, a 3-fluorophenyl group, a 4-fluorophenyl group, a 2,4-difluorophenyl group, a 2,6-difluorophenyl group, a 2,4,6-trifluorophenyl group or the like; an aryl group having 6 carbon atoms, in which a hydrogen atom bonded to the carbon atoms is substituted by a chlorine atom (having a chlorine atom as a substituent), such as, for example, a 2-chlorophenyl group, a 3-chlorophenyl group, a 4-chlorophenyl group, a 2,4-dichlorophenyl group, a 2,6-dichlorophenyl group, a 2,4,6-trichlorophenyl group or the like; an aryl group having 6 carbon atoms, in which a hydrogen atom bonded to the carbon atoms is substituted by a bromine atom (having a bromine atom as a substituent), such as, for example, a 2-bromophenyl group, a 3-bromophenyl group, a 4-bromophenyl group, a 2,4-dibromophenyl group, a 2,6-dibromophenyl group, a 2,4,6-tribromophenyl group or the like; and an aryl group having 6 carbon atoms, in which a hydrogen atom bonded to the carbon atoms is substituted by an iodine atom (having an iodine atom as a substituent), such as, for example, a 2-iodophenyl group, a 3-iodophenyl group, a 4-iodophenyl group, a 2,4-diiodophenyl group, a 2,6-diiodophenyl group, a 2,4,6-triiodophenyl group or the like; an aryl group having 6 carbon atoms, in which a hydrogen atom bonded to the carbon atoms is substituted by an alkyl group having 1 to 4 carbon atoms (having an alkyl group having 1 to 4 carbon atoms as a substituent), such as, for example, an aryl group having 6 carbon atoms, in which a hydrogen atom bonded to the carbon atoms is substituted by a methyl group (having a methyl group as a substituent), such as, for example, a 2-tolyl group, a 3-tolyl group, a 4-tolyl group, a 2,4-xylyl group, a 2,6-xylyl group, a mesityl group (a 2,4,6-trimethylphenyl group) or the like; an aryl group having 6 carbon atoms, in which a hydrogen atom bonded to the carbon atoms is substituted by an ethyl group (having an ethyl group as a substituent), such as, for example, a 2-ethylphenyl group, a 3-ethylphenyl group, a 4-ethylphenyl group, a 2,4-diethylphenyl group, a 2,6-diethylphenyl group, a 2,4,6-triethylphenyl group or the like; an aryl group having 6 carbon atoms, in which a hydrogen atom bonded to the carbon atoms is substituted by a propyl group (having a propyl group as a substituent), such as, for example, a 2-propylphenyl group, a 3-propylphenyl group, a 4-propylphenyl group, a 2,4-dipropylphenyl group, a 2,6-dipropylphenyl group, a 2,4,6-tripropylphenyl group or the like; and an aryl group having 6 carbon atoms, in which a hydrogen atom bonded to the carbon atoms is substituted by a butyl group (having a butyl group as a substituent), such as, for example, a 2-butylphenyl group, a 3-butylphenyl group, a 4-butylphenyl group, a 2,4-dibutylphenyl group, a 2,6-dibutylphenyl group, a 2,4,6-tributylphenyl group or the like; and an aryl group having 6 carbon atoms, in which a hydrogen atom bonded to the carbon atoms is substituted by a haloalkyl group having 1 to 4 carbon atoms (having a haloalkyl group having 1 to 4 carbon atoms as a substituent), such as, for example, a fluoroalkyl group having 1 to 4 carbon atoms or a chloroalkyl group having 1 to 4 carbon atoms, such as, for example, an aryl group having 6 carbon atoms, in which a hydrogen atom bonded to the carbon atoms is substituted by a fluoromethyl group (having a fluoromethyl group as a substituent), such as, for example, a 2-trifluoromethylphenyl group, a 3-trifluoromethylphenyl group, a 4-trifluoromethylphenyl group, a 2,4-bis(trifluoromethyl)phenyl group, a 2,6-bis(trifluoromethyl)phenyl group, a 2,4,6-tris(trifluoromethyl)phenyl group or the like; an aryl group having 6 carbon atoms, in which a hydrogen atom bonded to the carbon atoms is substituted by a chloromethyl group (having a chloromethyl group as a substituent), such as, for example, a 2-trichloromethylphenyl group, a 3-trichloromethylphenyl group, a 4-trichloromethylphenyl group, a 2,4-bis(trichloromethyl)phenyl group, a 2,6-bis(trichloromethyl)phenyl group, a 2,4,6-tris(trichloromethyl)phenyl group or the like; an aryl group having 6 carbon atoms, in which a hydrogen atom bonded to the carbon atoms is substituted by a fluoroethyl group (having a fluoroethyl group as a substituent), such as, for example, a 2-pentafluoroethylphenyl group, a 3-pentafluoroethylphenyl group, a 4-pentafluoroethylphenyl group, a 2,4-bis(pentafluoroethyl)phenyl group, a 2,6-bis(pentafluoroethyl)phenyl group, a 2,4,6-tris(pentafluoroethyl)phenyl group or the like; an aryl group having 6 carbon atoms, in which a hydrogen atom bonded to the carbon atoms is substituted by a chloroethyl group (having a chloroethyl group as a substituent), such as, for example, a 2-pentachloroethylphenyl group, a 3-pentachloroethylphenyl group, a 4-pentachloroethylphenyl group, a 2,4-bis(pentachloroethyl)phenyl group, a 2,6-bis(pentachloroethyl)phenyl group, a 2,4,6-tris(pentachloroethyl)phenyl group or the like; an aryl group having 6 carbon atoms, in which a hydrogen atom bonded to the carbon atoms is substituted by a fluoropropyl group (having a fluoropropyl group as a substituent), such as, for example, a 2-heptafluoropropylphenyl group, a 3-heptafluoropropylphenyl group, a 4-heptafluoropropylphenyl group, a 2,4-bis(heptafluoropropyl)phenyl group, a 2,6-bis(heptafluoropropyl)phenyl group, a 2,4,6-tris(heptafluoropropyl)phenyl group or the like; an aryl group having 6 carbon atoms, in which a hydrogen atom bonded to the carbon atoms is substituted by a chloropropyl group (having a chloropropyl group as a substituent), such as, for example, a 2-heptachloropropylphenyl group, a 3-heptachloropropylphenyl group, a 4-heptachloropropylphenyl group, a 2,4-bis(heptachloropropyl)phenyl group, a 2,6-bis(heptachloropropyl)phenyl group, a 2,4,6-tris(heptachloropropyl)phenyl group or the like; an aryl group having 6 carbon atoms, in which a hydrogen atom bonded to the carbon atoms is substituted by a fluorobutyl group (having a fluorobutyl group as a substituent), such as, for example, a 2-nonafluorobutylphenyl group, a 3-nonafluorobutylphenyl group, a 4-nonafluorobutylphenyl group, a 2,4-bis(nonafluorobutyl)phenyl group, a 2,6-bis(nonafluorobutyl)phenyl group, a 2,4,6-tris(nonafluorobutyl)phenyl group or the like; and an aryl group having 6 carbon atoms, in which a hydrogen atom bonded to the carbon atoms is substituted by a chlorobutyl group (having a chlorobutyl group as a substituent), such as, for example, 2-nonachlorobutylphenyl group, a 3-nonachlorobutylphenyl group, a 4-nonachlorobutylphenyl group, a 2,4-bis(nonachlorobutyl)phenyl group, a 2,6-bis(nonachlorobutyl)phenyl group, a 2,4,6-tris(nonachlorobutyl)phenyl group or the like are preferable; and among them, an unsubstituted (having no substituent) aryl group having 6 carbon atoms, such as, for example, a phenyl group; an aryl group having 6 carbon atoms, in which a hydrogen atom bonded to the carbon atoms is substituted by a fluorine atom (having a fluorine atom as a substituent), such as, for example, a 2-fluorophenyl group, a 3-fluorophenyl group, a 4-fluorophenyl group, a 2,4-difluorophenyl group, a 2,6-difluorophenyl group, a 2,4,6-trifluorophenyl group or the like; an aryl group having 6 carbon atoms, in which a hydrogen atom bonded to the carbon atoms is substituted by a chlorine atom (having a chlorine atom as a substituent), such as, for example, a 2-chlorophenyl group, a 3-chlorophenyl group, a 4-chlorophenyl group, a 2,4-dichlorophenyl group, a 2,6-dichlorophenyl group, a 2,4,6-trichlorophenyl group or the like; an aryl group having 6 carbon atoms, in which a hydrogen atom bonded to the carbon atoms is substituted by a methyl group (having a methyl group as a substituent), such as, for example, a 2-tolyl group, a 3-tolyl group, a 4-tolyl group, a 2,4-xylyl group, a 2,6-xylyl group, a mesityl group (a 2,4,6-trimethylphenyl group) or the like; an aryl group having 6 carbon atoms, in which a hydrogen atom bonded to the carbon atoms is substituted by a fluoromethyl group (having a fluoromethyl group as a substituent), such as, for example, a 2-trifluoromethylphenyl group, a 3-trifluoromethylphenyl group, a 4-trifluoromethylphenyl group, a 2,4-bis(trifluoromethyl)phenyl group, a 2,6-bis(trifluoromethyl)phenyl group, a 2,4,6-tris(trifluoromethyl)phenyl group or the like; and an aryl group having 6 carbon atoms, in which a hydrogen atom bonded to the carbon atoms is substituted by a chloromethyl group (having a chloromethyl group as a substituent), such as, for example, a 2-trichloromethylphenyl group, a 3-trichloromethylphenyl group, a 4-trichloromethylphenyl group, a 2,4-bis(trichloromethyl)phenyl group, a 2,6-bis(trichloromethyl)phenyl group, a 2,4,6-tris(trichloromethyl)phenyl group or the like; are more preferable, and among them, a phenyl group, a 4-fluorophenyl group, a 4-chlorophenyl group, a 4-tolyl group, a 4-trifluoromethylphenyl group and 4-trichloromethylphenyl group are further preferable.

An aryloxy group having 6 to 10 carbon atoms, in which a hydrogen atom may be substituted by a halogen atom, an alkyl group or a haloalkyl group, represented by $R^1$ in the general formula (A), may be any of a monocyclic or a condensed polycyclic group, and specifically includes an unsubstituted (having no substituent) aryloxy group having 6 to 10 carbon atoms, such as, for example, a phenoxy group, a naphthyloxy group or the like; an aryloxy group having 6 to 10 carbon atoms, in which a hydrogen atom bonded to the carbon atoms is substituted by a halogen atom (having a halogen atom as a substituent), such as, for example, an aryloxy group having 6 to 10 carbon atoms, in which a hydrogen atom bonded to the carbon atoms is substituted by a fluorine atom (having a fluorine atom as a substituent), such as, for example, a 2-fluorophenoxy group, a 3-fluorophenoxy group, a 4-fluorophenoxy group, a 2,4-difluorophenoxy group, a 2,6-difluorophenoxy group, a 2,4,6-trifluorophenoxy group, a 1-fluoronaphthyloxy group, a 2-fluoronaphthyloxy group, a 3-fluoronaphthyloxy group, a 4-fluoronaphthyloxy group, a 5-fluoronaphthyloxy group, a 6-fluoronaphthyloxy group, a 7-fluoronaphthyloxy group, a 8-fluoronaphthyloxy group or the like; an aryloxy group having 6 to 10 carbon atoms, in which a hydrogen atom bonded to the carbon atoms is substituted by a chlorine atom (having a chlorine atom as a substituent), such as, for example, a 2-chlorophenoxy group, a 3-chlorophenoxy group, a 4-chlorophenoxy group, a 2,4-dichlorophenoxy group, a 2,6-dichlorophenoxy group, a 2,4,6-trichlorophenoxy group, a 1-chloronaphthyloxy group, 2-chloronaphthyloxy group, a 3-chloronaphthyloxy group, a 4-chloronaphthyloxy group, a 5-chloronaphthyloxy group, a 6-chloronaphthyloxy group, a 7-chloronaphthyloxy group, a 8-chloronaphthyloxy group or the like; an aryloxy group having 6 to 10 carbon atoms, in which a hydrogen atom bonded to the carbon atoms is substituted by a bromine atom (having a bromine atom as a substituent), such as, for example, a 2-bromophenoxy group, a 3-bromophenoxy group, a 4-bromophenoxy group, a 2,4-dibromophenoxy group, a 2,6-dibromophenoxy group, a 2,4,6-tribromophenoxy group, a 1-bromonaphthyloxy group, a 2-bromonaphthyloxy group, a 3-bromonaphthyloxy group, a 4-bromonaphthyloxy group, a 5-bromonaphthyloxy group, a 6-bromonaphthyloxy group, a 7-bromonaphthyloxy group, a 8-bromonaphthyloxy group or the like; an aryloxy group having 6 to 10 carbon atoms, in which a hydrogen atom bonded to the carbon atoms is substituted by an iodine atom (having an iodine atom as a substituent), such as, for example, a 2-iodophenoxy group, a 3-iodophenoxy group, a 4-iodophenoxy group, a 2,4-diiodophenoxy group, a 2,6-diiodophenoxy group, a 2,4,6-triiodophenoxy group, a 1-iodonaphthyloxy group, a 2-iodonaphthyloxy group, a 3-iodonaphthyloxy group, a 4-iodonaphthyloxy group, a 5-iodonaphthyloxy group, a 6-iodonaphthyloxy group, a 7-iodonaphthyloxy group, a 8-iodonaphthyloxy group or the like; an aryloxy group having 6 to 10 carbon atoms, in which a hydrogen atom bonded to the carbon atoms is substituted by an alkyl group having 1 to 4 carbon atoms (having an alkyl group having 1 to 4 carbon atoms as a substituent), such as, for example, an aryloxy group having 6 to 10 carbon atoms, in which a hydrogen atom bonded to the carbon atoms is substituted by a methyl group (having a methyl group as a substituent), such as, for example, a 2-tolyloxy group, a 3-tolyloxy group, a 4-tolyloxy group, a 2,4-xylyloxy group, a 2,6-xylyloxy group, a mesityloxy group (a 2,4,6-trimethylphenoxy group), a 1-methylnaphthyloxy group, a 2-methylnaphthyloxy group, a 3-methylnaphthyloxy group, a 4-methylnaphthyloxy group, a 5-methylnaphthyloxy group, a 6-methylnaphthyloxy group, a 7-methylnaphthyloxy group, a 8-methylnaphthyloxy group or the like; an aryloxy group having 6 to 10 carbon atoms, in which a hydrogen atom bonded to the carbon atoms is substituted by an ethyl group (having an ethyl group as a substituent), such as, for example, a 2-ethylphenoxy group, a 3-ethylphenoxy group, a 4-ethylphenoxy group, a 2,4-diethylphenoxy group, a 2,6-diethylphenoxy group, a 2,4,6-triethylphenoxy group, a 1-ethylnaphthyloxy group, a 2-ethylnaphthyloxy group, a 3-ethylnaphthyloxy group, a 4-ethylnaphthyloxy group, a 5-ethylnaphthyloxy group, a 6-ethylnaphthyloxy group, a 7-ethylnaphthyloxy group, a 8-ethylnaphthyloxy group or the like; an aryloxy group having 6 to 10 carbon atoms, in which a hydrogen atom bonded to the carbon atoms is substituted by a propyl group (having a propyl group as a substituent), such as, for example, a 2-propylphenoxy group, a 3-propylphenoxy group, a 4-propylphenoxy group, a 2,4-dipropylphenoxy group, a 2,6-dipropylphenoxy group, a 2,4,6-tripropylphenoxy group, a 1-propylnaphthyloxy group, a 2-propylnaphthyloxy group, a 3-propylnaphthyloxy group, a 4-propylnaphthyloxy group, a 5-propylnaphthyloxy group, a 6-propylnaphthyloxy group, a 7-propylnaphthyloxy group, a 8-propylnaphthyloxy group or the like; an aryloxy group having 6 to 10 carbon atoms, in which a hydrogen atom bonded to the carbon atoms is substituted by a butyl group (having a butyl group as a substituent), such as, for example, a 2-butylphenoxy group, a 3-butylphenoxy group, a 4-butylphenoxy group, a 2,4-dibutylphenoxy group, a 2,6-dibutylphenoxy group, a 2,4,6-tributylphenoxy group, a 1-butylnaphthyloxy group, a 2-butylnaphthyloxy group, a 3-butylnaphthyloxy group, a 4-butylnaphthyloxy group, a 5-butylnaphthyloxy group, a 6-butylnaphthyloxy group, a 7-butylnaphthyloxy group, a 8-butylnaphthyloxy group or the like; an aryloxy group having 6 to 10 carbon atoms, in which a hydrogen atom bonded to the carbon atoms is substituted by a haloalkyl group having 1 to 4 carbon atoms (having a haloalkyl group having 1 to 4 carbon atoms as a substituent), such as, for example, a fluoroalkyl group or a chloroalkyl group having 1 to 4 carbon atoms, such as, for example, an aryloxy group having 6 to 10 carbon atoms, in which a hydrogen atom bonded to the carbon atoms is substituted by a fluoromethyl group (having a fluoromethyl group as a substituent), such as, for example, a 2-trifluoromethylphenoxy group, a 3-trifluoromethylphenoxy group, a 4-trifluoromethylphenoxy group, a 2,4-bis(trifluoromethyl)phenoxy group, a 2,6-bis(trifluoromethyl)phenoxy group, a 2,4,6-tris(trifluoromethyl)phenoxy group, a 1-trifluoromethylnaphthyloxy group, a 2-trifluoromethylnaphthyloxy group, a 3-trifluoromethylnaphthyloxy group, a 4-trifluoromethylnaphthyloxy group, a 5-trifluoromethylnaphthyloxy group, a 6-trifluoromethylnaphthyloxy group, a 7-trifluoromethylnaphthyloxy group, a 8-trifluoromethylnaphthyloxy group or the like; an aryloxy group having 6 to 10 carbon atoms, in which a hydrogen atom bonded to the carbon atoms is substituted by a chloromethyl group (having a chloromethyl group as a substituent), such as, for example, a 2-trichloromethylphenoxy group, a 3-trichloromethylphenoxy group, a 4-trichloromethylphenoxy group, a 2,4-bis(trichloromethyl)phenoxy group, a 2,6-bis(trichloromethyl)phenoxy group, a 2,4,6-tris(trichloromethyl)phenoxy group, a 1-trichloromethylnaphthyloxy group, a 2-trichloromethylnaphthyloxy group, a 3-trichloromethylnaphthyloxy group, a 4-trichloromethylnaphthyloxy group, a 5-trichloromethylnaphthyloxy group, a 6-trichloromethylnaphthyloxy group, a 7-trichloromethylnaphthyloxy group, a 8-trichloromethylnaphthyloxy group or the like; an aryloxy group having 6 to 10 carbon atoms, in which a hydrogen atom bonded to the carbon atoms is substituted by a fluoroethyl group (having a fluoroethyl group as a substituent), such as, for example, a 2-pentafluoroethylphenoxy group, a 3-pentafluoroethylphenoxy group, a 4-pentafluoroethylphenoxy group, a 2,4-bis(pentafluoroethyl)phenoxy group, a 2,6-bis(pentafluoroethyl)phenoxy group, a 2,4,6-tris(pentafluoroethyl)phenoxy group, a 1-pentafluoroethylnaphthyloxy group, a 2-pentafluoroethylnaphthyloxy group, a 3-pentafluoroethylnaphthyloxy group, a 4-pentafluoroethylnaphthyloxy group, a 5-pentafluoroethylnaphthyloxy group, a 6-pentafluoroethylnaphthyloxy group, a 7-pentafluoroethylnaphthyloxy group, a 8-pentafluoroethylnaphthyloxy group or the like; an aryloxy group having 6 to 10 carbon atoms, in which a hydrogen atom bonded to the carbon atoms is substituted by a chloroethyl group (having a chloroethyl group as a substituent), such as, for example, a 2-pentachloroethylphenoxy group, a 3-pentachloroethylphenoxy group, a 4-pentachloroethylphenoxy group, a 2,4-bis(pentachloroethyl)phenoxy group, a 2,6-bis(pentachloroethyl)phenoxy group, a 2,4,6-tris(pentachloroethyl)phenoxy group, a 1-pentachloroethylnaphthyloxy group, a 2-pentachloroethylnaphthyloxy group, a 3-pentachloroethylnaphthyloxy group, a 4-pentachloroethylnaphthyloxy group, a 5-pentachloroethylnaphthyloxy group, a 6-pentachloroethylnaphthyloxy group, a 7-pentachloroethylnaphthyloxy group, a 8-pentachloroethylnaphthyloxy group or the like; an aryloxy group having 6 to 10 carbon atoms, in which a hydrogen atom bonded to the carbon atoms is substituted by a fluoropropyl group (having a fluoropropyl group as a substituent), such as, for example, a 2-heptafluoropropylphenoxy group, a 3-heptafluoropropylphenoxy group, a 4-heptafluoropropylphenoxy group, a 2,4-bis(heptafluoropropyl)phenoxy group, a 2,6-bis(heptafluoropropyl)phenoxy group, a 2,4,6-tris(heptafluoropropyl)phenoxy group, a 1-heptafluoropropylnaphthyloxy group, a 2-heptafluoropropylnaphthyloxy group, a 3-heptafluoropropylnaphthyloxy group, a 4-heptafluoropropylnaphthyloxy group, a 5-heptafluoropropylnaphthyloxy group, a 6-heptafluoropropylnaphthyloxy group, a 7-heptafluoropropylnaphthyloxy group, a 8-heptafluoropropylnaphthyloxy group or the like; an aryloxy group having 6 to 10 carbon atoms, in which a hydrogen atom bonded to the carbon atoms is substituted by a chloropropyl group (having a chloropropyl group as a substituent), such as, for example, a 2-heptachloropropylphenoxy group, a 3-heptachloropropylphenoxy group, a 4-heptachloropropylphenoxy group, a 2,4-bis(heptachloropropyl)phenoxy group, a 2,6-bis(heptachloropropyl)phenoxy group, a 2,4,6-tris(heptachloropropyl)phenoxy group, a 1-heptachloropropylnaphthyloxy group, a 2-heptachloropropylnaphthyloxy group, a 3-heptachloropropylnaphthyloxy group, a 4-heptachloropropylnaphthyloxy group, a 5-heptachloropropylnaphthyloxy group, a 6-heptachloropropylnaphthyloxy group, a 7-heptachloropropylnaphthyloxy group, a 8-heptachloropropylnaphthyloxy group or the like; an aryloxy group having 6 to 10 carbon atoms, in which a hydrogen atom bonded to the carbon atoms is substituted by a fluorobutyl group (having a fluorobutyl group as a substituent), such as, for example, a 2-nonafluorobutylphenoxy group, a 3-nonafluorobutylphenoxy group, a 4-nonafluorobutylphenoxy group, a 2,4-bis(nonafluorobutyl)phenoxy group, a 2,6-bis(nonafluorobutyl)phenoxy group, a 2,4,6-tris(nonafluorobutyl)phenoxy group, a 1-nonafluorobutylnaphthyloxy group, a 2-nonafluorobutylnaphthyloxy group, a 3-nonafluorobutylnaphthyloxy group, a 4-nonafluorobutylnaphthyloxy group, a 5-nonafluorobutylnaphthyloxy group, a 6-nonafluorobutylnaphthyloxy group, a 7-nonafluorobutylnaphthyloxy group, a 8-nonafluorobutylnaphthyloxy group or the like; an aryloxy group having 6 to 10 carbon atoms, in which a hydrogen atom bonded to the carbon atoms is substituted by a chlorobutyl group (having a chlorobutyl group as a substituent), such as, for example, a 2-nonachlorobutylphenoxy group, a 3-nonachlorobutylphenoxy group, a 4-nonachlorobutylphenoxy group, a 2,4-bis(nonachlorobutyl)phenoxy group, a 2,6-bis(nonachlorobutyl)phenoxy group, a 2,4,6-tris(nonachlorobutyl)phenoxy group, a 1-nonachlorobutylnaphthyloxy group, a 2-nonachlorobutylnaphthyloxy group, a 3-nonachlorobutylnaphthyloxy group, a 4-nonachlorobutylnaphthyloxy group, a 5-nonachlorobutylnaphthyloxy group, a 6-nonachlorobutylnaphthyloxy group, a 7-nonachlorobutylnaphthyloxy group, a 8-nonachlorobutylnaphthyloxy group or the like. It should be noted that, in the above-described specific examples, an alkyl group or a haloalkyl group substituted (bonded) to an aryloxy group is not limited to a normal-form, and may be an alkyl group or a haloalkyl group of a branched group, such as, for example, a sec-form, a tert-form, an iso-form and a neo-form, or an alkyl group or a haloalkyl group of a cyclic group, such as, for example, a cyclo-form. In addition, the carbon atoms constituting an alkyl group or a haloalkyl group substituted (bonded) to an aryloxy group should not be contained in number of the carbon atoms constituting an aryloxy group to which they bond (6 to 10 carbon atoms). In other words, sum of the carbon atoms of an aryloxy group in which 1 to 3 pieces of a hydrogen atom in hydrogen atoms bonded to the carbon atoms are substituted by an alkyl group or a haloalkyl group having 1 to 4 carbon atoms (having an alkyl group or a haloalkyl group having 1 to 4 carbon atoms as a substituent), are 7 to 22.

Among these aryloxy groups, an unsubstituted (having no substituent) aryloxy group having 6 carbon atoms, such as, for example, a phenoxy group; an aryloxy group having 6 carbon atoms, in which a hydrogen atom bonded to the carbon atoms is substituted by a halogen atom (having a halogen atom as a substituent), such as, for example, an aryloxy group having 6 carbon atoms, in which a hydrogen atom bonded to the carbon atoms is substituted by a fluorine atom (having a fluorine atom as a substituent), such as, for example, a 2-fluorophenoxy group, a 3-fluorophenoxy group, a 4-fluorophenoxy group, a 2,4-difluorophenoxy group, a 2,6-difluorophenoxy group, a 2,4,6-trifluorophenoxy group or the like; an aryloxy group having 6 carbon atoms, in which a hydrogen atom bonded to the carbon atoms is substituted by a chlorine atom (having a chlorine atom as a substituent), such as, for example, a 2-chlorophenoxy group, a 3-chlorophenoxy group, 4-chlorophenoxy group, a 2,4-dichlorophenoxy group, a 2,6-dichlorophenoxy group, a 2,4,6-trichlorophenoxy group or the like; an aryloxy group having 6 carbon atoms, in which a hydrogen atom bonded to the carbon atoms is substituted by a bromine atom (having a bromine atom as a substituent), such as, for example, a 2-bromophenoxy group, a 3-bromophenoxy group, a 4-bromophenoxy group, a 2,4-dibromophenoxy group, a 2,6-dibromophenoxy group, a 2,4,6-tribromophenoxy group or the like; and an aryloxy group having 6 carbon atoms, in which a hydrogen atom bonded to the carbon atoms is substituted by an iodine atom (having an iodine atom as a substituent), such as, for example, a 2-iodophenoxy group, a 3-iodophenoxy group, a 4-iodophenoxy group, a 2,4-diiodophenoxy group, a 2,6-diiodophenoxy group, a 2,4,6-triiodophenoxy group or the like; an aryloxy group having 6 carbon atoms, in which a hydrogen atom bonded to the carbon atoms is substituted by an alkyl group having 1 to 4 carbon atoms (having an alkyl group having 1 to 4 carbon atoms as a substituent), such as, for example, an aryloxy group having 6 carbon atoms, in which a hydrogen atom bonded to the carbon atoms is substituted by a methyl group (having a methyl group as a substituent), such as, for example, a 2-tolyloxy group, a 3-tolyloxy group, a 4-tolyloxy group, a 2,4-xylyloxy group, a 2,6-xylyloxy group, a mesityloxy group (a 2,4,6-trimethylphenoxy group) or the like; an aryloxy group having 6 carbon atoms, in which a hydrogen atom bonded to the carbon atoms is substituted by an ethyl group (having an ethyl group as a substituent), such as, for example, a 2-ethylphenoxy group, a 3-ethylphenoxy group, a 4-ethylphenoxy group, a 2,4-diethylphenoxy group, a 2,6-diethylphenoxy group, a 2,4,6-triethylphenoxy group or the like; an aryloxy group having 6 carbon atoms, in which a hydrogen atom bonded to the carbon atoms is substituted by a propyl group (having a propyl group as a substituent), such as, for example, a 2-propylphenoxy group, a 3-propylphenoxy group, a 4-propylphenoxy group, a 2,4-dipropylphenoxy group, a 2,6-dipropylphenoxy group, a 2,4,6-tripropylphenoxy group or the like; and an aryloxy group having 6 carbon atoms, in which a hydrogen atom bonded to the carbon atoms is substituted by a butyl group (having a butyl group as a substituent), such as, for example, a 2-butylphenoxy group, a 3-butylphenoxy group, a 4-butylphenoxy group, a 2,4-dibutylphenoxy group, a 2,6-dibutylphenoxy group, a 2,4,6-tributylphenoxy group or the like; and an aryloxy group having 6 carbon atoms, in which a hydrogen atom bonded to the carbon atoms is substituted by a haloalkyl group having 1 to 4 carbon atoms (having a haloalkyl group having 1 to 4 carbon atoms as a substituent), such as, for example, a fluoroalkyl group or a chloroalkyl group having 1 to 4 carbon atoms, such as, for example, an aryloxy group having 6 carbon atoms, in which a hydrogen atom bonded to the carbon atoms is substituted by a fluoromethyl group (having a fluoromethyl group as a substituent), such as, for example, a 2-trifluoromethylphenoxy group, a 3-trifluoromethylphenoxy group, a 4-trifluoromethylphenoxy group, a 2,4-bis(trifluoromethyl)phenoxy group, a 2,6-bis(trifluoromethyl)phenoxy group, a 2,4,6-tris(trifluoromethyl)phenoxy group or the like; an aryloxy group having 6 carbon atoms, in which a hydrogen atom bonded to the carbon atoms is substituted by a chloromethyl group (having a chloromethyl group as a substituent), such as, for example, a 2-trichloromethylphenoxy group, a 3-trichloromethylphenoxy group, a 4-trichloromethylphenoxy group, a 2,4-bis(trichloromethyl)phenoxy group, a 2,6-bis(trichloromethyl)phenoxy group, a 2,4,6-tris(trichloromethyl)phenoxy group or the like; an aryloxy group having 6 carbon atoms, in which a hydrogen atom bonded to the carbon atoms is substituted by a fluoroethyl group (having a fluoroethyl group as a substituent), such as, for example, a 2-pentafluoroethylphenoxy group, a 3-pentafluoroethylphenoxy group, a 4-pentafluoroethylphenoxy group, a 2,4-bis(pentafluoroethyl)phenoxy group, a 2,6-bis(pentafluoroethyl)phenoxy group, a 2,4,6-tris(pentafluoroethyl)phenoxy group or the like; an aryloxy group having 6 carbon atoms, in which a hydrogen atom bonded to the carbon atoms is substituted by a chloroethyl group (having a chloroethyl group as a substituent), such as, for example, a 2-pentachloroethylphenoxy group, a 3-pentachloroethylphenoxy group, a 4-pentachloroethylphenoxy group, a 2,4-bis(pentachloroethyl)phenoxy group, a 2,6-bis(pentachloroethyl)phenoxy group, a 2,4,6-tris(pentachloroethyl)phenoxy group or the like; an aryloxy group having 6 carbon atoms, in which a hydrogen atom bonded to the carbon atoms is substituted by a fluoropropyl group (having a fluoropropyl group as a substituent), such as, for example, a 2-heptafluoropropylphenoxy group, a 3-heptafluoropropylphenoxy group, a 4-heptafluoropropylphenoxy group, a 2,4-bis(heptafluoropropyl)phenoxy group, a 2,6-bis(heptafluoropropyl)phenoxy group, a 2,4,6-tris(heptafluoropropyl)phenoxy group or the like; an aryloxy group having 6 carbon atoms, in which a hydrogen atom bonded to the carbon atoms is substituted by a chloropropyl group (having a chloropropyl group as a substituent), such as, for example, a 2-heptachloropropylphenoxy group, a 3-heptachloropropylphenoxy group, a 4-heptachloropropylphenoxy group, a 2,4-bis(heptachloropropyl)phenoxy group, a 2,6-bis(heptachloropropyl)phenoxy group, a 2,4,6-tris(heptachloropropyl)phenoxy group or the like; an aryloxy group having 6 carbon atoms, in which a hydrogen atom bonded to the carbon atoms is substituted by a fluorobutyl group (having a fluorobutyl group as a substituent), such as, for example, a 2-nonafluorobutylphenoxy group, a 3-nonafluorobutylphenoxy group, a 4-nonafluorobutylphenoxy group, a 2,4-bis(nonafluorobutyl)phenoxy group, a 2,6-bis(nonafluorobutyl)phenoxy group, a 2,4,6-tris(nonafluorobutyl)phenoxy group or the like; and an aryloxy group having 6 carbon atoms, in which a hydrogen atom bonded to the carbon atoms is substituted by a chlorobutyl group (having a chlorobutyl group as a substituent), such as, for example, a 2-nonachlorobutylphenoxy group, a 3-nonachlorobutylphenoxy group, a 4-nonachlorobutylphenoxy group, a 2,4-bis(nonachlorobutyl)phenoxy group, a 2,6-bis(nonachlorobutyl)phenoxy group, a 2,4,6-tris(nonachlorobutyl)phenoxy group or the like are preferable, and among them, an unsubstituted (having no substituent) aryloxy group having 6 carbon atoms, such as, for example, a phenoxy group; an aryloxy group having 6 carbon atoms, in which a hydrogen atom bonded to the carbon atoms is substituted by a fluorine atom (having a fluorine atom as a substituent), such as, for example, a 2-fluorophenoxy group, a 3-fluorophenoxy group, a 4-fluorophenoxy group, a 2,4-difluorophenoxy group, a 2,6-difluorophenoxy group, a 2,4,6-trifluorophenoxy group or the like; an aryloxy group having 6 carbon atoms, in which a hydrogen atom bonded to the carbon atoms is substituted by a chlorine atom (having a chlorine atom as a substituent), such as, for example, a 2-chlorophenoxy group, a 3-chlorophenoxy group, a 4-chlorophenoxy group, a 2,4-dichlorophenoxy group, a 2,6-dichlorophenoxy group, a 2,4,6-trichlorophenoxy group or the like; an aryloxy group having 6 carbon atoms, in which a hydrogen atom bonded to the carbon atoms is substituted by a methyl group (having a methyl group as a substituent), such as, for example, a 2-tolyloxy group, a 3-tolyloxy group, a 4-tolyloxy group, a 2,4-xylyloxy group, a 2,6-xylyloxy group, a mesityloxy group (a 2,4,6-trimethylphenoxy group) or the like; an aryloxy group having 6 carbon atoms, in which a hydrogen atom bonded to the carbon atoms is substituted by a fluoromethyl group (having a fluoromethyl group as a substituent), such as, for example, a 2-trifluoromethylphenoxy group, a 3-trifluoromethylphenoxy group, a 4-trifluoromethylphenoxy group, a 2,4-bis(trifluoromethyl)phenoxy group, a 2,6-bis(trifluoromethyl)phenoxy group, a 2,4,6-tris(trifluoromethyl)phenoxy group or the like; and an aryloxy group having 6 carbon atoms, in which a hydrogen atom bonded to the carbon atom is substituted by a chloromethyl group (having a chloromethyl group as a substituent), such as, for example, a 2-trichloromethylphenoxy group, a 3-trichloromethylphenoxy group, a 4-trichloromethylphenoxy group, a 2,4-bis(trichloromethyl)phenoxy group, a 2,6-bis(trichloromethyl)phenoxy group, a 2,4,6-tris(trichloromethyl)phenoxy group or the like are more preferable, and among them, a phenoxy group, a 4-fluorophenoxy group, a 4-chlorophenoxy group, a 4-tolyloxy group, a 4-trifluoromethylphenoxy group and a 4-trichloromethylphenoxy group are further preferable.

An arylalkyl group having 7 to 15 carbon atoms, in which a hydrogen atom may be substituted by a halogen atom, an alkyl group or a haloalkyl group, represented by $R^1$ in the general formula (A), may be any of a monocyclic or a condensed polycyclic group, and specifically includes an unsubstituted (having no substituent) arylalkyl group having 7 to 15 carbon atoms, such as, for example, a benzyl group, a phenethyl group, a methylbenzyl group, a phenylpropyl group, a 1-methylphenylethyl group, a phenylbutyl group, a 2-methylphenylpropyl group, a tetrahydronaphthyl group, a naphthylmethyl group, a naphthylethyl group, an indenyl group, a fluorenyl group, or the like; an arylalkyl group having 7 to 15 carbon atoms, in which a hydrogen atom bonded to the carbon atoms is substituted by a halogen atom (having a halogen atom as a substituent), such as, for example, an arylalkyl group having 7 to 15 carbon atoms, in which a hydrogen atom bonded to the carbon atoms is substituted by a fluorine atom (having a fluorine atom as a substituent), such as, for example, a 2-fluorophenylmethyl group, a 3-fluorophenylmethyl group, a 4-fluorophenylmethyl group, a 2,4-difluorophenylmethyl group, a 2,6-difluorophenylmethyl group, a 2,4,6-trifluorophenylmethyl group, a 2-fluorophenylethyl group, a 3-fluorophenylethyl group, a 4-fluorophenylethyl group, a 2,4-difluorophenylethyl group, a 2,6-difluorophenylethyl group, a 2,4,6-trifluorophenylethyl group, a methyl(2-fluorophenyl)methyl group, a methyl(3-fluorophenyl)methyl group, a methyl(4-fluorophenyl)methyl group, a methyl(2,4-difluorophenyl)methyl group, a methyl(2,6-difluorophenyl)methyl group, a methyl(2,4,6-trifluorophenyl)methyl group, a 2-fluorophenylpropyl group, a 3-fluorophenylpropyl group, a 4-fluorophenylpropyl group, a 2,4-difluorophenylpropyl group, a 2,6-difluorophenylpropyl group, a 2,4,6-trifluorophenylpropyl group, a 1-methyl(2-fluorophenyl)ethyl group, a 1-methyl(3-fluorophenyl)ethyl group, a 1-methyl(4-fluorophenyl)ethyl group, a 1-methyl(2,4-difluorophenyl)ethyl group, a 1-methyl(2,6-difluorophenyl)ethyl group, a 1-methyl(2,4,6-trifluorophenyl)ethyl group, a 2-fluorophenylbutyl group, a 3-fluorophenylbutyl group, a 4-fluorophenylbutyl group, a 2,4-difluorophenylbutyl group, a 2,6-difluorophenylbutyl group, a 2,4,6-trifluorophenylbutyl group, a 2-methyl(2-fluorophenyl)propyl group, a 2-methyl(3-fluorophenyl)propyl group, a 2-methyl(4-fluorophenyl)propyl group, 2-methyl(2,4-difluorophenyl)propyl group, 2-methyl(2,6-difluorophenyl)propyl group, a 2-methyl(2,4,6-trifluorophenyl)propyl group, a tetrahydrofluoronaphthyl group, a fluoronaphthylmethyl group, a fluoronaphthylethyl group, a fluoroindenyl group, a fluorofluorenyl group or the like; an arylalkyl group having 7 to 15 carbon atoms, in which a hydrogen atom bonded to the carbon atoms is substituted by a chlorine atom (having a chlorine atom as a substituent), such as, for example, a 2-chlorophenylmethyl group, a 3-chlorophenylmethyl group, a 4-chlorophenylmethyl group, a 2,4-dichlorophenylmethyl group, a 2,6-dichlorophenylmethyl group, a 2,4,6-trichlorophenylmethyl group, a 2-chlorophenylethyl group, a 3-chlorophenylethyl group, a 4-chlorophenylethyl group, a 2,4-dichlorophenylethyl group, a 2,6-dichlorophenylethyl group, a 2,4,6-trichlorophenylethyl group, a methyl(2-chlorophenyl)methyl group, a methyl(3-chlorophenyl)methyl group, a methyl(4-chlorophenyl)methyl group, a methyl(2,4-dichlorophenyl)methyl group, a methyl(2,6-dichlorophenyl)methyl group, a methyl(2,4,6-trichlorophenyl)methyl group, a 2-chlorophenylpropyl group, a 3-chlorophenylpropyl group, a 4-chlorophenylpropyl group, a 2,4-dichlorophenylpropyl group, a 2,6-dichlorophenylpropyl group, a 2,4,6-trichlorophenylpropyl group, a 1-methyl(2-chlorophenyl)ethyl group, a 1-methyl(3-chlorophenyl)ethyl group, a 1-methyl(4-chlorophenyl)ethyl group, a 1-methyl(2,4-dichlorophenyl)ethyl group, a 1-methyl(2,6-dichlorophenyl)ethyl group, a 1-methyl(2,4,6-trichlorophenyl)ethyl group, a 2-chlorophenylbutyl group, a 3-chlorophenylbutyl group, a 4-chlorophenylbutyl group, a 2,4-dichlorophenylbutyl group, a 2,6-dichlorophenylbutylgroup, a 2,4,6-trichlorophenylbutyl group, a 2-methyl(2-chlorophenyl)propyl group, a 2-methyl(3-chlorophenyl)propyl group, a 2-methyl(4-chlorophenyl)propyl group, a 2-methyl(2,4-dichlorophenyl)propyl group, a 2-methyl(2,6-dichlorophenyl)propyl group, a 2-methyl(2,4,6-trichlorophenyl)propyl group, a tetrahydrochloronaphthyl group, a chloronaphthylmethyl group, a chloronaphthylethyl group, a chloroindenyl group, a chlorofluorenyl group or the like; an arylalkyl group having 7 to 15 carbon atoms, in which a hydrogen atom bonded to the carbon atoms is substituted by a bromine atom (having a bromine atom as a substituent), such as, for example, a 2-bromophenylmethyl group, a 3-bromophenylmethyl group, a 4-bromophenylmethyl group, a 2,4-dibromophenylmethyl group, a 2,6-dibromophenylmethyl group, a 2,4,6-tribromophenylmethyl group, a 2-bromophenylethyl group, a 3-bromophenylethyl group, a 4-bromophenylethyl group, a 2,4-dibromophenylethyl group, a 2,6-dibromophenylethyl group, a 2,4,6-tribromophenylethyl group, a methyl(2-bromophenyl)methyl group, a methyl(3-bromophenyl)methyl group, a methyl(4-bromophenyl)methyl group, a methyl(2,4-dibromophenyl)methyl group, a methyl(2,6-dibromophenyl)methyl group, a methyl(2,4,6-tribromophenyl)methyl group, a 2-bromophenylpropyl group, a 3-bromophenylpropyl group, a 4-bromophenylpropyl group, a 2,4-dibromophenylpropyl group, a 2,6-dibromophenylpropyl group, a 2,4,6-tribromophenylpropyl group, a 1-methyl(2-bromophenyl)ethyl group, a 1-methyl(3-bromophenyl)ethyl group, a 1-methyl(4-bromophenyl)ethyl group, a 1-methyl(2,4-dibromophenyl)ethyl group, a 1-methyl(2,6-dibromophenyl)ethyl group, a 1-methyl(2,4,6-tribromophenyl)ethyl group, a 2-bromophenylbutyl group, a 3-bromophenylbutyl group, a 4-bromophenylbutyl group, a 2,4-dibromophenylbutyl group, a 2,6-dibromophenylbutyl group, a 2,4,6-tribromophenylbutyl group, a 2-methyl(2-bromophenyl)propyl group, a 2-methyl(3-bromophenyl)propyl group, a 2-methyl(4-bromophenyl)propyl group, a 2-methyl(2,4-dibromophenyl)propyl group, a 2-methyl(2,6-dibromophenyl)propyl group, a 2-methyl(2,4,6-tribromophenyl)propyl group, a tetrahydrobromonaphthyl group, a bromonaphthylmethyl group, a bromonaphthylethyl group, a bromoindenyl group, a bromofluorenyl group or the like; an arylalkyl group having 7 to 15 carbon atoms, in which a hydrogen atom bonded to the carbon atoms is substituted by an iodine atom (having an iodine atom as a substituent), such as, for example, a 2-iodophenylmethyl group, a 3-iodophenylmethyl group, a 4-iodophenylmethyl group, a 2,4-diiodophenylmethyl group, a 2,6-diiodophenylmethyl group, a 2,4,6-triiodophenylmethyl group, a 2-iodophenylethyl group, a 3-iodophenylethyl group, a 4-iodophenylethyl group, a 2,4-diiodophenylethyl group, a 2,6-diiodophenylethyl group, a 2,4,6-triiodophenylethyl group, a methyl(2-iodophenyl)methyl group, a methyl(3-iodophenyl)methyl group, a methyl(4-iodophenyl)methyl group, a methyl(2,4-diiodophenyl)methyl group, a methyl(2,6-diiodophenyl)methyl group, a methyl(2,4,6-triiodophenyl)methyl group, a 2-iodophenylpropyl group, a 3-iodophenylpropyl group, a 4-iodophenylpropyl group, a 2,4- diiodophenylpropyl group, a 2,6-diiodophenylpropyl group, a 2,4,6-triiodophenylpropyl group, a 1-methyl(2-iodophenyl)ethyl group, a 1-methyl(3-iodophenyl)ethyl group, a 1-methyl(4-iodophenyl)ethyl group, a 1-methyl(2,4-diiodophenyl)ethyl group, a 1-methyl(2,6-diiodophenyl)ethyl group, a 1-methyl(2,4,6-triiodophenyl)ethyl group, a 2-iodophenylbutyl group, a 3-iodophenylbutyl group, a 4-iodophenylbutyl group, a 2,4-diiodophenylbutyl group, a 2,6-diiodophenylbutyl group, a 2,4,6-triiodophenylbutyl group, a 2-methyl(2-iodophenyl)propyl group, a 2-methyl(3-iodophenyl)propyl group, a 2-methyl(4-iodophenyl)propyl group, a 2-methyl(2,4-diiodophenyl)propyl group, a 2-methyl(2,6-diiodophenyl)propyl group, a 2-methyl(2,4,6-triiodophenyl)propyl group, a tetrahydroiodonaphthyl group, an iodonaphthylmethyl group, an iodonaphthylethyl group, an iodoindenyl group, an iodofluorenyl group or the like; an arylalkyl group having 7 to 15 carbon atoms, in which a hydrogen atom bonded to the carbon atoms is substituted by an alkyl group having 1 to 4 carbon atoms (having an alkyl group having 1 to 4 carbon atoms as a substituent), such as, for example, an arylalkyl group having 7 to 15 carbon atoms, in which a hydrogen atom bonded to the carbon atoms is substituted by a methyl group (having a methyl group as a substituent), such as, for example, a 2-tolylmethyl group, a 3-tolylmethyl group, a 4-tolylmethyl group, a 2,4-xylylmethyl group, a 2,6-xylylmethyl group, a mesitylmethyl group (a 2,4,6-trimethylphenylmethyl group), a 2-tolylethyl group, a 3-tolylethyl group, a 4-tolylethyl group, a 2,4-xylylethyl group, a 2,6-xylylethyl group, a mesitylethyl group (a 2,4,6-trimethylphenylethyl group), a methyl(2-tolyl)methyl group, a methyl(3-tolyl)methyl group, a methyl(4-tolyl)methyl group, a methyl(2,4-xylyl)methyl group, a methyl(2,6-xylyl)methyl group, a methyl(mesityl)methyl group, a (methyl(2,4,6-trimethylphenyl)methyl group), a 2-tolylpropyl group, a 3-tolylpropyl group, a 4-tolylpropyl group, a 2,4-xylylpropyl group, a 2,6-xylylpropyl group, a mesitylpropyl group (a 2,4,6-trimethylphenylpropyl group), a 1-methyl(2-tolyl)ethyl group, a 1-methyl(3-tolyl)ethyl group, a 1-methyl(4-tolyl)ethyl group, a 1-methyl(2,4-xylyl)ethyl group, a 1-methyl(2,6-xylyl)ethyl group, a 1-methyl(mesityl)ethyl group, (a 1-methyl(2,4,6-trimethylphenyl)ethyl group), a 2-tolylbutyl group, a 3-tolylbutyl group, a 4-tolylbutyl group, a 2,4-xylylbutyl group, a 2,6-xylylbutyl group, a mesitylbutyl group, (a 2,4,6-trimethylphenylbutyl group), a 2-methyl(2-tolyl)propyl group, a 2-methyl(3-tolyl)propyl group, a 2-methyl(4-tolyl)propyl group, a 2-methyl(2,4-xylyl)propyl group, a 2-methyl(2,6-xylyl)propyl group, a 2-methyl(mesityl)propyl group, (a 2-methyl(2,4,6-trimethylphenyl)propyl group), a tetrahydromethylnaphthyl group, a methylnaphthylmethyl group, a methylnaphthylethyl group, a methylindenyl group, a methylfluorenyl group or the like; an arylalkyl group having 7 to 15 carbon atoms, in which a hydrogen atom bonded to the carbon atoms is substituted by an ethyl group (having an ethyl group as a substituent), such as, for example, a 2-ethylphenylmethyl group, a 3-ethylphenylmethyl group, a 4-ethylphenylmethyl group, a 2,4-diethylphenylmethyl group, a 2,6-diethylphenylmethyl group, a 2,4,6-triethylphenylmethyl group, a 2-ethylphenylethyl group, a 3-ethylphenylethyl group, a 4-ethylphenylethyl group, a 2,4-diethylphenylethyl group, a 2,6-diethylphenylethyl group, a 2,4,6-triethylphenylethyl group, a methyl(2-ethylphenyl)methyl group, a methyl(3-ethylphenyl)methyl group, a methyl(4-ethylphenyl)methyl group, a methyl(2,4-diethylphenyl)methyl group, a methyl(2,6-diethylphenyl)methyl group, a methyl(2,4,6-triethylphenyl)methyl group, a 2-ethylphenylpropyl group, a 3-ethylphenylpropyl group, a 4-ethylphenylpropyl group, a 2,4-diethylphenylpropyl group, a 2,6-diethylphenylpropyl group, a 2,4,6-triethylphenylpropyl group, a 1-methyl(2-ethylphenyl)ethyl group, a 1-methyl(3-ethylphenyl)ethyl group, a 1-methyl(4-ethylphenyl)ethyl group, a 1-methyl(2,4-diethylphenyl)ethyl group, a 1-methyl(2,6-diethylphenyl)ethyl group, a 1-methyl(2,4,6-triethylphenyl)ethyl group, a 2-ethylphenylbutyl group, a 3-ethylphenylbutyl group, a 4-ethylphenylbutyl group, a 2,4-diethylphenylbutyl group, a 2,6-diethylphenylbutyl group, a 2,4,6-triethylphenylbutyl group, a 2-methyl(2-ethylphenyl)propyl group, a 2-methyl(3-ethylphenyl)propyl group, a 2-methyl(4-ethylphenyl)propyl group, a 2-methyl(2,4-diethylphenyl)propyl group, a 2-methyl(2,6-diethylphenyl)propyl group, a 2-methyl(2,4,6-triethylphenyl)propyl group, a tetrahydroethylnaphthyl group, an ethylnaphthylmethyl group, an ethylnaphthylethyl group, an ethylindenyl group, an ethylfluorenyl group or the like; an arylalkyl group having 7 to 15 carbon atoms, in which a hydrogen atom bonded to the carbon atoms is substituted by a propyl group (having a propyl group as a substituent), such as, for example, a 2-propylphenylmethyl group, a 3-propylphenylmethyl group, a 4-propylphenylmethyl group, a 2,4-dipropylphenylmethyl group, a 2,6-dipropylphenylmethyl group, a 2,4,6-tripropylphenylmethyl group, a 2-propylphenylethyl group, a 3-propylphenylethyl group, a 4-propylphenylethyl group, a 2,4-dipropylphenylethyl group, a 2,6-dipropylphenylethyl group, a 2,4,6-tripropylphenylethyl group, a methyl(2-propylphenyl)methyl group, a methyl(3-propylphenyl)methyl group, a methyl(4-propylphenyl)methyl group, a methyl(2,4-dipropylphenyl)methyl group, a methyl(2,6-dipropylphenyl)methyl group, a methyl(2,4,6-tripropylphenyl)methyl group, a 2-propylphenylpropyl group, a 3-propylphenylpropyl group, a 4-propylphenylpropyl group, a 2,4-dipropylphenylpropyl group, a 2,6-dipropylphenylpropyl group, a 2,4,6-tripropylphenylpropyl group, a 1-methyl(2-propylphenyl)ethyl group, a 1-methyl(3-propylphenyl)ethyl group, a 1-methyl(4-propylphenyl)ethyl group, a 1-methyl(2,4-dipropylphenyl)ethyl group, a 1-methyl(2,6-dipropylphenyl)ethyl group, a 1-methyl(2,4,6-triopylphenyl)ethyl group, a 2-propylphenylbutyl group, a 3-propylphenylbutyl group, a 4-propylphenylbutyl group, a 2,4-dipropylphenylbutyl group, a 2,6-dipropylphenylbutyl group, a 2,4,6-tripropylphenylbutyl group, a 2-methyl(2-propylphenyl)propyl group, a 2-methyl(3-propylphenyl)propyl group, a 2-methyl(4-propylphenyl)propyl group, a 2-methyl(2,4-dipropylphenyl)propyl group, a 2-methyl(2,6-dipropylphenyl)propyl group, a 2-methyl(2,4,6-tripropylphenyl)propyl group, a tetrahydropropylnaphthyl group, a propylnaphthylmethyl group, a propylnaphthylethyl group, a propylindenyl group, a propylfluorenyl group or the like; an arylalkyl group having 7 to 15 carbon atoms, in which a hydrogen atom bonded to the carbon atoms is substituted by a butyl group (having a butyl group as a substituent), such as, for example, a 2-butylphenylmethyl group, a 3-butylphenylmethyl group, a 4-butylphenylmethyl group, a 2,4-dibutylphenylmethyl group, a 2,6-dibutylphenylmethyl group, a 2,4,6-tributylphenylmethyl group, a 2-butylphenylethyl group, a 3-butylphenylethyl group, a 4-butylphenylethyl group, a 2,4-dibutylphenylethyl group, a 2,6-dibutylphenylethyl group, a 2,4,6-tributylphenylethyl group, a methyl(2-butylphenyl)methyl group, a methyl(3-butylphenyl)methyl group, a methyl(4-butylphenyl)methyl group, a methyl(2,4-dibutylphenyl)methyl group, a methyl(2,6-dibutylphenyl)methyl group, a methyl(2,4,6-tributylphenyl)methyl group, a 2-butylphenylpropyl group, a 3-butylphenylpropyl group, a 4-butylphenylpropyl group, a 2,4-dibutylphenylpropyl group, a 2,6-dibutylphenylpropyl group, a 2,4,6-tributylphenylpropyl group, a 1-methyl(2-butylphenyl)ethyl group, a 1-methyl(3-butylphenyl)ethyl group, a 1-methyl(4-butylphenyl)ethyl group, a 1-methyl(2,4-dibutylphenyl)ethyl group, a 1-methyl(2,6-dibutylphenyl) ethyl group, a 1-methyl(2,4,6-tributylphenyl)ethyl group, a 2-butylphenylbutyl group, a 3-butylphenylbutyl group, a 4-butylphenylbutyl group, a 2,4-dibutylphenylbutyl group, a 2,6-dibutylphenylbutyl group, a 2,4,6-tributylphenylbutyl group, a 2-methyl(2-butylphenyl)propyl group, a 2-methyl(3-butylphenyl)propyl group, a 2-methyl(4-butylphenyl) propyl group, a 2-methyl(2,4-dibutylphenyl)propyl group, a 2-methyl(2,6-dibutylphenyl)propyl group, a 2-methyl(2,4,6-tributylphenyl)propyl group, a tetrahydrobutylnaphthyl group, a butylnaphthylmethyl group, a butylnaphthylethyl group, a butylindenyl group, a butylfluorenyl group or the like; an arylalkyl group having 7 to 15 carbon atoms, in which a hydrogen atom bonded to the carbon atoms is substituted by a haloalkyl group having 1 to 4 carbon atoms (having a haloalkyl group having 1 to 4 carbon atoms), such as, for example, a fluoroalkyl group or a chloroalkyl group having 1 to 4 carbon atoms, such as, for example, an arylalkyl group having 7 to 15 carbon atoms, in which a hydrogen atom bonded to the carbon atoms is substituted by a fluoromethyl group (having a fluoromethyl group as a substituent), such as, for example, a 2-trifluoromethylphenylmethyl group, a 3-trifluoromethylphenylmethyl group, a 4-trifluoromethylphenylmethyl group, a 2,4-bis(trifluoromethyl)phenylmethyl group, a 2,6-bis(trifluoromethyl)phenylmethyl group, a 2,4,6-tris(trifluoromethyl)phenylmethyl group, a 2-trifluoromethylphenylethyl group, a 3-trifluoromethylphenylethyl group, a 4-trifluoromethylphenylethyl group, a 2,4-bis(trifluoromethyl)phenylethyl group, a 2,6-bis(trifluoromethyl)phenylethyl group, a 2,4,6-tris(trifluoromethyl)phenylethyl group, a methyl(2-trifluoromethylphenyl)methyl group, a methyl(3-trifluoromethylphenyl) methyl group, a methyl(4-trifluoromethylphenyl)methyl group, a methyl[2,4-bis(trifluoromethyl)phenyl]methyl group, a methyl[2,6-bis(trifluoromethyl)phenyl]methyl group, a methyl[2,4,6-tris(trifluoromethyl)phenyl]methyl group, a 2-trifluoromethylphenylpropyl group, a 3-trifluoromethylphenylpropyl group, a 4-trifluoromethylphenylpropyl group, a 2,4-bis(trifluoromethyl)phenylpropyl group, a 2,6-bis(trifluoromethyl)phenylpropyl group, a 2,4,6-tris(trifluoromethyl)phenylpropyl group, a 1-methyl[2-(trifluoromethyl)phenyl]ethyl group, a 1-methyl[3-(trifluoromethyl)phenyl]ethyl group, a 1-methyl[4-(trifluoromethyl)phenyl]ethyl group, a 1-methyl[2,4-bis(trifluoromethyl)phenyl]ethyl group, a 1-methyl[2,6-bis(trifluoromethyl)phenyl]ethyl group, a 1-methyl[2,4,6-tris(trifluoromethyl)phenyl]ethyl group, a 2-trifluoromethylphenylbutyl group, a 3-trifluoromethylphenylbutyl group, a 4-trifluoromethylphenylbutyl group, a 2,4-bis(trifluoromethyl)phenylbutyl group, a 2,6-bis(trifluoromethyl)phenylbutyl group, a 2,4,6-tris(trifluoromethyl)phenylbutyl group, a 2-methyl[2-(trifluoromethyl)phenyl]propyl group, a 2-methyl[3-(trifluoromethyl)phenyl]propyl group, a 2-methyl[4-(trifluoromethyl)phenyl]propyl group, a 2-methyl[2,4-bis(trifluoromethyl)phenyl]propyl group, a 2-methyl[2,6-bis(trifluoromethyl)phenyl]propyl group, a 2-methyl[2,4,6-tris(trifluoromethyl)phenyl]propyl group, a tetrahydro(trifluoromethyl)naphthyl group, a trifluoromethylnaphthylmethyl group, a trifluoromethylnaphthylethyl group, a trifluoromethylindenyl group, a trifluoromethylfluorenyl group or the like; an arylalkyl group having 7 to 15 carbon atoms, in which a hydrogen atom bonded to the carbon atoms is substituted by a chloromethyl group (having a chloromethyl group as a substituent), such as, for example, a 2-trichloromethylphenylmethyl group, a 3-trichloromethylphenylmethyl group, a 4-trichloromethylphenylmethyl group, a 2,4-bis(trichloromethyl)phenylmethyl group, a 2,6-bis(trichloromethyl)phenylmethyl group, a 2,4,6-tris(trichloromethyl)phenylmethyl group, a 2-trichloromethylphenylethyl group, a 3-trichloromethylphenylethyl group, a 4-trichloromethylphenylethyl group, a 2,4-bis(trichloromethyl)phenylethyl group, a 2,6-bis(trichloromethyl)phenylethyl group, a 2,4,6-tris(trichloromethyl)phenylethyl group, a methyl(2-trichloromethylphenyl)methyl group, a methyl(3-trichloromethylphenyl)methyl group, a methyl(4-trichloromethylphenyl)methyl group, a methyl[2,4-bis(trichloromethyl)phenyl]methyl group, a methyl[2,6-bis(trichloromethyl)phenyl]methyl group, a methyl[2,4,6-tris(trichloromethyl)phenyl]methyl group, a 2-trichloromethylphenylpropyl group, a 3-trichloromethylphenylpropyl group, a 4-trichloromethylphenylpropyl group, a 2,4-bis(trichloromethyl)phenylpropyl group, a 2,6-bis(trichloromethyl)phenylpropyl group, a 2,4,6-tris(trichloromethyl)phenylpropyl group, a 1-methyl[2-(trichloromethyl)phenyl]ethyl group, a 1-methyl[3-(trichloromethyl)phenyl]ethyl group, a 1-methyl[4-(trichloromethyl)phenyl]ethyl group, a 1-methyl[2,4-bis(trichloromethyl)phenyl]ethyl group, a 1-methyl[2,6-bis(trichloromethyl)phenyl]ethyl group, a 1-methyl[2,4,6-tris(trichloromethyl)phenyl]ethyl group, a 2-trichloromethylphenylbutyl group, a 3-trichloromethylphenylbutyl group, a 4-trichloromethylphenylbutyl group, a 2,4-bis(trichloromethyl)phenylbutyl group, a 2,6-bis(trichloromethyl)phenylbutyl group, a 2,4,6-tris(trichloromethyl)phenylbutyl group, a 2-methyl[2-(trichloromethyl)phenyl]propyl group, a 2-methyl[3-(trichloromethyl)phenyl]propyl group, a 2-methyl[4-(trichloromethyl)phenyl]propyl group, a 2-methyl[2,4-bis(trichloromethyl)phenyl]propyl group, a 2-methyl[2,6-bis(trichloromethyl)phenyl]propyl group, a 2-methyl[2,4,6-tris(trichloromethyl)phenyl]propyl group, a tetrahydro(trichloromethyl)naphthyl group, a trichloromethylnaphthylmethyl group, a trichloromethylnaphthylethyl group, a trichloromethylindenyl group, a trichloromethylfluorenyl group or the like; an arylalkyl group having 7 to 15 carbon atoms, in which a hydrogen atom bonded to the carbon atoms is substituted by a fluoroethyl group (having a fluoroethyl group as a substituent), such as, for example, a 2-pentafluoroethylphenylmethyl group, a 3-pentafluoroethylphenylmethyl group, a 4-pentafluoroethylphenylmethyl group, a 2,4-bis(pentafluoroethyl)phenylmethyl group, a 2,6-bis(pentafluoroethyl)phenylmethyl group, a 2,4,6-tris(pentafluoroethyl)phenylmethyl group, a 2-pentafluoroethylphenylethyl group, a 3-pentafluoroethylphenylethyl group, a 4-pentafluoroethylphenylethyl group, a 2,4-bis(pentafluoroethyl)phenylethyl group, a 2,6-bis(pentafluoroethyl)phenylethyl group, a 2,4,6-tris(pentafluoroethyl)phenylethyl group, a methyl(2-pentafluoroethylphenyl)methyl group, a methyl(3-pentafluoroethylphenyl)methyl group, a methyl(4-pentafluoroethylphenyl)methyl group, a methyl[2,4-bis(pentafluoroethyl)phenyl]methyl group, a methyl[2,6-bis(pentafluoroethyl)phenyl]methyl group, a methyl[2,4,6-tris(pentafluoroethyl)phenyl]methyl group, a 2-pentafluoroethylphenylpropyl group, a 3-pentafluoroethylphenylpropyl group, a 4-pentafluoroethylphenylpropyl group, a 2,4-bis(pentafluoroethyl)phenylpropyl group, a 2,6-bis(pentafluoroethyl)phenylpropyl group, a 2,4,6-tris(pentafluoroethyl)phenylpropyl group, 1-methyl[2-(pentafluoroethyl)phenyl]ethyl group, a 1-methyl[3-(pentafluoroethyl)phenyl]ethyl group, a 1-methyl[4-(pentafluoroethyl)phenyl]ethyl group, a 1-methyl[2,4-bis(pentafluoroethyl)phenyl]ethyl group, a 1-methyl[2,6-bis(pentafluoroethyl)phenyl]ethyl group, a 1-methyl[2,4,6-tris(pentafluoroethyl)phenyl]ethyl group, 2-pentafluoroethylphenylbutyl group, a 3-pentafluoroethylphenylbutyl group, a 4-pentafluoroethylphenylbutyl group, a 2,4-bis(pentafluoroethyl)phenylbutyl group, a 2,6-bis(pentafluoroethyl)phenylbutyl group, a 2,4,6-tris(pentafluoroethyl)phenylbutyl group, a 2-methyl[2-(pentafluoroethyl)phenyl]propyl group, a 2-methyl[3-(pentafluoroethyl)phenyl]propyl group, a 2-methyl[4-(pentafluoroethyl)phenyl]propyl group, a 2-methyl[2,4-bis(pentafluoroethyl)phenyl]propyl group, a 2-methyl[2,6-bis(pentafluoroethyl)phenyl]propyl group, a 2-methyl[2,4,6-tris(pentafluoroethyl)phenyl]propyl group, a tetrahydro(pentafluoroethyl)naphthyl group, a pentafluoroethylnaphthylmethyl group, a pentafluoroethylnaphthylethyl group, a pentafluoroethylindenyl group, a pentafluoroethylfluorenyl group or the like; an arylalkyl group having 7 to 15 carbon atoms, in which a hydrogen atom bonded to the carbon atoms is substituted by a chloroethyl group (having a chloroethyl group as a substituent), such as, for example, a 2-pentachloroethylphenylmethyl group, a 3-pentachloroethylphenylmethyl group, a 4-pentachloroethylphenylmethyl group, a 2,4-bis(pentachloroethyl)phenylmethyl group, a 2,6-bis(pentachloroethyl)phenylmethyl group, a 2,4,6-tris(pentachloroethyl)phenylmethyl group, a 2-pentachloroethylphenylethyl group, a 3-pentachloroethylphenylethyl group, a 4-pentachloroethylphenylethyl group, a 2,4-bis(pentachloroethyl)phenylethyl group, a 2,6-bis(pentachloroethyl)phenylethyl group, a 2,4,6-tris(pentachloroethyl)phenylethyl group, a methyl(2-pentachloroethylphenyl)methyl group, a methyl(3-pentachloroethylphenyl)methyl group, a methyl(4-pentachloroethylphenyl)methyl group, a methyl[2,4-bis(pentachloroethyl)phenyl]methyl group, a methyl[2,6-bis(pentachloroethyl)phenyl]methyl group, a methyl[2,4,6-tris(pentachloroethyl)phenyl]methyl group, a 2-pentachloroethylphenylpropyl group, a 3-pentachloroethylphenylpropyl group, a 4-pentachloroethylphenylpropyl group, a 2,4-bis(pentachloroethyl)phenylpropyl group, a 2,6-bis(pentachloroethyl)phenylpropyl group, a 2,4,6-tris(pentachloroethyl)phenylpropyl group, a 1-methyl[2-(pentachloroethyl)phenyl]ethyl group, a 1-methyl[3-(pentachloroethyl)phenyl]ethyl group, a 1-methyl[4-(pentachloroethyl)phenyl]ethyl group, a 1-methyl[2,4-bis(pentachloroethyl)phenyl]ethyl group, a 1-methyl[2,6-bis(pentachloroethyl)phenyl]ethyl group, a 1-methyl[2,4,6-tris(pentachloroethyl)phenyl]ethyl group, a 2-pentachloroethylphenylbutyl group, a 3-pentachloroethylphenylbutyl group, a 4-pentachloroethylphenylbutyl group, a 2,4-bis(pentachloroethyl)phenylbutyl group, a 2,6-bis(pentachloroethyl)phenylbutyl group, a 2,4,6-tris(pentachloroethyl)phenylbutyl group, a 2-methyl[2-(pentachloroethyl)phenyl]propyl group, a 2-methyl[3-(pentachloroethyl)phenyl]propyl group, a 2-methyl[4-(pentachloroethyl)phenyl]propyl group, a 2-methyl[2,4-bis(pentachloroethyl)phenyl]propyl group, a 2-methyl[2,6-bis(pentachloroethyl)phenyl]propyl group, a 2-methyl[2,4,6-tris(pentachloroethyl)phenyl]propyl group, a tetrahydro(pentachloroethyl)naphthyl group, a pentachloroethylnaphthylmethyl group, a pentachloroethylnaphthylethyl group, a pentachloroethylindenyl group, a pentachloroethylfluorenyl group or the like; an arylalkyl group having 7 to 15 carbon atoms, in which a hydrogen atom bonded to the carbon atoms is substituted by a fluoropropyl group (having a fluoropropyl group as a substituent), such as, for example, a 2-heptafluoropropylphenylmethyl group, a 3-heptafluoropropylphenylmethyl group, a 4-heptafluoropropylphenylmethyl group, a 2,4-bis(heptafluoropropyl)phenylmethyl group, a 2,6-bis(heptafluoropropyl)phenylmethyl group, a 2,4,6-tris(heptafluoropropyl)phenylmethyl group, a 2-heptafluoropropylphenylethyl group, a 3-heptafluoropropylphenylethyl group, a 4-heptafluoropropylphenylethyl group, a 2,4-bis(heptafluoropropyl)phenylethyl group, a 2,6-bis(heptafluoropropyl)phenylethyl group, a 2,4,6-tris(heptafluoropropyl)phenylethyl group, a methyl(2-heptafluoropropylphenyl)methyl group, a methyl(3-heptafluoropropylphenyl)methyl group, a methyl(4-heptafluoropropylphenyl)methyl group, a methyl[2,4-bis(heptafluoropropyl)phenyl]methyl group, a methyl[2,6-bis(heptafluoropropyl)phenyl]methyl group, a methyl[2,4,6-tris(heptafluoropropyl)phenyl]methyl group, a 2-heptafluoropropylphenylpropyl group, a 3-heptafluoropropylphenylpropyl group, a 4-heptafluoropropylphenylpropyl group, a 2,4-bis(heptafluoropropyl)phenylpropyl group, a 2,6-bis(heptafluoropropyl)phenylpropyl group, a 2,4,6-tris(heptafluoropropyl)phenylpropyl group, a 1-methyl[2-(heptafluoropropyl)phenyl]ethyl group, a 1-methyl[3-(heptafluoropropyl)phenyl]ethyl group, a 1-methyl[4-(heptafluoropropyl)phenyl]ethyl group, a 1-methyl[2,4-bis(heptafluoropropyl)phenyl]ethyl group, a 1-methyl[2,6-bis(heptafluoropropyl)phenyl]ethyl group, a 1-methyl[2,4,6-tris(heptafluoropropyl)phenyl]ethyl group, a 2-heptafluoropropylphenylbutyl group, a 3-heptafluoropropylphenylbutyl group, a 4-heptafluoropropylphenylbutyl group, a 2,4-bis(heptafluoropropyl)phenylbutyl group, a 2,6-bis(heptafluoropropyl)phenylbutyl group, a 2,4,6-tris(heptafluoropropyl)phenylbutyl group, a 2-methyl[2-(heptafluoropropyl)phenyl]propyl group, a 2-methyl[3-(heptafluoropropyl)phenyl]propyl group, a 2-methyl[4-(heptafluoropropyl)phenyl]propyl group, a 2-methyl[2,4-bis(heptafluoropropyl)phenyl]propyl group, a 2-methyl[2,6-bis(heptafluoropropyl)phenyl]propyl group, a 2-methyl[2,4,6-tris(heptafluoropropyl)phenyl]propyl group, a tetrahydro(heptafluoropropyl)naphthyl group, a heptafluoropropylnaphthylmethyl group, a heptafluoropropylnaphthylethyl group, a heptafluoropropylindenyl group, a heptafluoropropylfluorenyl group or the like; an arylalkyl group having 7 to 15 carbon atoms, in which a hydrogen atom bonded to the carbon atoms is substituted by a chloropropyl group (having a chloropropyl group as a substituent), such as, for example, a 2-heptachloropropylphenylmethyl group, a 3-heptachloropropylphenylmethyl group, a 4-heptachloropropylphenylmethyl group, a 2,4-bis(heptachloropropyl)phenylmethyl group, a 2,6-bis(heptachloropropyl)phenylmethyl group, a 2,4,6-tris(heptachloropropyl)phenylmethyl group, a 2-heptachloropropylphenylethyl group, a 3-heptachloropropylphenylethyl group, a 4-heptachloropropylphenylethyl group, a 2,4-bis(heptachloropropyl)phenylethyl group, a 2,6-bis(heptachloropropyl)phenylethyl group, a 2,4,6-tris(heptachloropropyl)phenylethyl group, a methyl(2-heptachloropropylphenyl)methyl group, a methyl(3-heptachloropropylphenyl)methyl group, a methyl(4-heptachloropropylphenyl)methyl group, a methyl[2,4-bis(heptachloropropyl)phenyl]methyl group, a methyl[2,6-bis(heptachloropropyl)phenyl]methyl group, a methyl[2,4,6-tris(heptachloropropyl)phenyl]methyl group, a 2-heptachloropropylphenylpropyl group, a 3-heptachloropropylphenylpropyl group, a 4-heptachloropropylphenylpropyl group, a 2,4-bis(heptachloropropyl)phenylpropyl group, a 2,6-bis(heptachloropropyl)phenylpropyl group, a 2,4,6-tris(heptachloropropyl)phenylpropyl group, a 1-methyl[2-(heptachloropropyl)phenyl]ethyl group, a 1-methyl[3-(heptachloropropyl)phenyl]ethyl group, a 1-methyl[4-(heptachloropropyl)phenyl]ethyl group, a 1-methyl[2,4-bis(heptachloropropyl)phenyl]ethyl group, a 1-methyl[2,6-bis(heptachloropropyl)phenyl]ethyl group, a 1-methyl[2,4,6-tris(heptachloropropyl)phenyl]ethyl group, a 2-heptachloropropylphenylbutyl group, a 3-heptachloropropylphenylbutyl group, a 4-heptachloropropylphenylbutyl group, a 2,4-bis(heptachloropropyl)phenylbutyl group, a 2,6-bis(heptachloropropyl)phenylbutyl group, a 2,4,6-tris(heptachloropropyl)phenylbutyl group, a 2-methyl[2-(heptachloropropyl)phenyl]propyl group, a 2-methyl[3-(heptachloropropyl)phenyl]propyl group, a 2-methyl[4-(heptachloropropyl)phenyl]propyl group, a 2-methyl[2,4-bis(heptachloropropyl)phenyl]propyl group, a 2-methyl[2,6-bis(heptachloropropyl)phenyl]propyl group, a 2-methyl[2,4,6-tris(heptachloropropyl)phenyl]propyl group, a tetrahydro(heptachloropropyl)naphthyl group, a heptachloropropylnaphthylmethyl group, a heptachloropropylnaphthylethyl group, a heptachloropropylindenyl group, a heptachloropropylfluorenyl group or the like; an arylalkyl group having 7 to 15 carbon atoms, in which a hydrogen atom bonded to the carbon atoms is substituted by a fluorobutyl group (having a fluorobutyl group as a substituent), such as, for example, a 2-nonafluorobutylphenylmethyl group, a 3-nonafluorobutylphenylmethyl group, a 4-nonafluorobutylphenylmethyl group, a 2,4-bis(nonafluorobutyl)phenylmethyl group, a 2,6-bis(nonafluorobutyl)phenylmethyl group, a 2,4,6-tris(nonafluorobutyl)phenylmethyl group, a 2-nonafluorobutylphenylethyl group, a 3-nonafluorobutylphenylethyl group, a 4-nonafluorobutylphenylethyl group, a 2,4-bis(nonafluorobutyl)phenylethyl group, a 2,6-bis(nonafluorobutyl)phenylethyl group, a 2,4,6-tris(nonafluorobutyl)phenylethyl group, a methyl(2-nonafluorobutylphenyl)methyl group, a methyl(3-nonafluorobutylphenyl)methyl group, a methyl(4-nonafluorobutylphenyl)methyl group, a methyl[2,4-bis(nonafluorobutyl)phenyl]methyl group, a methyl[2,6-bis(nonafluorobutyl)phenyl]methyl group, a methyl[2,4,6-tris(nonafluorobutyl)phenyl]methyl group, a 2-nonafluorobutylphenylpropyl group, a 3-nonafluorobutylphenylpropyl group, a 4-nonafluorobutylphenylpropyl group, a 2,4-bis(nonafluorobutyl)phenylpropyl group, a 2,6-bis(nonafluorobutyl)phenylpropyl group, a 2,4,6-tris(nonafluorobutyl)phenylpropyl group, a 1-methyl[2-(nonafluorobutyl)phenyl]ethyl group, a 1-methyl[3-(nonafluorobutyl)phenyl]ethyl group, a 1-methyl[4-(nonafluorobutyl)phenyl]ethyl group, a 1-methyl[2,4-bis(nonafluorobutyl)phenyl]ethyl group, a 1-methyl[2,6-bis(nonafluorobutyl)phenyl]ethyl group, a 1-methyl[2,4,6-tris(nonafluorobutyl)phenyl]ethyl group, a 2-nonafluorobutylphenylbutyl group, a 3-nonafluorobutylphenylbutyl group, a 4-nonafluorobutylphenylbutyl group, a 2,4-bis(nonafluorobutyl)phenylbutyl group, a 2,6-bis(nonafluorobutyl)phenylbutyl group, a 2,4,6-tris(nonafluorobutyl)phenylbutyl group, a 2-methyl[2-(nonafluorobutyl)phenyl]propyl group, a 2-methyl[3-(nonafluorobutyl)phenyl]propyl group, a 2-methyl[4-(nonafluorobutyl)phenyl]propyl group, a 2-methyl[2,4-bis(nonafluorobutyl)phenyl]propyl group, a 2-methyl[2,6-bis(nonafluorobutyl)phenyl]propyl group, a 2-methyl[2,4,6-tris(nonafluorobutyl)phenyl]propyl group, a tetrahydro(nonafluorobutyl)naphthyl group, a nonafluorobutylnaphthylmethyl group, a nonafluorobutylnaphthylethyl group, a nonafluorobutylindenyl group, a nonafluorobutylfluorenyl group or the like; an arylalkyl group having 7 to 15 carbon atoms, in which a hydrogen atom bonded to the carbon atoms is substituted by a chlorobutyl group (having a chlorobutyl group as a substituent), such as, for example, a 2-nonachlorobutylphenylmethyl group, a 3-nonachlorobutylphenylmethyl group, a 4-nonachlorobutylphenylmethyl group, a 2,4-bis(nonachlorobutyl)phenylmethyl group, a 2,6-bis(nonachlorobutyl)phenylmethyl group, a 2,4,6-tris(nonachlorobutyl)phenylmethyl group, a 2-nonachlorobutylphenylethyl group, a 3-nonachlorobutylphenylethyl group, a 4-nonachlorobutylphenylethyl group, a 2,4-bis(nonachlorobutyl)phenylethyl group, a 2,6-bis(nonachlorobutyl)phenylethyl group, a 2,4,6-tris(nonachlorobutyl)phenylethyl group, a methyl(2-nonachlorobutylphenyl)methyl group, a methyl(3-nonachlorobutylphenyl)methyl group, a methyl(4-nonachlorobutylphenyl)methyl group, a methyl[2,4-bis(nonachlorobutyl)phenyl]methyl group, a methyl[2,6-bis(nonachlorobutyl)phenyl]methyl group, a methyl[2,4,6-tris(nonachlorobutyl)phenyl]methyl group, a 2-nonachlorobutylphenylpropyl group, a 3-nonachlorobutylphenylpropyl group, a 4-nonachlorobutylphenylpropyl group, a 2,4-bis(nonachlorobutyl)phenylpropyl group, a 2,6-bis(nonachlorobutyl)phenylpropyl group, a 2,4,6-tris(nonachlorobutyl)phenylpropyl group, 1-methyl[2-(nonachlorobutyl)phenyl]ethyl group, a 1-methyl[3-(nonachlorobutyl)phenyl]ethyl group, a 1-methyl[4-(nonachlorobutyl)phenyl]ethyl group, a 1-methyl[2,4-bis(nonachlorobutyl)phenyl]ethyl group, a 1-methyl[2,6-bis(nonachlorobutyl)phenyl]ethyl group, a 1-methyl[2,4,6-tris(nonachlorobutyl)phenyl]ethyl group, a 2-nonachlorobutylphenylbutyl group, a 3-nonachlorobutylphenylbutyl group, a 4-nonachlorobutylphenylbutyl group, a 2,4-bis(nonachlorobutyl)phenylbutyl group, a 2,6-bis(nonachlorobutyl)phenylbutyl group, a 2,4,6-tris(nonachlorobutyl)phenylbutyl group, a 2-methyl[2-(nonachlorobutyl)phenyl]propyl group, a 2-methyl[3-(nonachlorobutyl)phenyl]propyl group, a 2-methyl[4-(nonachlorobutyl)phenyl]propyl group, a 2-methyl[2,4-bis(nonachlorobutyl)phenyl]propyl group, a 2-methyl[2,6-bis(nonachlorobutyl)phenyl]propyl group, a 2-methyl[2,4,6-tris(nonachlorobutyl)phenyl]propyl group, a tetrahydro(nonachlorobutyl)naphthyl group, a nonachlorobutylnaphthylmethyl group, a nonachlorobutylnaphthylethyl group, a nonachlorobutylindenyl group, a nonachlorobutylfluorenyl group or the like. It should be noted that, in the above-described specific examples, an alkyl group or a haloalkyl group substituted (bonded) to an aryl group in an arylalkyl group is not limited to a normal-form, and may be an alkyl group or a haloalkyl group of a branched group, such as, for example, a sec-form, a tert-form, an iso-form and a neo-form, or an alkyl group or a haloalkyl group of a cyclic group, such as, for example, a cyclo-form. In addition, the carbon atoms constituting an alkyl group or a haloalkyl group substituted (bonded) to an aryl group in an arylalkyl group should not be contained in number of the carbon atoms constituting an arylalkyl group to which they bond (7 to 15 carbon atoms). In other words, sum of the carbon atoms of an arylalkyl group in which 1 to 3 pieces of a hydrogen atom in hydrogen atoms bonded to the carbon atoms are substituted by an alkyl group or a haloalkyl group having 1 to 4 carbon atoms (having an alkyl group or a haloalkyl group having 1 to 4 carbon atoms as a substituent), are 8 to 27.

Among these arylalkyl groups, an unsubstituted (having no substituent) arylalkyl group having 7 to 9 carbon atoms, such as, for example, a benzyl group, a phenethyl group, a methylbenzyl group, a phenylpropyl group, a 1-methylphenylethyl group or the like; an arylalkyl group having 7 to 9 carbon atoms, in which a hydrogen atom bonded to the carbon atoms is substituted by a halogen atom (having a halogen atom as a substituent), such as, for example, an arylalkyl group having 7 to 9 carbon atoms, in which a hydrogen atom bonded to the carbon atoms is substituted by a fluorine atom (having a fluorine atom as a substituent), such as, for example, a 2-fluorophenylmethyl group, a 3-fluorophenylmethyl group, a 4-fluorophenylmethyl group, a 2,4-difluorophenylmethyl group, a 2,6-difluorophenylmethyl group, a 2,4,6-trifluorophenylmethyl group, a 2-fluorophenylethyl group, a 3-fluorophenylethyl group, a 4-fluorophenylethyl group, a 2,4-difluorophenylethyl group, a 2,6-difluorophenylethyl group, a 2,4,6-trifluorophenylethyl group, a methyl(2-fluorophenyl)methyl group, a methyl(3-fluorophenyl)methyl group, a methyl(4-fluorophenyl)methyl group, a methyl(2,4-difluorophenyl)methyl group, a methyl(2,6-difluorophenyl)methyl group, a methyl(2,4,6-trifluorophenyl)methyl group, a 2-fluorophenylpropyl group, a 3-fluorophenylpropyl group, a 4-fluorophenylpropyl group, a 2,4-difluorophenylpropyl group, a 2,6-difluorophenylpropyl group, a 2,4,6-trifluorophenylpropyl group, a 1-methyl(2-fluorophenyl)ethyl group, a 1-methyl(3-fluorophenyl)ethyl group, a 1-methyl(4-fluorophenyl)ethyl group, a 1-methyl(2,4-difluorophenyl)ethyl group, a 1-methyl(2,6-difluorophenyl)ethyl group, a 1-methyl(2,4,6-trifluorophenyl)ethyl group or the like; an arylalkyl group having 7 to 9 carbon atoms, in which a hydrogen atom bonded to the carbon atoms is substituted by a chlorine atom (having a chlorine atom as a substituent), such as, for example, a 2-chlorophenylmethyl group, a 3-chlorophenylmethyl group, a 4-chlorophenylmethyl group, a 2,4-dichlorophenylmethyl group, a 2,6-dichlorophenylmethyl group, a 2,4,6-trichlorophenylmethyl group, a 2-chlorophenylethyl group, a 3-chlorophenylethyl group, a 4-chlorophenylethyl group, a 2,4-dichlorophenylethyl group, a 2,6-dichlorophenylethyl group, a 2,4,6-trichlorophenylethyl group, a methyl(2-chlorophenyl)methyl group, a methyl(3-chlorophenyl)methyl group, a methyl(4-chlorophenyl)methyl group, a methyl(2,4-dichlorophenyl)methyl group, a methyl(2,6-dichlorophenyl)methyl group, a methyl(2,4,6-trichlorophenyl)methyl group, a 2-chlorophenylpropyl group, a 3-chlorophenylpropyl group, a 4-chlorophenylpropyl group, a 2,4-dichlorophenylpropyl group, a 2,6-dichlorophenylpropyl group, a 2,4,6-trichlorophenylpropyl group, a 1-methyl(2-chlorophenyl)ethyl group, a 1-methyl(3-chlorophenyl)ethyl group, a 1-methyl(4-chlorophenyl)ethyl group, a 1-methyl(2,4-dichlorophenyl)ethyl group, a 1-methyl(2,6-dichlorophenyl)ethyl group, a 1-methyl(2,4,6-trichlorophenyl)ethyl group or the like; an arylalkyl group having 7 to 9 carbon atoms, in which a hydrogen atom bonded to the carbon atoms is substituted by a bromine atom (having a bromine atom as a substituent), such as, for example, a 2-bromophenylmethyl group, a 3-bromophenylmethyl group, a 4-bromophenylmethyl group, a 2,4-dibromophenylmethyl group, a 2,6-dibromophenylmethyl group, a 2,4,6-tribromophenylmethyl group, a 2-bromophenylethyl group, a 3-bromophenylethyl group, a 4-bromophenylethyl group, a 2,4-dibromophenylethyl group, a 2,6-dibromophenylethyl group, a 2,4,6-tribromophenylethyl group, a methyl(2-bromophenyl)methyl group, a methyl(3-bromophenyl)methyl group, a methyl(4-bromophenyl)methyl group, a methyl(2,4-dibromophenyl)methyl group, a methyl(2,6-dibromophenyl)methyl group, a methyl(2,4,6-tribromophenyl)methyl group, a 2-bromophenylpropyl group, a 3-bromophenylpropyl group, a 4-bromophenylpropyl group, a 2,4-dibromophenylpropyl group, a 2,6-dibromophenylpropyl group, a 2,4,6-tribromophenylpropyl group, a 1-methyl(2-bromophenyl)ethyl group, a 1-methyl(3-bromophenyl)ethyl group, a 1-methyl(4-bromophenyl)ethyl group, a 1-methyl(2,4-dibromophenyl)ethyl group, a 1-methyl(2,6-dibromophenyl)ethyl group, a 1-methyl(2,4,6-tribromophenyl)ethyl group or the like; and an arylalkyl group having 7 to 9 carbon atoms, in which a hydrogen atom bonded to the carbon atoms is substituted by an iodine atom (having an iodine atom as a substituent), such as, for example, a 2-iodophenylmethyl group, a 3-iodophenylmethyl group, a 4-iodophenylmethyl group, a 2,4-diiodophenylmethyl group, a 2,6-diiodophenylmethyl group, a 2,4,6-triiodophenylmethyl group, a 2-iodophenylethyl group, a 3-iodophenylethyl group, a 4-iodophenylethyl group, a 2,4-diiodophenylethyl group, a 2,6-diiodophenylethyl group, a 2,4,6-triiodophenylethyl group, a methyl(2-iodophenyl)methyl group, a methyl(3-iodophenyl)methyl group, a methyl(4-iodophenyl)methyl group, a methyl(2,4-diiodophenyl)methyl group, a methyl(2,6-diiodophenyl)methyl group, a methyl(2,4,6-triiodophenyl)methyl group, a 2-iodophenylpropyl group, a 3-iodophenylpropyl group, a 4-iodophenylpropyl group, a 2,4-diiodophenylpropyl group, a 2,6-diiodophenylpropyl group, a 2,4,6-triiodophenylpropyl group, a 1-methyl(2-iodophenyl)ethyl group, a 1-methyl(3-iodophenyl)ethyl group, a 1-methyl(4-iodophenyl)ethyl group, a 1-methyl(2,4-diiodophenyl)ethyl group, a 1-methyl(2,6-diiodophenyl)ethyl group, a 1-methyl(2,4,6-triiodophenyl)ethyl group or the like; an arylalkyl group having 7 to 9 carbon atoms, in which a hydrogen atom bonded to the carbon atoms is substituted by an alkyl group having 1 to 4 carbon atoms (having an alkyl group having 1 to 4 carbon atoms as a substituent), such as, for example, an arylalkyl group having 7 to 9 carbon atoms, in which a hydrogen atom bonded to the carbon atoms is substituted by a methyl group (having a methyl group as a substituent), such as, for example, a 2-tolylmethyl group, a 3-tolylmethyl group, a 4-tolylmethyl group, a 2,4-xylylmethyl group, a 2,6-xylylmethyl group, a mesitylmethyl group (a 2,4,6-trimethylphenylmethyl group), a 2-tolylethyl group, a 3-tolylethyl group, a 4-tolylethyl group, a 2,4-xylylethyl group, a 2,6-xylylethyl group, a mesitylethyl group (a 2,4,6-trimethylphenylethyl group), a methyl(2-tolyl)methyl group, a methyl(3-tolyl)methyl group, a methyl(4-tolyl)methyl group, a methyl(2,4-xylyl)methyl group, a methyl(2,6-xylyl)methyl group, a methyl(mesityl)methyl group (a methyl(2,4,6-trimethylphenyl)methyl group), a 2-tolylpropyl group, a 3-tolylpropyl group, a 4-tolylpropyl group, a 2,4-xylylpropyl group, a 2,6-xylylpropyl group, a mesitylpropyl group (a 2,4,6-trimethylphenylpropyl group), a 1-methyl(2-tolyl)ethyl group, a 1-methyl(3-tolyl)ethyl group, a 1-methyl(4-tolyl)ethyl group, a 1-methyl(2,4-xylyl)ethyl group, a 1-methyl(2,6-xylyl)ethyl group, a 1-methyl(mesityl)ethyl group (a 1-methyl(2,4,6-trimethylphenyl)ethyl group) or the like; an arylalkyl group having 7 to 9 carbon atoms, in which a hydrogen atom bonded to the carbon atoms is substituted by an ethyl group (having an ethyl group as a substituent), such as, for example, a 2-ethylphenylmethyl group, a 3-ethylphenylmethyl group, a 4-ethylphenylmethyl group, a 2,4-diethylphenylmethyl group, a 2,6-diethylphenylmethyl group, a 2,4,6-triethylphenylmethyl group, a 2-ethylphenylethyl group, a 3-ethylphenylethyl group, a 4-ethylphenylethyl group, a 2,4-diethylphenylethyl group, a 2,6-diethylphenylethyl group, a 2,4,6-triethylphenylethyl group, a methyl(2-ethylphenyl)methyl group, a methyl(3-ethylphenyl)methyl group, a methyl(4-ethylphenyl)methyl group, a methyl(2,4-diethylphenyl)methyl group, a methyl(2,6-diethylphenyl)methyl group, a methyl(2,4,6-triethylphenyl)methyl group, a 2-ethylphenylpropyl group, a 3-ethylphenylpropyl group, a 4-ethylphenylpropyl group, a 2,4-diethylphenylpropyl group, a 2,6-diethylphenylpropyl group, a 2,4,6-triethylphenylpropyl group, a 1-methyl(2-ethylphenyl)ethyl group, a 1-methyl(3-ethylphenyl)ethyl group, a 1-methyl(4-ethylphenyl)ethyl group, a 1-methyl(2,4-diethylphenyl)ethyl group, a 1-methyl(2,6-diethylphenyl)ethyl group, a 1-methyl(2,4,6-triethylphenyl)ethyl group or the like; an arylalkyl group having 7 to 9 carbon atoms, in which a hydrogen atom bonded to the carbon atoms is substituted by a propyl group (having a propyl group as a substituent), such as, for example, a 2-propylphenylmethyl group, a 3-propylphenylmethyl group, a 4-propylphenylmethyl group, a 2,4-dipropylphenylmethyl group, a 2,6-dipropylphenylmethyl group, a 2,4,6-tripropylphenylmethyl group, a 2-propylphenylethyl group, a 3-propylphenylethyl group, a 4-propylphenylethyl group, a 2,4-dipropylphenylethyl group, a 2,6-dipropylphenylethyl group, a 2,4,6-tripropylphenylethyl group, a methyl(2-propylphenyl)methyl group, a methyl(3-propylphenyl)methyl group, a methyl(4-propylphenyl)methyl group, a methyl(2,4-dipropylphenyl)methyl group, a methyl(2,6-dipropylphenyl)methyl group, a methyl(2,4,6-tripropylphenyl)methyl group, a 2-propylphenylpropyl group, a 3-propylphenylpropyl group, a 4-propylphenylpropyl group, a 2,4-dipropylphenylpropyl group, a 2,6-dipropylphenylpropyl group, a 2,4,6-tripropylphenylpropyl group, a 1-methyl(2-propylphenyl)ethyl group, a 1-methyl(3-propylphenyl)ethyl group, a 1-methyl(4-propylphenyl)ethyl group, a 1-methyl(2,4-dipropylphenyl)ethyl group, a 1-methyl(2,6-dipropylphenyl)ethyl group, a 1-methyl(2,4,6-tripropylphenyl)ethyl group or the like; and an arylalkyl group having 7 to 9 carbon atoms, of in which a hydrogen atom bonded to the carbon atoms is substituted by a butyl group (having a butyl group as a substituent), such as, for example, a 2-butylphenylmethyl group, a 3-butylphenylmethyl group, a 4-butylphenylmethyl group, a 2,4-dibutylphenylmethyl group, a 2,6-dibutylphenylmethyl group, a 2,4,6-tributylphenylmethyl group, a 2-butylphenylethyl group, a 3-butylphenylethyl group, a 4-butylphenylethyl group, a 2,4-dibutylphenylethyl group, a 2,6-dibutylphenylethyl group, a 2,4,6-tributylphenylethyl group, a methyl(2-butylphenyl)methyl group, a methyl(3-butylphenyl)methyl group, a methyl(4-butylphenyl)methyl group, a methyl(2,4-dibutylphenyl)methyl group, a methyl(2,6-dibutylphenyl)methyl group, a methyl(2,4,6-tributylphenyl)methyl group, a 2-butylphenylpropyl group, a 3-butylphenylpropyl group, a 4-butylphenylpropyl group, a 2,4-dibutylphenylpropyl group, a 2,6-dibutylphenylpropyl group, a 2,4,6-tributylphenylpropyl group, a 1-methyl(2-butylphenyl)ethyl group, a 1-methyl(3-butylphenyl)ethyl group, a 1-methyl(4-butylphenyl)ethyl group, a 1-methyl(2,4-dibutylphenyl)ethyl group, a 1-methyl(2,6-dibutylphenyl)ethyl group, a 1-methyl(2,4,6-tributylphenyl)ethyl group or the like; and an arylalkyl group having 7 to 9 carbon atoms, in which a hydrogen atom bonded to the carbon atoms is substituted by a haloalkyl group having 1 to 4 carbon atoms (having a haloalkyl group having 1 to 4 carbon atoms as a substituent), such as, for example, a fluoroalkyl group or a chloroalkyl group having 1 to 4 carbon atoms, such as, for example, an arylalkyl group having 7 to 9 carbon atoms, in which a hydrogen atom bonded to the carbon atoms is substituted by a fluoromethyl group (having a fluoromethyl group as a substituent), such as, for example, a 2-trifluoromethylphenylmethyl group, a 3-trifluoromethylphenylmethyl group, a 4-trifluoromethylphenylmethyl group, a 2,4-bis(trifluoromethyl)phenylmethyl group, a 2,6-bis(trifluoromethyl)phenylmethyl group, a 2,4,6-tris(trifluoromethyl)phenylmethyl group, a 2-trifluoromethylphenylethyl group, a 3-trifluoromethylphenylethyl group, a 4-trifluoromethylphenylethyl group, a 2,4-bis(trifluoromethyl)phenylethyl group, a 2,6-bis(trifluoromethyl)phenylethyl group, a 2,4,6-tris(trifluoromethyl)phenylethyl group, a methyl(2-trifluoromethylphenyl)methyl group, a methyl(3-trifluoromethylphenyl)methyl group, a methyl(4-trifluoromethylphenyl)methyl group, a methyl[2,4-bis(trifluoromethyl)phenyl]methyl group, a methyl[2,6-bis(trifluoromethyl)phenyl]methyl group, a methyl[2,4,6-tris(trifluoromethyl)phenyl]methyl group, a 2-trifluoromethylphenylpropyl group, a 3-trifluoromethylphenylpropyl group, a 4-trifluoromethylphenylpropyl group, a 2,4-bis(trifluoromethyl)phenylpropyl group, a 2,6-bis(trifluoromethyl)phenylpropyl group, a 2,4,6-tris(trifluoromethyl)phenylpropyl group, a 1-methyl[2-(trifluoromethyl)phenyl]ethyl group, a 1-methyl[3-(trifluoromethyl)phenyl]ethyl group, a 1-methyl[4-(trifluoromethyl)phenyl]ethyl group, a 1-methyl[2,4-bis(trifluoromethyl)phenyl]ethyl group, a 1-methyl[2,6-bis(trifluoromethyl)phenyl]ethyl group, a 1-methyl[2,4,6-tris(trifluoromethyl)phenyl]ethyl group or the like; an arylalkyl group having 7 to 9 carbon atoms, in which a hydrogen atom bonded to the carbon atoms is substituted by a chloromethyl group (having a chloromethyl group as a substituent), such as, for example, a 2-trichloromethylphenylmethyl group, a 3-trichloromethylphenylmethyl group, a 4-trichloromethylphenylmethyl group, a 2,4-bis(trichloromethyl)phenylmethyl group, a 2,6-bis(trichloromethyl)phenylmethyl group, a 2,4,6-tris(trichloromethyl)phenylmethyl group, a 2-trichloromethylphenylethyl group, a 3-trichloromethylphenylethyl group, a 4-trichloromethylphenylethyl group, a 2,4-bis(trichloromethyl)phenylethyl group, a 2,6-bis(trichloromethyl)phenylethyl group, a 2,4,6-tris(trichloromethyl)phenylethyl group, a methyl(2-trichloromethylphenyl)methyl group, a methyl(3-trichloromethylphenyl)methyl group, a methyl(4-trichloromethylphenyl)methyl group, a methyl[2,4-bis(trichloromethyl)phenyl]methyl group, a methyl[2,6-bis(trichloromethyl)phenyl]methyl group, a methyl[2,4,6-tris(trichloromethyl)phenyl]methyl group, a 2-trichloromethylphenylpropyl group, a 3-trichloromethylphenylpropyl group, a 4-trichloromethylphenylpropyl group, a 2,4-bis(trichloromethyl)phenylpropyl group, a 2,6-bis(trichloromethyl)phenylpropyl group, a 2,4,6-tris(trichloromethyl)phenylpropyl group, a 1-methyl[2-(trichloromethyl)phenyl]ethyl group, a 1-methyl[3-(trichloromethyl)phenyl]ethyl group, a 1-methyl[4-(trichloromethyl)phenyl]ethyl group, a 1-methyl[2,4-bis(trichloromethyl)phenyl]ethyl group, a 1-methyl[2,6-bis(trichloromethyl)phenyl]ethyl group, a 1-methyl[2,4,6-tris(trichloromethyl)phenyl]ethyl group or the like; an arylalkyl group having 7 to 9 carbon atoms, in which a hydrogen atom bonded to the carbon atoms is substituted by a fluoroethyl group (having a fluoroethyl group as a substituent), such as, for example, a 2-pentafluoroethylphenylmethyl group, a 3-pentafluoroethylphenylmethyl group, a 4-pentafluoroethylphenylmethyl group, a 2,4-bis(pentafluoroethyl)phenylmethyl group, a 2,6-bis(pentafluoroethyl)phenylmethyl group, a 2,4,6-tris(pentafluoroethyl)phenylmethyl group, a 2-pentafluoroethylphenylethyl group, a 3-pentafluoroethylphenylethyl group, a 4-pentafluoroethylphenylethyl group, a 2,4-bis(pentafluoroethyl)phenylethyl group, a 2,6-bis(pentafluoroethyl)phenylethyl group, a 2,4,6-tris(pentafluoroethyl)phenylethyl group, a methyl(2-pentafluoroethylphenyl)methyl group, a methyl(3-pentafluoroethylphenyl)methyl group, a methyl(4-pentafluoroethylphenyl)methyl group, a methyl[2,4-bis(pentafluoroethyl)phenyl]methyl group, a methyl[2,6-bis(pentafluoroethyl)phenyl]methyl group, a methyl[2,4,6-tris(pentafluoroethyl)phenyl]methyl group, a 2-pentafluoroethylphenylpropyl group, a 3-pentafluoroethylphenylpropyl group, a 4-pentafluoroethylphenylpropyl group, a 2,4-bis(pentafluoroethyl)phenylpropyl group, a 2,6-bis(pentafluoroethyl)phenylpropyl group, a 2,4,6-tris(pentafluoroethyl)phenylpropyl group, 1-methyl[2-(pentafluoroethyl)phenyl]ethyl group, a 1-methyl[3-(pentafluoroethyl)phenyl]ethyl group, a 1-methyl[4-(pentafluoroethyl)phenyl]ethyl group, a 1-methyl[2,4-bis(pentafluoroethyl)phenyl]

ethyl group, a 1-methyl[2,6-bis(pentafluoroethyl)phenyl] ethyl group, a 1-methyl[2,4,6-tris(pentafluoroethyl)phenyl] ethyl group or the like; an arylalkyl group having 7 to 9 carbon atoms, in which a hydrogen atom bonded to the carbon atoms is substituted by a chloroethyl group (having a chloroethyl group as a substituent), such as, for example, a 2-pentachloroethylphenylmethyl group, a 3-pentachloroethylphenylmethyl group, a 4-pentachloroethylphenylmethyl group, a 2,4-bis(pentachloroethyl)phenylmethyl group, a 2,6-bis(pentachloroethyl)phenylmethyl group, a 2,4,6-tris(pentachloroethyl)phenylmethyl group, a 2-pentachloroethylphenylethyl group, a 3-pentachloroethylphenylethyl group, a 4-pentachloroethylphenylethyl group, a 2,4-bis(pentachloroethyl)phenylethyl group, a 2,6-bis(pentachloroethyl)phenylethyl group, a 2,4,6-tris(pentachloroethyl)phenylethyl group, a methyl(2-pentachloroethylphenyl)methyl group, a methyl(3-pentachloroethylphenyl)methyl group, a methyl(4-pentachloroethylphenyl)methyl group, a methyl[2,4-bis(pentachloroethyl)phenyl]methyl group, a methyl[2,6-bis(pentachloroethyl)phenyl]methyl group, a methyl[2,4,6-tris(pentachloroethyl)phenyl]methyl group, a 2-pentachloroethylphenylpropyl group, a 3-pentachloroethylphenylpropyl group, a 4-pentachloroethylphenylpropyl group, a 2,4-bis(pentachloroethyl)phenylpropyl group, a 2,6-bis(pentachloroethyl)phenylpropyl group, a 2,4,6-tris(pentachloroethyl)phenylpropyl group, a 1-methyl[2-(pentachloroethyl)phenyl]ethyl group, a 1-methyl[3-(pentachloroethyl)phenyl]ethyl group, a 1-methyl[4-(pentachloroethyl)phenyl]ethyl group, a 1-methyl[2,4-bis(pentachloroethyl)phenyl]ethyl group, a 1-methyl[2,6-bis(pentachloroethyl)phenyl]ethyl group, a 1-methyl[2,4,6-tris(pentachloroethyl)phenyl]ethyl group or the like; an arylalkyl group having 7 to 9 carbon atoms, in which a hydrogen atom bonded to the carbon atoms is substituted by a fluoropropyl group (having a fluoropropyl group as a substituent), such as, for example, a 2-heptafluoropropylphenylmethyl group, a 3-heptafluoropropylphenylmethyl group, a 4-heptafluoropropylphenylmethyl group, a 2,4-bis(heptafluoropropyl)phenylmethyl group, a 2,6-bis(heptafluoropropyl)phenylmethyl group, a 2,4,6-tris(heptafluoropropyl)phenylmethyl group, a 2-heptafluoropropylphenylethyl group, a 3-heptafluoropropylphenylethyl group, a 4-heptafluoropropylphenylethyl group, a 2,4-bis(heptafluoropropyl)phenylethyl group, a 2,6-bis(heptafluoropropyl)phenylethyl group, a 2,4,6-tris(heptafluoropropyl)phenylethyl group, a methyl(2-heptafluoropropylphenyl)methyl group, a methyl(3-heptafluoropropylphenyl)methyl group, a methyl(4-heptafluoropropylphenyl)methyl group, a methyl[2,4-bis(heptafluoropropyl)phenyl]methyl group, a methyl[2,6-bis(heptafluoropropyl)phenyl]methyl group, a methyl[2,4,6-tris(heptafluoropropyl)phenyl]methyl group, a 2-heptafluoropropylphenylpropyl group, a 3-heptafluoropropylphenylpropyl group, a 4-heptafluoropropylphenylpropyl group, a 2,4-bis(heptafluoropropyl)phenylpropyl group, a 2,6-bis(heptafluoropropyl)phenylpropyl group, a 2,4,6-tris(heptafluoropropyl)phenylpropyl group, a 1-methyl[2-(heptafluoropropyl)phenyl]ethyl group, a 1-methyl[3-(heptafluoropropyl)phenyl]ethyl group, a 1-methyl[4-(heptafluoropropyl)phenyl]ethyl group, a 1-methyl[2,4-bis(heptafluoropropyl)phenyl]ethyl group, a 1-methyl[2,6-bis(heptafluoropropyl)phenyl]ethyl group, a 1-methyl[2,4,6-tris(heptafluoropropyl)phenyl]ethyl group or the like; an arylalkyl group having 7 to 9 carbon atoms, in which a hydrogen atom bonded to the carbon atoms is substituted by a chloropropyl group (having a chloropropyl group as a substituent), such as, for example, a 2-heptachloropropylphenylmethyl group, a 3-heptachloropropylphenylmethyl group, a 4-heptachloropropylphenylmethyl group, a 2,4-bis(heptachloropropyl)phenylmethyl group, a 2,6-bis(heptachloropropyl)phenylmethyl group, a 2,4,6-tris(heptachloropropyl)phenylmethyl group, a 2-heptachloropropylphenylethyl group, a 3-heptachloropropylphenylethyl group, a 4-heptachloropropylphenylethyl group, a 2,4-bis(heptachloropropyl)phenylethyl group, a 2,6-bis(heptachloropropyl)phenylethyl group, a 2,4,6-tris(heptachloropropyl)phenylethyl group, a methyl(2-heptachloropropylphenyl)methyl group, a methyl(3-heptachloropropylphenyl)methyl group, a methyl(4-heptachloropropylphenyl)methyl group, a methyl[2,4-bis(heptachloropropyl)phenyl]methyl group, a methyl[2,6-bis(heptachloropropyl)phenyl]methyl group, a methyl[2,4,6-tris(heptachloropropyl)phenyl]methyl group, a 2-heptachloropropylphenylpropyl group, a 3-heptachloropropylphenylpropyl group, a 4-heptachloropropylphenylpropyl group, a 2,4-bis(heptachloropropyl)phenylpropyl group, a 2,6-bis(heptachloropropyl)phenylpropyl group, a 2,4,6-tris(heptachloropropyl)phenylpropyl group, a 1-methyl[2-(heptachloropropyl)phenyl]ethyl group, a 1-methyl[3-(heptachloropropyl)phenyl]ethyl group, a 1-methyl[4-(heptachloropropyl)phenyl]ethyl group, a 1-methyl[2,4-bis(heptachloropropyl)phenyl]ethyl group, a 1-methyl[2,6-bis(heptachloropropyl)phenyl]ethyl group, a 1-methyl[2,4,6-tris(heptachloropropyl)phenyl]ethyl group or the like; an arylalkyl group having 7 to 9 carbon atoms, in which a hydrogen atom bonded to the carbon atoms is substituted by a fluorobutyl group (having a fluorobutyl group as a substituent), such as, for example, a 2-nonafluorobutylphenylmethyl group, a 3-nonafluorobutylphenylmethyl group, a 4-nonafluorobutylphenylmethyl group, a 2,4-bis(nonafluorobutyl)phenylmethyl group, a 2,6-bis(nonafluorobutyl)phenylmethyl group, a 2,4,6-tris(nonafluorobutyl)phenylmethyl group, a 2-nonafluorobutylphenylethyl group, a 3-nonafluorobutylphenylethyl group, a 4-nonafluorobutylphenylethyl group, a 2,4-bis(nonafluorobutyl)phenylethyl group, a 2,6-bis(nonafluorobutyl)phenylethyl group, a 2,4,6-tris(nonafluorobutyl)phenylethyl group, a methyl(2-nonafluorobutylphenyl)methyl group, a methyl(3-nonafluorobutylphenyl)methyl group, a methyl(4-nonafluorobutylphenyl)methyl group, a methyl[2,4-bis(nonafluorobutyl)phenyl]methyl group, a methyl[2,6-bis(nonafluorobutyl)phenyl]methyl group, a methyl[2,4,6-tris(nonafluorobutyl)phenyl]methyl group, a 2-nonafluorobutylphenylpropyl group, a 3-nonafluorobutylphenylpropyl group, a 4-nonafluorobutylphenylpropyl group, a 2,4-bis(nonafluorobutyl)phenylpropyl group, a 2,6-bis(nonafluorobutyl)phenylpropyl group, a 2,4,6-tris(nonafluorobutyl)phenylpropyl group, a 1-methyl[2-(nonafluorobutyl)phenyl]ethyl group, a 1-methyl[3-(nonafluorobutyl)phenyl]ethyl group, a 1-methyl[4-(nonafluorobutyl)phenyl] ethyl group, a 1-methyl[2,4-bis(nonafluorobutyl)phenyl] ethyl group, a 1-methyl[2,6-bis(nonafluorobutyl)phenyl] ethyl group, a 1-methyl[2,4,6-tris(nonafluorobutyl)phenyl] ethyl group or the like; and an arylalkyl group having 7 to 9 carbon atoms, in which a hydrogen atom bonded to the carbon atoms is substituted by a chlorobutyl group (having a chlorobutyl group as a substituent), such as, for example, a 2-nonachlorobutylphenylmethyl group, a 3-nonachlorobutylphenylmethyl group, a 4-nonachlorobutylphenylmethyl group, a 2,4-bis(nonachlorobutyl)phenylmethyl group, a 2,6-bis(nonachlorobutyl)phenylmethyl group, a 2,4,6-tris (nonachlorobutyl)phenylmethyl group, a 2-nonachlorobutylphenylethyl group, a 3-nonachlorobutylphenylethyl group, a 4-nonachlorobutylphenylethyl group, a 2,4-bis (nonachlorobutyl)phenylethyl group, a 2,6-bis(nonachlorobutyl)phenylethyl group, a 2,4,6-tris(nonachlorobutyl)phenylethyl group, a methyl(2-nonachlorobutylphenyl)methyl group, a methyl(3-nonachlorobutylphenyl)methyl group, a methyl(4-nonachlorobutylphenyl)methyl group, a methyl[2,4-bis(nonachlorobutyl)phenyl]methyl group, a methyl[2,6-bis(nonachlorobutyl)phenyl]methyl group, a methyl[2,4,6-tris(nonachlorobutyl)phenyl]methyl group, a 2-nonachlorobutylphenylpropyl group, a 3-nonachlorobutylphenylpropyl group, a 4-nonachlorobutylphenylpropyl group, a 2,4-bis(nonachlorobutyl)phenylpropyl group, a 2,6-bis(nonachlorobutyl)phenylpropyl group, a 2,4,6-tris(nonachlorobutyl)phenylpropyl group, a 1-methyl[2-(nonachlorobutyl)phenyl]ethyl group, a 1-methyl[3-(nonachlorobutyl)phenyl]ethyl group, a 1-methyl[4-(nonachlorobutyl)phenyl]ethyl group, a 1-methyl[2,4-bis(nonachlorobutyl)phenyl]ethyl group, a 1-methyl[2,6-bis(nonachlorobutyl)phenyl]ethyl group, a 1-methyl[2,4,6-tris(nonachlorobutyl)phenyl]ethyl group or the like are preferable, and among them, an unsubstituted (having no substituent) arylalkyl group having 7 to 9 carbon atoms, such as, for example, a benzyl group, a phenethyl group, a methylbenzyl group, a phenylpropyl group, a 1-methylphenylethyl group or the like; an arylalkyl group having 7 to 9 carbon atoms, in which a hydrogen atom bonded to the carbon atoms is substituted by a fluorine atom (having a fluorine atom as a substituent), such as, for example, a 2-fluorophenylmethyl group, a 3-fluorophenylmethyl group, a 4-fluorophenylmethyl group, a 2,4-difluorophenylmethyl group, a 2,6-difluorophenylmethyl group, a 2,4,6-trifluorophenylmethyl group, a 2-fluorophenylethyl group, a 3-fluorophenylethyl group, a 4-fluorophenylethyl group, a 2,4-difluorophenylethyl group, a 2,6-difluorophenylethyl group, a 2,4,6-trifluorophenylethyl group, a methyl(2-fluorophenyl)methyl group, a methyl(3-fluorophenyl)methyl group, a methyl(4-fluorophenyl)methyl group, a methyl(2,4-difluorophenyl)methyl group, a methyl(2,6-difluorophenyl)methyl group, a methyl(2,4,6-trifluorophenyl)methyl group, a 2-fluorophenylpropyl group, a 3-fluorophenylpropyl group, a 4-fluorophenylpropyl group, a 2,4-difluorophenylpropyl group, a 2,6-difluorophenylpropyl group, a 2,4,6-trifluorophenylpropyl group, a 1-methyl(2-fluorophenyl)ethyl group, a 1-methyl(3-fluorophenyl)ethyl group, a 1-methyl(4-fluorophenyl)ethyl group, a 1-methyl(2,4-difluorophenyl)ethyl group, a 1-methyl(2,6-difluorophenyl)ethyl group, a 1-methyl(2,4,6-trifluorophenyl)ethyl group or the like; an arylalkyl group having 7 to 9 carbon atoms, in which a hydrogen atom bonded to the carbon atoms is substituted by a chlorine atom (having a chlorine atom as a substituent), such as, for example, a 2-chlorophenylmethyl group, a 3-chlorophenylmethyl group, a 4-chlorophenylmethyl group, a 2,4-dichlorophenylmethyl group, a 2,6-dichlorophenylmethyl group, a 2,4,6-trichlorophenylmethyl group, a 2-chlorophenylethyl group, a 3-chlorophenylethyl group, a 4-chlorophenylethyl group, a 2,4-dichlorophenylethyl group, a 2,6-dichlorophenylethyl group, a 2,4,6-trichlorophenylethyl group, a methyl(2-chlorophenyl)methyl group, a methyl(3-chlorophenyl)methyl group, a methyl(4-chlorophenyl)methyl group, a methyl(2,4-dichlorophenyl)methyl group, a methyl(2,6-dichlorophenyl)methyl group, a methyl(2,4,6-trichlorophenyl)methyl group, a 2-chlorophenylpropyl group, a 3-chlorophenylpropyl group, a 4-chlorophenylpropyl group, a 2,4-dichlorophenylpropyl group, a 2,6-dichlorophenylpropyl group, a 2,4,6-trichlorophenylpropyl group, a 1-methyl(2-chlorophenyl)ethyl group, a 1-methyl(3-chlorophenyl)ethyl group, a 1-methyl(4-chlorophenyl)ethyl group, a 1-methyl(2,4-dichlorophenyl)ethyl group, a 1-methyl(2,6-dichlorophenyl)ethyl group, a 1-methyl(2,4,6-trichlorophenyl)ethyl group or the like; an arylalkyl group having 7 to 9 carbon atoms, in which a hydrogen atom bonded to the carbon atoms is substituted by a methyl group (having a methyl group as a substituent), such as, for example, a 2-tolylmethyl group, a 3-tolylmethyl group, a 4-tolylmethyl group, a 2,4-xylylmethyl group, a 2,6-xylylmethyl group, a mesitylmethyl group (a 2,4,6-trimethylphenylmethyl group), a 2-tolylethyl group, a 3-tolylethyl group, a 4-tolylethyl group, a 2,4-xylylethyl group, a 2,6-xylylethyl group, a mesitylethyl group (a 2,4,6-trimethylphenylethyl group), a methyl(2-tolyl)methyl group, a methyl(3-tolyl)methyl group, a methyl(4-tolyl)methyl group, a methyl(2,4-xylyl)methyl group, a methyl(2,6-xylyl)methyl group, a methyl(mesityl)methyl group (a methyl(2,4,6-trimethylphenyl)methyl group), a 2-tolylpropyl group, a 3-tolylpropyl group, a 4-tolylpropyl group, a 2,4-xylylpropyl group, a 2,6-xylylpropyl group, a mesitylpropyl group (a 2,4,6-trimethylphenylpropyl group), a 1-methyl(2-tolyl)ethyl group, a 1-methyl(3-tolyl)ethyl group, a 1-methyl(4-tolyl)ethyl group, a 1-methyl(2,4-xylyl)ethyl group, a 1-methyl(2,6-xylyl)ethyl group, a 1-methyl(mesityl)ethyl group (a 1-methyl(2,4,6-trimethylphenyl)ethyl group) or the like; an arylalkyl group having 7 to 9 carbon atoms, in which a hydrogen atom bonded to the carbon atoms is substituted by a fluoromethyl group (having a fluoromethyl group as a substituent), such as, for example, a 2-trifluoromethylphenylmethyl group, a 3-trifluoromethylphenylmethyl group, a 4-trifluoromethylphenylmethyl group, a 2,4-bis(trifluoromethyl)phenylmethyl group, a 2,6-bis(trifluoromethyl)phenylmethyl group, a 2,4,6-tris(trifluoromethyl)phenylmethyl group, a 2-trifluoromethylphenylethyl group, a 3-trifluoromethylphenylethyl group, a 4-trifluoromethylphenylethyl group, a 2,4-bis(trifluoromethyl)phenylethyl group, a 2,6-bis(trifluoromethyl)phenylethyl group, a 2,4,6-tris(trifluoromethyl)phenylethyl group, a methyl(2-trifluoromethylphenyl)methyl group, a methyl(3-trifluoromethylphenyl)methyl group, a methyl(4-trifluoromethylphenyl)methyl group, a methyl[2,4-bis(trifluoromethyl)phenyl]methyl group, a methyl[2,6-bis(trifluoromethyl)phenyl]methyl group, a methyl[2,4,6-tris(trifluoromethyl)phenyl]methyl group, a 2-trifluoromethylphenylpropyl group, a 3-trifluoromethylphenylpropyl group, a 4-trifluoromethylphenylpropyl group, a 2,4-bis(trifluoromethyl)phenylpropyl group, a 2,6-bis(trifluoromethyl)phenylpropyl group, a 2,4,6-tris(trifluoromethyl)phenylpropyl group, a 1-methyl[2-(trifluoromethyl)phenyl]ethyl group, a 1-methyl[3-(trifluoromethyl)phenyl]ethyl group, a 1-methyl[4-(trifluoromethyl)phenyl]ethyl group, a 1-methyl[2,4-bis(trifluoromethyl)phenyl]ethyl group, a 1-methyl[2,6-bis(trifluoromethyl)phenyl]ethyl group, a 1-methyl[2,4,6-tris(trifluoromethyl)phenyl]ethyl group or the like; and an arylalkyl group having 7 to 9 carbon atoms, in which a hydrogen atom bonded to the carbon atoms is substituted by a chloromethyl group (having a chloromethyl group as a substituent), such as, for example, a 2-trichloromethylphenylmethyl group, a 3-trichloromethylphenylmethyl group, a 4-trichloromethylphenylmethyl group, a 2,4-bis(trichloromethyl)phenylmethyl group, a 2,6-bis(trichloromethyl)phenylmethyl group, a 2,4,6-tris(trichloromethyl)phenylmethyl group, a 2-trichloromethylphenylethyl group, a 3-trichloromethylphenylethyl group, a 4-trichloromethylphenylethyl group, a 2,4-bis(trichloromethyl)phenylethyl group, a 2,6-bis(trichloromethyl)phenylethyl group, a 2,4,6-tris(trichloromethyl)phenylethyl group, a methyl(2-trichloromethylphenyl)methyl group, a methyl(3-trichloromethylphenyl)methyl group, a methyl(4-trichloromethylphenyl)methyl group, a methyl[2,4-bis(trichloromethyl)phenyl]methyl group, a methyl[2,6-bis(trichloromethyl)phenyl]methyl group, a methyl[2,4,6-tris(trichloromethyl)phenyl]methyl group, a 2-trichloromethylphenylpropyl group, a 3-trichloromethylphenylpropyl group, a 4-trichloromethylphenylpropyl group, a 2,4-bis(trichloromethyl)phenylpropyl group, a 2,6-bis(trichloromethyl)phenylpropyl group, a 2,4,6-tris(trichloromethyl)phenylpropyl group, a 1-methyl[2-(trichloromethyl)phenyl]ethyl group, a 1-methyl[3-(trichloromethyl)phenyl]ethyl group, a 1-methyl[4-(trichloromethyl)phenyl]ethyl group, a 1-methyl[2,4-bis(trichloromethyl)phenyl]ethyl group, a 1-methyl[2,6-bis(trichloromethyl)phenyl]ethyl group, a 1-methyl[2,4,6-tris(trichloromethyl)phenyl]ethyl group or the like are more preferable, and among them, an unsubstituted (having no substituent) arylalkyl group having 7 to 9 carbon atoms, such as, for example, a benzyl group, a phenethyl group, a methylbenzyl group, a phenylpropyl group, a 1-methylphenylethyl group or the like; an arylalkyl group having 7 to 9 carbon atoms, in which a hydrogen atom bonded to the carbon atom at 4 position of a phenyl group is substituted by a fluorine atom (having a fluorine atom at 4 position of a phenyl group as a substituent), such as, for example, a 4-fluorophenylmethyl group, a 4-fluorophenylethyl group, a methyl(4-fluorophenyl)methyl group, a 4-fluorophenylpropyl group, a 1-methyl(4-fluorophenyl)ethyl group or the like; an arylalkyl group having 7 to 9 carbon atoms, in which a hydrogen atom bonded to the carbon atom at 4 position of a phenyl group is substituted by a chlorine atom (having a chlorine atom at 4 position of a phenyl group as a substituent), such as, for example, a 4-chlorophenylmethyl group, a 4-chlorophenylethyl group, a methyl(4-chlorophenyl)methyl group, a 4-chlorophenylpropyl group, a 1-methyl(4-chlorophenyl)ethyl group or the like; an arylalkyl group having 7 to 9 carbon atoms, in which a hydrogen atom bonded to the carbon atom at 4 position of a phenyl group is substituted by a methyl group (having a methyl group at 4 position of a phenyl group as a substituent), such as, for example, a 4-tolylmethyl group, a 4-tolylethyl group, a methyl(4-tolyl)methyl group, a 4-tolylpropyl group, a 1-methyl(4-tolyl)ethyl group or the like; an arylalkyl group having 7 to 9 carbon atoms, in which a hydrogen atom bonded to the carbon atom at 4 position of a phenyl group is substituted by a fluoromethyl group (having a fluoromethyl group at 4 position of a phenyl group as a substituent), such as, for example, a 4-trifluoromethylphenylmethyl group, a 4-trifluoromethylphenylethyl group, a methyl(4-trifluoromethylphenyl)methyl group, a 4-trifluoromethylphenylpropyl group, a 1-methyl[4-(trifluoromethyl)phenyl]ethyl group or the like; and an arylalkyl group having 7 to 9 carbon atoms, in which a hydrogen atom bonded to the carbon atom at 4 position of a phenyl group is substituted by a chloromethyl group (having a chloromethyl group at 4 position of a phenyl group as a substituent), such as, for example, a 4-trichloromethylphenylmethyl group, a 4-trichloromethylphenylethyl group, a methyl(4-trichloromethylphenyl)methyl group, a 4-trichloromethylphenylpropyl group, a 1-methyl[4-(trichloromethyl)phenyl]ethyl group or the like are further preferable, and furthermore among them, a benzyl group, a 4-fluorophenylmethyl group, a 4-chlorophenylmethyl group, a 4-tolylmethyl group, a 4-trifluoromethylphenylmethyl group and a 4-trichloromethylphenylmethyl group are particularly preferable.

An arylalkyloxy group having 7 to 15 carbon atoms, in which a hydrogen atom may be substituted by a halogen atom, an alkyl group or haloalkyl group, represented by $R^1$ in the general formula (A), may be any of a monocyclic or a condensed polycyclic group, and specifically includes an unsubstituted (having no substituent) arylalkyloxy group having 7 to 15 carbon atoms, such as, for example, a benzyloxy group, a phenethyloxy group, a methylbenzyloxy group, a phenylpropoxy group, a 1-methylphenylethoxy group, a phenylbutoxy group, a 2-methylphenylpropoxy group, a tetrahydronaphthyloxy group, a naphthylmethoxy group, a naphthylethoxy group, an indenyloxy group, a fluorenyloxy group or the like; an arylalkyloxy group having 7 to 15 carbon atoms, in which a hydrogen atom bonded to the carbon atoms is substituted by a halogen atom (having a halogen atom as a substituent), such as, for example, an arylalkyloxy group having 7 to 15 carbon atoms, in which a hydrogen atom bonded to the carbon atoms is substituted by a fluorine atom (having a fluorine atom as a substituent), such as, for example, a 2-fluorophenylmethoxy group, a 3-fluorophenylmethoxy group, a 4-fluorophenylmethoxy group, a 2,4-difluorophenylmethoxy group, a 2,6-difluorophenylmethoxy group, a 2,4,6-trifluorophenylmethoxy group, a 2-fluorophenylethoxy group, a 3-fluorophenylethoxy group, a 4-fluorophenylethoxy group, a 2,4-difluorophenylethoxy group, a 2,6-difluorophenylethoxy group, a 2,4,6-trifluorophenylethoxy group, a methyl(2-fluorophenyl)methoxy group, a methyl(3-fluorophenyl)methoxy group, a methyl(4-fluorophenyl)methoxy group, a methyl(2,4-difluorophenyl)methoxy group, a methyl(2,6-difluorophenyl)methoxy group, a methyl(2,4,6-trifluorophenyl)methoxy group, a 2-fluorophenylpropoxy group, a 3-fluorophenylpropoxy group, a 4-fluorophenylpropoxy group, a 2,4-difluorophenylpropoxy group, a 2,6-difluorophenylpropoxy group, a 2,4,6-trifluorophenylpropoxy group, a 1-methyl(2-fluorophenyl)ethoxy group, a 1-methyl(3-fluorophenyl)ethoxy group, a 1-methyl(4-fluorophenyl)ethoxy group, a 1-methyl(2,4-difluorophenyl)ethoxy group, a 1-methyl(2,6-difluorophenyl)ethoxy group, a 1-methyl(2,4,6-trifluorophenyl)ethoxy group, a 2-fluorophenylbutoxy group, a 3-fluorophenylbutoxy group, a 4-fluorophenylbutoxy group, a 2,4-difluorophenylbutoxy group, a 2,6-difluorophenylbutoxy group, a 2,4,6-trifluorophenylbutoxy group, a 2-methyl(2-fluorophenyl)propoxy group, a 2-methyl(3-fluorophenyl)propoxy group, a 2-methyl(4-fluorophenyl)propoxy group, a 2-methyl(2,4-difluorophenyl)propoxy group, a 2-methyl(2,6-difluorophenyl)propoxy group, a 2-methyl(2,4,6-trifluorophenyl)propoxy group, a tetrahydrofluoronaphthyloxy group, a fluoronaphthylmethoxy group, a fluoronaphthylethoxy group, a fluoroindenyloxy group, a fluorofluorenyloxy group or the like; an arylalkyloxy group having 7 to 15 carbon atoms, in which a hydrogen atom bonded to the carbon atoms is substituted by a chlorine atom (having a chlorine atom as a substituent), such as, for example, a 2-chlorophenylmethoxy group, a 3-chlorophenylmethoxy group, a 4-chlorophenylmethoxy group, a 2,4-dichlorophenylmethoxy group, a 2,6-dichlorophenylmethoxy group, a 2,4,6-trichlorophenylmethoxy group, a 2-chlorophenylethoxy group, a 3-chlorophenylethoxy group, a 4-chlorophenylethoxy group, a 2,4-dichlorophenylethoxy group, a 2,6-dichlorophenylethoxy group, a 2,4,6-trichlorophenylethoxy group, a methyl(2-chlorophenyl)methoxy group, a methyl(3-chlorophenyl)methoxy group, a methyl(4-chlorophenyl)methoxy group, a methyl(2,4-dichlorophenyl)methoxy group, a methyl(2,6-dichlorophenyl)methoxy group, a methyl(2,4,6-trichlorophenyl)methoxy group, a 2-chlorophenylpropoxy group, a 3-chlorophenylpropoxy group, a 4-chlorophenylpropoxy group, a 2,4-dichlorophenylpropoxy group, a 2,6-dichlorophenylpropoxy group, a 2,4,6-trichlorophenylpropoxy group, a 1-methyl(2-chlorophenyl)ethoxy group, a 1-methyl (3-chlorophenyl)ethoxy group, a 1-methyl(4-chlorophenyl) ethoxy group, a 1-methyl(2,4-dichlorophenyl)ethoxy group, a 1-methyl(2,6-dichlorophenyl)ethoxy group, a 1-methyl(2,4,6-trichlorophenyl)ethoxy group, a 2-chlorophenylbutoxy group, a 3-chlorophenylbutoxy group, a 4-chlorophenylbutoxy group, a 2,4-dichlorophenylbutoxy group, a 2,6-dichlorophenylbutoxy group, a 2,4,6-trichlorophenylbutoxy group, a 2-methyl(2-chlorophenyl)propoxy group, a 2-methyl(3-chlorophenyl)propoxy group, a 2-methyl(4-chlorophenyl)propoxy group, a 2-methyl(2,4-dichlorophenyl)propoxy group, a 2-methyl(2,6-dichlorophenyl)propoxy group, a 2-methyl(2,4,6-trichlorophenyl)propoxy group, a tetrahydrochloronaphthyloxy group, a chloronaphthylmethoxy group, a chloronaphthylethoxy group, a chloroindenyloxy group, a chlorofluorenyloxy group or the like; an arylalkyloxy group having 7 to 15 carbon atoms, in which a hydrogen atom bonded to the carbon atoms is substituted by a bromine atom (having a bromine atom as a substituent), such as, for example, a 2-bromophenylmethoxy group, a 3-bromophenylmethoxy group, a 4-bromophenylmethoxy group, a 2,4-dibromophenylmethoxy group, a 2,6-dibromophenylmethoxy group, a 2,4,6-tribromophenylmethoxy group, a 2-bromophenylethoxy group, a 3-bromophenylethoxy group, a 4-bromophenylethoxy group, a 2,4-dibromophenylethoxy group, a 2,6-dibromophenylethoxy group, a 2,4,6-tribromophenylethoxy group, a methyl(2-bromophenyl)methoxy group, a methyl(3-bromophenyl)methoxy group, a methyl(4-bromophenyl)methoxy group, a methyl(2,4-dibromophenyl)methoxy group, a methyl(2,6-dibromophenyl)methoxy group, a methyl(2,4,6-tribromophenyl) methoxy group, a 2-bromophenylpropoxy group, a 3-bromophenylpropoxy group, a 4-bromophenylpropoxy group, a 2,4-dibromophenylpropoxy group, a 2,6-dibromophenylpropoxy group, a 2,4,6-tribromophenylpropoxy group, a 1-methyl(2-bromophenyl)ethoxy group, a 1-methyl(3-bromophenyl)ethoxy group,1-methyl(4-bromophenyl)ethoxy group, a 1-methyl(2,4-dibromophenyl)ethoxy group, a 1-methyl(2,6-dibromophenyl)ethoxy group, a 1-methyl(2,4,6-tribromophenyl)ethoxy group, a 2-bromophenylbutoxy group, a 3-bromophenylbutoxy group, a 4-bromophenylbutoxy group, a 2,4-dibromophenylbutoxy group, a 2,6-dibromophenylbutoxy group, a 2,4,6-tribromophenylbutoxy group, a 2-methyl(2-bromophenyl)propoxy group, a 2-methyl(3-bromophenyl)propoxy group, a 2-methyl(4-bromophenyl)propoxy group, 2-methyl(2,4-dibromophenyl)propoxy group, a 2-methyl(2,6-dibromophenyl)propoxy group, a 2-methyl(2,4,6-tribromophenyl)propoxy group, a tetrahydrobromonaphthyloxy group, a bromonaphthylmethoxy group, a bromonaphthylethoxy group, a bromoindenyloxy group, a bromofluorenyloxy group or the like; an arylalkyloxy group having 7 to 15 carbon atoms, in which a hydrogen atom bonded to the carbon atoms is substituted by an iodine atom (having an iodine atom as a substituent), such as, for example, a 2-iodophenylmethoxy group, a 3-iodophenylmethoxy group, a 4-iodophenylmethoxy group, a 2,4-diiodophenylmethoxy group, a 2,6-diiodophenylmethoxy group, a 2,4,6-triiodophenylmethoxy group, a 2-iodophenylethoxy group, a 3-iodophenylethoxy group, a 4-iodophenylethoxy group, a 2,4-diiodophenylethoxy group, a 2,6-diiodophenylethoxy group, a 2,4,6-triiodophenylethoxy group, a methyl(2-iodophenyl)methoxy group, a methyl(3-iodophenyl)methoxy group, a methyl(4-iodophenyl) methoxy group, a methyl(2,4-diiodophenyl)methoxy group, a methyl(2,6-diiodophenyl)methoxy group, a methyl(2,4,6-triiodophenyl)methoxy group, a 2-iodophenylpropoxy group, a 3-iodophenylpropoxy group, a 4-iodophenylpropoxy group, a 2,4-diiodophenylpropoxy group, a 2,6-diiodophenylpropoxy group, a 2,4,6-triiodophenylpropoxy group, a 1-methyl(2-iodophenyl)ethoxy group, a 1-methyl(3-iodophenyl)ethoxy group, a 1-methyl(4-iodophenyl) ethoxy group, a 1-methyl(2,4-diiodophenyl)ethoxy group, a 1-methyl(2,6-diiodophenyl)ethoxy group, a 1-methyl(2,4,6-triiodophenyl)ethoxy group, a 2-iodophenylbutoxy group, a 3-iodophenylbutoxy group, a 4-iodophenylbutoxy group, a 2,4-diiodophenylbutoxy group, a 2,6-diiodophenylbutoxy group, a 2,4,6-triiodophenylbutoxy group, a 2-methyl(2-iodophenyl)propoxy group, 2-methyl(3-iodophenyl) propoxy group, a 2-methyl(4-iodophenyl)propoxy group, a 2-methyl(2,4-diiodophenyl)propoxy group, a 2-methyl(2,6-di iodophenyl)propoxy group, a 2-methyl(2,4,6-triiodophenyl)propoxy group, a tetrahydroiodonaphthyloxy group, an iodonaphthylmethoxy group, an iodonaphthylethoxy group, an iodoindenyloxy group, an iodofluorenyloxy group or the like; an arylalkyloxy group having 7 to 15 carbon atoms, in which a hydrogen atom bonded to the carbon atoms is substituted by an alkyl group having 1 to 4 carbon atoms (having an alkyl group having 1 to 4 carbon atoms as a substituent), such as, for example, an arylalkyloxy group having 7 to 15 carbon atoms, in which a hydrogen atom bonded to the carbon atoms is substituted by a methyl group (having a methyl group as a substituent), such as, for example, a 2-tolylmethoxy group, a 3-tolylmethoxy group, a 4-tolylmethoxy group, a 2,4-xylylmethoxy group, a 2,6-xylylmethoxy group, a mesitylmethoxy group (a 2,4,6-trimethylphenylmethoxy group), a 2-tolylethoxy group, a 3-tolylethoxy group, a 4-tolylethoxy group, a 2,4-xylylethoxy group, a 2,6-xylylethoxy group, a mesitylethoxy group (a 2,4,6-trimethylphenylethoxy group), a methyl(2-tolyl)methoxy group, a methyl(3-tolyl)methoxy group, a methyl(4-tolyl)methoxy group, a methyl(2,4-xylyl)methoxy group, a methyl(2,6-xylyl)methoxy group, a methyl(mesityl)methoxy group (a methyl(2,4,6-trimethylphenyl) methoxy group), a 2-tolylpropoxy group, a 3-tolylpropoxy group, a 4-tolylpropoxy group, a 2,4-xylylpropoxy group, a 2,6-xylylpropoxy group, a mesitylpropoxy group (a 2,4,6-trimethylphenylpropoxy group), a 1-methyl(2-tolyl)ethoxy group, a 1-methyl(3-tolyl)ethoxy group, a 1-methyl(4-tolyl) ethoxy group, a 1-methyl(2,4-xylyl)ethoxy group, a 1-methyl(2,6-xylyl)ethoxy group, a 1-methyl(mesityl) ethoxy group (a 1-methyl(2,4,6-trimethylphenyl)ethoxy group), a 2-tolylbutoxy group, a 3-tolylbutoxy group, a 4-tolylbutoxy group, a 2,4-xylylbutoxy group, a 2,6-xylylbutoxy group, a mesitylbutoxy group (a 2,4,6-trimethylphenylbutoxy group), a 2-methyl(2-tolyl)propoxy group, a 2-methyl(3-tolyl)propoxy group, a 2-methyl(4-tolyl) propoxy group, a 2-methyl(2,4-xylyl)propoxy group, a 2-methyl(2,6-xylyl)propoxy group, a 2-methyl(mesityl) propoxy group (a 2-methyl(2,4,6-trimethylphenyl)propoxy group), a tetrahydromethylnaphthyloxy group, a methylnaphthylmethoxy group, a methylnaphthylethoxy group, a methylindenyloxy group, a methylfluorenyloxy group or the like; an arylalkyloxy group having 7 to 15 carbon atoms, in which a hydrogen atom bonded to the carbon atoms is substituted by an ethyl group (having an ethyl group as a substituent), such as, for example, a 2-ethylphenylmethoxy group, a 3-ethylphenylmethoxy group, a 4-ethylphenylmethoxy group, a 2,4-diethylphenylmethoxy group, a 2,6-diethylphenylmethoxy group, a 2,4,6-triethylphenylmethoxy group, a 2-ethylphenylethoxy group, a 3-ethylphenylethoxy group, a 4-ethylphenylethoxy group, a 2,4-diethylphenylethoxy group, a 2,6-diethylphenylethoxy group, a 2,4,6-triethylphenylethoxy group, a methyl(2-ethylphenyl)methoxy group, a methyl(3-ethylphenyl)methoxy group, a methyl(4-ethylphenyl)methoxy group, a methyl(2, 4-diethylphenyl)methoxy group, a methyl(2,6-diethylphenyl)methoxy group, a methyl(2,4,6-triethylphenyl)methoxy group, a 2-ethylphenylpropoxy group, a 3-ethylphenylpropoxy group, a 4-ethylphenylpropoxy group, a 2,4-diethylphenylpropoxy group, a 2,6-diethylphenylpropoxy group, a 2,4,6-triethylphenylpropoxy group, a 1-methyl(2-ethylphenyl)ethoxy group, a 1-methyl(3-ethylphenyl)ethoxy group, a 1-methyl(4-ethylphenyl)ethoxy group, a 1-methyl(2,4-diethylphenyl)ethoxy group, a 1-methyl(2,6-diethylphenyl)ethoxy group, a 1-methyl(2,4,6-triethylphenyl)ethoxy group, a 2-ethylphenylbutoxy group, a 3-ethylphenylbutoxy group, a 4-ethylphenylbutoxy group, a 2,4-diethylphenylbutoxy group, a 2,6-diethylphenylbutoxy group, a 2,4,6-triethylphenylbutoxy group, a 2-methyl(2-ethylphenyl)propoxy group, a 2-methyl(3-ethylphenyl)propoxy group, a 2-methyl(4-ethylphenyl)propoxy group, a 2-methyl(2,4-diethylphenyl)propoxy group, a 2-methyl(2,6-diethylphenyl)propoxy group, a 2-methyl(2,4,6-triethylphenyl)propoxy group, a tetrahydroethylnaphthyloxy group, an ethylnaphthylmethoxy group, an ethylnaphthylethoxy group, an ethylindenyloxy group, an ethylfluorenyloxy group or the like; an arylalkyloxy group having 7 to 15 carbon atoms, in which a hydrogen atom bonded to the carbon atoms is substituted by a propyl group (having a propyl group as a substituent), such as, for example, 2-propylphenylmethoxy group, a 3-propylphenylmethoxy group, a 4-propylphenylmethoxy group, a 2,4-dipropylphenylmethoxy group, a 2,6-dipropylphenylmethoxy group, a 2,4,6-tripropylphenylmethoxy group, a 2-propylphenylethoxy group, a 3-propylphenylethoxy group, a 4-propylphenylethoxy group, a 2,4-dipropylphenylethoxy group, a 2,6-dipropylphenylethoxy group, a 2,4,6-tripropylphenylethoxy group, a methyl(2-propylphenyl)methoxy group, a methyl(3-propylphenyl)methoxy group, a methyl(4-propylphenyl)methoxy group, a methyl(2,4-dipropylphenyl)methoxy group, a methyl(2,6-dipropylphenyl)methoxy group, a methyl(2,4,6-tripropylphenyl)methoxy group, a 2-propylphenylpropoxy group, a 3-propylphenylpropoxy group, a 4-propylphenylpropoxy group, a 2,4-dipropylphenylpropoxy group, a 2,6-dipropylphenylpropoxy group, a 2,4,6-tripropylphenylpropoxy group, a 1-methyl(2-propylphenyl)ethoxy group, a 1-methyl(3-propylphenyl)ethoxy group, a 1-methyl(4-propylphenyl)ethoxy group, a 1-methyl(2,4-dipropylphenyl)ethoxy group, a 1-methyl(2,6-dipropylphenyl)ethoxy group, a 1-methyl(2,4,6-tripropylphenyl)ethoxy group, a 2-propylphenylbutoxy group, a 3-propylphenylbutoxy group, a 4-propylphenylbutoxy group, a 2,4-dipropylphenylbutoxy group, a 2,6-dipropylphenylbutoxy group, a 2,4,6-tripropylphenylbutoxy group, a 2-methyl(2-propylphenyl)propoxy group, a 2-methyl(3-propylphenyl)propoxy group, a 2-methyl(4-propylphenyl)propoxy group, a 2-methyl(2,4-dipropylphenyl)propoxy group, a 2-methyl(2,6-dipropylphenyl)propoxy group, a 2-methyl(2,4,6-tripropylphenyl)propoxy group, a tetrahydropropylnaphthyloxy group, a propylnaphthylmethoxy group, a propylnaphthylethoxy group, a propylindenyloxy group, a propylfluorenyloxy group or the like; an arylalkyloxy group having 7 to 15 carbon atoms, in which a hydrogen atom bonded to the carbon atoms is substituted by a butyl group (having a butyl group as a substituent), such as, for example, a 2-butylphenylmethoxy group, a 3-butylphenylmethoxy group, a 4-butylphenylmethoxy group, a 2,4-dibutylphenylmethoxy group, a 2,6-dibutylphenylmethoxy group, a 2,4,6-tributylphenylmethoxy group, a 2-butylphenylethoxy group, a 3-butylphenylethoxy group, a 4-butylphenylethoxy group, a 2,4-dibutylphenylethoxy group, a 2,6-dibutylphenylethoxy group, a 2,4,6-tributylphenylethoxy group, a methyl(2-butylphenyl)methoxy group, a methyl(3-butylphenyl)methoxy group, a methyl(4-butylphenyl)methoxy group, a methyl(2,4-dibutylphenyl)methoxy group, a methyl(2,6-dibutylphenyl)methoxy group, a methyl(2,4,6-tributylphenyl)methoxy group, a 2-butylphenylpropoxy group, a 3-butylphenylpropoxy group, a 4-butylphenylpropoxy group, a 2,4-dibutylphenylpropoxy group, a 2,6-dibutylphenylpropoxy group, a 2,4,6-tributylphenylpropoxy group, a 1-methyl(2-butylphenyl)ethoxy group, a 1-methyl(3-butylphenyl)ethoxy group, a 1-methyl(4-butylphenyl)ethoxy group, a 1-methyl(2,4-dibutylphenyl)ethoxy group, a 1-methyl(2,6-dibutylphenyl)ethoxy group, a 1-methyl(2,4,6-tributylphenyl)ethoxy group, a 2-butylphenylbutoxy group, a 3-butylphenylbutoxy group, a 4-butylphenylbutoxy group, a 2,4-dibutylphenylbutoxy group, a 2,6-dibutylphenylbutoxy group, a 2,4,6-tributylphenylbutoxy group, a 2-methyl(2-butylphenyl)propoxy group, a 2-methyl(3-butylphenyl)propoxy group, a 2-methyl(4-butylphenyl)propoxy group, a 2-methyl(2,4-dibutylphenyl)propoxy group, a 2-methyl(2,6-dibutylphenyl)propoxy group, a 2-methyl(2,4,6-tributylphenyl)propoxy group, a tetrahydrobutylnaphthyloxy group, a butylnaphthylmethoxy group, a butylnaphthylethoxy group, a butylindenyloxy group, a butylfluorenyloxy group or the like; an arylalkyloxy group having 7 to 15 carbon atoms, in which a hydrogen atom bonded to the carbon atoms is substituted by a haloalkyl group having 1 to 4 carbon atoms (having a haloalkyl group having 1 to 4 carbon atoms as a substituent), such as, for example, a fluoroalkyl group or a chloroalkyl group having 1 to 4 carbon atoms, such as, for example, an arylalkyloxy group having 7 to 15 carbon atoms, in which a hydrogen atom bonded to the carbon atoms is substituted by a fluoromethyl group (having a fluoromethyl group as a substituent), such as, for example, a 2-trifluoromethylphenylmethoxy group, a 3-trifluoromethylphenylmethoxy group, a 4-trifluoromethylphenylmethoxy group, a 2,4-bis(trifluoromethyl)phenylmethoxy group, a 2,6-bis(trifluoromethyl)phenylmethoxy group, a 2,4,6-tris(trifluoromethyl)phenylmethoxy group, a 2-trifluoromethylphenylethoxy group, a 3-trifluoromethylphenylethoxy group, a 4-trifluoromethylphenylethoxy group, a 2,4-bis(trifluoromethyl)phenylethoxy group, a 2,6-bis(trifluoromethyl)phenylethoxy group, a 2,4,6-tris(trifluoromethyl)phenylethoxy group, a methyl(2-trifluoromethylphenyl)methoxy group, a methyl(3-trifluoromethylphenyl)methoxy group, a methyl(4-trifluoromethylphenyl)methoxy group, a methyl[2,4-bis(trifluoromethyl)phenyl]methoxy group, a methyl[2,6-bis(trifluoromethyl)phenyl]methoxy group, a methyl[2,4,6-tris(trifluoromethyl)phenyl]methoxy group, a 2-trifluoromethylphenylpropoxy group, a 3-trifluoromethylphenylpropoxy group, a 4-trifluoromethylphenylpropoxy group, a 2,4-bis(trifluoromethyl)phenylpropoxy group, a 2,6-bis(trifluoromethyl)phenylpropoxy group, a 2,4,6-tris(trifluoromethyl)phenylpropoxy group, a 1-methyl[2-(trifluoromethyl)phenyl]ethoxy group, a 1-methyl[3-(trifluoromethyl)phenyl]ethoxy group, a 1-methyl[4-(trifluoromethyl)phenyl]ethoxy group, a 1-methyl[2,4-bis(trifluoromethyl)phenyl]ethoxy group, a 1-methyl[2,6-bis(trifluoromethyl)phenyl]ethoxy group, a 1-methyl[2,4,6-tris(trifluoromethyl)phenyl]ethoxy group, a 2-trifluoromethylphenylbutoxy group, a 3-trifluoromethylphenylbutoxy group, a 4-trifluoromethylphenylbutoxy group, a 2,4-bis(trifluoromethyl)phenylbutoxy group, a 2,6-bis(trifluoromethyl)phenylbutoxy group, a 2,4,6-tris(trifluoromethyl)phenylbutoxy group, a 2-methyl[2-(trifluoromethyl)phenyl]propoxy group, a 2-methyl[3-(trifluoromethyl)phenyl]propoxy group, a 2-methyl[4-(trifluoromethyl)phenyl]propoxy group, a 2-methyl[2,4-bis(trifluoromethyl)

phenyl]propoxy group, a 2-methyl[2,6-bis(trifluoromethyl)phenyl]propoxy group, a 2-methyl[2,4,6-tris(trifluoromethyl)phenyl]propoxy group, a tetrahydro(trifluoromethyl)naphthyloxy group, a trifluoromethylnaphthylmethoxy group, a trifluoromethylnaphthylethoxy group, a trifluoromethylindenyloxy group, a trifluoromethylfluorenyloxy group or the like; an arylalkyloxy group having 7 to 15 carbon atoms, in which a hydrogen atom bonded to the carbon atoms is substituted by a chloromethyl group (having a chloromethyl group as a substituent), such as, for example, a 2-trichloromethylphenylmethoxy group, a 3-trichloromethylphenylmethoxy group, a 4-trichloromethylphenylmethoxy group, a 2,4-bis(trichloromethyl)phenylmethoxy group, a 2,6-bis(trichloromethyl)phenylmethoxy group, a 2,4,6-tris(trichloromethyl)phenylmethoxy group, a 2-trichloromethylphenylethoxy group, a 3-trichloromethylphenylethoxy group, a 4-trichloromethylphenylethoxy group, a 2,4-bis(trichloromethyl)phenylethoxy group, a 2,6-bis(trichloromethyl)phenylethoxy group, a 2,4,6-tris(trichloromethyl)phenylethoxy group, a methyl(2-trichloromethylphenyl)methoxy group, a methyl(3-trichloromethylphenyl)methoxy group, a methyl(4-trichloromethylphenyl)methoxy group, a methyl[2,4-bis(trichloromethyl)phenyl]methoxy group, a methyl[2,6-bis(trichloromethyl)phenyl]methoxy group, a methyl[2,4,6-tris(trichloromethyl)phenyl]methoxy group, a 2-trichloromethylphenylpropoxy group, a 3-trichloromethylphenylpropoxy group, a 4-trichloromethylphenylpropoxy group, a 2,4-bis(trichloromethyl)phenylpropoxy group, a 2,6-bis(trichloromethyl)phenylpropoxy group, a 2,4,6-tris(trichloromethyl)phenylpropoxy group, a 1-methyl[2-(trichloromethyl)phenyl]ethoxy group, a 1-methyl[3-(trichloromethyl)phenyl]ethoxy group, a 1-methyl[4-(trichloromethyl)phenyl]ethoxy group, a 1-methyl[2,4-bis(trichloromethyl)phenyl]ethoxy group, a 1-methyl[2,6-bis(trichloromethyl)phenyl]ethoxy group, a 1-methyl[2,4,6-tris(trichloromethyl)phenyl]ethoxy group, a 2-trichloromethylphenylbutoxy group, a 3-trichloromethylphenylbutoxy group, a 4-trichloromethylphenylbutoxy group, a 2,4-bis(trichloromethyl)phenylbutoxy group, a 2,6-bis(trichloromethyl)phenylbutoxy group, a 2,4,6-tris(trichloromethyl)phenylbutoxy group, a 2-methyl[2-(trichloromethyl)phenyl]propoxy group, a 2-methyl[3-(trichloromethyl)phenyl]propoxy group, a 2-methyl[4-(trichloromethyl)phenyl]propoxy group, a 2-methyl[2,4-bis(trichloromethyl)phenyl]propoxy group, a 2-methyl[2,6-bis(trichloromethyl)phenyl]propoxy group, a 2-methyl[2,4,6-tris(trichloromethyl)phenyl]propoxy group, a tetrahydro(trichloromethyl)naphthyloxy group, a trichloromethylnaphthylmethoxy group, a trichloromethylnaphthylethoxy group, a trichloromethylindenyloxy group, a trichloromethylfluorenyloxy group or the like; an arylalkyloxy group having 7 to 15 carbon atoms, in which a hydrogen atom bonded to the carbon atoms is substituted by a fluoroethyl group (having a fluoroethyl group as a substituent), such as, for example, a 2-pentafluoroethylphenylmethoxy group, a 3-pentafluoroethylphenylmethoxy group, a 4-pentafluoroethylphenylmethoxy group, a 2,4-bis(pentafluoroethyl)phenylmethoxy group, a 2,6-bis(pentafluoroethyl)phenylmethoxy group, a 2,4,6-tris(pentafluoroethyl)phenylmethoxy group, a 2-pentafluoroethylphenylethoxy group, a 3-pentafluoroethylphenylethoxy group, a 4-pentafluoroethylphenylethoxy group, a 2,4-bis(pentafluoroethyl)phenylethoxy group, a 2,6-bis(pentafluoroethyl)phenylethoxy group, a 2,4,6-tris(pentafluoroethyl)phenylethoxy group, a methyl(2-pentafluoroethylphenyl)methoxy group, a methyl(3-pentafluoroethylphenyl)methoxy group, a methyl(4-pentafluoroethylphenyl)methoxy group, a methyl[2,4-bis(pentafluoroethyl)phenyl]methoxy group, a methyl[2,6-bis(pentafluoroethyl)phenyl]methoxy group, a methyl[2,4,6-tris(pentafluoroethyl)phenyl]methoxy group, a 2-pentafluoroethylphenylpropoxy group, a 3-pentafluoroethylphenylpropoxy group, a 4-pentafluoroethylphenylpropoxy group, a 2,4-bis(pentafluoroethyl)phenylpropoxy group, a 2,6-bis(pentafluoroethyl)phenylpropoxy group, a 2,4,6-tris(pentafluoroethyl)phenylpropoxy group, a 1-methyl[2-(pentafluoroethyl)phenyl]ethoxy group, a 1-methyl[3-(pentafluoroethyl)phenyl]ethoxy group, a 1-methyl[4-(pentafluoroethyl)phenyl]ethoxy group, a 1-methyl[2,4-bis(pentafluoroethyl)phenyl]ethoxy group, a 1-methyl[2,6-bis(pentafluoroethyl)phenyl]ethoxy group, a 1-methyl[2,4,6-tris(pentafluoroethyl)phenyl]ethoxy group, a 2-pentafluoroethylphenylbutoxy group, a 3-pentafluoroethylphenylbutoxy group, a 4-pentafluoroethylphenylbutoxy group, a 2,4-bis(pentafluoroethyl)phenylbutoxy group, a 2,6-bis(pentafluoroethyl)phenylbutoxy group, a 2,4,6-tris(pentafluoroethyl)phenylbutoxy group, a 2-methyl[2-(pentafluoroethyl)phenyl]propoxy group, a 2-methyl[3-(pentafluoroethyl)phenyl]propoxy group, a 2-methyl[4-(pentafluoroethyl)phenyl]propoxy group, a 2-methyl[2,4-bis(pentafluoroethyl)phenyl]propoxy group, a 2-methyl[2,6-bis(pentafluoroethyl)phenyl]propoxy group, a 2-methyl[2,4,6-tris(pentafluoroethyl)phenyl]propoxy group, a tetrahydro(pentafluoroethyl)naphthyloxy group, a pentafluoroethylnaphthylmethoxy group, a pentafluoroethylnaphthylethoxy group, a pentafluoroethylindenyloxy group, a pentafluoroethylfluorenyloxy group or the like; an arylalkyloxy group having 7 to 15 carbon atoms, in which a hydrogen atom bonded to the carbon atoms is substituted by a chloroethyl group (having a chloroethyl group as a substituent), such as, for example, a 2-pentachloroethylphenylmethoxy group, a 3-pentachloroethylphenylmethoxy group, a 4-pentachloroethyl phenylmethoxy group, a 2,4-bis(pentachloroethyl)phenylmethoxy group, a 2,6-bis(pentachloroethyl)phenylmethoxy group, a 2,4,6-tris(pentachloroethyl)phenylmethoxy group, a 2-pentachloroethylphenylethoxy group, a 3-pentachloroethylphenylethoxy group, a 4-pentachloroethylphenylethoxy group, a 2,4-bis(pentachloroethyl)phenylethoxy group, a 2,6-bis(pentachloroethyl)phenylethoxy group, a 2,4,6-tris(pentachloroethyl)phenylethoxy group, a methyl(2-pentachloroethylphenyl)methoxy group, a methyl(3-pentachloroethylphenyl)methoxy group, a methyl(4-pentachloroethylphenyl)methoxy group, a methyl[2,4-bis(pentachloroethyl)phenyl]methoxy group, a methyl[2,6-bis(pentachloroethyl)phenyl]methoxy group, a methyl[2,4,6-tris(pentachloroethyl)phenyl]methoxy group, a 2-pentachloroethylphenylpropoxy group, a 3-pentachloroethylphenylpropoxy group, a 4-pentachloroethylphenylpropoxy group, a 2,4-bis(pentachloroethyl)phenylpropoxy group, a 2,6-bis(pentachloroethyl)phenylpropoxy group, a 2,4,6-tris(pentachloroethyl)phenylpropoxy group, a 1-methyl[2-(pentachloroethyl)phenyl]ethoxy group, a 1-methyl[3-(pentachloroethyl)phenyl]ethoxy group, a 1-methyl[4-(pentachloroethyl)phenyl]ethoxy group, a 1-methyl[2,4-bis(pentachloroethyl)phenyl]ethoxy group, a 1-methyl[2,6-bis(pentachloroethyl)phenyl]ethoxy group, a 1-methyl[2,4,6-tris(pentachloroethyl)phenyl]ethoxy group, a 2-pentachloroethylphenylbutoxy group, a 3-pentachloroethylphenylbutoxy group, a 4-pentachloroethylphenylbutoxy group, a 2,4-bis(pentachloroethyl)phenylbutoxy group, a 2,6-bis(pentachloroethyl)phenylbutoxy group, a 2,4,6-tris(pentachloroethyl)phenylbutoxy group, a 2-methyl[2-(pentachloroethyl)phenyl]propoxy group, a 2-methyl[3-(pentachloroethyl)phenyl]propoxy group, a 2-methyl[4-(pentachloroethyl)phenyl]propoxy group, a 2-methyl[2,4-bis(pentachloroethyl)phenyl]propoxy group, a 2-methyl[2,6-bis(pentachloroethyl)phenyl]propoxy group, a 2-methyl[2,4,6-tris(pentachloroethyl)phenyl]propoxy group, a tetrahydro(pentachloroethyl)naphthyloxy group, a pentachloroethylnaphthylmethoxy group, a pentachloroethylnaphthylethoxy group, a pentachloroethylindenyloxy group, a pentachloroethylfluorenyloxy group or the like; an arylalkyloxy group having 7 to 15 carbon atoms, in which a hydrogen atom bonded to the carbon atoms is substituted by a fluoropropyl group (having a fluoropropyl group as a substituent), such as, for example, a 2-heptafluoropropylphenylmethoxy group, a 3-heptafluoropropylphenylmethoxy group, a 4-heptafluoropropylphenylmethoxy group, a 2,4-bis(heptafluoropropyl)phenylmethoxy group, a 2,6-bis(heptafluoropropyl)phenylmethoxy group, a 2,4,6-tris(heptafluoropropyl)phenylmethoxy group, a 2-heptafluoropropylphenylethoxy group, a 3-heptafluoropropylphenylethoxy group, a 4-heptafluoropropylphenylethoxy group, a 2,4-bis(heptafluoropropyl)phenylethoxy group, a 2,6-bis(heptafluoropropyl)phenylethoxy group, a 2,4,6-tris(heptafluoropropyl)phenylethoxy group, a methyl(2-heptafluoropropylphenyl)methoxy group, a methyl(3-heptafluoropropylphenyl)methoxy group, a methyl(4-heptafluoropropylphenyl)methoxy group, a methyl[2,4-bis(heptafluoropropyl)phenyl]methoxy group, a methyl[2,6-bis(heptafluoropropyl)phenyl]methoxy group, a methyl[2,4,6-tris(heptafluoropropyl)phenyl]methoxy group, a 2-heptafluoropropylphenylpropoxy group, a 3-heptafluoropropylphenylpropoxy group, a 4-heptafluoropropylphenylpropoxy group, a 2,4-bis(heptafluoropropyl)phenylpropoxy group, a 2,6-bis(heptafluoropropyl)phenylpropoxy group, a 2,4,6-tris(heptafluoropropyl)phenylpropoxy group, a 1-methyl[2-(heptafluoropropyl)phenyl]ethoxy group, a 1-methyl[3-(heptafluoropropyl)phenyl]ethoxy group, a 1-methyl[4-(heptafluoropropyl)phenyl]ethoxy group, a 1-methyl[2,4-bis(heptafluoropropyl)phenyl]ethoxy group, a 1-methyl[2,6-bis(heptafluoropropyl)phenyl]ethoxy group, a 1-methyl[2,4,6-tris(heptafluoropropyl)phenyl]ethoxy group, a 2-heptafluoropropylphenylbutoxy group, a 3-heptafluoropropylphenylbutoxy group, a 4-heptafluoropropylphenylbutoxy group, a 2,4-bis(heptafluoropropyl)phenylbutoxy group, a 2,6-bis(heptafluoropropyl)phenylbutoxy group, a 2,4,6-tris(heptafluoropropyl)phenylbutoxy group, a 2-methyl[2-(heptafluoropropyl)phenyl]propoxy group, a 2-methyl[3-(heptafluoropropyl)phenyl]propoxy group, a 2-methyl[4-(heptafluoropropyl)phenyl]propoxy group, a 2-methyl[2,4-bis(heptafluoropropyl)phenyl]propoxy group, a 2-methyl[2,6-bis(heptafluoropropyl)phenyl]propoxy group, a 2-methyl[2,4,6-tris(heptafluoropropyl)phenyl]propoxy group, a tetrahydro(heptafluoropropyl)naphthyloxy group, a heptafluoropropylnaphthylmethoxy group, a heptafluoropropylnaphthylethoxy group, a heptafluoropropylindenyloxy group, a heptafluoropropylfluorenyloxy group or the like; an arylalkyloxy group having 7 to 15 carbon atoms, in which a hydrogen atom bonded to the carbon atoms is substituted by a chloropropyl group (having a chloropropyl group as a substituent), such as, for example, a 2-heptachloropropylphenylmethoxy group, a 3-heptachloropropylphenylmethoxy group, a 4-heptachloropropylphenylmethoxy group, a 2,4-bis(heptachloropropyl)phenylmethoxy group, a 2,6-bis(heptachloropropyl)phenylmethoxy group, a 2,4,6-tris(heptachloropropyl)phenylmethoxy group, a 2-heptachloropropylphenylethoxy group, a 3-heptachloropropylphenylethoxy group, a 4-heptachloropropylphenylethoxy group, a 2,4-bis(heptachloropropyl)phenylethoxy group, a 2,6-bis(heptachloropropyl)phenylethoxy group, a 2,4,6-tris(heptachloropropyl)phenylethoxy group, a methyl(2-heptachloropropylphenyl)methoxy group, a methyl(3-heptachloropropylphenyl)methoxy group, a methyl(4-heptachloropropylphenyl)methoxy group, a methyl[2,4-bis(heptachloropropyl)phenyl]methoxy group, a methyl[2,6-bis(heptachloropropyl)phenyl]methoxy group, a methyl[2,4,6-tris(heptachloropropyl)phenyl]methoxy group, a 2-heptachloropropylphenylpropoxy group, a 3-heptachloropropylphenylpropoxy group, a 4-heptachloropropylphenylpropoxy group, a 2,4-bis(heptachloropropyl)phenylpropoxy group, a 2,6-bis(heptachloropropyl)phenylpropoxy group, a 2,4,6-tris(heptachloropropyl)phenylpropoxy group, a 1-methyl[2-(heptachloropropyl)phenyl]ethoxy group, a 1-methyl[3-(heptachloropropyl)phenyl]ethoxy group, a 1-methyl[4-(heptachloropropyl)phenyl]ethoxy group, a 1-methyl[2,4-bis(heptachloropropyl)phenyl]ethoxy group, a 1-methyl[2,6-bis(heptachloropropyl)phenyl]ethoxy group, a 1-methyl[2,4,6-tris(heptachloropropyl)phenyl]ethoxy group, a 2-heptachloropropylphenylbutoxy group, a 3-heptachloropropylphenylbutoxy group, a 4-heptachloropropylphenylbutoxy group, a 2,4-bis(heptachloropropyl)phenylbutoxy group, a 2,6-bis(heptachloropropyl)phenylbutoxy group, a 2,4,6-tris(heptachloropropyl)phenylbutoxy group, a 2-methyl[2-(heptachloropropyl)phenyl]propoxy group, a 2-methyl[3-(heptachloropropyl)phenyl]propoxy group, a 2-methyl[4-(heptachloropropyl)phenyl]propoxy group, a 2-methyl[2,4-bis(heptachloropropyl)phenyl]propoxy group, a 2-methyl[2,6-bis(heptachloropropyl)phenyl]propoxy group, a 2-methyl[2,4,6-tris(heptachloropropyl)phenyl]propoxy group, a tetrahydro(heptachloropropyl)naphthyloxy group, a heptachloropropylnaphthylmethoxy group, a heptachloropropylnaphthylethoxy group, a heptachloropropylindenyloxy group, a heptachloropropylfluorenyloxy group or the like; an arylalkyloxy group having 7 to 15 carbon atoms, in which a hydrogen atom bonded to the carbon atoms is substituted by a fluorobutyl group (having a fluorobutyl group as a substituent), such as, for example, a 2-nonafluorobutylphenylmethoxy group, a 3-nonafluorobutylphenylmethoxy group, a 4-nonafluorobutylphenylmethoxy group, a 2,4-bis(nonafluorobutyl)phenylmethoxy group, a 2,6-bis(nonafluorobutyl)phenylmethoxy group, a 2,4,6-tris(nonafluorobutyl)phenylmethoxy group, a 2-nonafluorobutylphenylethoxy group, a 3-nonafluorobutylphenylethoxy group, a 4-nonafluorobutylphenylethoxy group, a 2,4-bis(nonafluorobutyl)phenylethoxy group, a 2,6-bis(nonafluorobutyl)phenylethoxy group, a 2,4,6-tris(nonafluorobutyl)phenylethoxy group, a methyl(2-nonafluorobutylphenyl)methoxy group, a methyl(3-nonafluorobutylphenyl)methoxy group, a methyl(4-nonafluorobutylphenyl)methoxy group, a methyl[2,4-bis(nonafluorobutyl)phenyl]methoxy group, a methyl[2,6-bis(nonafluorobutyl)phenyl]methoxy group, a methyl[2,4,6-tris(nonafluorobutyl)phenyl]methoxy group, a 2-nonafluorobutylphenylpropoxy group, a 3-nonafluorobutylphenylpropoxy group, a 4-nonafluorobutylphenylpropoxy group, a 2,4-bis(nonafluorobutyl)phenylpropoxy group, a 2,6-bis(nonafluorobutyl)phenylpropoxy group, a 2,4,6-tris(nonafluorobutyl)phenylpropoxy group, a 1-methyl[2-(nonafluorobutyl)phenyl]ethoxy group, a 1-methyl[3-(nonafluorobutyl)phenyl]ethoxy group, a 1-methyl[4-(nonafluorobutyl)phenyl]ethoxy group, a 1-methyl[2,4-bis(nonafluorobutyl)phenyl]ethoxy group, a 1-methyl[2,6-bis(nonafluorobutyl)phenyl]ethoxy group, a 1-methyl[2,4,6-tris(nonafluorobutyl)phenyl]ethoxy group, a 2-nonafluorobutylphenylbutoxy group, a 3-nonafluorobutylphenylbutoxy group, a 4-nonafluorobutylphenylbutoxy group, a 2,4-bis(nonafluorobutyl)phenylbutoxy group, a 2,6-bis(nonafluorobutyl)phenylbutoxy group, a 2,4,6-tris(nonafluorobutyl)phenylbutoxy group, a 2-methyl[2-(nonafluorobutyl)phenyl]propoxy group, a 2-methyl[3-(nonafluorobutyl)phenyl]propoxy group, a 2-methyl[4-(nonafluorobutyl)phenyl]propoxy group, a 2-methyl[2,4-bis(nonafluorobutyl)phenyl]propoxy group, a 2-methyl[2,6-bis(nonafluorobutyl)phenyl]propoxy group, a 2-methyl[2,4,6-tris(nonafluorobutyl)phenyl]propoxy group, a tetrahydro(nonafluorobutyl)naphthyloxy group, a nonafluorobutylnaphthylmethoxy group, a nonafluorobutylnaphthylethoxy group, a nonafluorobutylindenyloxy group, a nonafluorobutylfluorenyloxy group or the like; an arylalkyloxy group having 7 to 15 carbon atoms, in which a hydrogen atom bonded to the carbon atoms is substituted by a chlorobutyl group (having a chlorobutyl group as a substituent), such as, for example, a 2-nonachlorobutylphenylmethoxy group, a 3-nonachlorobutylphenylmethoxy group, a 4-nonachlorobutylphenylmethoxy group, a 2,4-bis(nonachlorobutyl)phenylmethoxy group, a 2,6-bis(nonachlorobutyl)phenylmethoxy group, a 2,4,6-tris(nonachlorobutyl)phenylmethoxy group, a 2-nonachlorobutylphenylethoxy group, a 3-nonachlorobutylphenylethoxy group, a 4-nonachlorobutylphenylethoxy group, a 2,4-bis(nonachlorobutyl)phenylethoxy group, a 2,6-bis(nonachlorobutyl)phenylethoxy group, a 2,4,6-tris(nonachlorobutyl)phenylethoxy group, a methyl(2-nonachlorobutylphenyl)methoxy group, a methyl(3-nonachlorobutylphenyl)methoxy group, a methyl(4-nonachlorobutylphenyl)methoxy group, a methyl[2,4-bis(nonachlorobutyl)phenyl]methoxy group, a methyl[2,6-bis(nonachlorobutyl)phenyl]methoxy group, a methyl[2,4,6-tris(nonachlorobutyl)phenyl]methoxy group, a 2-nonachlorobutylphenylpropoxy group, a 3-nonachlorobutylphenylpropoxy group, a 4-nonachlorobutylphenylpropoxy group, a 2,4-bis(nonachlorobutyl)phenylpropoxy group, a 2,6-bis(nonachlorobutyl)phenylpropoxy group, a 2,4,6-tris(nonachlorobutyl)phenylpropoxy group, a 1-methyl[2-(nonachlorobutyl)phenyl]ethoxy group, a 1-methyl[3-(nonachlorobutyl)phenyl]ethoxy group, a 1-methyl[4-(nonachlorobutyl)phenyl]ethoxy group, a 1-methyl[2,4-bis(nonachlorobutyl)phenyl]ethoxy group, a 1-methyl[2,6-bis(nonachlorobutyl)phenyl]ethoxy group, a 1-methyl[2,4,6-tris(nonachlorobutyl)phenyl]ethoxy group, a 2-nonachlorobutylphenylbutoxy group, a 3-nonachlorobutylphenylbutoxy group, a 4-nonachlorobutylphenylbutoxy group, a 2,4-bis(nonachlorobutyl)phenylbutoxy group, a 2,6-bis(nonachlorobutyl)phenylbutoxy group, a 2,4,6-tris(nonachlorobutyl)phenylbutoxy group, a 2-methyl[2-(nonachlorobutyl)phenyl]propoxy group, a 2-methyl[3-(nonachlorobutyl)phenyl]propoxy group, a 2-methyl[4-(nonachlorobutyl)phenyl]propoxy group, a 2-methyl[2,4-bis(nonachlorobutyl)phenyl]propoxy group, a 2-methyl[2,6-bis(nonachlorobutyl)phenyl]propoxy group, a 2-methyl[2,4,6-tris(nonachlorobutyl)phenyl]propoxy group, a tetrahydro(nonachlorobutyl)naphthyloxy group, a nonachlorobutylnaphthylmethoxy group, a nonachlorobutylnaphthylethoxy group, a nonachlorobutylindenyloxy group, a nonachlorobutylfluorenyloxy group or the like. It should be noted that, in the above-described specific examples, an alkyl group or a haloalkyl group substituted (bonded) to an aryl group in an arylalkyloxy group is not limited to a normal-form, and may be an alkyl group or a haloalkyl group of a branched group, such as, for example, a sec-form, a tert-form, an iso-form and a neo-form, or an alkyl group or a haloalkyl group of a cyclic group, such as, for example, a cyclo-form. In addition, the carbon atoms constituting an alkyl group or a haloalkyl group substituted (bonded) to an aryl group in an arylalkyloxy group should not be contained in number of the carbon atoms constituting an arylalkyloxy group to which they bond (7 to 15 carbon atoms). In other words, sum of the carbon atoms of an arylalkyloxy group in which 1 to 3 pieces of a hydrogen atom in hydrogen atoms bonded to the carbon atoms are substituted by an alkyl group or a haloalkyl group having 1 to 4 carbon atoms (having an alkyl group or a haloalkyl group having 1 to 4 carbon atoms as a substituent), are 8 to 27.

Among these arylalkyloxy groups, an unsubstituted (having no substituent) arylalkyloxy group having 7 to 9 carbon atoms, such as, for example, a benzyloxy group, a phenethyloxy group, a methylbenzyloxy group, a phenylpropoxy group, a 1-methylphenylethoxy group or the like; an arylalkyloxy group having 7 to 9 carbon atoms, in which a hydrogen atom bonded to the carbon atoms is substituted by a halogen atom (having a halogen atom as a substituent), such as, for example, an arylalkyloxy group having 7 to 9 carbon atoms, in which a hydrogen atom bonded to the carbon atoms is substituted by a fluorine atom (having a fluorine atom as a substituent), such as, for example, a 2-fluorophenylmethoxy group, a 3-fluorophenylmethoxy group, a 4-fluorophenylmethoxy group, a 2,4-difluorophenylmethoxy group, a 2,6-difluorophenylmethoxy group, a 2,4,6-trifluorophenylmethoxy group, a 2-fluorophenylethoxy group, a 3-fluorophenylethoxy group, a 4-fluorophenylethoxy group, a 2,4-difluorophenylethoxy group, a 2,6-difluorophenylethoxy group, a 2,4,6-trifluorophenylethoxy group, a methyl(2-fluorophenyl)methoxy group, a methyl(3-fluorophenyl)methoxy group, a methyl(4-fluorophenyl)methoxy group, a methyl(2,4-difluorophenyl)methoxy group, a methyl(2,6-difluorophenyl)methoxy group, a methyl(2,4,6-trifluorophenyl)methoxy group, a 2-fluorophenylpropoxy group, a 3-fluorophenylpropoxy group, a 4-fluorophenylpropoxy group, a 2,4-difluorophenylpropoxy group, a 2,6-difluorophenylpropoxy group, a 2,4,6-trifluorophenylpropoxy group, a 1-methyl(2-fluorophenyl)ethoxy group, a 1-methyl(3-fluorophenyl)ethoxy group, a 1-methyl(4-fluorophenyl)ethoxy group, a 1-methyl(2,4-difluorophenyl)ethoxy group, a 1-methyl(2,6-difluorophenyl)ethoxy group, a 1-methyl(2,4,6-trifluorophenyl)ethoxy group or the like; an arylalkyloxy group having 7 to 9 carbon atoms, in which a hydrogen atom bonded to the carbon atoms is substituted by a chlorine atom (having a chlorine atom as a substituent), such as, for example, a 2-chlorophenylmethoxy group, a 3-chlorophenylmethoxy group, a 4-chlorophenylmethoxy group, a 2,4-dichlorophenylmethoxy group, a 2,6-dichlorophenylmethoxy group, a 2,4,6-trichlorophenylmethoxy group, a 2-chlorophenylethoxy group, a 3-chlorophenylethoxy group, a 4-chlorophenylethoxy group, a 2,4-dichlorophenylethoxy group, a 2,6-dichlorophenylethoxy group, a 2,4,6-trichlorophenylethoxy group, a methyl(2-chlorophenyl)methoxy group, a methyl(3-chlorophenyl)methoxy group, a methyl(4-chlorophenyl)methoxy group, a methyl(2,4-dichlorophenyl)methoxy group, a methyl(2,6-dichlorophenyl)methoxy group, a methyl(2,4,6-trichlorophenyl)methoxy group, a 2-chlorophenylpropoxy group, a 3-chlorophenylpropoxy group, a 4-chlorophenylpropoxy group, a 2,4-dichlorophenylpropoxy group, a 2,6-dichlorophenylpropoxy group, a 2,4,6-trichlorophenylpropoxy group, a 1-methyl(2-chlorophenyl)ethoxy group, a 1-methyl(3-chlorophenyl)ethoxy group, a 1-methyl(4-chlorophenyl)ethoxy group, a 1-methyl(2,4-dichlorophenyl)ethoxy group, a 1-methyl(2,6-dichlorophenyl)ethoxy group, a 1-methyl(2,4,6-trichlorophenyl)ethoxy group or the like; an arylalkyloxy group having 7 to 9 carbon atoms, in which a hydrogen atom bonded to the carbon atoms is substituted by a bromine atom (having a bromine atom as a substituent), such as, for example, a 2-bromophenylmethoxy group, a 3-bromophenylmethoxy group, a 4-bromophenylmethoxy group, a 2,4-dibromophenylmethoxy group, a 2,6-dibromophenylmethoxy group, a 2,4,6-tribromophenylmethoxy group, a 2-bromophenylethoxy group, a 3-bromophenylethoxy group, a 4-bromophenylethoxy group, a 2,4-dibromophenylethoxy group, a 2,6-dibromophenylethoxy group, a 2,4,6-tribromophenylethoxy group, a methyl(2-bromophenyl)methoxy group, a methyl(3-bromophenyl)methoxy group, a methyl(4-bromophenyl)methoxy group, a methyl(2,4-dibromophenyl)methoxy group, a methyl(2,6-dibromophenyl)methoxy group, a methyl(2,4,6-tribromophenyl)methoxy group, a 2-bromophenylpropoxy group, a 3-bromophenylpropoxy group, a 4-bromophenylpropoxy group, a 2,4-dibromophenylpropoxy group, a 2,6-dibromophenylpropoxy group, a 2,4,6-tribromophenylpropoxy group, a 1-methyl(2-bromophenyl)ethoxy group, a 1-methyl(3-bromophenyl)ethoxy group, a 1-methyl(4-bromophenyl)ethoxy group, a 1-methyl(2,4-dibromophenyl)ethoxy group, a 1-methyl(2,6-dibromophenyl)ethoxy group, a 1-methyl(2,4,6-tribromophenyl)ethoxy group or the like; and an arylalkyloxy group having 7 to 9 carbon atoms, in which a hydrogen atom bonded to the carbon atoms is substituted by an iodine atom (having an iodine atom as a substituent), such as, for example, a 2-iodophenylmethoxy group, a 3-iodophenylmethoxy group, a 4-iodophenylmethoxy group, a 2,4-diiodophenylmethoxy group, a 2,6-diiodophenylmethoxy group, a 2,4,6-triiodophenylmethoxy group, a 2-iodophenylethoxy group, a 3-iodophenylethoxy group, a 4-iodophenylethoxy group, a 2,4-diiodophenylethoxy group, a 2,6-diiodophenylethoxy group, a 2,4,6-triiodophenylethoxy group, a methyl(2-iodophenyl)methoxy group, a methyl(3-iodophenyl)methoxy group, a methyl(4-iodophenyl)methoxy group, a methyl(2,4-diiodophenyl)methoxy group, a methyl(2,6-diiodophenyl)methoxy group, a methyl(2,4,6-triiodophenyl)methoxy group, a 2-iodophenylpropoxy group, a 3-iodophenylpropoxy group, a 4-iodophenylpropoxy group, a 2,4-diiodophenylpropoxy group, a 2,6-diiodophenylpropoxy group, a 2,4,6-triiodophenylpropoxy group, a 1-methyl(2-iodophenyl)ethoxy group, a 1-methyl(3-iodophenyl)ethoxy group, a 1-methyl(4-iodophenyl)ethoxy group, a 1-methyl(2,4-diiodophenyl)ethoxy group, a 1-methyl(2,6-diiodophenyl)ethoxy group, a 1-methyl(2,4,6-triiodophenyl)ethoxy group or the like; an arylalkyloxy group having 7 to 9 carbon atoms, in which a hydrogen atom bonded to the carbon atoms is substituted by an alkyl group having 1 to 4 carbon atoms (having an alkyl group having 1 to 4 carbon atoms as a substituent), such as, for example, an arylalkyloxy group having 7 to 9 carbon atoms, in which a hydrogen atom bonded to the carbon atoms is substituted by a methyl group (having a methyl group as a substituent), such as, for example, a 2-tolylmethoxy group, a 3-tolylmethoxy group, a 4-tolylmethoxy group, a 2,4-xylylmethoxy group, a 2,6-xylylmethoxy group, a mesitylmethoxy group (a 2,4,6-trimethylphenylmethoxy group), a 2-tolylethoxy group, a 3-tolylethoxy group, a 4-tolylethoxy group, a 2,4-xylylethoxy group, a 2,6-xylylethoxy group, a mesitylethoxy group (a 2,4,6-trimethylphenylethoxy group), a methyl(2-tolyl)methoxy group, a methyl(3-tolyl)methoxy group, a methyl(4-tolyl)methoxy group, a methyl(2,4-xylyl)methoxy group, a methyl(2,6-xylyl)methoxy group, a methyl(mesityl)methoxy group, (a methyl(2,4,6-trimethylphenyl)methoxy group), a 2-tolylpropoxy group, a 3-tolylpropoxy group, a 4-tolylpropoxy group, a 2,4-xylylpropoxy group, a 2,6-xylylpropoxy group, a mesitylpropoxy group (a 2,4,6-trimethylphenylpropoxy group), a 1-methyl(2-tolyl)ethoxy group, a 1-methyl(3-tolyl)ethoxy group, a 1-methyl(4-tolyl)ethoxy group, a 1-methyl(2,4-xylyl)ethoxy group, a 1-methyl(2,6-xylyl)ethoxy group, a 1-methyl(mesityl)ethoxy group (a 1-methyl(2,4,6-trimethylphenyl)ethoxy group) or the like; an arylalkyloxy group having 7 to 9 carbon atoms, in which a hydrogen atom bonded to the carbon atoms is substituted by an ethyl group (having an ethyl group as a substituent), such as, for example, a 2-ethylphenylmethoxy group, a 3-ethylphenylmethoxy group, a 4-ethylphenylmethoxy group, a 2,4-diethylphenylmethoxy group, a 2,6-diethylphenylmethoxy group, a 2,4,6-triethylphenylmethoxy group, a 2-ethylphenylethoxy group, a 3-ethylphenylethoxy group, a 4-ethylphenylethoxy group, a 2,4-diethylphenylethoxy group, a 2,6-diethylphenylethoxy group, a 2,4,6-triethylphenylethoxy group, a methyl(2-ethylphenyl)methoxy group, a methyl(3-ethylphenyl)methoxy group, a methyl(4-ethylphenyl)methoxy group, a methyl(2,4-diethylphenyl)methoxy group, a methyl(2,6-diethylphenyl)methoxy group, a methyl(2,4,6-triethylphenyl)methoxy group, a 2-ethylphenylpropoxy group, a 3-ethylphenylpropoxy group, a 4-ethylphenylpropoxy group, a 2,4-diethylphenylpropoxy group, a 2,6-diethylphenylpropoxy group, a 2,4,6-triethylphenylpropoxy group, a 1-methyl(2-ethylphenyl)ethoxy group, a 1-methyl(3-ethylphenyl)ethoxy group, a 1-methyl(4-ethylphenyl)ethoxy group, a 1-methyl(2,4-diethylphenyl)ethoxy group, a 1-methyl(2,6-diethylphenyl)ethoxy group, a 1-methyl(2,4,6-triethylphenyl)ethoxy group or the like; an arylalkyloxy group having 7 to 9 carbon atoms, in which a hydrogen atom bonded to the carbon atoms is substituted by a propyl group (having a propyl group as a substituent), such as, for example, a 2-propylphenylmethoxy group, a 3-propylphenylmethoxy group, a 4-propylphenylmethoxy group, a 2,4-dipropylphenylmethoxy group, a 2,6-dipropylphenylmethoxy group, a 2,4,6-tripropylphenylmethoxy group, a 2-propylphenylethoxy group, a 3-propylphenylethoxy group, a 4-propylphenylethoxy group, a 2,4-dipropylphenylethoxy group, a 2,6-dipropylphenylethoxy group, a 2,4,6-tripropylphenylethoxy group, a methyl(2-propylphenyl)methoxy group, a methyl(3-propylphenyl)methoxy group, a methyl(4-propylphenyl)methoxy group, a methyl(2,4-dipropylphenyl)methoxy group, a methyl(2,6-dipropylphenyl)methoxy group, a methyl(2,4,6-tripropylphenyl)methoxy group, a 2-propylphenylpropoxy group, a 3-propylphenylpropoxy group, a 4-propylphenylpropoxy group, a 2,4-dipropylphenylpropoxy group, a 2,6-dipropylphenylpropoxy group, a 2,4,6-tripropylphenylpropoxy group, a 1-methyl(2-propylphenyl)ethoxy group, a 1-methyl(3-propylphenyl)ethoxy group, a 1-methyl(4-propylphenyl)ethoxy group, a 1-methyl(2,4-dipropylphenyl)ethoxy group, a 1-methyl(2,6-dipropylphenyl)ethoxy group, a 1-methyl(2,4,6-tripropylphenyl)ethoxy group or the like; and an arylalkyloxy group having 7 to 9 carbon atoms, in which a hydrogen atom bonded to the carbon atoms is substituted by a butyl group (having a butyl group as a substituent), such as, for example, a 2-butylphenylmethoxy group, a 3-butylphenylmethoxy group, a 4-butylphenylmethoxy group, a 2,4-dibutylphenylmethoxy group, a 2,6-dibutylphenylmethoxy group, a 2,4,6-tributylphenylmethoxy group, a 2-butylphenylethoxy group, a 3-butylphenylethoxy group, a 4-butylphenylethoxy group, a 2,4-dibutylphenylethoxy group, a 2,6-dibutylphenylethoxy group, a 2,4,6-tributylphenylethoxy group, a methyl(2-butylphenyl)methoxy group, a methyl(3-butylphenyl)methoxy group, a methyl(4-butylphenyl)methoxy group, a methyl(2,4-dibutylphenyl)methoxy group, a methyl(2,6-dibutylphenyl)methoxy group, a methyl(2,4,6-tributylphenyl)methoxy group, a 2-butylphenylpropoxy group, a 3-butylphenylpropoxy group, a 4-butylphenylpropoxy group, a 2,4-dibutylphenylpropoxy group, a 2,6-dibutylphenylpropoxy group, a 2,4,6-tributylphenylpropoxy group, a 1-methyl(2-butylphenyl)ethoxy group, a 1-methyl(3-butylphenyl)ethoxy group, a 1-methyl(4-butylphenyl)ethoxy group, a 1-methyl(2,4-dibutylphenyl)ethoxy group, a 1-methyl(2,6-dibutylphenyl)ethoxy group, a 1-methyl(2,4,6-tributylphenyl)ethoxy group or the like; and an arylalkyloxy group having 7 to 9 carbon atoms, in which a hydrogen atom bonded to the carbon atoms is substituted by a haloalkyl group having 1 to 4 carbon atoms (having a haloalkyl group having 1 to 4 carbon atoms as a substituent), such as, for example, a fluoroalkyl group or a chloroalkyl group having 1 to 4 carbon atoms, such as, for example, an arylalkyloxy group having 7 to 9 carbon atoms, in which a hydrogen atom bonded to the carbon atoms is substituted by a fluoromethyl group (having a fluoromethyl group as a substituent), such as, for example, a 2-trifluoromethylphenylmethoxy group, a 3-trifluoromethylphenylmethoxy group, a 4-trifluoromethylphenylmethoxy group, a 2,4-bis(trifluoromethyl)phenylmethoxy group, a 2,6-bis(trifluoromethyl)phenylmethoxy group, a 2,4,6-tris(trifluoromethyl)phenylmethoxy group, a 2-trifluoromethylphenylethoxy group, a 3-trifluoromethylphenylethoxy group, a 4-trifluoromethylphenylethoxy group, a 2,4-bis(trifluoromethyl)phenylethoxy group, a 2,6-bis(trifluoromethyl)phenylethoxy group, a 2,4,6-tris(trifluoromethyl)phenylethoxy group, a methyl(2-trifluoromethylphenyl)methoxy group, a methyl(3-trifluoromethylphenyl)methoxy group, a methyl(4-trifluoromethylphenyl)methoxy group, a methyl[2,4-bis(trifluoromethyl)phenyl]methoxy group, a methyl[2,6-bis(trifluoromethyl)phenyl]methoxy group, a methyl[2,4,6-tris(trifluoromethyl)phenyl]methoxy group, a 2-trifluoromethylphenylpropoxy group, a 3-trifluoromethylphenylpropoxy group, a 4-trifluoromethylphenylpropoxy group, a 2,4-bis(trifluoromethyl)phenylpropoxy group, a 2,6-bis(trifluoromethyl)phenylpropoxy group, a 2,4,6-tris(trifluoromethyl)phenylpropoxy group, a 1-methyl[2-(trifluoromethyl)phenyl]ethoxy group, a 1-methyl[3-(trifluoromethyl)phenyl]ethoxy group, a 1-methyl[4-(trifluoromethyl)phenyl]ethoxy group, a 1-methyl[2,4-bis(trifluoromethyl)phenyl]ethoxy group, a 1-methyl[2,6-bis(trifluoromethyl)phenyl]ethoxy group, a 1-methyl[2,4,6-tris(trifluoromethyl)phenyl]ethoxy group or the like; an arylalkyloxy group having 7 to 9 carbon atoms, in which a hydrogen atom bonded to the carbon atoms is substituted by a chloromethyl group (having a chloromethyl group as a substituent), such as, for example, a 2-trichloromethylphenylmethoxy group, a 3-trichloromethylphenylmethoxy group, a 4-trichloromethylphenylmethoxy group, a 2,4-bis(trichloromethyl)phenylmethoxy group, a 2,6-bis(trichloromethyl)phenylmethoxy group, a 2,4,6-tris(trichloromethyl)phenylmethoxy group, a 2-trichloromethylphenylethoxy group, a 3-trichloromethylphenylethoxy group, a 4-trichloromethylphenylethoxy group, a 2,4-bis(trichloromethyl)phenylethoxy group, a 2,6-bis(trichloromethyl)phenylethoxy group, a 2,4,6-tris(trichloromethyl)phenylethoxy group, a methyl(2-trichloromethylphenyl)methoxy group, a methyl(3-trichloromethylphenyl)methoxy group, a methyl(4-trichloromethylphenyl)methoxy group, a methyl[2,4-bis(trichloromethyl)phenyl]methoxy group, a methyl[2,6-bis(trichloromethyl)phenyl]methoxy group, a methyl[2,4,6-tris(trichloromethyl)phenyl]methoxy group, a 2-trichloromethylphenylpropoxy group, a 3-trichloromethylphenylpropoxy group, a 4-trichloromethylphenylpropoxy group, a 2,4-bis(trichloromethyl)phenylpropoxy group, a 2,6-bis(trichloromethyl)phenylpropoxy group, a 2,4,6-tris(trichloromethyl)phenylpropoxy group, a 1-methyl[2-(trichloromethyl)phenyl]ethoxy group, a 1-methyl[3-(trichloromethyl)phenyl]ethoxy group, a 1-methyl[4-(trichloromethyl)phenyl]ethoxy group, a 1-methyl[2,4-bis(trichloromethyl)phenyl]ethoxy group, a 1-methyl[2,6-bis(trichloromethyl)phenyl]ethoxy group, a 1-methyl[2,4,6-tris(trichloromethyl)phenyl]ethoxy group or the like; an arylalkyloxy group having 7 to 9 carbon atoms, in which a hydrogen atom bonded to the carbon atoms is substituted by a fluoroethyl group (having a fluoroethyl group as a substituent), such as, for example, a 2-pentafluoroethylphenylmethoxy group, a 3-pentafluoroethylphenylmethoxy group, a 4-pentafluoroethylphenylmethoxy group, a 2,4-bis(pentafluoroethyl)phenylmethoxy group, a 2,6-bis(pentafluoroethyl)phenylmethoxy group, a 2,4,6-tris(pentafluoroethyl)phenylmethoxy group, a 2-pentafluoroethylphenylethoxy group, a 3-pentafluoroethylphenylethoxy group, a 4-pentafluoroethylphenylethoxy group, a 2,4-bis(pentafluoroethyl)phenylethoxy group, a 2,6-bis(pentafluoroethyl)phenylethoxy group, a 2,4,6-tris(pentafluoroethyl)phenylethoxy group, a methyl(2-pentafluoroethylphenyl)methoxy group, a methyl(3-pentafluoroethylphenyl)methoxy group, a methyl(4-pentafluoroethylphenyl)methoxy group, a methyl[2,4-bis(pentafluoroethyl)phenyl]methoxy group, a methyl[2,6-bis(pentafluoroethyl)phenyl]methoxy group, a methyl[2,4,6-tris(pentafluoroethyl)phenyl]methoxy group, a 2-pentafluoroethylphenylpropoxy group, a 3-pentafluoroethylphenylpropoxy group, a 4-pentafluoroethylphenylpropoxy group, a 2,4-bis(pentafluoroethyl)phenylpropoxy group, a 2,6-bis(pentafluoroethyl)phenylpropoxy group, a 2,4,6-tris(pentafluoroethyl)phenylpropoxy group, a 1-methyl[2-(pentafluoroethyl)phenyl]ethoxy group, a 1-methyl[3-(pentafluoroethyl)phenyl]ethoxy group, a 1-methyl[4-(pentafluoroethyl)phenyl]ethoxy group, a 1-methyl[2,4-bis(pentafluoroethyl)phenyl]ethoxy group, a 1-methyl[2,6-bis(pentafluoroethyl)phenyl]ethoxy group, a 1-methyl[2,4,6-tris(pentafluoroethyl)phenyl]ethoxy group or the like; an arylalkyloxy group having 7 to 9 carbon atoms, in which a hydrogen atom bonded to the carbon atoms is substituted by a chloroethyl group (having a chloroethyl group as a substituent), such as, for example, a 2-pentachloroethylphenylmethoxy group, a 3-pentachloroethylphenylmethoxy group, a 4-pentachloroethyl phenylmethoxy group, a 2,4-bis(pentachloroethyl)phenylmethoxy group, a 2,6-bis(pentachloroethyl)phenylmethoxy group, a 2,4,6-tris(pentachloroethyl)phenylmethoxy group, a 2-pentachloroethylphenylethoxy group, a 3-pentachloroethylphenylethoxy group, a 4-pentachloroethylphenylethoxy group, a 2,4-bis(pentachloroethyl)phenylethoxy group, a 2,6-bis(pentachloroethyl)phenylethoxy group, a 2,4,6-tris(pentachloroethyl)phenylethoxy group, a methyl(2-pentachloroethylphenyl)methoxy group, a methyl(3-pentachloroethylphenyl)methoxy group, a methyl(4-pentachloroethylphenyl)methoxy group, a methyl[2,4-bis(pentachloroethyl)phenyl]methoxy group, a methyl[2,6-bis(pentachloroethyl)phenyl]methoxy group, a methyl[2,4,6-tris(pentachloroethyl)phenyl]methoxy group, a 2-pentachloroethylphenylpropoxy group, a 3-pentachloroethylphenylpropoxy group, a 4-pentachloroethylphenylpropoxy group, a 2,4-bis(pentachloroethyl)phenylpropoxy group, a 2,6-bis(pentachloroethyl)phenylpropoxy group, a 2,4,6-tris(pentachloroethyl)phenylpropoxy group, a 1-methyl[2-(pentachloroethyl)phenyl]ethoxy group, a 1-methyl[3-(pentachloroethyl)phenyl]ethoxy group, a 1-methyl[4-(pentachloroethyl)phenyl]ethoxy group, a 1-methyl[2,4-bis(pentachloroethyl)phenyl]ethoxy group, a 1-methyl[2,6-bis(pentachloroethyl)phenyl]ethoxy group, a 1-methyl[2,4,6-tris(pentachloroethyl)phenyl]ethoxy group or the like; an arylalkyloxy group having 7 to 9 carbon atoms, in which a hydrogen atom bonded to the carbon atoms is substituted by a fluoropropyl group (having a fluoropropyl group as a substituent), such as, for example, a 2-heptafluoropropylphenylmethoxy group, a 3-heptafluoropropylphenylmethoxy group, a 4-heptafluoropropylphenylmethoxy group, a 2,4-bis(heptafluoropropyl)phenylmethoxy group, a 2,6-bis(heptafluoropropyl)phenylmethoxy group, a 2,4,6-tris(heptafluoropropyl)phenylmethoxy group, a 2-heptafluoropropylphenylethoxy group, a 3-heptafluoropropylphenylethoxy group, a 4-heptafluoropropylphenylethoxy group, a 2,4-bis(heptafluoropropyl)phenylethoxy group, a 2,6-bis(heptafluoropropyl)phenylethoxy group, a 2,4,6-tris(heptafluoropropyl)phenylethoxy group, a methyl(2-heptafluoropropylphenyl)methoxy group, a methyl(3-heptafluoropropylphenyl)methoxy group, a methyl(4-heptafluoropropylphenyl)methoxy group, a methyl[2,4-bis(heptafluoropropyl)phenyl]methoxy group, a methyl[2,6-bis(heptafluoropropyl)phenyl]methoxy group, a methyl[2,4,6-tris(heptafluoropropyl)phenyl]methoxy group, a 2-heptafluoropropylphenylpropoxy group, a 3-heptafluoropropylphenylpropoxy group, a 4-heptafluoropropylphenylpropoxy group, a 2,4-bis(heptafluoropropyl)phenylpropoxy group, a 2,6-bis(heptafluoropropyl)phenylpropoxy group, a 2,4,6-tris(heptafluoropropyl)phenylpropoxy group, a 1-methyl[2-(heptafluoropropyl)phenyl]ethoxy group, a 1-methyl[3-(heptafluoropropyl)phenyl]ethoxy group, a 1-methyl[4-(heptafluoropropyl)phenyl]ethoxy group, a 1-methyl[2,4-bis(heptafluoropropyl)phenyl]ethoxy group, a 1-methyl[2,6-bis(heptafluoropropyl)phenyl]ethoxy group, a 1-methyl[2,4,6-tris(heptafluoropropyl)phenyl]ethoxy group or the like; an arylalkyloxy group having 7 to 9 carbon atoms, in which a hydrogen atom bonded to the carbon atoms is substituted by a chloropropyl group (having a chloropropyl group as a substituent), such as, for example, a 2-heptachloropropylphenylmethoxy group, a 3-heptachloropropylphenylmethoxy group, a 4-heptachloropropylphenylmethoxy group, a 2,4-bis(heptachloropropyl)phenylmethoxy group, a 2,6-bis(heptachloropropyl)phenylmethoxy group, a 2,4,6-tris(heptachloropropyl)phenylmethoxy group, a 2-heptachloropropylphenylethoxy group, a 3-heptachloropropylphenylethoxy group, a 4-heptachloropropylphenylethoxy group, a 2,4-bis(heptachloropropyl)phenylethoxy group, a 2,6-bis(heptachloropropyl)phenylethoxy group, a 2,4,6-tris(heptachloropropyl)phenylethoxy group, a methyl(2-heptachloropropylphenyl)methoxy group, a methyl(3-heptachloropropylphenyl)methoxy group, a methyl(4-heptachloropropylphenyl)methoxy group, a methyl[2,4-bis(heptachloropropyl)phenyl]methoxy group, a methyl[2,6-bis(heptachloropropyl)phenyl]methoxy group, a methyl[2,4,6-tris(heptachloropropyl)phenyl]methoxy group, a 2-heptachloropropylphenylpropoxy group, a 3-heptachloropropylphenylpropoxy group, a 4-heptachloropropylphenylpropoxy group, a 2,4-bis(heptachloropropyl)phenylpropoxy group, a 2,6-bis(heptachloropropyl)phenylpropoxy group, a 2,4,6-tris(heptachloropropyl)phenylpropoxy group, a 1-methyl[2-(heptachloropropyl)phenyl]ethoxy group, a 1-methyl[3-(heptachloropropyl)phenyl]ethoxy group, a 1-methyl[4-(heptachloropropyl)phenyl]ethoxy group, a 1-methyl[2,4-bis(heptachloropropyl)phenyl]ethoxy group, a 1-methyl[2,6-bis(heptachloropropyl)phenyl]ethoxy group, a 1-methyl[2,4,6-tris(heptachloropropyl)phenyl]ethoxy group or the like; an arylalkyloxy group having 7 to 9 carbon atoms, in which a hydrogen atom bonded to the carbon atoms is substituted by a fluorobutyl group (having a fluorobutyl group as a substituent), such as, for example, a 2-nonafluorobutylphenylmethoxy group, a 3-nonafluorobutylphenylmethoxy group, a 4-nonafluorobutylphenylmethoxy group, a 2,4-bis(nonafluorobutyl)phenylmethoxy group, a 2,6-bis(nonafluorobutyl)phenylmethoxy group, a 2,4,6-tris(nonafluorobutyl)phenylmethoxy group, a 2-nonafluorobutylphenylethoxy group, a 3-nonafluorobutylphenylethoxy group, a 4-nonafluorobutylphenylethoxy group, a 2,4-bis(nonafluorobutyl)phenylethoxy group, a 2,6-bis(nonafluorobutyl)phenylethoxy group, a 2,4,6-tris(nonafluorobutyl)phenylethoxy group, a methyl(2-nonafluorobutylphenyl)methoxy group, a methyl(3-nonafluorobutylphenyl)methoxy group, a methyl(4-nonafluorobutylphenyl)methoxy group, a methyl[2,4-bis(nonafluorobutyl)phenyl]methoxy group, a methyl[2,6-bis(nonafluorobutyl)phenyl]methoxy group, a methyl[2,4,6-tris(nonafluorobutyl)phenyl]methoxy group, a 2-nonafluorobutylphenylpropoxy group, a 3-nonafluorobutylphenylpropoxy group, a 4-nonafluorobutylphenylpropoxy group, a 2,4-bis(nonafluorobutyl)phenylpropoxy group, a 2,6-bis(nonafluorobutyl)phenylpropoxy group, a 2,4,6-tris(nonafluorobutyl)phenylpropoxy group, a 1-methyl[2-(nonafluorobutyl)phenyl]ethoxy group, a 1-methyl[3-(nonafluorobutyl)phenyl]ethoxy group, a 1-methyl[4-(nonafluorobutyl)phenyl]ethoxy group, a 1-methyl[2,4-bis(nonafluorobutyl)phenyl]ethoxy group, a 1-methyl[2,6-bis(nonafluorobutyl)phenyl]ethoxy group, a 1-methyl[2,4,6-tris(nonafluorobutyl)phenyl]ethoxy group or the like; and an arylalkyloxy group having 7 to 9 carbon atoms, in which a hydrogen atom bonded to the carbon atoms is substituted by a chlorobutyl group (having a chlorobutyl group as a substituent), such as, for example, a 2-nonachlorobutylphenylmethoxy group, a 3-nonachlorobutylphenylmethoxy group, a 4-nonachlorobutylphenylmethoxy group, a 2,4-bis(nonachlorobutyl)phenylmethoxy group, a 2,6-bis(nonachlorobutyl)phenylmethoxy group, a 2,4,6-tris(nonachlorobutyl)phenylmethoxy group, a 2-nonachlorobutylphenylethoxy group, a 3-nonachlorobutylphenylethoxy group, a 4-nonachlorobutylphenylethoxy group, a 2,4-bis(nonachlorobutyl)phenylethoxy group, a 2,6-bis(nonachlorobutyl)phenylethoxy group, a 2,4,6-tris(nonachlorobutyl)phenylethoxy group, a methyl(2-nonachlorobutylphenyl)methoxy group, a methyl(3-nonachlorobutylphenyl)methoxy group, a methyl(4-nonachlorobutylphenyl)methoxy group, a methyl[2,4-bis(nonachlorobutyl)phenyl]methoxy group, a methyl[2,6-bis(nonachlorobutyl)phenyl]methoxy group, a methyl[2,4,6-tris(nonachlorobutyl)phenyl]methoxy group, a 2-nonachlorobutylphenylpropoxy group, a 3-nonachlorobutylphenylpropoxy group, a 4-nonachlorobutylphenylpropoxy group, a 2,4-bis(nonachlorobutyl)phenylpropoxy group, a 2,6-bis(nonachlorobutyl)phenylpropoxy group, a 2,4,6-tris(nonachlorobutyl)phenylpropoxy group, a 1-methyl[2-(nonachlorobutyl)phenyl]ethoxy group, a 1-methyl[3-(nonachlorobutyl)phenyl]ethoxy group, a 1-methyl[4-(nonachlorobutyl)phenyl]ethoxy group, a 1-methyl[2,4-bis(nonachlorobutyl)phenyl]ethoxy group, a 1-methyl[2,6-bis(nonachlorobutyl)phenyl]ethoxy group, a 1-methyl[2,4,6-tris(nonachlorobutyl)phenyl]ethoxy group or the like are preferable, and among them, an unsubstituted (having no substituent) arylalkyloxy group having 7 to 9 carbon atoms, such as, for example, a benzyloxy group, a phenethyloxy group, a methylbenzyloxy group, a phenylpropoxy group, a 1-methylphenylethoxy group or the like; an arylalkyloxy group having 7 to 9 carbon atoms, in which a hydrogen atom bonded to the carbon atoms is substituted by a fluorine atom (having a fluorine atom as a substituent), such as, for example, a 2-fluorophenylmethoxy group, a 3-fluorophenylmethoxy group, a 4-fluorophenylmethoxy group, a 2,4-difluorophenylmethoxy group, a 2,6-difluorophenylmethoxy group, a 2,4,6-trifluorophenylmethoxy group, a 2-fluorophenylethoxy group, a 3-fluorophenylethoxy group, a 4-fluorophenylethoxy group, a 2,4-difluorophenylethoxy group, a 2,6-difluorophenylethoxy group, a 2,4,6-trifluorophenylethoxy group, a methyl(2-fluorophenyl)methoxy group, a methyl(3-fluorophenyl)methoxy group, a methyl(4-fluorophenyl)methoxy group, a methyl(2,4-difluorophenyl)methoxy group, a methyl(2,6-difluorophenyl)methoxy group, a methyl(2,4,6-trifluorophenyl)methoxy group, a 2-fluorophenylpropoxy group, a 3-fluorophenylpropoxy group, a 4-fluorophenylpropoxy group, a 2,4-difluorophenylpropoxy group, a 2,6-difluorophenylpropoxy group, a 2,4,6-trifluorophenylpropoxy group, a 1-methyl(2-fluorophenyl)ethoxy group, a 1-methyl(3-fluorophenyl)ethoxy group, a 1-methyl(4-fluorophenyl)ethoxy group, a 1-methyl(2,4-difluorophenyl)ethoxy group, a 1-methyl(2,6-difluorophenyl)ethoxy group, a 1-methyl(2,4,6-trifluorophenyl)ethoxy group or the like; an arylalkyloxy group having 7 to 9 carbon atoms, in which a hydrogen atom bonded to the carbon atoms is substituted by a chlorine atom (having a chlorine atom as a substituent), such as, for example, a 2-chlorophenylmethoxy group, a 3-chlorophenylmethoxy group, a 4-chlorophenylmethoxy group, a 2,4-dichlorophenylmethoxy group, a 2,6-dichlorophenylmethoxy group, a 2,4,6-trichlorophenylmethoxy group, a 2-chlorophenylethoxy group, a 3-chlorophenylethoxy group, a 4-chlorophenylethoxy group, a 2,4-dichlorophenylethoxy group, a 2,6-dichlorophenylethoxy group, a 2,4,6-trichlorophenylethoxy group, a methyl(2-chlorophenyl)methoxy group, a methyl(3-chlorophenyl)methoxy group, a methyl(4-chlorophenyl)methoxy group, a methyl(2,4-dichlorophenyl)methoxy group, a methyl(2,6-dichlorophenyl)methoxy group, a methyl(2,4,6-trichlorophenyl)methoxy group, a 2-chlorophenylpropoxy group, a 3-chlorophenylpropoxy group, a 4-chlorophenylpropoxy group, a 2,4-dichlorophenylpropoxy group, a 2,6-dichlorophenylpropoxy group, a 2,4,6-trichlorophenylpropoxy group, a 1-methyl(2-chlorophenyl)ethoxy group, a 1-methyl(3-chlorophenyl)ethoxy group, a 1-methyl(4-chlorophenyl)ethoxy group, a 1-methyl(2,4-dichlorophenyl)ethoxy group, a 1-methyl(2,6-dichlorophenyl)ethoxy group, a 1-methyl(2,4,6-trichlorophenyl)ethoxy group or the like; an arylalkyloxy group having 7 to 9 carbon atoms, in which a hydrogen atom bonded to the carbon atoms is substituted by a methyl group (having a methyl group as a substituent), such as, for example, a 2-tolylmethoxy group, a 3-tolylmethoxy group, a 4-tolylmethoxy group, a 2,4-xylylmethoxy group, a 2,6-xylylmethoxy group, a mesitylmethoxy group (a 2,4,6-trimethylphenylmethoxy group), a 2-tolylethoxy group, a 3-tolylethoxy group, a 4-tolylethoxy group, a 2,4-xylylethoxy group, a 2,6-xylylethoxy group, a mesitylethoxy group (a 2,4,6-trimethylphenylethoxy group), a methyl(2-tolyl)methoxy group, a methyl(3-tolyl)methoxy group, a methyl(4-tolyl)methoxy group, a methyl(2,4-xylyl)methoxy group, a methyl(2,6-xylyl)methoxy group, a methyl(mesityl)methoxy group (a methyl(2,4,6-trimethylphenyl)methoxy group), a 2-tolylpropoxy group, a 3-tolylpropoxy group, a 4-tolylpropoxy group, a 2,4-xylylpropoxy group, a 2,6-xylylpropoxy group, a mesitylpropoxy group (a 2,4,6-trimethylphenylpropoxy group), a 1-methyl(2-tolyl)ethoxy group, a 1-methyl(3-tolyl)ethoxy group, a 1-methyl(4-tolyl)ethoxy group, a 1-methyl(2,4-xylyl)ethoxy group, a 1-methyl(2,6-xylyl)ethoxy group, a 1-methyl(mesityl)ethoxy group (a 1-methyl(2,4,6-trimethylphenyl)ethoxy group); an arylalkyloxy group having 7 to 9 carbon atoms, in which a hydrogen atom bonded to the carbon atoms is substituted by a fluoromethyl group (having a fluoromethyl group as a substituent), such as, for example, a 2-trifluoromethylphenylmethoxy group, a 3-trifluoromethylphenylmethoxy group, a 4-trifluoromethylphenylmethoxy group, a 2,4-bis(trifluoromethyl)phenylmethoxy group, a 2,6-bis(trifluoromethyl)phenylmethoxy group, a 2,4,6-tris(trifluoromethyl)phenylmethoxy group, a 2-trifluoromethylphenylethoxy group, a 3-trifluoromethylphenylethoxy group, a 4-trifluoromethylphenylethoxy group, a 2,4-bis(trifluoromethyl)phenylethoxy group, a 2,6-bis(trifluoromethyl)phenylethoxy group, a 2,4,6-tris(trifluoromethyl)phenylethoxy group, a methyl(2-trifluoromethylphenyl)methoxy group, a methyl(3-trifluoromethylphenyl)methoxy group, a methyl(4-trifluoromethylphenyl)methoxy group, a methyl[2,4-bis(trifluoromethyl)phenyl]methoxy group, a methyl[2,6-bis(trifluoromethyl)phenyl]methoxy group, a methyl[2,4,6-tris(trifluoromethyl)phenyl]methoxy group, a 2-trifluoromethylphenylpropoxy group, a 3-trifluoromethylphenylpropoxy group, a 4-trifluoromethylphenylpropoxy group, a 2,4-bis(trifluoromethyl)phenylpropoxy group, a 2,6-bis(trifluoromethyl)phenylpropoxy group, a 2,4,6-tris(trifluoromethyl)phenylpropoxy group, a 1-methyl[2-(trifluoromethyl)phenyl]ethoxy group, a 1-methyl[3-(trifluoromethyl)phenyl]ethoxy group, a 1-methyl[4-(trifluoromethyl)phenyl]ethoxy group, a 1-methyl[2,4-bis(trifluoromethyl)phenyl]ethoxy group, a 1-methyl[2,6-bis(trifluoromethyl)phenyl]ethoxy group, a 1-methyl[2,4,6-tris(trifluoromethyl)phenyl]ethoxy group or the like; and an arylalkyloxy group having 7 to 9 carbon atoms, in which a hydrogen atom bonded to the carbon atoms is substituted by a chloromethyl group (having a chloromethyl group as a substituent), such as, for example, a 2-trichloromethylphenylmethoxy group, a 3-trichloromethylphenylmethoxy group, a 4-trichloromethylphenylmethoxy group, a 2,4-bis(trichloromethyl)phenylmethoxy group, a 2,6-bis(trichloromethyl)phenylmethoxy group, a 2,4,6-tris(trichloromethyl)phenylmethoxy group, a 2-trichloromethylphenylethoxy group, a 3-trichloromethylphenylethoxy group, a 4-trichloromethylphenylethoxy group, a 2,4-bis(trichloromethyl)phenylethoxy group, a 2,6-bis(trichloromethyl)phenylethoxy group, a 2,4,6-tris(trichloromethyl)phenylethoxy group, a methyl(2-trichloromethylphenyl)methoxy group, a methyl(3-trichloromethylphenyl)methoxy group, a methyl(4-trichloromethylphenyl)methoxy group, a methyl[2,4-bis(trichloromethyl)phenyl]methoxy group, a methyl[2,6-bis(trichloromethyl)phenyl]methoxy group, a methyl[2,4,6-tris(trichloromethyl)phenyl]methoxy group, a 2-trichloromethylphenylpropoxy group, a 3-trichloromethylphenylpropoxy group, a 4-trichloromethylphenylpropoxy group, a 2,4-bis(trichloromethyl)phenylpropoxy group, a 2,6-bis(trichloromethyl)phenylpropoxy group, a 2,4,6-tris(trichloromethyl)phenylpropoxy group, a 1-methyl[2-(trichloromethyl)phenyl]ethoxy group, a 1-methyl[3-(trichloromethyl)phenyl]ethoxy group, a 1-methyl[4-(trichloromethyl)phenyl]ethoxy group, a 1-methyl[2,4-bis(trichloromethyl)phenyl]ethoxy group, a 1-methyl[2,6-bis(trichloromethyl)phenyl]ethoxy group, a 1-methyl[2,4,6-tris(trichloromethyl)phenyl]ethoxy group or the like are more preferable, and among them, an unsubstituted (having no substituent) arylalkyloxy group having 7 to 9 carbon atoms, such as, for example, a benzyloxy group, a phenethyloxy group, a methylbenzyloxy group, a phenylpropoxy group, a 1-methylphenylethoxy group or the like; an arylalkyloxy group having 7 to 9 carbon atoms, in which a hydrogen atom bonded to the carbon atom at 4 position of a phenyl group is substituted by a fluorine atom (having a fluorine atom at 4 position of a phenyl group as a substituent), such as, for example, a 4-fluorophenylmethoxy group, a 4-fluorophenylethoxy group, a methyl(4-fluorophenyl)methoxy group, a 4-fluorophenylpropoxy group, a 1-methyl(4-fluorophenyl) ethoxy group or the like; an arylalkyloxy group having 7 to 9 carbon atoms, in which a hydrogen atom bonded to the carbon atom at 4 position of a phenyl group is substituted by a chlorine atom (having a chlorine atom at 4 position of a phenyl group as a substituent), such as, for example, a 4-chlorophenylmethoxy group, a 4-chlorophenylethoxy group, a methyl(4-chlorophenyl)methoxy group, a 4-chlorophenylpropoxy group, a 1-methyl(4-chlorophenyl)ethoxy group or the like; an arylalkyloxy group having 7 to 9 carbon atoms, in which a hydrogen atom bonded to the carbon atom at 4 position of a phenyl group is substituted by a methyl group (having a methyl group at 4 position of a phenyl group as a substituent), such as, for example, a 4-tolylmethoxy group, a 4-tolylethoxy group, a methyl(4-tolyl)methoxy group, a 4-tolylpropoxy group, a 1-methyl(4-tolyl)ethoxy group or the like; an arylalkyloxy group having 7 to 9 carbon atoms, in which a hydrogen atom bonded to the carbon atom at 4 position of a phenyl group is substituted by a fluoromethyl group (having a fluoromethyl group at 4 position of a phenyl group as a substituent), such as, for example, a 4-trifluoromethylphenylmethoxy group, a 4-trifluoromethylphenylethoxy group, a methyl(4-trifluoromethylphenyl) methoxy group, a 4-trifluoromethylphenylpropoxy group, a 1-methyl[4-(trifluoromethyl)phenyl]ethoxy group or the like; and an arylalkyloxy group having 7 to 9 carbon atoms, in which a hydrogen atom bonded to the carbon atom at 4 position of a phenyl group is substituted by a chloromethyl group (having a chloromethyl group at 4 position of a phenyl group as a substituent), such as, for example, a 4-trichloromethylphenylmethoxy group, a 4-trichloromethylphenylethoxy group, a methyl(4-trichloromethylphenyl)methoxy group, a 4-trichloromethylphenylpropoxy group, a 1-methyl [4-(trichloromethyl)phenyl]ethoxy group or the like are further preferable, and furthermore among them, a benzyloxy group, a 4-fluorophenylmethoxy group, a 4-chlorophenylmethoxy group, a 4-tolylmethoxy group, a 4-trifluoromethylphenylmethoxy group and a 4-trichloromethylphenylmethoxy group are particularly preferable.

n pieces of $R^1$ in the general formula (A) may be the same or may be different.

An alkyl group having 1 to 10 carbon atoms, represented by $R^2$ and $R^3$ in the general formula (A), may be any of a straight chained, branched or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group, a n-heptyl group, an isoheptyl group, a sec-heptyl group, a tert-heptyl group, a neoheptyl group, a cycloheptyl group, a n-octyl group, an isooctyl group, a sec-octyl group, a tert-octyl group, a neooctyl group, a 2-ethylhexyl group, a cyclooctyl group, a n-nonyl group, an isononyl group, a sec-nonyl group, a tert-nonyl group, a neononyl group, a cyclononyl group, a n-decyl group, an isodecyl group, a sec-decyl group, a tert-decyl group, a neodecyl group, a cyclodecyl group, a norbornyl group (a norbornane-χ-yl group), a bornyl group (a bornane-χ-yl group), a menthyl group (a mentha-χ-yl group), an adamantyl group, a decahydronaphthyl group or the like, and among them, a straight chained, branched or cyclic alkyl group having 1 to 6 carbon atoms, such as, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group and a cyclohexyl group are preferable, and among them, a straight chained, branched or cyclic alkyl group having 1 to 4 carbon atoms, such as, for example, a methyl group, an ethyl group, a n-propyl group, an isopropyl group, a n-butyl group, an isobutyl group, a sec-butyl group, a tert-butyl group and a cyclobutyl group are more preferable, and furthermore among them, a methyl group, which is an alkyl group having one carbon atom, is further preferable.

An alkoxycarbonyl group having 2 to 7 carbon atoms, represented by $R^2$ and $R^3$ in the general formula (A), may be any of a straight chained, branched or cyclic group, and specifically includes, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a cyclobutoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a 2-methylbutoxycarbonyl group, a 1,2-dimethylpropoxycarbonyl group, a 1-ethylpropoxycarbonyl group, a cyclopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a 2-methylpentyloxycarbonyl group, a 1,2-dimethylbutoxycarbonyl group, a 2,3-dimethylbutoxycarbonyl group, a 1-ethylbutoxycarbonyl group, a cyclohexyloxycarbonyl group or the like, and among them, a straight chained, branched or cyclic alkoxycarbonyl group having 2 to 5 carbon atoms, such as, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group and a cyclobutoxycarbonyl group are preferable.

n pieces of $R^2$ and n pieces of $R^3$ in the general formula (A) may be the same or may be different.

A halogen atom represented by $R^4$ to $R^7$ in the general formula (A) specifically includes, for example, a fluorine atom, a chlorine atom, a bromine atom, an iodine atom or the like, and among them, a chlorine atom and a bromine atom are preferable.

An alkyl group having 1 to 6 carbon atoms, represented by $R^4$ and $R^7$ in the general formula (A), may be any of a straight chained, branched or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group or the like, and among them, a straight chained, branched or cyclic alkyl group having 1 to 4 carbon atoms, such as, for example, a methyl group, an ethyl group, a n-propyl group, an isopropyl group, a n-butyl group, an isobutyl group, a sec-butyl group, a tert-butyl group and a cyclobutyl group are preferable, and among them, a methyl group, which is an alkyl group having one carbon atom, is more preferable.

An alkoxy group having 1 to 6 carbon atoms, represented by $R^4$ and $R^7$ in the general formula (A), may be any of a straight chained, branched or cyclic group, and specifically includes, for example, a methoxy group, an ethoxy group, a n-propoxy group, an isopropoxy group, a n-butoxy group, an isobutoxy group, a sec-butoxy group, a tert-butoxy group, a cyclobutoxy group, a n-pentyloxy group, an isopentyloxy group, a sec-pentyloxy group, a tert-pentyloxy group, a neopentyloxy group, a 2-methylbutoxy group, a 1,2-dimethylpropoxy group, a 1-ethylpropoxy group, a cyclopentyloxy group, a n-hexyloxy group, an isohexyloxy group, a sec-hexyloxy group, a tert-hexyloxy group, a neohexyloxy group, a 2-methylpentyloxy group, a 1,2-dimethylbutoxy group, a 2,3-dimethylbutoxy group, a 1-ethylbutoxy group, a cyclohexyloxy group or the like, and among them, a straight chained, branched or cyclic alkoxy group having 1 to 4 carbon atoms, such as, for example, a methoxy group, an ethoxy group, a n-propoxy group, an isopropoxy group, a n-butoxy group, an isobutoxy group, a sec-butoxy group, a tert-butoxy group and a cyclobutoxy group are preferable, and among them, a methoxy group, which is an alkoxy group having one carbon atom, is more preferable.

An alkenyl group having 2 to 6 carbon atoms, represented by $R^4$ and $R^7$ in the general formula (A), may be any of a straight chained, branched or cyclic group, and specifically includes, for example, a vinyl group, a 1-propenyl group, a 2-propenyl group (an allyl group), an isopropenyl group, a crotyl group, an isocrotyl group (an isobutenyl group), a methallyl group (a 2-methylallyl group), a prenyl group (a dimethylallyl group), an isopentenyl group, a cyclopentenyl group, a sorbyl group (a (2E,4E)-hexa-2,4-diene-1-yl group), a cyclohexenyl group or the like, and among them, for example, a straight chained or branched alkenyl group having 2 to 3 carbon atoms, such as, for example, a vinyl group, a 1-propenyl group, a 2-propenyl group (an allyl group) and an isopropenyl group are preferable.

An aryl group having 6 to 10 carbon atoms, represented by $R^4$ and $R^7$ in the general formula (A), may be any of a monocyclic or a condensed polycyclic group, and specifically includes, for example, a phenyl group, a naphthyl group or the like, and among them, a phenyl group, which is an aryl group having 6 carbon atoms, is preferable.

An alkoxycarbonyl group having 2 to 7 carbon atoms, represented by $R^4$ and $R^7$ in the general formula (A), may be any of a straight chained, branched or cyclic group, and specifically includes, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a cyclobutoxycarbonyl group, a n-pentyloxycarbonyl group, an isopentyloxycarbonyl group, a sec-pentyloxycarbonyl group, a tert-pentyloxycarbonyl group, a neopentyloxycarbonyl group, a 2-methylbutoxycarbonyl group, a 1,2-dimethylpropoxycarbonyl group, a 1-ethylpropoxycarbonyl group, a cyclopentyloxycarbonyl group, a n-hexyloxycarbonyl group, an isohexyloxycarbonyl group, a sec-hexyloxycarbonyl group, a tert-hexyloxycarbonyl group, a neohexyloxycarbonyl group, a 2-methylpentyloxycarbonyl group, a 1,2-dimethylbutoxycarbonyl group, a 2,3-dimethylbutoxycarbonyl group, a 1-ethylbutoxycarbonyl group, a cyclohexyloxycarbonyl group or the like; and among them, a straight chained, branched or cyclic alkoxycarbonyl group having 2 to 5 carbon atoms, such as, for example, a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group and a cyclobutoxycarbonyl group are preferable.

A dialkylamino group having 2 to 8 carbon atoms, represented by $R^4$ and $R^7$ in the general formula (A), may be any of a straight chained, branched or cyclic group, and specifically includes, for example, a dimethylamino group, a diethylamino group, a di-n-propylamino group, a diisopropylamino group, a di-n-butylamino group, a diisobutylamino group, a di-sec-butylamino group, a di-tert-butylamino group, a dicyclobutylamino group, an ethylmethylamino group, a methyl-n-propylamino group, a methylisopropylamino group, a n-butylmethylamino group, an isobutylmethylamino group, a sec-butylmethylamino group, a tert-butylmethylamino group, a cyclobutylmethylamino group, an ethyl-n-propylamino group, an ethylisopropylamino group, a n-butyl-n-propylamino group, an isobutyl-n-propylamino group, a sec-butyl-n-propylamino group, a tert-butyl-n-propylamino group, a cyclobutyl-n-propylamino group, a n-butylisopropylamino group, an isobutylisopropylamino group, a sec-butylisopropylamino group, a tert-butylisopropylamino group, a cyclobutylisopropylamino group or the like, and among them, a straight chained, branched or cyclic dialkylamino group having 2 to 4 carbon atoms, such as, for example, a dimethylamino group, a diethylamino group, a methyl-n-propylamino group and a methylisopropylamino group are preferable.

As $R^1$ in the general formula (A), an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an aryl group having 6 to 10 carbon atoms, in which a hydrogen atom may be substituted by a halogen atom, an alkyl group or a haloalkyl group; and an arylalkyl group having 7 to 15 carbon atoms, in which a hydrogen atom may be substituted by a halogen atom, an alkyl group or a haloalkyl group are more preferable, and among them, an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; and an aryl group having 6 to 10 carbon atoms, in which a hydrogen atom may be substituted by a halogen atom, an alkyl group or a haloalkyl group are further preferable.

As $R^2$ in the general formula (A), a hydrogen atom and an alkyl group having 1 to 10 carbon atoms are more preferable, and among them, an alkyl group having 1 to 10 carbon atoms is further preferable.

As $R^3$ in the general formula (A), a hydrogen atom and an alkyl group having 1 to 10 carbon atoms are more preferable, and among them, a hydrogen atom is further preferable.

As $R^2$ and $R^3$ in the general formula (A), the one where at least either of $R^2$ and $R^3$ is a hydrogen atom is preferable.

As $R^4$ to $R^7$ in the general formula (A), a hydrogen atom is more preferable.

Y in the general formula (A) represents an oxygen atom, a sulfur atom or a carbonyl group, and among them, an oxygen atom, and a carbonyl group are more preferable.

Z in the general formula (A) represents a sulfonyl group (—SO₂— group) or an alkoxyphosphoryl group (—P(O)OR$^{12}$— group) having 1 to 6 carbon atoms, and among them, a sulfonyl group (—SO₂— group) is more preferable.

$R^{12}$ in an alkoxyphosphoryl group (—P(O)OR$^{12}$— group) having 1 to 6 carbon atoms, represented by Z in the general formula (A), represents a straight chained, branched or cyclic alkyl group having 1 to 6 carbon atoms or an aryl group having 6 carbon atoms, and specifically includes, for example, an alkyl group having 1 to 6 carbon atoms, such as, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group or the like; and an aryl group having 6 carbon atoms, such as, for example, a phenyl group or the like, and among them, a straight chained or branched alkyl group having 1 to 4 carbon atoms, such as, for example, a methyl group, an ethyl group, a n-propyl group, an isopropyl group, a n-butyl group, an isobutyl group, a sec-butyl group, a tert-butyl group or the like; and a phenyl group, which is an aryl group having 6 carbon atoms, are preferable, and among them, an ethyl group, which is an alkyl group having 2 carbon atoms, is more preferable.

A specific example of an alkoxyphosphoryl group (—P(O)OR$^{12}$— group) having 1 to 6 carbon atoms, represented by Z in the general formula (A), specifically includes, for example, a methoxyphosphoryl group, an ethoxyphosphoryl group, a n-propoxyphosphoryl group, an isopropoxyphosphoryl group, a n-butoxyphosphoryl group, an isobutoxyphosphoryl group, a sec-butoxyphosphoryl group, a tert-butoxyphosphoryl group, a cyclobutoxyphosphoryl group, a n-pentyloxyphosphoryl group, an isopentyloxyphosphoryl group, a sec-pentyloxyphosphoryl group, a tert-pentyloxyphosphoryl group, a neopentyloxyphosphoryl group, a 2-methylbutoxyphosphoryl group, a 1,2-dimethylpropoxyphosphoryl group, a 1-ethylpropoxyphosphoryl group, a cyclopentyloxyphosphoryl group, a n-hexyloxyphosphoryl group, an isohexyloxyphosphoryl group, a sec-hexyloxyphosphoryl a group, a tert-hexyloxyphosphoryl group, a neohexyloxyphosphoryl group, a 2-methylpentyloxyphosphoryl group, a 1,2-dimethylbutoxyphosphoryl group, a 2,3-dimethylbutoxyphosphoryl group, a 1-ethylbutoxyphosphoryl group, a cyclohexyloxyphosphoryl group, a phenyloxyphosphoryl group or the like, and among them, a methoxyphosphoryl group, an ethoxyphosphoryl group, a n-propoxyphosphoryl group, an isopropoxyphosphoryl group, a n-butoxyphosphoryl group, an isobutoxyphosphoryl group, a sec-butoxyphosphoryl group, a tert-butoxyphosphoryl group and phenyloxyphosphoryl group are preferable, and among them, an ethoxyphosphoryl group is more preferable.

n pieces of Z in the general formula (A) may be the same or may be different.

n in the general formula (A) represents 1 or 2, and among them, 2 is more preferable.

Among the compounds represented by the above-described general formula (A) of the present invention, the compound represented by the following general formula (A'-1), and the compound represented by the following general formula (A'-2) are included as preferable ones. The compounds represented by the general formulae (A'-1) and (A'-2) are preferable ones among the compounds represented by the general formula (A), in view of enabling to be produced easily in short steps and in low cost, and to provide an acid-generating agent with high general-purpose properties.

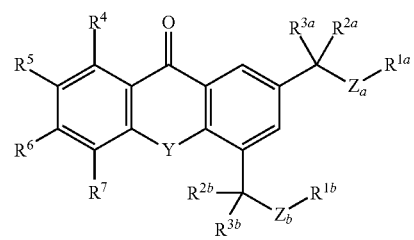

(A'-1)

(wherein $R^{1a}$ and $R^{1b}$ each independently represent an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an alkoxy group having 1 to 10 carbon atoms, in which a hydrogen atom may be substituted by a halogen atom; an aryl group having 6 to 10 carbon atoms, in which a hydrogen atom may be substituted by a halogen atom; an alkyl group or a haloalkyl group; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group; $R^{2a}$, $R^{2b}$, $R^{3a}$ and $R^{3b}$ each independently represent a hydrogen atom, an alkyl group having 1 to 10 carbon atoms or an alkoxycarbonyl group having 2 to 7 carbon atoms; $Z_a$ and $Z_b$ each independently represent a sulfonyl group or an alkoxyphosphoryl group having 1 to 6 carbon atoms; $R^4$ to $R^7$ and Y are the same as described above.)

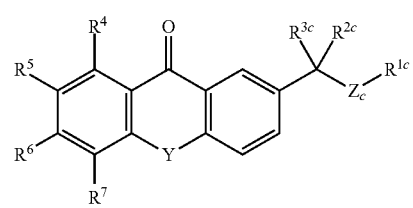

(A'-2)

(wherein $R^{1c}$ represents an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an alkoxy group having 1 to 10 carbon atoms, in which a hydrogen atom may be substituted by a halogen atom; an aryl group having 6 to 10 carbon atoms, in which a hydrogen atom may be substituted by a halogen atom, an alkyl group or a haloalkyl group; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group; $R^{2c}$ and $R^{3c}$ each independently represent a hydrogen atom, an alkyl group having 1 to 10 carbon atoms or an alkoxycarbonyl group having 2 to 7 carbon atoms; $Z_c$ represents a sulfonyl group or an alkoxyphosphoryl group having 1 to 6 carbon atoms; $R^4$ to $R^7$ and Y are the same as described above.)

In an alkyl group having 1 to 20 carbon atoms, which may have a functional group selected from the group consisting of a carbonyloxy group, a carbonylamino group, an ether group and a sulfide in the chain, or in which a hydrogen atom may be substituted by a halogen atom, represented by $R^{1a}$ and $R^{1b}$ in the general formula (A'-1) and $R^{1c}$ in the general formula (A'-2); a specific example of an alkyl group having 1 to 20 carbon atoms, in which a hydrogen atom may be substituted by a halogen atom, includes the same as a specific example of an alkyl group having 1 to 20 carbon atoms, in which a hydrogen atom may be substituted by a halogen atom represented by $R^1$ in the general formula (A), and a preferable specific example of an alkyl group also includes the same one.

A specific example of an alkyl group having 1 to 20 carbon atoms, in which a hydrogen atom may be substituted by a halogen atom, in the case of having a functional group selected from the group consisting of a carbonyloxy group, a carbonylamino group, an ether group and a sulfide group in the chain, represented by $R^{1a}$ and $R^{1b}$ in the general formula (A'-1) and $R^{1c}$ in the general formula (A'-2), includes the same as a specific example represented by the above-described general formulae (B-1) and (B-2). A preferable specific example and a more preferable specific example also include the same ones.

A specific example of an alkoxy group having 1 to 10 carbon atoms, in which a hydrogen atom may be substituted by a halogen atom, represented by $R^{1a}$ and $R^{1b}$ in the general formula (A'-1) and $R^{1c}$ in the general formula (A'-2), includes the same as a specific example of an alkoxy group having 1 to 10 carbon atoms, in which a hydrogen atom may be substituted by a halogen atom, represented by $R^1$ in the general formula (A), and a preferable specific example of an alkoxy group, a more preferable specific example of an alkoxy group and a further preferable specific example of an alkoxy group also include the same ones.

A specific example of an aryl group having 6 to 10 carbon atoms, in which a hydrogen atom may be substituted by a halogen atom, an alkyl group or a haloalkyl group, represented by $R^{1a}$ and $R^{1b}$ in the general formula (A'-1) and $R^{1c}$ in the general formula (A'-2), includes the same as a specific example of an aryl group having 6 to 10 carbon atoms, in which a hydrogen atom may be substituted by a halogen atom, an alkyl group or a haloalkyl group, represented by $R^1$ in the general formula (A), and a preferable specific example of an aryl group, a more preferable specific example of an aryl group and a further preferable specific example of an aryl group also include the same ones.

A specific example of an aryloxy group having 6 to 10 carbon atoms, in which a hydrogen atom may be substituted by a halogen atom, an alkyl group or a haloalkyl group, represented by $R^{1a}$ and $R^{1b}$ in the general formula (A'-1) and $R^{1c}$ in the general formula (A'-2), includes the same as a specific example of an aryloxy group having 6 to 10 carbon atoms, in which a hydrogen atom may be substituted by a halogen atom, an alkyl group or a haloalkyl group, represented by $R^1$ in the general formula (A), and a preferable specific example of an aryloxy group, a more preferable specific example of an aryloxy group and a further preferable specific example of an aryloxy group also include the same ones.

A specific example of an arylalkyl group having 7 to 15 carbon atoms, in which a hydrogen atom may be substituted by a halogen atom, an alkyl group or a haloalkyl group, represented by $R^{1a}$ and $R^{1b}$ in the general formula (A'-1) and $R^{1c}$ in the general formula (A'-2), includes the same as a specific example of an arylalkyl group having 7 to 15 carbon atoms, in which a hydrogen atom may be substituted by a halogen atom, an alkyl group or a haloalkyl group, represented by $R^1$ in the general formula (A), and a preferable specific example of an arylalkyl group, a more preferable specific example of an arylalkyl group, a further preferable specific example of an arylalkyl group and a particularly preferable specific example of an arylalkyl group also include the same ones.

A specific example of an arylalkyloxy group having 7 to 15 carbon atoms, in which a hydrogen atom may be substituted by a halogen atom, an alkyl group or a haloalkyl group, represented by $R^{1a}$ and $R^{1b}$ in the general formula (A'-1) and $R^{1c}$ in the general formula (A'-2), includes the same as a specific example of an arylalkyloxy group having 7 to 15 carbon atoms, in which a hydrogen atom may be substituted by a halogen atom, an alkyl group or a haloalkyl group, represented by $R^1$ in the general formula (A), and a preferable specific example of an arylalkyloxy group, a more preferable specific example of an arylalkyloxy group, a further preferable specific example of an arylalkyloxy group and a particularly preferable specific example of an arylalkyloxy group also include the same ones.

A specific example of an alkyl group having 1 to 10 carbon atoms, represented by $R^{2a}$, $R^{2b}$, $R^{3a}$ and $R^{3b}$ in the general formula (A'-1) and $R^{2c}$ and $R^{3c}$ in the general formula (A'-2), includes the same as a specific example of an alkyl group having 1 to 10 carbon atoms, represented by $R^2$ and $R^3$ in the general formula (A), and a preferable specific example of an alkyl group, a more preferable specific example of an alkyl group and a further preferable specific example of an alkyl group also include the same ones.

A specific example of an alkoxycarbonyl group having 2 to 7 carbon atoms, represented by $R^{2a}$, $R^{2b}$, $R^{3a}$ and $R^{3b}$ in the general formula (A'-1) and $R^{2c}$ and $R^{3c}$ in the general formula (A'-2), includes the same as a specific example of an alkoxycarbonyl group having 2 to 7 carbon atoms, represented by $R^2$ and $R^3$ in the general formula (A), and a preferable specific example of an alkoxycarbonyl group also includes the same one.

As $R^{1a}$ and $R^{1b}$ in the general formula (A'-1) and $R^{1c}$ in the general formula (A'-2), an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an aryl group having 6 to 10 carbon atoms, in which a hydrogen atom may be substituted by a halogen atom, an alkyl group or a haloalkyl group; and an arylalkyl group having 7 to 15 carbon atoms, in which a hydrogen atom may be substituted by a halogen atom, an alkyl group or a haloalkyl group are more preferable, and among them, an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; and an aryl group having 6 to 10 carbon atoms, in which a hydrogen atom may be substituted by a halogen atom, an alkyl group or a haloalkyl group are further preferable.

As $R^{2a}$ and $R^{2b}$ in the general formula (A'-1) and $R^{2c}$ in the general formula (A'-2), a hydrogen atom and an alkyl group having 1 to 10 carbon atoms are more preferable, and among them, an alkyl group having 1 to 10 carbon atoms is further preferable.

As $R^{3a}$ and $R^{3b}$ in the general formula (A'-1) and $R^{3c}$ in the general formula (A'-2), a hydrogen atom and an alkyl group having 1 to 10 carbon atoms are more preferable, and among them, a hydrogen atom is further preferable.

As $R^{2a}$ and $R^{3a}$ in the general formula (A'-1), the one where at least either of $R^{2a}$ and $R^{3a}$ is a hydrogen atom is preferable.

As $R^{2b}$ and $R^{3b}$ in the general formula (A'-1), the one where at least either of $R^{2b}$ and $R^{3b}$ is a hydrogen atom is preferable.

As $R^{2c}$ and $R^{3c}$ in the general formula (A'-2), the one where at least either of $R^{2c}$ and $R^{3c}$ is a hydrogen atom is preferable.

$Z_a$ and $Z_b$ in the general formula (A'-1) and $Z_c$ in the general formula (A'-2) represent a sulfonyl group (—SO$_2$— group) or an alkoxyphosphoryl group (—P(O)OR$^{12}$— group) having 1 to 6 carbon atoms, and among them, a sulfonyl group (—SO$_2$— group) is more preferable.

A specific example of $R^{12}$ in an alkoxyphosphoryl group (—P(O)OR$^{12}$— group) having 1 to 6 carbon atoms, represented by $Z_a$ and $Z_b$ in the general formula (A'-1) and $Z_c$ in the general formula (A'-2), includes the same as a specific example of $R^{12}$ in an alkoxyphosphoryl group (—P(O)OR$^{12}$— group) having 1 to 6 carbon atoms, represented by Z in the general formula (A) and a preferable specific example of $R^{12}$ and a more preferable specific example of $R^{12}$ also include the same ones.

A specific example of an alkoxyphosphoryl group (—P(O)OR$^{12}$— group) having 1 to 6 carbon atoms, represented by $Z_a$ and $Z_b$ in the general formula (A'-1) and $Z_c$ in the general formula (A'-2), includes the same as a specific example of an alkoxyphosphoryl group having 1 to 6 carbon atoms, represented by Z in the general formula (A), and a preferable specific example of an alkoxyphosphoryl group and a more preferable specific example of an alkoxyphosphoryl group also include the same ones.

$R^4$ to $R^7$ and Z in the general formulae (A'-1) and (A'-2) are the same as $R^4$ to $R^7$ and Z in the general formula (A), and preferable ones and more preferable ones are also the same.

Among the compounds represented by the above-described general formula (A) of the present invention, the compound represented by the following general formula (A"-1), and the compound represented by the following general formula (A"-2) are included as more preferable ones. The compounds represented by the general formulae (A"-1) and (A"-2) are more preferable ones among the compounds represented by the general formula (A), in view of enabling to be produced easily and conveniently, and in very low cost from commercially available raw materials, and to provide an acid-generating agent with high general-purpose properties.

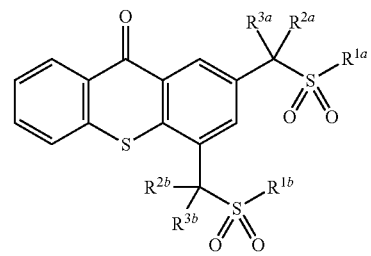

(A"-1)

(wherein $R^{1a}$, $R^{1b}$, $R^{2a}$, $R^{2b}$, $R^{3a}$, and $R^{3b}$ are the same as described above.)

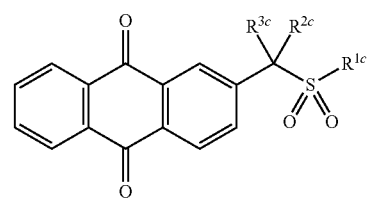

(A"-2)

(wherein $R^{1c}$, $R^{2c}$ and $R^{3c}$ are the same as described above.)

Among the compounds represented by the above-described general formula (A) of the present invention, the compound represented by the following general formula (A'''-1), and the compound represented by the following general formula (A'''-2) are included as further preferable ones. The compounds represented by the general formulae (A'''-1) and (A'''-2) are further preferable ones among the compounds represented by the general formula (A), in particular, in view of enabling to provide an acid-generating agent with high general-purpose properties.

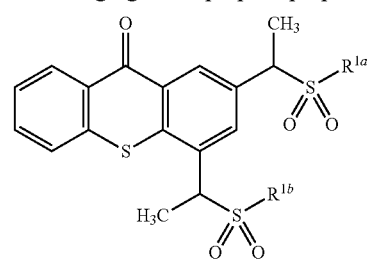

(A'''-1)

(wherein $R^{1a}$ and $R^{1b}$ are the same as described above.)

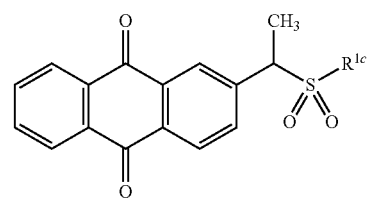

(A'''-2)

(wherein $R^{1c}$ is the same as described above.)

A specific example of the compound represented by the general formula (A) of the present invention includes, for example, compounds represented by the following formula (2), formula (3), formula (4), formula (5), and formula (6).

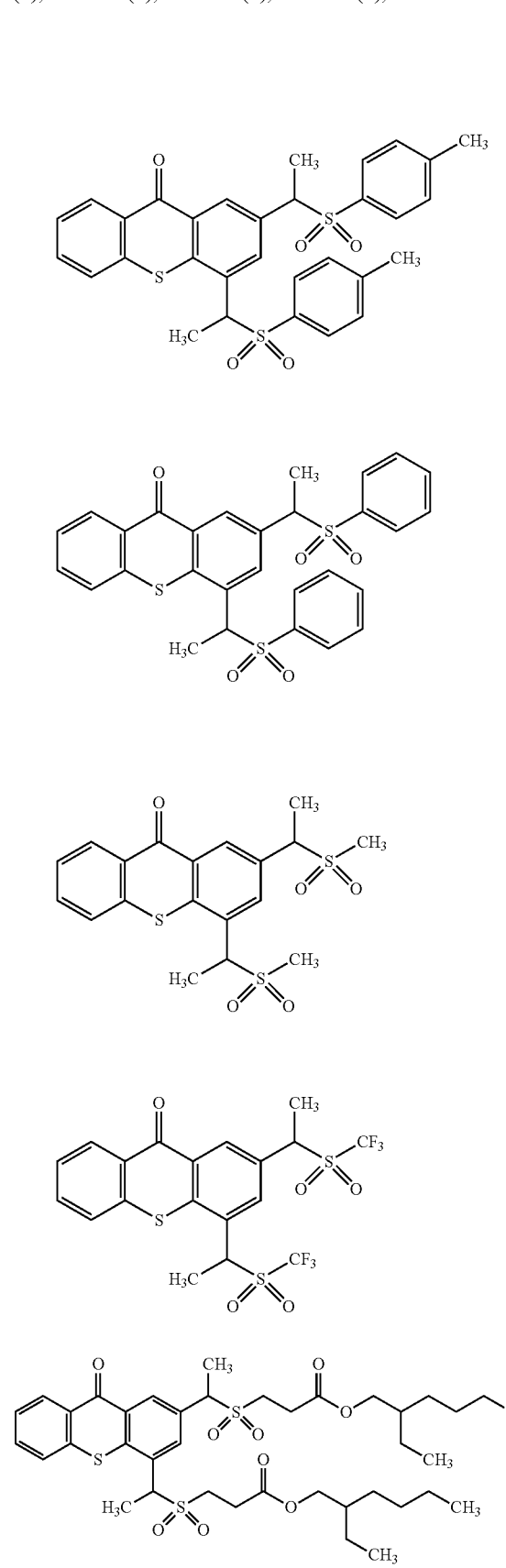

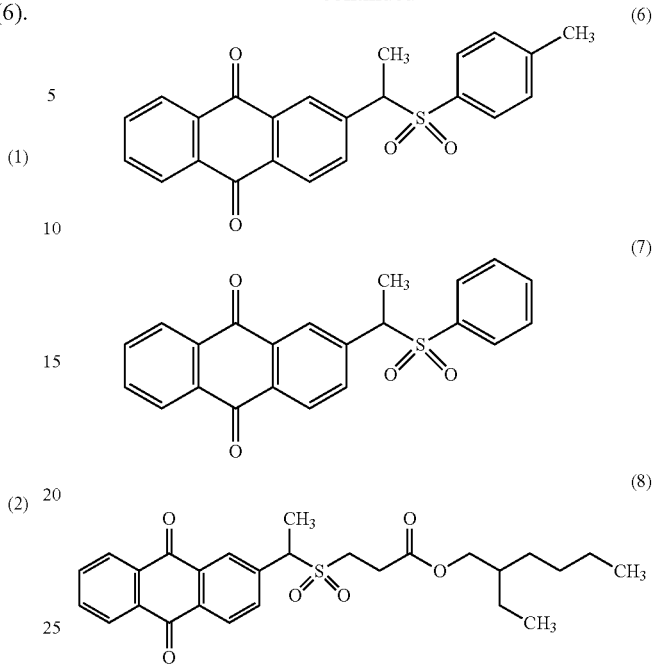

In the compound represented by the above-described general formula (A), the compound represented by the formula (1) corresponds to a compound in which n pieces of $R^1$ are a phenyl group which is an aryl group having 6 carbon atoms, having a methyl group as a substituent; n pieces of $R^2$ are a methyl group which is an alkyl group having one carbon atom; n pieces of $R^3$ are a hydrogen atom; all of $R^4$ to $R^7$ are a hydrogen atom; Y is a sulfur atom; n pieces of Z are a sulfonyl group; n is 2; and groups bundled by n are bonded at 2 position and 4 position.

In the compound represented by the above-described general formula (A), the compound represented by the formula (2) corresponds to a compound in which n pieces of $R^1$ are a phenyl group which is an aryl group having 6 carbon atoms; n pieces of $R^2$ are a methyl group which is an alkyl group having one carbon atom; n pieces of $R^3$ are a hydrogen atom; all of $R^4$ to $R^7$ are a hydrogen atom; Y is a sulfur atom; n pieces of Z are a sulfonyl group; n is 2; and groups bundled by n are bonded at 2 position and 4 position.

In the compound represented by the above-described general formula (A), the compound represented by the formula (3) corresponds a compound in which n pieces of $R^1$ are a methyl group which is an alkyl group having one carbon atom; n pieces of $R^2$ are a methyl group which is an alkyl group having one carbon atom; n pieces of $R^3$ are a hydrogen atom; all of $R^4$ to $R^7$ are a hydrogen atom; Y is a sulfur atom; n pieces of Z are a sulfonyl group; n is 2; and groups bundled by n are bonded at 2 position and at 4 position.

In the compound represented by the above-described general formula (A), the compound represented by the formula (4) corresponds to a compound in which n pieces of $R^1$ are a trifluoromethyl group which is a fluoroalkyl group having one carbon atom; n pieces of $R^2$ are a methyl group which is an alkyl group having one carbon atom; n pieces of $R^3$ are a hydrogen atom; all of $R^4$ to $R^7$ are a hydrogen atom; Y is a sulfur atom; n pieces of Z are a sulfonyl group; n is 2; and groups bundled by n are bonded at 2 position and 4 position.

In the compound represented by the above-described general formula (A), the compound represented by the formula (5) corresponds to a compound in which n pieces of $R^1$ are a 2-(2-ethylhexyloxycarbonyl)ethyl group which is an alkyl group having 11 carbon atoms which has a carbonyloxy group as a functional group in the chain; n pieces of $R^2$ are a methyl group which is an alkyl group having one carbon atom; n pieces of $R^3$ are a hydrogen atom; all of $R^4$ to $R^7$ are a hydrogen atom; Y is a sulfur atom; n pieces of Z are a sulfonyl group; n is 2; and groups bundled by n are bonded at 2 position and 4 position.

In the compound represented by the above-described general formula (A), the compound represented by the formula (6) corresponds to a compound in which n pieces of $R^1$ are a phenyl group, which is an aryl group having 6 carbon atoms, which has a methyl group as a substituent; n pieces of $R^2$ are a methyl group which is an alkyl group having one carbon atom; n pieces of $R^3$ are a hydrogen atom; all of $R^4$ to $R^7$ are a hydrogen atom; Y is a carbonyl group; n pieces of Z are a sulfonyl group; n is 1; and a group bundled by n is bonded at 2 position.

In the compound represented by the above-described general formula (A), the compound represented by the formula (7) corresponds to a compound in which n pieces of $R^1$ are a phenyl group which is an aryl group having 6 carbon atoms; n pieces of $R^2$ are a methyl group which is an alkyl group having one carbon atom; n pieces of $R^3$ are a hydrogen atom; all of $R^4$ to $R^7$ are a hydrogen atom; Y is a carbonyl group; n pieces of Z are a sulfonyl group; n is 1; and a group bundled by n is bonded at 2 position.

In the compound represented by the above-described general formula (A), the compound represented by the formula (8) corresponds to a compound in which n pieces of $R^1$ are a 2-(2-ethylhexyloxycarbonyl)ethyl group which is an alkyl group having 11 carbon atoms which has a carbonyloxy group as a functional group in the chain; n pieces of $R^2$ are a methyl group which is an alkyl group having one carbon atom; n pieces of $R^3$ are a hydrogen atom; all of $R^4$ to $R^7$ are a hydrogen atom; Y is a carbonyl group; n pieces of Z are a sulfonyl group; n is 1; and a group bundled by n is bonded at 2 position.

—A Production Method of the Compound Represented by the General Formula (A) of the Present Invention—

The compound represented by the above-described general formula (A) of the present invention can be produced by a method represented by, for example, the following scheme.

That is, [1]: among the compounds represented by the general formula (A), the compound in which Z is a sulfonyl group can be synthesized, after obtaining a compound represented by the general formula (II) by reacting, for example, a xanthene-9-one derivative, a thioxanthene-9-one derivative or an anthraquinone derivative represented by the general formula (I), with a halogenating agent, for example, N-bromosuccinimide under the presence of a radical initiator, for example, 2,2'-azobis(4-methoxy-2,4-dimethylvaleronitrile), by reacting the compound represented by the general formula (II) with a sulfinate salt represented by the general formula (III) or by reacting the compound represented by the general formula (II) with a thiol compound represented by the general formula (IV), subsequently, by oxidizing a resulting sulfide compound represented by the general formula (V). In addition, [2]: among the compounds represented by the general formula (A), the compound in which Z is a sulfonate group can be synthesized, after reacting a compound represented by the general formula (II) with a hydrogen sulfite salt represented by general formula (VI), by carrying out a halogenation reaction using, for example, thionyl chloride, subsequently, by carrying out a sulfonation reaction using an alcohol and a base. Furthermore, [3]: among the compounds represented by the general formula (A), the compound in which Z is an alkoxyphosphoryl group can be synthesized, after obtaining a compound represented by the general formula (II) by reacting, for example, a xanthene-9-one derivative, a thioxanthene-9-one derivative or an anthraquinone derivative represented by the general formula (I), with a halogenating agent, for example, N-bromosuccinimide under the presence of a radical initiator, for example, 2,2'-azobis(4-methoxy-2,4-dimethylvaleronitrile), by reacting the compound represented by the general formula (II) with a phosphite ester represented by the general formula (IX), subsequently, by reacting, for example, Grignard reagent. In addition, when a derivative represented by the general formula (I) is commercially unavailable, after carrying out, for example, an aromatic halogenation reaction for xanthene-9-one, thioxanthene-9-one or anthraquinone, by carrying out Buchwald-Hartwig cross-coupling reaction or Ulmann reaction, a derivative having a hetero-atom is synthesized, or after carrying out a carbon-increasing reaction with Heck reaction, Sonogashira reaction, by carrying out a reduction reaction using hydrogen gas, or the like, a derivative having a long chain alkyl group is synthesized. Then, these derivatives may be used.

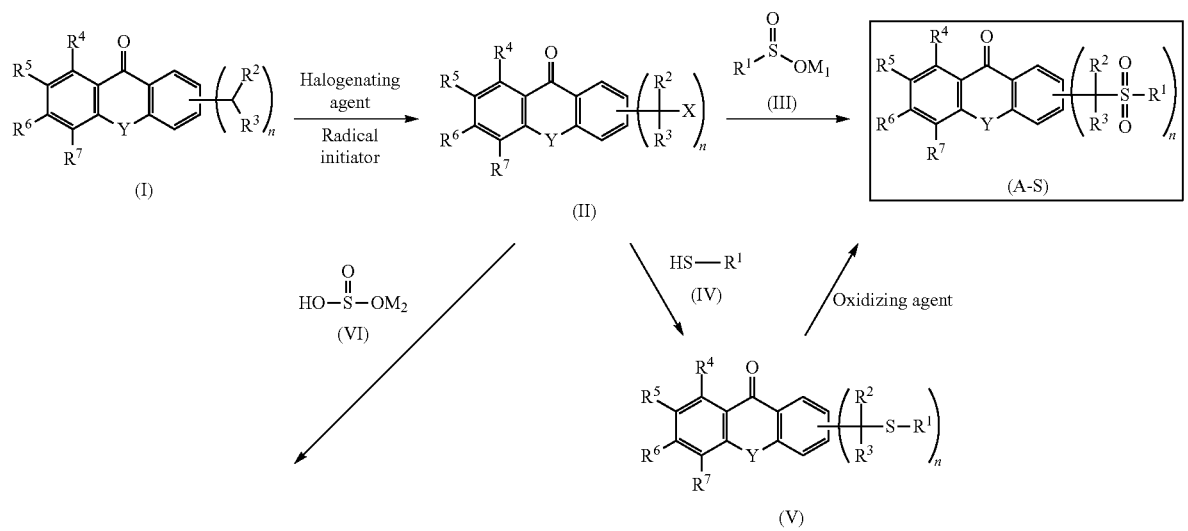

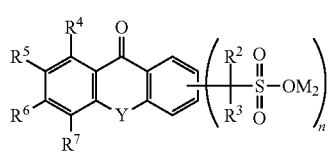 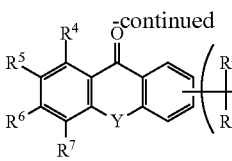 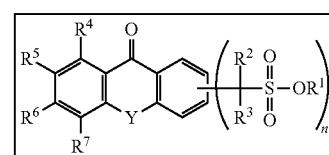

(VII) → (VIII) → (A-S)

(wherein X in the general formula (II) represents a halogen atom, $M_1$ in the general formula (III) represents an alkali metal atom, $M_2$ in the general formula (VI) represents an alkali metal atom or an ammonium group, and n pieces of $R^1$ to $R^3$, $R^4$ to $R^7$, Y and n are the same as described above.)

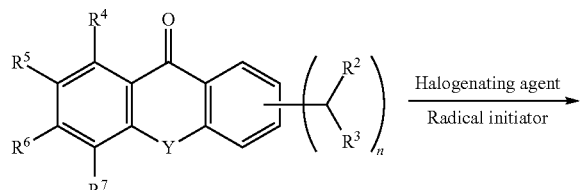

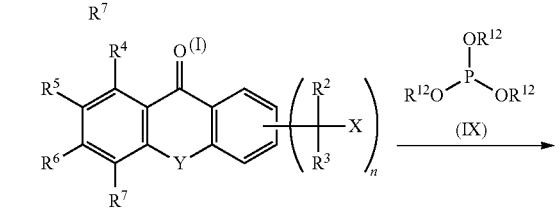

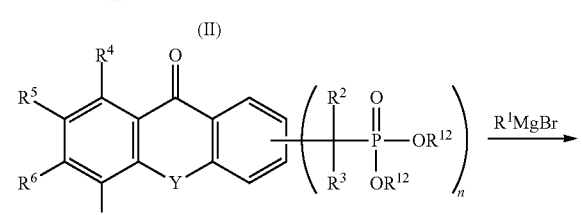

(wherein X in the general formula (II) represents a halogen atom, 3 pieces of $R^{12}$ each independently represent an alkyl group having 1 to 6 carbon atoms or an aryl group having 6 carbon atoms, and n pieces of $R^1$ to $R^3$, $R^4$ to $R^7$, Y and n are the same as described above.)

A halogen atom represented by X in the general formula (II) specifically includes, for example, a chlorine atom, a bromine atom, an iodine atom or the like, and among them, a bromine atom is preferable.

An alkali metal atom represented by $M_1$ in the general formula (III) and $M_2$ in the general formula (VI) specifically includes, for example, a lithium atom, a sodium atom, a potassium atom, a rubidium atom, a cesium atom or the like, and among them, a sodium atom is preferable.

An alkyl group having 1 to 6 carbon atoms, represented by $R^{12}$ in the general formula (VI), may be any of a straight chained, branched or cyclic group, and specifically includes, for example, a methyl group, an ethyl group, a n-propyl group, an isopropyl group, a n-butyl group, an isobutyl group, a sec-butyl group, a tert-butyl group, a cyclobutyl group, a n-pentyl group, an isopentyl group, a sec-pentyl group, a tert-pentyl group, a neopentyl group, a 2-methylbutyl group, a 1,2-dimethylpropyl group, a 1-ethylpropyl group, a cyclopentyl group, a n-hexyl group, an isohexyl group, a sec-hexyl group, a tert-hexyl group, a neohexyl group, a 2-methylpentyl group, a 1,2-dimethylbutyl group, a 2,3-dimethylbutyl group, a 1-ethylbutyl group, a cyclohexyl group or the like, and among them, a straight chained or branched an alkyl group having 1 to 4 carbon atoms, such as, for example, a methyl group, an ethyl group, a n-propyl group, an isopropyl group, a n-butyl group, an isobutyl group, a sec-butyl group and a tert-butyl group are preferable, and among them, an ethyl group, which is an alkyl group having 2 carbon atoms, is more preferable.

An aryl group having 6 carbon atoms, represented by $R^{12}$ in the general formula (VI), specifically includes an aryl group having 6 carbon atoms, such as, for example, a phenyl group or the like, and among them, a phenyl group, which is an aryl group having 6 carbon atoms, is preferable.

A specific example of a xanthene-9-one derivative represented by the general formula (I) in the production method of the compound represented by the general formula (A) of the present invention includes, for example, 1-methylxanthene-9-one, 2-methylxanthene-9-one, 3-methylxanthene-9-one, 4-methylxanthene-9-one, 1-ethylxanthene-9-one, 2-ethylxanthene-9-one, 3-ethylxanthene-9-one, 4-ethylxanthene-9-one, 1-propylxanthene-9-one, 2-propylxanthene-9-one, 3-propylxanthene-9-one, 4-propylxanthene-9-one, 1-butylxanthene-9-one, 2-butylxanthene-9-one, 3-butylxanthene-9-one, 4-butylxanthene-9-one, 1,3-dimethylxanthene-9-one, 2,4-dimethylxanthene-9-one, 1,3-diethylxanthene-9-one, 2,4-diethylxanthene-9-one, 1,3-dipropylxanthene-9-one, 2,4-dipropylxanthene-9-one, 1,3-dibutylxanthene-9-one, 2,4-dibutylxanthene-9-one or the like. It should be noted that, as for the xanthene-9-one derivative represented by the general formula (I), a commercially available one, or the one synthesized as appropriate by the above-described method known per se may be used.

A specific example of a thioxanthene-9-one derivative represented by the general formula (I) in the production method of the compound represented by the general formula (A) of the present invention includes, for example, 1-methylthioxanthene-9-one, 2-methylthioxanthene-9-one, 3-methylthioxanthene-9-one, 4-methylthioxanthene-9-one, 1-ethylthioxanthene-9-one, 2-ethylthioxanthene-9-one, 3-ethylthioxanthene-9-one, 4-ethylthioxanthene-9-one, 1-propylthioxanthene-9-one, 2-propylthioxanthene-9-one, 3-propylthioxanthene-9-one, 4-propylthioxanthene-9-one, 1-isopropylthioxanthene-9-one, 2-isopropylthioxanthene-9-one, 3-isopropylthioxanthene-9-one, 4-isopropylthioxanthene-9-one, 1-butylthioxanthene-9-one, 2-butylthioxanthene-9-one, 3-butylthioxanthene-9-one, 4-butylthioxanthene-9-one, 1,3-dimethylthioxanthene-9-one, 2,4-dimethylthioxanthene-9-one, 1,3-diethylthioxanthene-9-one, 2,4-diethylthioxanthene-9-one, 1,3-dipropylthioxanthene-9-one, 2,4-dipropylthioxanthene-9-one, 1,3-dibutylthioxanthene-9-one, 2,4-dibutylthioxanthene-9-one or the like. It should be noted that, as for the thioxanthene-9-one derivative represented by the general formula (I), a commercially available one, or the one synthesized as appropriate by the above-described method known per se may be used.

A specific example of an anthraquinone derivative represented by the general formula (I) in the production method of the compound represented by the general formula (A) of the present invention includes, for example, 1-methylanthraquinone, 2-methylanthraquinone, 3-methylanthraquinone, 4-methylanthraquinone, 1-ethylanthraquinone, 2-ethylanthraquinone, 3-ethylanthraquinone, 4-ethylanthraquinone, 1-propylanthraquinone, 2-propylanthraquinone, 3-propylanthraquinone, 4-propylanthraquinone, 1-butylanthraquinone, 2-butylanthraquinone, 3-butylanthraquinone, 4-butylanthraquinone, 1,3-dimethylanthraquinone, 2,4-dimethylanthraquinone, 1,3-diethylanthraquinone, 2,4-diethylanthraquinone, 1,3-dipropylanthraquinone, 2,4-dipropylanthraquinone, 1,3-dibutylanthraquinone, 2,4-dibutylanthraquinone or the like. It should be noted that, as for the anthraquinone derivative represented by the general formula (I), a commercially available one, or the one synthesized as appropriate by the above-described method known per se may be used.

A specific example of a sulfinate salt represented by the general formula (III) in the production method of the compound represented by the general formula (A) of the present invention includes, for example, an aromatic sulfinate salt, such as, for example, an aryl sulfinate salt or the like, such as, for example, lithium benzenesulfinate, sodium benzenesulfinate, potassium benzenesulfinate, lithium o-toluenesulfinate, sodium o-toluenesulfinate, potassium o-toluenesulfinate, lithium m-toluenesulfinate, sodium m-toluenesulfinate, potassium m-toluenesulfinate, lithium p-toluenesulfinate, sodium p-toluenesulfinate, potassium p-toluenesulfinate, lithium o-ethylbenzenesulfinate, sodium o-ethylbenzenesulfinate, potassium o-ethylbenzenesulfinate, lithium m-ethylbenzenesulfinate, sodium m-ethylbenzenesulfinate, potassium m-ethylbenzenesulfinate, lithium p-ethylbenzenesulfinate, sodium p-ethylbenzenesulfinate, potassium p-ethylbenzenesulfinate, lithium 2,4-xylenesulfinate, sodium 2,4-xylenesulfinate, potassium 2,4-xylenesulfinate, lithium 2,6-xylenesulfinate, sodium 2,6-xylenesulfinate, potassium 2,6-xylenesulfinate, lithium pentafluorobenzenesulfinate, sodium pentafluorobenzenesulfinate, potassium pentafluorobenzenesulfinate or the like; for example, an aliphatic sulfinate salt, such as, for example, an alkyl sulfinate salt, such as, for example, lithium methanesulfinate, sodium methanesulfinate, potassium methanesulfinate, lithium ethanesulfinate, sodium ethanesulfinate, potassium ethanesulfinate, lithium propanesulfinate, sodium propanesulfinate, potassium propanesulfinate, lithium butanesulfinate, sodium butanesulfinate, potassium butanesulfinate or the like; and a haloalkyl sulfinate salt, such as, for example, lithium trifluoromethanesulfinate, sodium trifluoromethanesulfinate, potassium trifluoromethanesulfinate, lithium pentafluoroethanesulfinate, sodium pentafluoroethanesulfinate, potassium pentafluoroethanesulfinate, lithium heptafluoropropanesulfinate, sodium heptafluoropropanesulfinate, potassium heptafluoropropanesulfinate, lithium nonafluorobutanesulfinate, sodium nonafluorobutanesulfinate, potassium nonafluorobutanesulfinate or the like. It should be noted that, as for the sulfinate salt represented by the general formula (III), a commercially available one, or the one synthesized as appropriate by the above-described method known per se may be used.

A specific example of a thiol compound represented by the general formula (IV) in the production method of the compound represented by the general formula (A) of the present invention includes, for example, ethylmercaptan, isopropylmercaptan, tert-butylmercaptan, 2-ethylhexyl 3-mercaptopropionate or the like. It should be noted that, as for the thiol compound, a commercially available one, or the one synthesized as appropriate by the above-described method known per se may be used.

A specific example of a hydrogen sulfite salt represented by the general formula (VI) in the production method of the compound represented by the general formula (A) of the present invention includes, for example, lithium hydrogen sulfite, sodium hydrogen sulfite, potassium hydrogen sulfite, ammonium hydrogen sulfite or the like. It should be noted that, as for the hydrogen sulfite salt represented by the general formula (VI), a commercially available one, or the one synthesized as appropriate by the above-described method known per se may be used.

A specific example of an alcohol to be used in the sulfonation reaction in the production method of the compound represented by the general formula (A) of the present invention includes, for example, methanol, ethanol, propanol, isopropanol, phenol or the like. It should be noted that as for the alcohol, a commercially available one, or the one synthesized as appropriate by a method known per se may be used.

A specific example of a phosphite ester represented by the general formula (IX) in the production method of the compound represented by the general formula (A) of the present invention includes, for example, trimethyl phosphite, triethyl phosphite, tripropyl phosphite, triisopropyl phosphite, triphenyl phosphite or the like. It should be noted that, as for the phosphite ester represented by the general formula (IX), a commercially available one or the one synthesized as appropriate by the above-described method known per se may be used.

A specific example of the above-described Grignard reagent in the production method of the compound represented by the general formula (A) of the present invention includes, for example, methylmagnesium bromide, ethylmagnesium bromide, propylmagnesium bromide, isopropylmagnesium bromide, phenylmagnesium bromide or the like. It should be noted that, as for the Grignard reagent, a commercially available one or the one synthesized as appropriate by the above-described method known per se may be used.

In the production method of the compound represented by the general formula (A) of the present invention, use amount of the sulfinate salt represented by the above-described general formula (III) is not especially limited, as long as being practical amount, and it is, for example, usually 0.8 to 10 equivalents, preferably 0.9 to 5 equivalents, and more preferably 0.95 to 2 equivalents, relative to mole number of the halogen atom represented by X in the compound represented by the above-described general formula (II). When use amount of the above-described sulfinate salt is extremely low, yield of the compound represented by the above-described general formula (A-S) tends to reduce. Meanwhile, when use amount of the above-described sulfinate salt is very high, problems of impairing economic performance occur.

In the production method of the compound represented by the general formula (A) of the present invention, use amount of the thiol compound represented by the above general formula (IV) is not especially limited, as long as being practical amount, and it is, for example, usually 0.8 to 10 equivalents, preferably 0.9 to 5 equivalents, and more preferably 0.95 to 2 equivalents, relative to mole number of the halogen atom represented by X in the compound represented by the above-described general formula (II). When use amount of the above-described thiol compound is extremely low, yield of the sulfide compound represented by the above-described general formula (V) tends to reduce. Meanwhile, when use amount of the above-described thiol compound is very high, problems of impairing economic performance occur.

In the production method of the compound represented by the general formula (A) of the present invention, use amount of the hydrogen sulfite salt represented by the above-described general formula (VI) is not especially limited, as long as being practical amount, and it is, for example, usually 0.8 to 10 equivalents, preferably 0.9 to 5 equivalents, and more preferably 0.95 to 2 equivalents, relative to mole number of the halogen atom represented by X in the compound represented by the above-described general formula (II). When use amount of the above-described hydrogen sulfite salt is extremely low, yield of the compound represented by the above-described general formula (VII) tends to reduce. Meanwhile, when use amount of the above-described hydrogen sulfite salt is very high, problems of impairing economic performance occur.

In the production method of the compound represented by the general formula (A) of the present invention, use amount of the above-described alcohol is not especially limited, as long as being practical amount, and it is, for example, usually 0.8 to 10 equivalents, preferably 0.9 to 5 equivalents, and more preferably 0.95 to 2 equivalents, relative to mole number of the chlorine atom in the compound represented by the above-described general formula (VIII). When use amount of the above-described alcohol is extremely low, yield of the compound represented by the above-described general formula (A-S) tends to reduce. Meanwhile, when use amount of the above-described alcohol is very high, problems of impairing economic performance occur.

In the production method of the compound represented by the general formula (A) of the present invention, use amount of the phosphite ester represented by the above-described general formula (IX) is not especially limited, as long as being practical amount, and it is, for example, usually 0.8 to 10 equivalents, preferably 0.9 to 5 equivalents, and more preferably 0.95 to 2 equivalents, relative to mole number of the halogen atom represented by X in the compound represented by the above-described general formula (II). When use amount of the above-described phosphite ester is extremely low, yield of the compound represented by the above-described general formula (X) tends to reduce. Meanwhile, when use amount of the above-described phosphite ester is very high, problems of impairing economic performance occur.

In the production method of the compound represented by the general formula (A) of the present invention, use amount of the above-described Grignard agent is not especially limited, as long as being practical amount, and it is, for example, usually 0.8 to 10 equivalents, preferably 0.9 to 5 equivalents, and more preferably 0.95 to 2 equivalents, relative to mole number of the —$OR^{12}$ group in the compound represented by the above-described general formula (X). When use amount of the above-described Grignard agent is extremely low, yield of the compound represented by the above-described general formula (A-P) tends to reduce. Meanwhile, when use amount of the above-described Grignard agent is very high, problems of impairing economic performance occur.

A series of reactions, in the production method of the compound represented by the general formula (A) of the present invention, may be carried out without a solvent or in an organic solvent. A specific example of the organic solvent is not especially limited, as long as it is an organic solvent which does not react with the xanthene-9-one derivative, the thioxanthene-9-one derivative or the anthraquinone derivative, represented by the above-described general formula (I), the compound represented by the general formula (II), the sulfinate salt represented by the general formula (III), the thiol compound represented by the general formula (IV), the sulfide compound represented by the general formula (V), the hydrogen sulfite salt represented by the general formula (VI), the compounds represented by general formulae (VII) and (VIII), the alcohol used in the sulfonation reaction, the phosphite ester represented by the general formula (IX), the compound represented by the general formula (X) and the Grignard reagent, and includes, for example, an aliphatic hydrocarbon type solvent, such as, for example, hexane, heptane, octane or the like; an aromatic hydrocarbon type solvent, such as, for example, benzene, toluene, xylene or the like; a halogen type solvent, such as, for example, dichloromethane, trichloromethane (chloroform), tetrachloromethane (carbon tetrachloride) or the like; an ether type solvent, such as, for example, diethyl ether, diisopropyl ether, methyl tert-butyl ether, cyclopentyl methyl ether, tetrahydrofuran, 2-methyltetrahydrofuran, 1,4-dioxane or the like; a glycol ether type solvent, such as, for example, ethylene glycol dimethyl ether, propylene glycol dimethyl ether, ethylene glycol diethyl ether, propylene glycol diethyl ether, diethylene glycol dimethyl ether, dipropylene glycol dimethyl ether, dipropylene glycol diethyl ether or the like; a glycol ether acetate type solvent, such as, for example, ethylene glycol monoethyl ether acetate, diethylene glycol monoethyl ether acetate, diethylene glycol monobutyl ether acetate, propylene glycol monomethyl ether acetate, propylene glycol monoethyl ether acetate, dipropylene glycol monomethyl ether acetate, dipropylene glycol monoethyl ether acetate or the like; a ketone type solvent, such as, for example, 2-propanone (acetone), 2-butanone (ethyl methyl ketone), 4-methyl-2-pentanone (methyl isobutyl ketone) or the like; an ester type solvent, such as, for example, ethyl acetate, n-propyl acetate, isopropyl acetate, isobutyl acetate, sec-butyl acetate, tert-butyl acetate, ethyl butyrate, isoamyl butyrate or the like; an amide type solvent, such as, for example, N, N-dimethylformamide, N, N-dimethylacetamide, 1-methyl-2-pyrrolidinone (N-methylpyrrolidone), 1,3-dimethyl-2-imidazolidinone (dimethylethylene urea) or the like; a nitrile type solvent, such as, for example, acetonitrile or the like. It should be noted that, as for the organic solvent, one kind of the organic solvent may be used alone, or two or more kinds of the organic solvents may be used in combination. In addition, as for the organic solvent, commercially available one may be used.

Use amount of the above-described organic solvent is not especially limited, as long as being practical amount, and it is, for example, usually 0.01 to 500 mL, and preferably 0.1 to 100 mL, relative to 1 mmol of the xanthene-9-one derivative, the thioxanthene-9-one derivative or the anthraquinone derivative, represented by the general formula (I), the compound represented by the general formula (II), the sulfide compound represented by the general formula (V), and the compounds represented by the general formulae (VII), (VIII) and (X).

It is desirable that a series of reactions, in the production method of the compound represented by the general formula (A) of the present invention, is carried out under the following conditions (reaction temperature, pressure and reaction time).

Temperature in a series of reactions in the production method of the compound represented by the general formula (A) of the present invention is not especially limited, as long as the series of reactions can be carried out without any delay, and it is, for example, usually 0 to 180° C.

Pressure in a series of reactions in the production method of the compound represented by the general formula (A) of the present invention is not especially limited, as long as the series of reactions can be carried out without any delay, and it is, for example, usually normal pressures.

Reaction time during a series of reaction, in the production method of the compound represented by the general formula (A) of the present invention, may be influenced by use amount of the sulfinate salt represented by the general formula (III), the thiol compound represented by the general formula (IV), the hydrogen sulfite salt represented by the general formula (VI), the alcohol used in the sulfonation reaction, the phosphite ester represented by the general formula (IX) and the Grignard reagent, relative to reactive raw materials, such as, for example, the xanthene-9-one derivative, the thioxanthene-9-one derivative or the anthraquinone derivative, represented by the general formula (I), the compound represented by the general formula (II), the sulfide compound represented by the general formula (V), and the compounds represented by the general formulae (VII), (VIII) and (X); the presence or absence of the organic solvent and the kind thereof; reaction temperature; pressure during the reaction or the like. Consequently, desirable reaction time cannot be said unconditionally, but it is, for example, usually 1 minute to 24 hours, and preferably 3 minutes to 12 hours.

A series of products after the reaction, in the production method of the compound represented by the general formula (A) of the present invention, can be isolated by a general post-treatment procedure and purification procedure, usually carried out in this field. A specific example of the isolation method includes a method for extraction of reaction solution, as needed, then concentration of extraction liquid under reduced pressure, and filtration of a resulting crystal, or the like. In addition, the products may be isolated by filtration or washing of reaction solution, as needed, by carrying out recrystallization, distillation, column chromatography or the like of a residue obtained by concentration of reaction solution.

—An Acid- and Radical-generating Agent of the Present Invention—

The acid- and radical-generating agent of the present invention is the one comprising the compound represented by the above-described general formula (A) of the present invention.

The acid- and radical-generating agent of the present invention generates an acid and a radical by irradiation of an active energy ray, such as, for example, an electromagnetic wave having a wavelength of a visible light region (visible rays); an electromagnetic wave having a wavelength of a non-visible light region, such as, for example, an electromagnetic wave having a wavelength of an ultraviolet light region (UV rays), an electromagnetic wave having a wavelength of an infrared light region (infrared rays), X-rays or the like. Among them, in particular, the acid- and radical-generating agent of the present invention is the one generating an acid and a radical by irradiation of an active energy ray having a wavelength of around 300 to 450 nm, which is a near-ultraviolet light region and a visible light region, and also generating an acid and a radical even by irradiation of an active energy ray (h-ray) having a wavelength of 405 nm. Because the acid- and radical-generating agent of the present invention has an absorption wavelength region where molar absorption coefficient is high, in such a region, it is capable of generating an acid and a radical efficiently. In this way, because the compound represented by the general formula (A) of the present invention is capable of generating both an acid and a radical, the compound can be used in any purposes as an acid-generating agent, a radical-generating agent, or both of an acid-generating agent and a radical-generating agent, so as to usage thereof. It should be noted that the acid- and radical-generating agent of the present invention is the one generating an acid and a radical by irradiation of an active energy ray, but it should not exclude generation of an acid by providing energy other than photo energy, for example, heating or the like.

It is preferable that the acid- and radical-generating agent of the present invention has a temperature over 200° C., when 5% weight is decreased from the initial weight by heating (hereafter, it may be abbreviated as 5% weight decrease temperature). In preparing a cured film using the acid- and radical-generating agent of the present invention, baking or the like may be carried out, and when 5% weight decrease temperature of the acid- and radical-generating agent of the present invention is high, it provides high general-purpose properties, such as baking temperature can be set high, deterioration of contrast between an exposed area (a cured area) and a non-exposed area (a non-cured area) can be suppressed, as well as residue of an organic solvent after baking can be reduced as low as possible and the like, and is thus preferable.

When the acid- and radical-generating agent of the present invention is used as an acid-generating agent, it can be used, for example, as an acid-generating agent for a resist material. In a negative type resist composition or a positive type resist composition utilizing, for example, the acid-generating agent of the present invention, as for an alkali-soluble resin, a solubility-inhibiting resin which becomes alkali-soluble by chemical change under the presence of an acid, a cross-linking type compound which makes the alkali-soluble resin alkali-insoluble by chemical change caused by action of an acid and the like, a conventionally known one can be used. In addition, the acid-generating agent of the present invention is capable of forming a cured film, since an acid generated from the acid-generating agent of the present invention can promote a hydrolysis reaction and a dehydration condensation reaction under the presence of a metal alkoxide. A specific example of such a resin and a compound includes the one described in, for example, WO 2003/045915, JP-A-2013-1821, JP-A-2013-100480 or the like.

When the acid- and radical-generating agent of the present invention is used as a radical-generating agent, it can be used, for example, as a radical-generating agent for a coating material. In a radical reactive composition utilizing, for example, the radical-generating agent of the present invention, as for a radical reactive compound which progresses a polymerization reaction caused by action of a radical, such as, for example, a compound having at least one polymerizable ethylenic unsaturated bond, a conventionally known one can be used. In addition, the radical-generating agent of the present invention is capable of forming a polythioether due to progressing of sequential polymerization by irradiation of an active energy ray under the presence of a compound having, for example, a thiol group and a carbon-carbon double bond. A specific example of such a compound includes in addition to the one described in, for example, JP-A-2014-28938, JP-A-2007-291313, such as a maleimide derivative, such as, for example, N,N'-1,3-phenylene dimaleimide, N,N'-1,4-phenylene dimaleimide, N,N',N''-1,3,5-phenylene trimaleimide, 4,4'-bismaleimide diphenylmethane, 1,2-bismaleimide ethane, 1,6-bismaleimide hexane, bis(3-ethyl-5-methyl-4-maleimidephenyl)methane or the like; an olefin compound having two or more double bonds, such as, for example, 1,3-butadiene, 1,3-pentadiene, 1,4-pentadiene, isoprene, 1,4-hexadiene, 1,5-hexadiene, 2,4-hexadiene, 2-methyl-1,4-pentadiene, 2,3-dimethyl-1,3-butadiene, 1,4-heptadiene, 1,5-heptadiene, 1,6-heptadiene, 2-methyl-1,5-hexadiene, 1,7-octadiene, 2,5-dimethyl-1,5-hexadiene, 1,5-cyclooctadiene, 1,8-nonadiene, 1,9-decadiene, 1,10-undecadiene, 1,11-dodecadiene, 1,12-tridecadiene, 1,13-tetradecadiene, tetraallyloxyethane, 1,3-divinylbenzene, 1,4-divinylbenzene, 1,3,5-trivinylbenzene, 1,3-diisopropenylbenzene, 1,4-diisopropenylbenzene, 1,3,5-triisopropenylbenzene, 3,3'-divinylbiphenyl, 3,4'-divinylbiphenyl, 4,4'-divinylbiphenyl, 4,4'-diisopropenylbiphenyl, 2,6-diisopropenylnaphthalene; a compound having two allyl groups, such as, for example, diethylene glycol diallyl ether, diallyl hexahydrophthalate, diallyl chlorendate, 1,2-bis(vinylphenyl)ethane or the like; a compound having three allyl groups, such as, for example, triallyl trimellitate or the like; a compound having four or more allyl groups, such as, for example, tetraallyl pyromellitate or the like.

When the acid- and radical-generating agent of the present invention is used as an acid-generating agent, a contained amount of the acid- and radical-generating agent of the present invention in a composition, such as, for example, a resist composition or the like, is not especially limited, as long as being practical amount, and it is, for example, usually 1 to 30% by weight, and preferably 3 to 20% by weight, relative to total amount of the resist composition.

When the acid- and radical-generating agent of the present invention is used as a radical-generating agent, a contained amount of the acid- and radical-generating agent of the present invention in a composition, such as, for example, a radical reactive composition or the like, is not especially limited, as long as being practical amount, and it is, for example, usually 5 to 0.01% by weight, and preferably 1 to 0.5% by weight, relative to total amount of the radical reactive composition.

—A Method for Generating an Acid and a Radical of the Present Invention—

The method for generating an acid and a radical of the present invention is the one characterized by irradiation of an active energy ray, such as, for example, an electromagnetic wave having a wavelength of a visible light region (visible rays); an electromagnetic wave having a wavelength of a non-visible light region, such as, for example, an electromagnetic wave having a wavelength of an ultraviolet light region (UV rays), an electromagnetic wave having a wavelength of an infrared light region (infrared rays), X-rays or the like, onto the compound represented by the general formula (A) of the present invention.

The method for generating an acid and a radical of the present invention is, in more specifically, a method for generating an acid and a radical by irradiation of an active energy ray having a wavelength of around 200 to 650 nm, and preferably around 300 to 450 nm, which is a near-ultraviolet light region and a visible light region, and also a method which is capable of generating an acid and a radical by irradiation of an active energy ray having a wavelength of 405 nm (h-ray), among the wavelength regions. In addition, the method for generating an acid and a radical of the present invention is a method enabling generation of an acid and a radical efficiently, by irradiation of an active energy ray having an exposure intensity of usually 0.1 to 100 mW/cm$^2$, and preferably 1.0 to 50 mW/cm$^2$, among the active energy rays of the above-described wavelength regions, for an irradiation time of 0.01 to 1000 seconds, and preferably 0.1 to 300 seconds.

EXAMPLES

The present invention will be explained specifically below based on Examples and Comparative Examples, however, the present invention should not be limited to these Examples.

Synthetic Example 1

Synthesis of 2,4-bis(1-bromoethyl)thioxanthene-9-one

Into 300 mL of ethyl acetate dissolved with 26.8 g of 2,4-diethylthioxanthene-9-one (100 mmol; produced by Wako Pure Chemical Industries, Ltd.), 19.6 g of N-bromosuccinimide (110 mmol; produced by Wako Pure Chemical Industries, Ltd.) and 1.54 g of 2,2'-azobis(4-methoxy-2,4-dimethylvaleronitrile) (5.0 mmol; produced by Wako Pure Chemical Industries, Ltd.) were added, and the resulting solution was stirred at 45° C. for 30 minutes. Then, after the reaction solution was once cooled to room temperature, 19.6 g of N-bromosuccinimide (110 mmol; produced by Wako Pure Chemical Industries, Ltd.) and 1.54 g of 2,2'-azobis(4-methoxy-2,4-dimethylvaleronitrile) (5.0 mmol; produced by Wako Pure Chemical Industries, Ltd.) were added to the reaction solution, and the resulting solution was stirred at 45° C. for 1 hour. After completion of the reaction, methanol was added to the reaction solution, which was cooled to 5° C. and solvent was removed from the resulting crystal to obtain 28.9 g of 2,4-bis(1-bromoethyl)thioxanthene-9-one (pale yellow powder, yield: 68%). Measurement results of $^1$H-NMR and a structural formula of 2,4-bis(1-bromoethyl)thioxanthene-9-one are shown below.

$^1$H-NMR (400 MHz, CDCl$_3$) δ (ppm): 2.14 (3H, d), 2.22 (3H, d), 5.33 (1H, q), 5.62 (1H, q), 7.51 (1H, t), 7.62-7.69 (2H, m), 8.00 (1H, d), 8.57 (1H, d), 8.68 (1H, d).

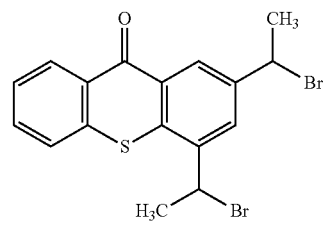 [SMILES: CC(Br)c1cc(C(C)Br)c2sc3ccccc3c(=O)c2c1]

Example 1

Synthesis of 2,4-bis(1-toluenesulfonylethyl)thioxanthene-9-one (the Compound Represented by the Formula (1))

4.26 g of 2,4-bis(1-bromoethyl)thioxanthene-9-one (10.0 mmol; produced by Wako Pure Chemical Industries, Ltd.)

obtained in Synthetic Example 1 and 5.0 g of sodium p-toluenesulfinate tetrahydrate (20.0 mmol; produced by Wako Pure Chemical Industries, Ltd.) were dissolved into 20 mL of dimethylformamide (DMF), and the resulting solution was stirred at room temperature for 1 hour. After completion of the reaction, water was added to the reaction solution, a precipitate formed by the addition of water was filtrated and the obtained filtrated residue was recrystallized in dioxane to obtain 0.84 g of 2,4-bis(1-toluenesulfonylethyl)thioxanthene-9-one (pale yellow powder, yield: 19%). Measurement results of $^1$H-NMR and a structural formula of 2,4-bis(1-toluenesulfonylethyl)thioxanthene-9-one are shown below.

$^1$H-NMR (400 MHz, CDCl$_3$) δ (ppm): 1.63 (3H, d), 1.82 (3H, d), 2.28 (3H, s), 2.38 (3H, s), 4.37 (1H, q), 4.81 (1H, q), 7.17-7.26 (4H, m), 7.48-7.63 (7H, m), 7.74 (1H, s), 8.41 (1H, s), 8.51 (1H, s).

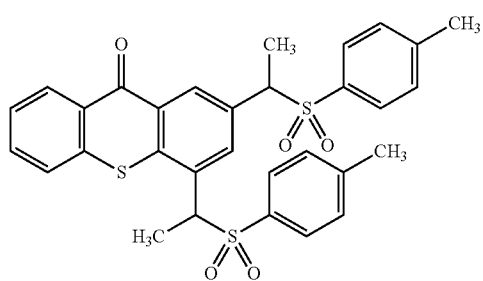

(1)

Example 2

Synthesis of 2,4-bis(1-benzenesulfonylethyl)thioxanthene-9-one (the Compound Represented by the Formula (2))

1.0 g of 2,4-bis(1-bromoethyl)thioxanthene-9-one (2.3 mmol; produced by Wako Pure Chemical Industries, Ltd.) obtained in Synthetic Example 1 and 1.0 g of sodium benzenesulfinate dihydrate (5.0 mmol; produced by Wako Pure Chemical Industries, Ltd.) were dissolved into 20 mL of dimethylformamide (DMF), and the resulting solution was stirred at room temperature for 4 hours. After completion of the reaction, water was added to the reaction solution, which was extracted with chloroform, and the resulting organic layer was washed with water. The organic layer after washing was concentrated under reduced pressure to obtain 1.21 g of a crude product (pale yellow powder). The crude product was purified by recrystallization using ethyl acetate/isopropanol to obtain 0.36 g of 2,4-bis(1-benzenesulfonylethyl)thioxanthene-9-one (pale yellow powder, yield: 29%). Measurement results of $^1$H-NMR and a structural formula of 2,4-bis(1-benzenesulfonylethyl)thioxanthene-9-one are shown below.

$^1$H-NMR (400 MHz, CDCl$_3$) δ (ppm): 1.60 (3H, d), 1.84 (3H, d), 4.41 (1H, q), 4.83 (1H, q), 7.26-7.77 (14H, m), 8.43 (1H, s), 8.50 (1H, d).

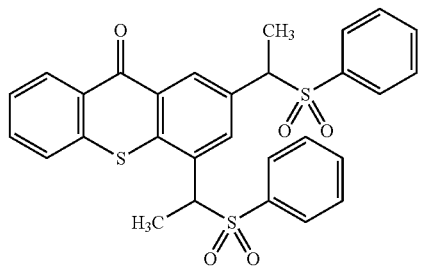

(2)

Example 3

Synthesis of 2,4-bis(1-methanesulfonylethyl)thioxanthene-9-one (the Compound Represented by the Formula (3))

2.1 g of 2,4-bis(1-bromoethyl)thioxanthene-9-one (5.0 mmol; produced by Wako Pure Chemical Industries, Ltd.) obtained in Synthetic Example 1 and 1.12 g of sodium methanesulfinate (11.0 mmol; produced by Wako Pure Chemical Industries, Ltd.) were dissolved into 10 mL of dimethylformamide (DMF), and the resulting solution was stirred at 70° C. for 4 hours. After completion of the reaction, water was added to the reaction solution, a precipitate formed by the addition of water was filtrated and the obtained filtrated residue was washed with toluene to obtain 0.78 g of 2,4-bis(1-methanesulfonylethyl)thioxanthene-9-one (pale yellow powder, yield: 37%). Measurement results of $^1$H-NMR and a structural formula of 2,4-bis(1-methanesulfonylethyl)thioxanthene-9-one are shown below.

$^1$H-NMR (400 MHz, CDCl$_3$) δ (ppm): 1.91-1.93 (6H, m), 2.76 (3H, s), 2.82 (3H, s), 4.39 (1H, q), 4.88 (1H, q), 7.56 (1H, t), 7.64 (1H, d), 7.69 (1H, t), 8.07 (1H, s), 8.59 (1H, d), 8.72 (1H, s).

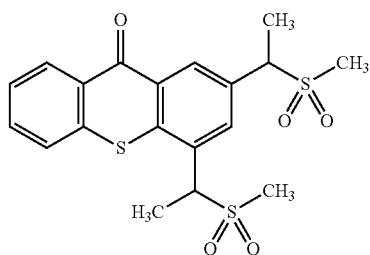

(3)

Example 4

Synthesis of 2,4-bis(1-trifluoromethanesulfonylethyl)thioxanthene-9-one (the Compound Represented by the Formula (4))

2.1 g of 2,4-bis(1-bromoethyl)thioxanthene-9-one (5.0 mmol; produced by Wako Pure Chemical Industries, Ltd.) obtained in Synthetic Example 1 and 1.7 g of sodium trifluoromethanesulfinate (11.0 mmol; produced by Wako Pure Chemical Industries, Ltd.) were dissolved into 10 mL of dimethylformamide (DMF), and the resulting solution was stirred at 80° C. for 4 hours. After completion of the reaction, water was added to the reaction solution, a precipitate formed by the addition of water was filtrated and the obtained filtrated residue was purified using a silica gel column chromatography (developing solvent: ethyl acetate/hexane) to obtain 0.6 g of 2,4-bis(1-trifluoromethanesulfonylethyl)thioxanthene-9-one (pale yellow powder, yield: 6%). Measurement results of $^1$H-NMR and a structural formula of 2,4-bis(1-trifluoromethanesulfonylethyl)thioxanthene-9-one are shown below.

$^1$H-NMR (400 MHz, CDCl$_3$) δ (ppm): 1.97 (3H, d), 2.04 (3H, d), 4.74 (1H, q), 5.24 (1H, q), 7.56-8.07 (4H, m), 8.58-8.82 (2H, m).

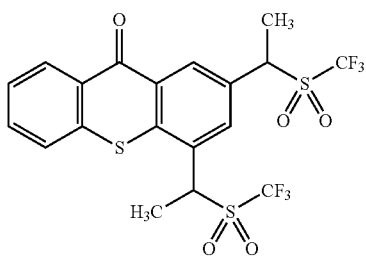

(4)

Example 5

Synthesis of 2,4-bis [1-{2-(2-ethyl hexyloxycarbonyl)ethanesulfonyl}ethyl]thioxanthene-9-one (the Compound Represented by the Formula (5))

2.1 g of 2,4-bis(1-bromoethyl)thioxanthene-9-one (5.0 mmol; produced by Wako Pure Chemical Industries, Ltd.) obtained in Synthetic Example 1, 1.1 g of triethylamine (11.0 mmol; produced by Wako Pure Chemical Industries, Ltd.) and 2.4 g of 2-ethylhexyl 3-mercaptopropionate (11.0 mmol; produced by Wako Pure Chemical Industries, Ltd.) were dissolved into 10 mL of dimethylformamide (DMF), and the resulting solution was stirred at 25° C. for 7 hours. After completion of the reaction, water was added to the reaction solution, which was extracted with ethyl acetate and the resulting organic layer was washed with water. After concentration of the organic layer after washing under reduced pressure, 6.2 mg of tungstic acid (0.025 mmol; produced by Wako Pure Chemical Industries, Ltd.), 13.0 mg of tridodecylamine (0.025 mmol; produced by Wako Pure Chemical Industries, Ltd.), 20 mL of toluene and 10 mL of acetonitrile were added into the resulting concentrated residue, which was warmed to 70° C. Then, 3.0 g of 35% hydrogen peroxide water (29.1 mmol; produced by Wako Pure Chemical Industries, Ltd.) was dropped into this solution and the resulting solution was stirred at 75° C. for 2 hours. After completion of the reaction, water was added to the reaction solution, which was extracted with ethyl acetate and the resulting organic layer was washed with sodium sulfite. After concentration of the organic layer after washing under reduced pressure and the obtained residue was purified using a silica gel column chromatography (developing solvent: ethyl acetate/hexane) to obtain 1.23 g of 2,4-bis[1-{2-(2-ethylhexyloxycarbonyl)ethanesulfonyl}ethyl]thioxanthene-9-one (pale yellow oil, yield: 31%). Measurement results of $^1$H-NMR and a structural formula of 2,4-bis[1-{2-(2-ethylhexyloxycarbonyl)ethanesulfonyl}ethyl]thioxanthene-9-one are shown below.

$^1$H-NMR (400 MHz, CDCl$_3$) δ (ppm): 0.85-0.89 (12H, m), 1.22-1.30 (16H, m), 1.53-1.56 (2H, m), 1.90 (3H, d), 1.93 (3H, d), 2.78-2.83 (4H, m), 3.15-3.28 (4H, m), 3.96-4.11 (4H, m), 4.44 (1H, q), 4.89 (1H, q), 7.55 (1H, t), 7.61 (1H, d), 7.69 (1H, t), 8.11 (1H, dd), 8.59 (1H, d), 8.73 (1H, dd).

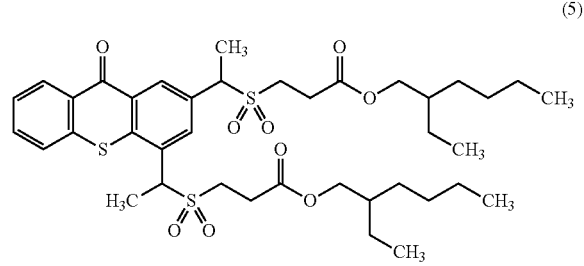 [SMILES: CCCCC(CC)COC(=O)CCS(=O)(=O)C(C)c1cc(C(C)S(=O)(=O)CCC(=O)OCC(CC)CCCC)c2sc3ccccc3c(=O)c2c1]

(5)

Synthetic Example 2

Synthesis of 2-(1-bromoethyl)anthraquinone

Into 300 mL ethyl acetate dissolved with 26.8 g of 2-ethylanthraquinone (100 mmol; produced by Wako Pure Chemical Industries, Ltd.), 8.9 g of N-bromosuccinimide (50 mmol; produced by Wako Pure Chemical Industries, Ltd.) and 1.54 g of 2,2'-azobis(4-methoxy-2,4-dimethylvaleronitrile) (5.0 mmol; produced by Wako Pure Chemical Industries, Ltd.) were added, and the resulting solution was stirred at 50° C. for 30 minutes. Then, after the reaction solution was once cooled to room temperature, 8.9 g of N-bromosuccinimide (50 mmol; produced by Wako Pure Chemical Industries, Ltd.) and 1.54 g of 2,2'-azobis(4-methoxy-2,4-dimethylvaleronitrile) (5.0 mmol; produced by Wako Pure Chemical Industries, Ltd.) were added to the reaction solution, and the resulting solution was stirred at 50° C. for 1 hour. After completion of the reaction, methanol was added to the reaction solution, which was cooled to 5° C. and solvent was removed from the resulting crystal, which was washed with ethyl acetate to obtain 21.3 g of 2-(1-bromoethyl)anthraquinone (pale yellow powder, yield: 68%). Measurement results of $^1$H-NMR and a structural formula of 2-(1-bromoethyl)anthraquinone are shown below.

$^1$H-NMR (400 MHz, CDCl$_3$) δ (ppm): 2.11 (3H, d), 5.28 (1H, q), 7.26-7.88 (3H, m), 8.29-8.34 (4H, m).

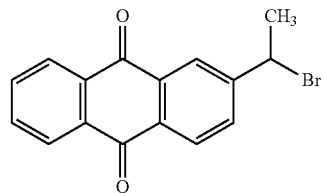 [SMILES: CC(Br)c1ccc2c(c1)C(=O)c1ccccc1C2=O]

Example 6

Synthesis of 2-(1-toluenesulfonylethyl)anthraquinone (the Compound Represented by the Formula (6))

1.58 g of 2-(1-bromoethyl)anthraquinone (5.0 mmol; produced by Wako Pure Chemical Industries, Ltd.) obtained in Synthetic Example 2 and 1.5 g of sodium p-toluenesulfinate tetrahydrate (6.0 mmol; produced by Wako Pure Chemical Industries, Ltd.) were dissolved into 10 mL of dimethylformamide (DMF), and the resulting solution was stirred at room temperature for 2 hours. After completion of the reaction, dichloromethane was added to the reaction solution, which was filtrated and the obtained filtrate was washed with water. Then, after concentration of the organic layer after washing under reduced pressure and the resulting crystal was dried to obtain 1.72 g of 2-(1-toluenesulfonylethyl)anthraquinone (pale yellow powder, yield: 88%). Measurement results of $^1$H-NMR and a structural formula of 2-(1-toluenesulfonylethyl)anthraquinone are shown below.

$^1$H-NMR (400 MHz, CDCl$_3$) δ (ppm): 1.83 (3H, d), 4.42 (1H, q), 7.22 (2H, d), 7.48 (2H, d), 7.69 (1H, d), 7.81 (2H, m), 8.01 (1H, s), 8.22-8.32 (3H, m).

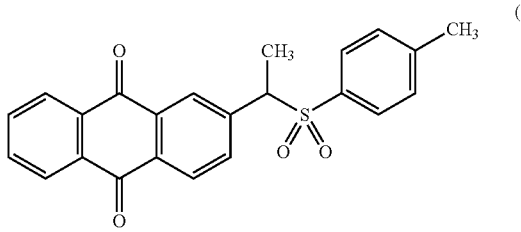

(6)

Example 7

Synthesis of 2-(1-benzenesulfonylethyl)anthraquinone (the Compound Represented by the Formula (7))

1.58 g of 2-(1-bromoethyl)anthraquinone (5.0 mmol; produced by Wako Pure Chemical Industries, Ltd.) obtained in Synthetic Example 2 and 1.2 g of sodium benzenesulfinate dihydrate (6.0 mmol; produced by Wako Pure Chemical Industries, Ltd.) were dissolved into 10 mL of dimethylformamide (DMF), and the resulting solution was stirred at room temperature for 2 hours. After completion of the reaction, dichloromethane was added to the reaction solution, which was filtrated and the obtained filtrate was washed with water. Then, after concentration of the organic layer after washing under reduced pressure and the resulting crystal was dried to obtain 1.74 g of 2-(1-benzenesulfonylethyl)anthraquinone (pale yellow powder, yield: 92%). Measurement results of $^1$H-NMR and a structural formula of 2-(1-benzenesulfonylethyl)anthraquinone are shown below.

$^1$H-NMR (400 MHz, CDCl$_3$) δ (ppm): 1.84 (3H, d), 4.44 (1H, q), 7.42 (2H, m), 7.57-7.63 (3H, m), 7.70 (1H, d), 7.80-7.83 (2H, m), 7.98 (1H, s), 8.23-8.32 (3H, m).

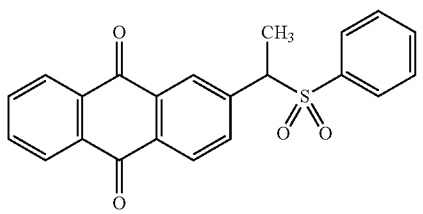

(7)

Example 8

Synthesis of 2-ethylhexyl 3-[1-(anthraquino-2-yl)-ethanesulfonyl]propionate (the Compound Represented by the Formula (8))

3.5 g of 2-(1-bromoethyl)anthraquinone (10.0 mmol; produced by Wako Pure Chemical Industries, Ltd.) obtained in Synthetic Example 2, 1.2 g of triethylamine (12.0 mmol; produced by Wako Pure Chemical Industries, Ltd.) and 2.6 g of 2-ethylhexyl 3-mercaptopropionate (12.0 mmol; produced by Wako Pure Chemical Industries, Ltd.) were dissolved into 20 mL of dimethylformamide (DMF), and the resulting solution was stirred at 25° C. for 7 hours. After completion of the reaction, water was added to the reaction solution, which was extracted with ethyl acetate and the resulting organic layer was washed with water. After concentration of the organic layer after washing under reduced pressure, 12.0 mg of tungstic acid (0.05 mmol; produced by Wako Pure Chemical Industries, Ltd.), 26.0 mg of tridodecylamine (0.05 mmol; produced by Wako Pure Chemical Industries, Ltd.), 20 mL of toluene and 10 mL of acetonitrile were dissolved into the resulting concentrated residue, which was warmed to 70° C. Then, 3.1 g of 35% hydrogen peroxide water (26.0 mmol; produced by Wako Pure Chemical Industries, Ltd.) was dropped into this solution and stirred at 75° C. for 2 hours. After completion of the reaction, water was added to the reaction solution, which was extracted with ethyl acetate and the resulting organic layer was washed with sodium sulfite. After concentration of the organic layer after washing under reduced pressure and the obtained residue was purified using a silica gel column chromatography (developing solvent: ethyl acetate/hexane) to obtain 2.2 g of 2-ethylhexyl 3-[1-(anthraquino-2-yl)-ethanesulfonyl]propionate (pale yellow powder, yield: 45%). Measurement results of $^1$H-NMR and a structural formula of 2-ethylhexyl 3-[1-(anthraquino-2-yl)-ethanesulfonyl]propionate are shown below.

$^1$H-NMR (400 MHz, CDCl$_3$) δ (ppm): 0.85-0.89 (12H, m), 1.22-1.30 (16H, m), 1.53-1.56 (2H, m), 1.90 (3H, d), 1.93 (3H, d), 2.78-2.83 (4H, m), 3.15-3.28 (4H, m), 3.96-4.11 (4H, m), 4.44 (1H, q), 4.89 (1H, q), 7.55 (1H, t), 7.61 (1H, d), 7.69 (1H, t), 8.11 (1H, dd), 8.59 (1H, d), 8.73 (1H, dd).

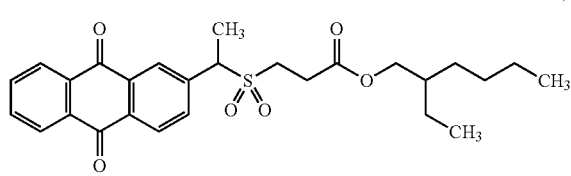

(8)

Experimental Example 1

A Heat Resistance Test

The compounds obtained in Examples 1 to 8 and the compound represented by the following formula (101) (2-methyl-2-[(4-methylphenyl)sulfonyl]-1-[(4-methylthio)phenyl]-1-propanone; produced by Wako Pure Chemical Industries, Ltd.) known as a photo-acid- and radical-generating agent, were each weighed by 10 mg, and as for these compounds, weight change was measured using TG-DTA 2000SA (manufactured by BRUKER AXS K.K.), in a range of 30° C. to 500° C. under a temperature increasing rate of 10/min., to calculate "5% weight decrease initiation temperature" of each compounds, and this temperature was used as decomposition initiation temperature to evaluate heat resistance of these compounds. The results thereof are shown in Table 1, as well as a structural formula of the compound represented by the formula (101) is shown below.

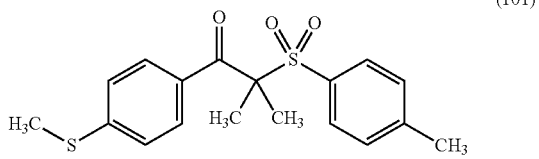

(101)

TABLE 1

| Compound | Decomposition initiation temperature |
| --- | --- |
| Compound represented by the formula (1) | 287° C. |
| Compound represented by the formula (2) | 289° C. |
| Compound represented by the formula (3) | 298° C. |
| Compound represented by the formula (4) | 208° C. |
| Compound represented by the formula (5) | 269° C. |
| Compound represented by the formula (6) | 285° C. |
| Compound represented by the formula (7) | 284° C. |
| Compound represented by the formula (8) | 254° C. |
| Compound represented by the formula (101) | 247° C. |

Experimental Example 2

An Acid Generating Test by Exposure (Irradiation of an Active Energy Ray)

The compounds obtained in Examples 1 to 8 and the compound represented by the above-described formula (101) (2-methyl-2-[(4-methylphenyl)sulfonyl]-1-[(4-methylthio)phenyl]-1-propanone; produced by Wako Pure Chemical Industries, Ltd.) known as a photo-acid- and radical-generating agent, were weighed each by 10 mg on a glass Petri dish, and 100 mg of methanol was added. Using an ultraviolet rays irradiation light source apparatus having specific exposure intensity, that is, REX-250 (manufactured by Asahi Spectra Co., Ltd.), and using a band-pass filter which transmits only specific wavelength, ultraviolet rays (an active energy ray) of only 365 nm (i-ray) or 405 nm (h-ray) were irradiated to the resulting solution, so as to attain an accumulated exposure amount of 1.0 J/cm². As for the solution after irradiation, 0.04 w/v % of a Thymol Blue solution was dropped to confirm the presence or absence of acid generation. The case where the solution presented red color was evaluated as [○], because the solution indicated sufficient acidity of a pH of 1.2 or lower by acid generation, while the case where the solution presented yellow color was evaluated as [x], because the solution indicated insufficient acidity of a pH of 2.8 to 8.0. The exposure intensity, when the band-pass filter and the ultraviolet rays irradiation light source apparatus REX-250 were used, is shown in Table 2, as well as evaluation results of the presence or absence of acid generation are shown in Table 3.

TABLE 2

| Wavelength | REX-250 Band-pass filter 365 | REX-250 Band-pass filter 405 |
| --- | --- | --- |
| 254 nm | — | — |
| 365 nm | 103 mW/cm² | — |
| 405 nm | — | 87 mW/cm² |

TABLE 3

| Compound | Irradiation of 365 nm 1.0 J/cm² | Irradiation of 405 nm 1.0 J/cm² |
| --- | --- | --- |
| Compound represented by the formula (1) | ○ | ○ |
| Compound represented by the formula (2) | ○ | ○ |
| Compound represented by the formula (3) | ○ | ○ |
| Compound represented by the formula (4) | ○ | ○ |
| Compound represented by the formula (5) | ○ | ○ |
| Compound represented by the formula (6) | ○ | ○ |
| Compound represented by the formula (7) | ○ | ○ |
| Compound represented by the formula (8) | ○ | ○ |
| Compound represented by the formula (101) | ○ | x |

Experimental Example 3

A Curing Test by a Sol-gel Method Using poly(3-propiotrimethoxysilanemethacrylate)

1.5 mL of a propylene glycol monomethyl ether acetate (PGMEA) solution containing 0.4 g of poly(3-propiotrimethoxysilanemethacrylate), and the compound obtained in Example 5, the compound obtained in Example 8 or the compound represented by the above-described formula (101) (2-methyl-2-[(4-methylphenyl)sulfonyl]-1-[(4-methylthio)phenyl]-1-propanone; produced by Wako Pure Chemical Industries, Ltd.) known as a photo-acid- and radical-generating agent, in 25% by weight relative to the poly(3-propiotrimethoxysilanemethacrylate), were bar-coated onto a glass plate, which was heated at 80° C. for 1 minute to prepare coated films. Using an ultraviolet rays irradiation light source apparatus having specific exposure intensity, that is, REX-250 (manufactured by Asahi Spectra Co., Ltd.), and using a band-pass filter which transmits only a wavelength of 405 nm (h-ray), ultraviolet rays (an active energy ray) of only 405 nm (h-ray) were irradiated to the coated films, so as to attain an accumulated exposure amount of 1.0 J/cm², and then by heating the coated films at 120° C. for 5 minutes, the coated films were hardened. Then, after these cured films were immersed into acetone for 30 seconds and the presence or absence of the cured films after immersion was confirmed visually. The results thereof are shown in Table 4.

TABLE 4

| Compound | Cured film |
| --- | --- |
| Compound represented by the formula (5) | Yes |
| Compound represented by the formula (8) | Yes |
| Compound represented by the formula (101) | No |

Experimental Example 4

A Radical Curing Test by Exposure (Irradiation of an Active Energy Ray)

10 mg of the compound obtained in Example 5, the compound obtained in Example 8 or the compound represented by the above-described formula (101) (2-methyl-2-[(4-methylphenyl)sulfonyl]-1-[(4-methylthio)phenyl]-1-propanone; produced by Wako Pure Chemical Industries, Ltd.) known as a photo-acid- and radical-generating agent was dissolved into 100 mg of pentaerythritol hexaacrylate (produced by Nippon Kayaku Co., Ltd.), and the resulting solution was bar-coated onto a glass plate to prepare coated films. Using an ultraviolet rays irradiation light source apparatus having specific exposure intensity, that is, REX-250 (manufactured by Asahi Spectra Co., Ltd.), and using a band-pass filter which transmits only specific wavelength, ultraviolet rays (an active energy ray) of only 365 nm (i-ray) or 405 nm (h-ray) were irradiated to the coated films, so as to attain an accumulated exposure amount of 0.5 $J/cm^2$, to harden the coated films. Then, curing performance of these coated films was confirmed by the presence or absence of stickiness by finger touch on the coated films. The case where there was no stickiness was evaluated as [○], because curing of the coated film was judged to be progressed sufficiently, while the case where there was stickiness was evaluated as [x], because curing of the coated film was judged not to be progressed sufficiently. The results thereof are shown in Table 5.

TABLE 5

| Compound | Irradiation of 365 nm 0.5 $J/cm^2$ | Irradiation of 405 nm 0.5 $J/cm^2$ |
| --- | --- | --- |
| Compound represented by the formula (5) | ○ | ○ |
| Compound represented by the formula (8) | ○ | ○ |
| Compound represented by the formula (101) | ○ | x |

Experimental Example 5

A Curing Test by a thiol-ene Reaction Using tetraallyl pyromellitate and pentaerythritol tetrakis(3-mercaptobutyrate)

10 mg of the compound obtained in Example 5, the compound obtained in Example 8 or the compound represented by the above-described formula (101) (2-methyl-2-[(4-methylphenyl)sulfonyl]-1-[(4-methylthio)phenyl]-1-propanone; produced by Wako Pure Chemical Industries, Ltd.) known as a photo-acid and radical-generating agent was dissolved into 414 mg of tetraallyl pyromellitate (produced by Wako Pure Chemical Industries, Ltd.), 544 mg of pentaerythritol tetrakis(3-mercaptobutyrate) (produced by Showa Denko K. K.) was added and mixed, and then the resulting solution was bar-coated onto a glass plate to prepare coated films. Using an ultraviolet rays irradiation light source apparatus having specific exposure intensity, that is, REX-250 (manufactured by Asahi Spectra Co., Ltd.), and using a band-pass filter which transmits only specific wavelength, ultraviolet rays (an active energy ray) of only 365 nm (i-ray) or 405 nm (h-ray) were irradiated to the coated films, so as to attain an accumulated exposure amount of 0.5 $J/cm^2$, to harden the coated films. Then, curing performance of these coated films was confirmed by the presence or absence of stickiness by finger touch on the coated films. The case where there was no stickiness was evaluated as [○], because curing of the coated film was judged to be progressed sufficiently, while the case where there was stickiness was evaluated as [x], because curing of the coated film was judged not to be progressed sufficiently. The results thereof are shown in Table 6.

TABLE 6

| Compound | Irradiation of 365 nm 0.5 $J/cm^2$ | Irradiation of 405 nm 0.5 $J/cm^2$ |
| --- | --- | --- |
| Compound represented by the formula (5) | ○ | ○ |
| Compound represented by the formula (8) | ○ | ○ |
| Compound represented by the formula (101) | ○ | x |

Experimental Example 6

A Curing Test by a thiol-ene Reaction and a Photo-sol-gel Method Using (3-mercaptopropyl)trimethoxysilane and 2,4,6-tris(allyloxy)-1,3,5-triazine Into 1.9 g of (3-mercaptopropyl)trimethoxysilane (produced by Wako Pure Chemical Industries, Ltd.), 92 mg of formic acid (produced by Wako Pure Chemical Industries, Ltd.) and 0.52 g of ion-exchanged water were added, the resulting solution was stirred at room temperature for 1 hour, and then by-produced methanol was removed under reduced pressure. Then, 0.15 g of the compound obtained in Example 5, the compound obtained in Example 8, the compound represented by the above-described formula (101) (2-methyl-2-[(4-methylphenyl)sulfonyl]-1-[(4-methylthio)phenyl]-1-propanone; produced by Wako Pure Chemical Industries, Ltd.) known as a photo-acid and radical-generating agent, the compound represented by the following formula (102) ((±)-camphorquinone; produced by Wako Pure Chemical Industries, Ltd.) known as a photo-radical-generating agent, the compound represented by the following formula (103) (1.2-octanedione,1-[4-(phenylthio)-,2-(O-benzoyloxime)]; produced by BASF Co., Ltd.) known as a photo-weak-base and radical-generating agent or the compound represented by the following formula (104) (ethanone,1-[9-ethyl-6-(2-methylbenzoyl)-9H-carbazol-3-yl]-,1-(O-acetyloxime); produced by BASF Co., Ltd.) known as a photo-weak-base- and radical-generating agent was dissolved into this solution, and still more 0.79 g of 2,4,6-tris(allyloxy)-1,3,5-triazine (produced by Wako Pure Chemical Industries, Ltd.) was added and mixed, and then the resulting solution was bar-coated onto a glass plate to prepare coated films. Using an ultraviolet rays irradiation light source apparatus having specific exposure intensity, that is, REX-250 (manufactured by Asahi Spectra Co., Ltd.), and using a band-pass filter which transmits only a wavelength of 405 nm (h-ray), ultraviolet rays (an active energy ray) of only 405 nm (h-ray) were irradiated to the coated films, so as to attain an accumulated exposure amount of 0.5 $J/cm^2$, to harden the coated films. Then, curing performance of these coated films was confirmed by the presence or absence of stickiness by finger touch on the coated films. The case where there was no stickiness was evaluated as [○], because curing of the coated film was judged to be progressed sufficiently, while the case where there was stickiness was evaluated as [x], because curing of the coated film was judged not to be progressed sufficiently. In addition, after these coated films were immersed into acetone and the presence or absence of solubility into acetone was confirmed visually. The case where curing performance of the coated film was sufficient and there was no dissolution into acetone was evaluated as [undissolved], while the case where curing performance of the coated film was insufficient and there was dissolution into acetone was evaluated as [dissolved]. These evaluation results are shown in Table 7, as well as structural formulae of the compounds represented by the formula (102), formula (103), and formula (104) are shown below.

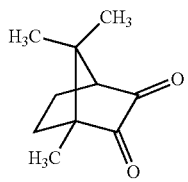
(102)

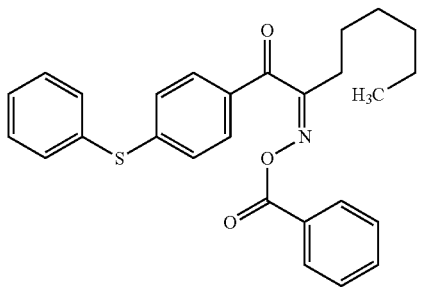
(103)

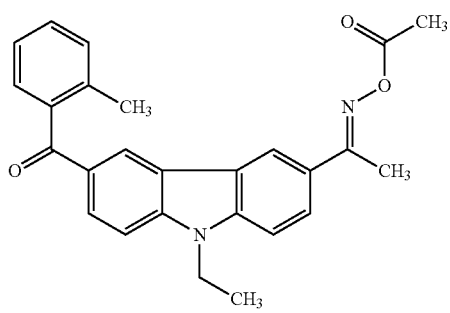
(104)

TABLE 7

| Compound | Irradiation of 405 nm 0.5 J/cm² | Solubility into acetone |
| --- | --- | --- |
| Compound represented by the formula (5) | ○ | Undissolved |
| Compound represented by the formula (8) | ○ | Undissolved |
| Compound represented by the formula (101) | x | Dissolved |
| Compound represented by the formula (102) | x | Dissolved |
| Compound represented by the formula (103) | x | Dissolved |
| Compound represented by the formula (104) | x | Dissolved |

From the results of Experimental Example 1 and Experimental Example 2, it was found that the compound represented by the general formula (A) of the present invention can exert as an acid-generating agent having heat resistance equivalent to or higher than that of conventionally known acid-generating agents, because the compound generates a strong acid by irradiation of an active energy ray, and still more decomposition initiation temperature is over 200° C. Therefore, when the compound represented by the general formula (A) of the present invention is used as an acid-generating agent, not only baking temperature can be set high, as well as deterioration of contrast between an exposed area (a cured area) and a non-exposed area (a non-cured area) can be suppressed, but also residue of an organic solvent after baking can be reduced as low as possible. In addition, from the results of Experimental Example 2 and Experimental Example 3, it was found that the compound represented by the general formula (A) of the present invention is capable of generating an acid by irradiation of an active energy ray having a wavelength of 300 nm or longer, in particular, capable of generating an acid even by irradiation of an active energy ray (h-ray) having a wavelength of 405 nm, to harden a coated film. Furthermore, from the results of Experimental Example 4 and Experimental Example 5, it was found that the compound represented by the general formula (A) of the present invention can exert as a radical-generating agent such as, what is called a polymerization initiator, because the compound generates a radical by irradiation of an active energy ray to progress a polymerization reaction of a compound having a double bond (a compound having a radically polymerizable ethylenic unsaturated bond). Still more, from the results of Experimental Example 4 and Experimental Example 5, it was found that the compound represented by the general formula (A) of the present invention is capable of generating a radical even by irradiation of an active energy ray having a long wavelength, for example, a wavelength of 405 nm (h-ray) or the like, to harden a coated film. Still further, from the result of Experimental Example 6, it was found that, although in using any of a conventionally known radical-generating agent, a conventionally known photo-acid- and radical-generating agent, and a conventionally known photo-weak-base- and radical-generating agent, a coated film cannot be hardened by irradiation of an active energy ray (h-ray) having a wavelength of 405 nm, because the compound represented by the general formula (A) of the present invention is capable of generating both of an acid and a radical even by irradiation of an active energy ray having a long wavelength, the compound is capable of hardening a coated film quickly, by well utilization of both functions. From the above-described results, it was found that the compound represented by the general formula (A) of the present invention is the one useful in any purposes as a photo-acid-generating agent, a photo-radical-generating agent, and a photo-acid- and radical-generating agent, suitable for a light emitting region (for example, 365 nm, 405 nm) of, such as, for example, an UV-LED light source, because the compound is the one of being capable of generating both of an acid and a radical by irradiation of an active energy ray having a long wavelength.

INDUSTRIAL APPLICABILITY

The compound represented by the general formula (A) of the present invention, and the acid- and radical-generating agent of the present invention are those which generate an acid and a radical by irradiation of an active energy ray, in particular, the compound, and the acid- and radical-generating agent which generate an acid and a radical even by irradiation of an active energy ray having a wavelength of around 300 to 450 nm, as well as have heat resistance. Therefore, the compound is useful as an acid- and radical-generating agent.

The method for generating an acid and a radical of the present invention is a method which comprises using the compound represented by the general formula (A) of the present invention, and is a method which is capable of generating an acid and a radical efficiently, by irradiation of an active energy ray, such as, for example, X-rays, UV rays, visible rays or the like, and in particular, generating an acid and a radical even by irradiation of an active energy ray (h-ray) having a wavelength of 405 nm.

The invention claimed is:

1. A compound represented by the general formula (A):

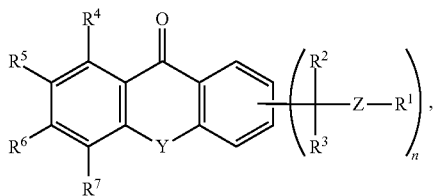

wherein Y represents an oxygen atom, a sulfur atom, or a carbonyl group;

when Y represents a carbonyl group,
n pieces of $R^1$ each independently represent an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group;
n pieces of $R^2$ and n pieces of $R^3$ each independently represent a hydrogen atom, an alkyl group having 1 to 10 carbon atoms or an alkoxycarbonyl group having 2 to 7 carbon atoms; $R^4$ to $R^7$ each independently represent a hydrogen atom, a halogen atom, an alkyl group having 1 to 6 carbon atoms, an alkoxy group having 1 to 6 carbon atoms, an alkenyl group having 2 to 6 carbon atoms, an aryl group having 6 to 10 carbon atoms, an alkoxycarbonyl group having 2 to 7 carbon atoms, a dialkylamino group having 2 to 8 carbon atoms, or a nitro group;
n pieces of Z each independently represent a sulfonyl group or an alkoxyphosphoryl group having 1 to 6 carbon atoms; and
n represents 1 or 2; and when Y represents an oxygen atom or a sulfur atom,
n pieces of $R^1$ each independently represent an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an alkoxy group having 1 to 10 carbon atoms, in which a hydrogen atom may be substituted by a halogen atom; an aryl group having 6 to 10 carbon atoms, in which a hydrogen atom may be substituted by a halogen atom, an alkyl group or a haloalkyl group; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group;
n pieces of $R^2$ and n pieces of $R^3$ each independently represent a hydrogen atom, an alkyl group having 1 to 10 carbon atoms or an alkoxycarbonyl group having 2 to 7 carbon atoms;
$R^4$ to $R^7$ each independently represent a hydrogen atom, a halogen atom, an alkyl group having 1 to 6 carbon atoms, an alkoxy group having 1 to 6 carbon atoms, an alkenyl group having 2 to 6 carbon atoms, an aryl group having 6 to 10 carbon atoms, an alkoxycarbonyl group having 2 to 7 carbon atoms, a dialkylamino group having 2 to 8 carbon atoms, or a nitro group;
n pieces of Z represent a sulfonyl group; and
n represents 1 or 2.

2. The compound according to claim 1, wherein the compound represented by the general formula (A) is a compound represented by the general formula (A'-1):

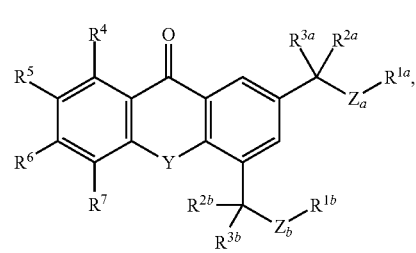

wherein Y represents an oxygen atom, a sulfur atom, or a carbonyl group;

when Y represents a carbonyl group,
$R^{1a}$ and $R^{1b}$ each independently represent an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group;
$R^{2a}$, $R^{2b}$, $R^{3a}$ and $R^{3b}$ each independently represent a hydrogen atom, an alkyl group having 1 to 10 carbon atoms or an alkoxycarbonyl group having 2 to 7 carbon atoms; and
$Z_a$ and $Z_b$ each independently represent a sulfonyl group or an alkoxyphosphoryl group having 1 to 6 carbon atoms; and when Y represents an oxygen atom or a sulfur atom,
$R^{1a}$ and $R^{1b}$ each independently represent an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an alkoxy group having 1 to 10 carbon atoms, in which a hydrogen atom may be substituted by a halogen atom; an aryl group having 6 to 10 carbon atoms, in which a hydrogen atom may be substituted by a halogen atom, an alkyl group or a haloalkyl group; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group;

$R^{2a}$, $R^{2b}$, $R^{3a}$ and $R^{3b}$ each independently represent a hydrogen atom, an alkyl group having 1 to 10 carbon atoms or an alkoxycarbonyl group having 2 to 7 carbon atoms; and $Z_a$ and $Z_b$ represent a sulfonyl group;

$R^4$ to $R^7$ are the same as described above.

3. The compound according to claim 1, wherein the compound represented by the general formula (A) is a compound represented by the general formula (A'-2):

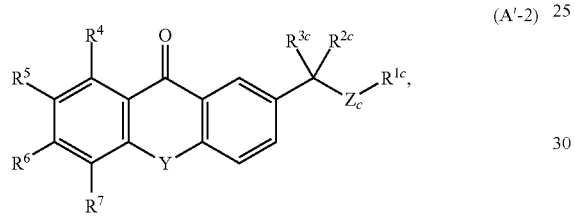

(A'-2)

wherein Y represents an oxygen atom, a sulfur atom, or a carbonyl group;

when Y represents a carbonyl group, $R^{1c}$ represents an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group;

$R^{2c}$ and $R^{3c}$ each independently represent a hydrogen atom, an alkyl group having 1 to 10 carbon atoms or an alkoxycarbonyl group having 2 to 7 carbon atoms; and $Z_c$ represents a sulfonyl group or an alkoxyphosphoryl group having 1 to 6 carbon atoms; and when Y represents an oxygen atom or a sulfur atom, $R^{1c}$ represents an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an alkoxy group having 1 to 10 carbon atoms, in which a hydrogen atom may be substituted by a halogen atom; an aryl group having 6 to 10 carbon atoms, in which a hydrogen atom may be substituted by a halogen atom, an alkyl group or a haloalkyl group; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group;

$R^{2c}$ and $R^{3c}$ each independently represent a hydrogen atom, an alkyl group having 1 to 10 carbon atoms or an alkoxycarbonyl group having 2 to 7 carbon atoms; and $Z_c$, represents a sulfonyl group;

$R^4$ to $R^7$ are the same as described above.

4. The compound according to claim 1, wherein the compound represented by the general formula (A) is a compound represented by the general formula (A"-1):

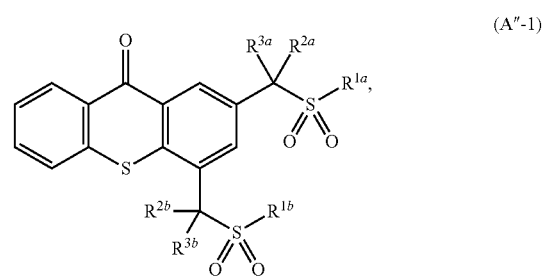

(A"-1)

wherein $R^{1a}$ and $R^{1b}$ each independently represent an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an alkoxy group having 1 to 10 carbon atoms, in which a hydrogen atom may be substituted by a halogen atom; an aryl group having 6 to 10 carbon atoms, in which a hydrogen atom may be substituted by a halogen atom, an alkyl group or a haloalkyl group; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group; and $R^{2a}$, $R^{2b}$, $R^{3a}$ and $R^{3b}$ each independently represent a hydrogen atom, an alkyl group having 1 to 10 carbon atoms or an alkoxycarbonyl group having 2 to 7 carbon atoms.

5. The compound according to claim 1, wherein the compound represented by the general formula (A) is a compound represented by the general formula (A"-2):

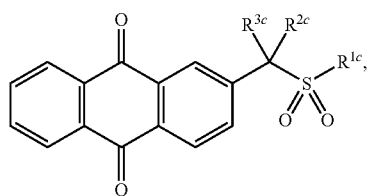

(A''-2)

wherein $R^{1c}$ represents an alkyl group having 1 to 20 carbon atoms, which may have a functional group selected from the group consisting of a carbonyloxy group, a carbonylamino group, an ether group and a sulfide group in the chain, or in which a hydrogen atom may be substituted by a halogen atom; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group; and $R^{2c}$ and $R^{3c}$ each independently represent a hydrogen atom, an alkyl group having 1 to 10 carbon atoms or an alkoxycarbonyl group having 2 to 7 carbon atoms.

6. The compound according to claim 1, wherein the compound represented by the general formula (A) is a compound represented by the general formula (A'''-1):

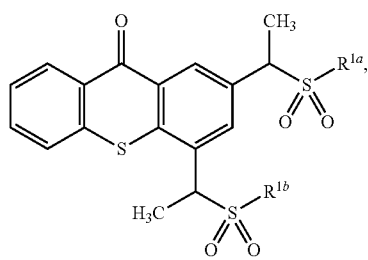

(A'''-1)

wherein $R^{1a}$ and $R^{1b}$ each independently represent an alkyl group having 1 to 15 carbon atoms, which may have a functional group selected from the group consisting of a carbonyloxy group, a carbonylamino group, an ether group and a sulfide group in the chain, or in which a hydrogen atom may be substituted by a fluorine atom; an alkoxy group having 1 to 10 carbon atoms, in which a hydrogen atom may be substituted by a halogen atom; an aryl group having 6 to 10 carbon atoms, in which a hydrogen atom may be substituted by a halogen atom, an alkyl group or a haloalkyl group; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group.

7. The compound according to claim 1, wherein the compound represented by the general formula (A) is a compound represented by the general formula (A'''-2):

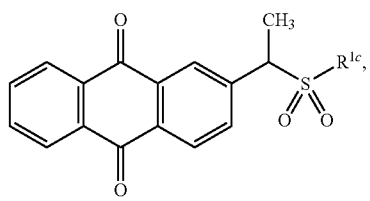

(A'''-2)

wherein $R^{1c}$ represents an alkyl group having 1 to 15 carbon atoms, which may have a functional group selected from the group consisting of a carbonyloxy group, a carbonylamino group, an ether group and a sulfide group in the chain, or in which a hydrogen atom may be substituted by a fluorine atom; an aryloxy group having 6 to 10 carbon atoms, in which a hydrogen atom may be substituted by a halogen atom, an alkyl group or a haloalkyl group; an arylalkyl group having 7 to 15 carbon atoms, in which a hydrogen atom may be substituted by a halogen atom, an alkyl group or a haloalkyl group; or an arylalkyloxy group having 7 to 15 carbon atoms, in which a hydrogen atom may be substituted by a halogen atom, an alkyl group or a haloalkyl group.

8. The compound according to claim 1, wherein the compound represented by the general formula (A) is the one represented by the formula (1), the formula (2), the formula (3), the formula (4), the formula (5), or the formula (8):

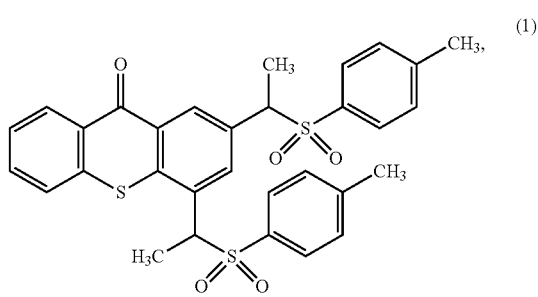

(1)

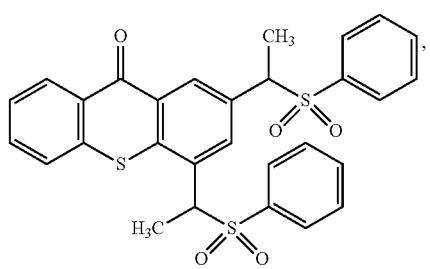

(2)

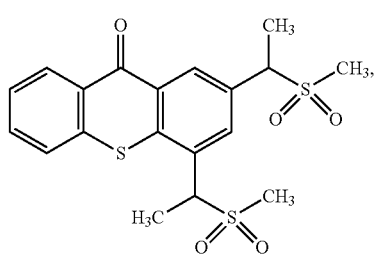

(3)

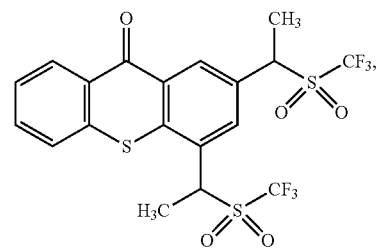
(4)

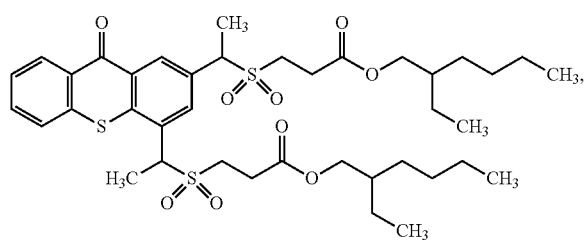
(5)

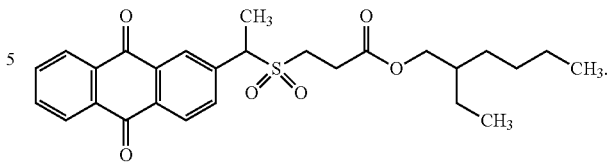
(8)

9. An acid- and radical-generating agent comprising the compound according to claim 1.

10. The acid- and radical-generating agent according to claim 9, wherein the acid- and radical-generating agent is the one generating an acid and a radical by irradiation of an active energy ray.

11. A method for generating an acid and a radical, which comprises irradiating an active energy ray onto the compound according to claim 1.

12. The method for generating an acid and a radical according to claim 11, wherein main wavelength of the active energy ray is 405 nm.

\* \* \* \* \*